(12) United States Patent
Jang et al.

(10) Patent No.: US 11,857,601 B2
(45) Date of Patent: *Jan. 2, 2024

(54) PHARMACEUTICAL COMPOSITION FOR CANCER TREATMENT COMPRISING FUSION PROTEIN INCLUDING IL-2 PROTEIN AND CD80 PROTEIN AND ANTICANCER DRUG

(71) Applicant: GI INNOVATION, INC., Seoul (KR)

(72) Inventors: Myung Ho Jang, Seoul (KR); Su Youn Nam, Seoul (KR); Young Jun Koh, Seoul (KR)

(73) Assignee: GI INNOVATION, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/911,891

(22) PCT Filed: Mar. 18, 2021

(86) PCT No.: PCT/KR2021/003375
§ 371 (c)(1),
(2) Date: Sep. 15, 2022

(87) PCT Pub. No.: WO2021/187922
PCT Pub. Date: Sep. 23, 2021

(65) Prior Publication Data
US 2023/0190876 A1 Jun. 22, 2023

(30) Foreign Application Priority Data

Mar. 18, 2020 (KR) .................. 10-2020-0033233
Feb. 16, 2021 (KR) .................. 10-2021-0020708

(51) Int. Cl.
| | |
|---|---|
| *A61P 35/00* | (2006.01) |
| *A61K 33/243* | (2019.01) |
| *A61K 31/337* | (2006.01) |
| *A61K 31/4439* | (2006.01) |
| *A61K 31/444* | (2006.01) |
| *A61K 31/47* | (2006.01) |
| *A61K 31/4709* | (2006.01) |
| *A61K 31/502* | (2006.01) |
| *A61K 31/5025* | (2006.01) |
| *A61K 31/506* | (2006.01) |
| *A61K 31/519* | (2006.01) |
| *A61K 31/708* | (2006.01) |
| *A61K 38/17* | (2006.01) |
| *A61K 39/395* | (2006.01) |
| *A61K 45/06* | (2006.01) |
| *A61K 38/20* | (2006.01) |

(52) U.S. Cl.
CPC ........ *A61K 38/2013* (2013.01); *A61K 31/337* (2013.01); *A61K 31/444* (2013.01); *A61K 31/4439* (2013.01); *A61K 31/47* (2013.01); *A61K 31/4709* (2013.01); *A61K 31/502* (2013.01); *A61K 31/506* (2013.01); *A61K 31/5025* (2013.01); *A61K 31/519* (2013.01); *A61K 31/708* (2013.01); *A61K 33/243* (2019.01); *A61K 38/1774* (2013.01); *A61K 39/3955* (2013.01); *A61K 45/06* (2013.01); *A61P 35/00* (2018.01)

(58) Field of Classification Search
CPC ............. A61K 38/2013; A61K 45/06; A61K 39/3955; A61K 33/243; A61K 31/337; A61K 31/708; A61P 35/00
See application file for complete search history.

(56) References Cited

FOREIGN PATENT DOCUMENTS

| | | | |
|---|---|---|---|
| JP | 2016-540042 A | 12/2016 | |
| KR | 10-2058846 B1 | 2/2020 | |
| KR | 10-2201086 B1 | 1/2021 | |
| WO | 2018/237158 A1 | 12/2018 | |
| WO | WO-2019051091 A1 * | 3/2019 | ............. A61K 39/00 |

OTHER PUBLICATIONS

Dandamudi et al. ("A Phase II Study of Bevacizumab and High-dose Interleukin-2 in Patients With Metastatic Renal Cell Carcinoma: A Cytokine Working Group (CWG) Study". Journal of Immunotherapy 36(9):p. 490-495, Nov./Dec. 2013) (Year: 2013).*
Carmenate et al. ("Human IL-2 Mutein with Higher Antitumor Efficacy Than Wild Type IL-2". J Immunol Jun. 15, 2013; 190 (12): 6230-6238) (Year: 2013).*
Arkin et al. ("Binding of small molecules to an adaptive protein-protein interface", Feb. 2003, 100(4) 1603-1608) (Year: 2003).*
Jae Chan Park, "3190-GI 101, a novel triple-targeting bispecific CD80-lgG4-IL2variant fusion protein, elicits synergistic anti-tumor effects in preclinical models", OncologyPROMeeting resourcesESMO 2019 Congress, Abstract 3190, Sep. 30, 2019, 3 pages, vol. 30, Supplement 5.
Korean Patent Office, Communication dated Oct. 26, 2021 in copending Korean Application No. 10-2021-0035517, with English translation.

(Continued)

*Primary Examiner* — Elly-Gerald Stoica
(74) *Attorney, Agent, or Firm* — Sughrue Mion, PLLC

(57) ABSTRACT

A pharmaceutical composition containing, as active ingredients, a fusion protein including an IL-2 protein and a CD80 protein, and an anticancer agent is disclosed. A fusion protein including a CD80 fragment, an immunoglobulin Fc, and an IL-2 variant, can activate immune cells such as natural killer cells, and at the same time, can control the immune cell regulatory activity of regulatory T cells. In addition, when an anticancer agent is administered in combination with the fusion protein, cancer can be effectively inhibited. Therefore, a pharmaceutical composition containing, as active ingredients, a fusion protein of an IL-2 protein and a CD80 protein, and an anticancer agent can increase the immune activity in the body and can be effectively utilized not only for cancer but also for an infectious disease, and thus has high industrial potential.

11 Claims, 95 Drawing Sheets
Specification includes a Sequence Listing.

(56) References Cited

OTHER PUBLICATIONS

Korean Patent Office, Communication dated Feb. 27, 2022 in copending Korean Application No. 10-2021-0035517, with English translation.
Korean Patent Office, Communication dated Jun. 29, 2022 in copending Korean Application No. 10-2021-0035517, with English translation.
Korean Patent Office, Notice of Allowance dated Aug. 29, 2022 in copending Korean Application No. 10-2021-0035517, with English translation.
"GI-101 showing the possibility of new immuno-cancer drugs, clinical confirmation next year", Oct. 28, 2019, pp. 1-3, <https://www.docdocdoc.co.kr/news/articleView.html?idxno=1073307, last edited Aug. 27, 2021>, with English translation.
Jae Chan Park, "3190—GI 101, a novel triple-targeting bispecific CD80-IgG4-IL2variant fusion protein, elicits synergistic anti-tumor effects in preclinical models", OncologyPROMeeting resourcesESMO 2019 Congress, Abstract 3190, Sep. 30, 2019, 3 pages, vol. 30, Supplement 5.
Lucas Chan et al., "IL-2/B7.1 (CD80) Fusagene Transduction of AML Blasts by a Self-Inactivating Lentiviral Vector Stimulates T Cell Responses in Vitro: a Strategy to Generate Whole Cell Vaccines for AML", Molecular Therapy, Jan. 2005, pp. 120-131, vol. 11, No. 1.
Nam Soo-Yeon, "GI-101, a new type of immuno-cancer drug, confirmed by clinical trials next year", https://www.docdocdoc.co.kr/news/articleView.html?idxno=1073307, Youth Doctor, Oct. 18, 2019, 5 pages.
International Search Report for PCT/KR2021/003375, dated Jul. 12, 2021.

\* cited by examiner

| Kon | Koff | Kd |
|---|---|---|
| 1.10X10 5 | 1.27X10-3 | 1.19X10-8 |

*; $p < 0.05$ vs. Vehicle
**; $p < 0.01$ vs. Vehicle

① ***; p < 0.001 vs. Vehicle
② ***; p < 0.001 vs. aTIGIT

*//* A significant difference at p<0.001/p<0.01/p<0.05 level compared to the Vehicle

SEQUENCE LISTING

<160> NUMBER OF SEQ ID NOS: 39

<210> SEQ ID NO 1
<211> LENGTH: 25
<212> TYPE: PRT
<213> ORGANISM: Artificial Sequence
<220> FEATURE:
<223> OTHER INFORMATION: Syntheic construct: signal peptide (TPA)

<400> SEQUENCE: 1

Met Asp Ala Met Leu Arg Gly Leu Cys Cys Val Leu Leu Cys Gly
1               5                   10                  15

Ala Val Phe Val Ser Pro Ser His Ala
            20                  25

<210> SEQ ID NO 2
<211> LENGTH: 208
<212> TYPE: PRT
<213> ORGANISM: Artificial Sequence
<220> FEATURE:
<223> OTHER INFORMATION: Sequence of hB7-1:35-242

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 3
<211> LENGTH: 30
<212> TYPE: PRT
<213> ORGANISM: Artificial Sequence
<220> FEATURE:
<223> OTHER INFORMATION: Sequence of hinge

<400> SEQUENCE: 3

Gly Ser Gly Gly Gly Gly Ser Gly Gly Gly Gly Ser Gly Gly Gly Gly
1               5                   10                  15

```
Ser Ala Glu Ser Lys Tyr Gly Pro Pro Cys Pro Pro Cys Pro
            20                  25                  30

<210> SEQ ID NO 4
<211> LENGTH: 216
<212> TYPE: PRT
<213> ORGANISM: Artificial Sequence
<220> FEATURE:
<223> OTHER INFORMATION: Sequence of immunoglobulin fc

<400> SEQUENCE: 4

Ala Pro Glu Ala Ala Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly
    210                 215

<210> SEQ ID NO 5
<211> LENGTH: 5
<212> TYPE: PRT
<213> ORGANISM: Artificial Sequence
<220> FEATURE:
<223> OTHER INFORMATION: Synthetic construct: linker

<400> SEQUENCE: 5

Gly Gly Gly Gly Ser
1               5

<210> SEQ ID NO 6
<211> LENGTH: 133
<212> TYPE: PRT
<213> ORGANISM: Artificial Sequence
<220> FEATURE:
<223> OTHER INFORMATION: Sequence of hIL-2M

<400> SEQUENCE: 6
```

-continued

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 7
<211> LENGTH: 617
<212> TYPE: PRT
<213> ORGANISM: Artificial Sequence
<220> FEATURE:
<223> OTHER INFORMATION: Fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220
```

Thr Lys Gln Glu His Phe Pro Asp Asn Gly Ser Gly Gly Gly Ser
225                 230                 235                 240

Gly Gly Gly Gly Ser Gly Gly Gly Ser Ala Glu Ser Lys Tyr Gly
            245                 250                 255

Pro Pro Cys Pro Pro Cys Pro Ala Pro Glu Ala Ala Gly Gly Pro Ser
        260                 265                 270

Val Phe Leu Phe Pro Pro Lys Pro Lys Asp Gln Leu Met Ile Ser Arg
        275                 280                 285

Thr Pro Glu Val Thr Cys Val Val Val Asp Val Ser Gln Glu Asp Pro
        290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
            325                 330                 335

Ser Val Leu Thr Val Leu His Gln Asp Trp Leu Asn Gly Lys Glu Tyr
            340                 345                 350

Lys Cys Lys Val Ser Asn Lys Gly Leu Pro Ser Ser Ile Glu Lys Thr
        355                 360                 365

Ile Ser Lys Ala Lys Gly Gln Pro Arg Glu Pro Gln Val Tyr Thr Leu
370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Arg Leu Thr Val Asp Lys Ser
        435                 440                 445

Arg Trp Gln Glu Gly Asn Val Phe Ser Cys Ser Val Leu His Glu Ala
450                 455                 460

Leu His Asn His Tyr Thr Gln Lys Ser Leu Ser Leu Ser Leu Gly Gly
465                 470                 475                 480

Gly Gly Gly Ser Ala Pro Thr Ser Ser Ser Thr Lys Lys Thr Gln Leu
            485                 490                 495

Gln Leu Glu His Leu Leu Leu Asp Leu Gln Met Ile Leu Asn Gly Ile
        500                 505                 510

Asn Asn Tyr Lys Asn Pro Lys Leu Thr Ala Met Leu Thr Ala Lys Phe
        515                 520                 525

Tyr Met Pro Lys Lys Ala Thr Glu Leu Lys His Leu Gln Cys Leu Glu
        530                 535                 540

Glu Glu Leu Lys Pro Leu Glu Glu Val Leu Asn Leu Ala Gln Ser Lys
545                 550                 555                 560

Asn Phe His Leu Arg Pro Arg Asp Leu Ile Ser Asn Ile Asn Val Ile
                565                 570                 575

Val Leu Glu Leu Lys Gly Ser Glu Thr Thr Phe Met Cys Glu Tyr Ala
            580                 585                 590

Asp Glu Thr Ala Thr Ile Val Glu Phe Leu Asn Arg Trp Ile Thr Phe
        595                 600                 605

Cys Gln Ser Ile Ile Ser Thr Leu Thr
        610                 615

<210> SEQ ID NO 8
<211> LENGTH: 1857

<212> TYPE: DNA
<213> ORGANISM: Artificial Sequence
<220> FEATURE:
<223> OTHER INFORMATION: Sequence of nucleotiedes coding fusion protein (GI101)

<400> SEQUENCE: 8

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120
tgcggccaca acgtttcagt ggaagaactg gcccagacca ggatctactg cagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540
tctcaggacc ccgaaaccga gctgtacgct gtgtcctcca gctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg aagcggagg cggaggatct gctgagtcta agtatggccc tccttgtcct      780
ccatgtcctg ctccagaagc tgctggcgga ccctctgtgt tcctgttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gtgtggtc cgtgctgacc      1020
gtgctgcacc aggattggct gaacggcaaa gagtacaagt gcaaggtgtc caacaagggc      1080
ctgccttcca gcatcgaaaa gaccatctcc aaggctaagg ccagcctag gaaccccag      1140
gtttacaccc tgcctccaag ccaagaggaa atgaccaaga ccaggtgtc cctgacctgc      1200
ctggtcaagg gcttctaccc ttccgacatt gccgtggaat gggagtccaa tggccagcct      1260
gagaacaact acaagaccac acctcctgtg ctggactccg acggctcctt ctttctgtac      1320
tctcgcctga ccgtggacaa gtctagatgg caagagggca acgtgttctc ctgctctgtg      1380
ctgcacgagg ccctgcacaa tcactacacc cagaagtccc tgtctctgtc tcttggaggt      1440
ggtgggggtt ctgcccctac cagctcctct accaagaaaa cccagctcca gttggagcat      1500
ctgctgctgg acctccagat gattctgaac gggatcaaca actataagaa ccccaagctg      1560
accgccatgc tgaccgctaa gttctacatg cccaagaagg ccaccgagct gaagcacctc      1620
cagtgcctgg aagaagaact gaagcccctg gaagaggtgc tgaatctggc ccagtccaag      1680
aacttccacc tgaggccacg ggacctgatc agcaacatca cgtgatcgt gctggaactg      1740
aagggctccg agacaacctt tatgtgcgag tacgccgacg agacagccac catcgtggaa      1800
tttctgaacc ggtggatcac cttctgccag agcatcatct ccacactgac ctgatga      1857
```

<210> SEQ ID NO 9
<211> LENGTH: 592
<212> TYPE: PRT
<213> ORGANISM: Artificial Sequence
<220> FEATURE:
<223> OTHER INFORMATION: Fusion protein (GI101)

<400> SEQUENCE: 9

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
50                      55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 10
<211> LENGTH: 133
<212> TYPE: PRT
<213> ORGANISM: Artificial Sequence
<220> FEATURE:
<223> OTHER INFORMATION: Sequence of hIL-2

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 11
<211> LENGTH: 288
<212> TYPE: PRT
<213> ORGANISM: Artificial Sequence
<220> FEATURE:
<223> OTHER INFORMATION: Sequennce of CD80

<400> SEQUENCE: 11
```

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 12
<211> LENGTH: 215
<212> TYPE: PRT
<213> ORGANISM: Artificial Sequence
<220> FEATURE:
<223> OTHER INFORMATION: Sequence of modified Fc

<400> SEQUENCE: 12

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80
```

```
Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215

<210> SEQ ID NO 13
<211> LENGTH: 306
<212> TYPE: PRT
<213> ORGANISM: Artificial Sequence
<220> FEATURE:
<223> OTHER INFORMATION: Sequence of mCD80

<400> SEQUENCE: 13

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220
```

```
Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
            245                 250                 255

Ala Val Ile Thr Val Val Val Ile Val Val Ile Ile Lys Cys Phe Cys
        260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
        290                 295                 300

Phe Leu
305

<210> SEQ ID NO 14
<211> LENGTH: 1848
<212> TYPE: DNA
<213> ORGANISM: Artificial Sequence
<220> FEATURE:
<223> OTHER INFORMATION: Sequence of nucleotiedes coding fusion protein
      (mGI101)

<400> SEQUENCE: 14
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct      480 aagcctcggt tctcttggct ggaaaacggc agagagctgc ccggcatcaa taccaccatt     540
tctcaggacc agagtccga gctgtacacc atctccagcc agctcgactt taacaccacc      600
agaaaccaca ccatcaagtg cctgattaag tacggcgacg cccacgtgtc cgaggacttt     660
acttgggaga acctcctga ggaccctcct gactctggat ctggcggcgg aggttctggc      720
ggaggtggaa gcggaggcgg aggatctgct gagtctaagt atggccctcc ttgtcctcca     780
tgtcctgctc cagaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca caacgccaag     960
accaagccta gagaggaaca gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga ccccaggtt     1140 tacaccctgc ctccaagcca gaggaaatg accaagaacc aggtgtccct gacctgcctg    1200
gtcaagggct ctacccttc cgacattgcc gtggaatggg agtccaatgg ccagcctgag    1260
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtctct ggaggtggt    1440 ggcggttctg cccctaccctc cagctctacc aagaaaaccc agctccagtt ggagcatctg    1500
```

```
ctgctggacc tccagatgat cctgaatggc atcaacaatt acaagaaccc caagctgacc     1560
gccatgctga ccgctaagtt ctacatgccc aagaaggcca ccgagctgaa gcacttgcag     1620
tgcctggaag aggaactgaa gcccctggaa gaagtgctga atctggccca gtccaagaac     1680
ttccacctga ggcctaggga cctgatctcc aacatcaacg tgatcgtgct ggaactgaaa     1740
ggctccgaga caaccttcat gtgcgagtac gccgacgaga cagccaccat cgtggaattt     1800
ctgaaccggt ggatcacctt ctgccagagc atcatctcca cactgacc                 1848
```

<210> SEQ ID NO 15
<211> LENGTH: 616
<212> TYPE: PRT
<213> ORGANISM: Artificial Sequence
<220> FEATURE:
<223> OTHER INFORMATION: Sequence of fusion protein (mGI101)

<400> SEQUENCE: 15

```
Met Asp Ala Met Leu Arg Gly Leu Cys Cys Val Leu Leu Cys Gly
1               5                   10                  15

Ala Val Phe Val Ser Pro Ser His Ala Val Asp Glu Gln Leu Ser Lys
                20                  25                  30

Ser Val Lys Asp Lys Val Leu Leu Pro Cys Arg Tyr Asn Ser Pro His
            35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300
```

```
Val Gln Phe Asn Trp Tyr Val Asp Gly Val Glu Val His Asn Ala Lys
305                 310                 315                 320

Thr Lys Pro Arg Glu Gln Phe Asn Ser Thr Tyr Arg Val Val Ser
            325                 330                 335

Val Leu Thr Val Leu His Gln Asp Trp Leu Asn Gly Lys Glu Tyr Lys
                340                 345                 350

Cys Lys Val Ser Asn Lys Gly Leu Pro Ser Ser Ile Glu Lys Thr Ile
            355                 360                 365

Ser Lys Ala Lys Gly Gln Pro Arg Glu Pro Gln Val Tyr Thr Leu Pro
370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
            515                 520                 525

Met Pro Lys Lys Ala Thr Glu Leu Lys His Leu Gln Cys Leu Glu Glu
530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
            595                 600                 605

Gln Ser Ile Ile Ser Thr Leu Thr
    610                 615
```

<210> SEQ ID NO 16
<211> LENGTH: 1437
<212> TYPE: DNA
<213> ORGANISM: Artificial Sequence
<220> FEATURE:
<223> OTHER INFORMATION: Sequence of nucleotiedes coding fusion protein
      (GI101C1)

<400> SEQUENCE: 16

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120 tgcggccaca acgtttcagt ggaagaactg gcccagacca ggatctactg cagaaagaa      180 aagaaaatgg tgctgaccat gatgtccggc gacatgaaca tctggcctga gtacaagaac      240
```

```
cggaccatct tcgacatcac caacaacctg tccatcgtga ttctggccct gaggccttct    300
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg aagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg ccagcctag ggaaccccag   1140 gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt ctttctgtac   1320
tctcgcctga ccgtggacaa gtctaggtgg caagagggca cgtgttctc ctgctctgtg   1380 ctgcacgagg ccctgcacaa tcactacacc cagaagtccc tgtctctgtc cctgggc     1437
```

<210> SEQ ID NO 17
<211> LENGTH: 454
<212> TYPE: PRT
<213> ORGANISM: Artificial Sequence
<220> FEATURE:
<223> OTHER INFORMATION: Sequence of fusion protein (GI101C1)

<400> SEQUENCE: 17

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
```

Thr Glu Leu Tyr Ala Val Ser Ser Lys Leu Asp Phe Asn Met Thr Thr
145                 150                 155                 160

Asn His Ser Phe Met Cys Leu Ile Lys Tyr Gly His Leu Arg Val Asn
        165                 170                 175

Gln Thr Phe Asn Trp Asn Thr Thr Lys Gln Glu His Phe Pro Asp Asn
            180                 185                 190

Gly Ser Gly Gly Gly Ser Gly Gly Gly Ser Gly Gly Gly
    195                 200                 205

Gly Ser Gly Gly Gly Gly Ser Gly Gly Gly Ser Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
            245                 250                 255

Asp Gln Leu Met Ile Ser Arg Thr Pro Glu Val Thr Cys Val Val Val
                260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Met Thr Lys
                355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
        435                 440                 445

Leu Ser Leu Ser Leu Gly
    450

<210> SEQ ID NO 18
<211> LENGTH: 1176
<212> TYPE: DNA
<213> ORGANISM: Artificial Sequence
<220> FEATURE:
<223> OTHER INFORMATION: Sequence of nucleotiedes coding fusion protein
      (GI101C2)

<400> SEQUENCE: 18
atggatgcta tgctgagagg cctgtgttgc gtgctgctgc tgtgtggcgc tgtgttcgtg     60
tctccatctc acgccgctga gtctaagtac ggccctcctt gtcctccatg tcctgctcca    120
gaagctgctg gcggacccte tgtgttcctg tttcctccaa agcctaagga ccagctcatg    180
atctctcgga cccctgaagt gacctgcgtg gtggtggatg tgtctcaaga ggaccctgag    240
gtgcagttca attggtacgt ggacggcgtg gaagtgcaca acgccaagac caagcctaga    300

```
gaggaacagt tcaactccac ctacagagtg gtgtccgtgc tgaccgtgct gcaccaggat    360
tggctgaacg gcaaagagta caagtgcaag gtgtccaaca agggcctgcc ttccagcatc    420
gaaaagacca tctccaaggc taagggccag cctagggaac ccaggttta caccctgcct    480
ccaagccaag aggaaatgac caagaaccag gtgtccctga cctgcctggt caagggcttc    540
taccctccg acattgccgt ggaatgggag tccaatggcc agcctgagaa caactacaag    600
accacacctc ctgtgctgga ctccgacggc tccttctttc tgtactctcg cctgaccgtg    660
gacaagtcta ggtggcaaga gggcaacgtg ttctcctgct ctgtgctgca cgaggccctg    720
cacaatcact acacccagaa gtccctgtct ctgtctcttg gcggaggcgg aggatctgct    780
cctacctcca gctccaccaa gaaaacccag ctccagttgg agcatctgct gctggacctc    840
cagatgatcc tgaatggcat caacaattac aagaaccca agctgaccgc catgctgacc    900
gctaagttct acatgcccaa gaaggccacc gagctgaagc acctccagtg cctggaagag    960
gaactgaagc ccctggaaga agtgctgaat ctggcccagt ccaagaactt ccacctgagg    1020
cctagggacc tgatctccaa catcaacgtg atcgtgctgg aactgaaagg ctccgagaca    1080
accttcatgt gcgagtacgc cgacgagaca gccaccatcg tggaatttct gaaccggtgg    1140
atcaccttct gccagtccat catctccaca ctgacc                              1176
```

<210> SEQ ID NO 19
<211> LENGTH: 367
<212> TYPE: PRT
<213> ORGANISM: Artificial Sequence
<220> FEATURE:
<223> OTHER INFORMATION: Sequence of fusion protein (GI101C2)

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205
```

```
Ser Val Leu His Glu Ala Leu His Asn His Tyr Thr Gln Lys Ser Leu
    210                 215                 220
Ser Leu Ser Leu Gly Gly Gly Gly Ser Ala Pro Thr Ser Ser Ser
225                 230                 235                 240
Thr Lys Lys Thr Gln Leu Gln Leu Glu His Leu Leu Asp Leu Gln
                245                 250                 255
Met Ile Leu Asn Gly Ile Asn Asn Tyr Lys Asn Pro Lys Leu Thr Ala
            260                 265                 270
Met Leu Thr Ala Lys Phe Tyr Met Pro Lys Lys Ala Thr Glu Leu Lys
            275                 280                 285
His Leu Gln Cys Leu Glu Glu Glu Leu Lys Pro Leu Glu Glu Val Leu
            290                 295                 300
Asn Leu Ala Gln Ser Lys Asn Phe His Leu Arg Pro Arg Asp Leu Ile
305                 310                 315                 320
Ser Asn Ile Asn Val Ile Val Leu Glu Leu Lys Gly Ser Glu Thr Thr
                325                 330                 335
Phe Met Cys Glu Tyr Ala Asp Glu Thr Ala Thr Ile Val Glu Phe Leu
            340                 345                 350
Asn Arg Trp Ile Thr Phe Cys Gln Ser Ile Ile Ser Thr Leu Thr
            355                 360                 365

<210> SEQ ID NO 20
<211> LENGTH: 1434
<212> TYPE: DNA
<213> ORGANISM: Artificial Sequence
<220> FEATURE:
<223> OTHER INFORMATION: Sequence of nucleotiedes coding fusion protein
      (mGI101C1)

<400> SEQUENCE: 20
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag     240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct     480 aagcctcggt tctcttggct ggaaaacggc agagagctgc ccggcatcaa taccaccatt     540
tctcaggacc cagagtccga gctgtacacc atctccagcc agctcgactt taacaccacc     600
agaaaccaca ccatcaagtg cctgattaag tacggcgacg cccacgtgtc cgaggacttt     660
acttgggaga aacctcctga ggaccctcct gactctggat ctggcggcgg aggttctggc     720
ggaggtggaa gcggaggcgg aggatctgct gagtctaagt atggcccctc cttgtcctcca    780 tgtcctgctc cagaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca aacgccaag     960 accaagccta gaggaacag gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga accccaggtt    1140
```

-continued

```
tacaccctgc ctccaagcca agaggaaatg accaagaacc aggtgtccct gacctgcctg    1200
gtcaagggct ctacccttc cgacattgcc gtggaatggg agtccaatgg ccagcctgag     1260
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtccct gggc          1434
```

<210> SEQ ID NO 21
<211> LENGTH: 478
<212> TYPE: PRT
<213> ORGANISM: Artificial Sequence
<220> FEATURE:
<223> OTHER INFORMATION: Sequence of fusion protein (mGI101C1)

<400> SEQUENCE: 21

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
```

```
                    305                 310                 315                 320
        Thr Lys Pro Arg Glu Glu Gln Phe Asn Ser Thr Tyr Arg Val Val Ser
                        325                 330                 335

Val Leu Thr Val Leu His Gln Asp Trp Leu Asn Gly Lys Glu Tyr Lys
                        340                 345                 350

Cys Lys Val Ser Asn Lys Gly Leu Pro Ser Ser Ile Glu Lys Thr Ile
                        355                 360                 365

Ser Lys Ala Lys Gly Gln Pro Arg Glu Pro Gln Val Tyr Thr Leu Pro
                        370                 375                 380

Pro Ser Gln Glu Glu Met Thr Lys Asn Gln Val Ser Leu Thr Cys Leu
        385                 390                 395                 400

Val Lys Gly Phe Tyr Pro Ser Asp Ile Ala Val Glu Trp Glu Ser Asn
                        405                 410                 415

Gly Gln Pro Glu Asn Asn Tyr Lys Thr Thr Pro Pro Val Leu Asp Ser
                        420                 425                 430

Asp Gly Ser Phe Phe Leu Tyr Ser Arg Leu Thr Val Asp Lys Ser Arg
                        435                 440                 445

Trp Gln Glu Gly Asn Val Phe Ser Cys Ser Val Leu His Glu Ala Leu
            450                 455                 460

His Asn His Tyr Thr Gln Lys Ser Leu Ser Leu Ser Leu Gly
        465                 470                 475

<210> SEQ ID NO 22
<211> LENGTH: 133
<212> TYPE: PRT
<213> ORGANISM: Artificial Sequence
<220> FEATURE:
<223> OTHER INFORMATION: Sequence of variants of IL-2 (3M, M45)

<400> SEQUENCE: 22

Ala Pro Thr Ser Ser Ser Thr Lys Lys Thr Gln Leu Gln Leu Glu His
        1               5                   10                  15

Leu Leu Leu Asp Leu Gln Met Ile Leu Asn Gly Ile Asn Asn Tyr Lys
                        20                  25                  30

Asn Pro Lys Leu Thr Ala Met Leu Thr Ala Lys Phe Ala Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
        65                  70                  75                  80

Arg Pro Arg Asp Leu Ile Ser Asn Ile Asn Val Ile Val Leu Glu Leu
                        85                  90                  95

Lys Gly Ser Glu Thr Thr Phe Met Cys Glu Tyr Ala Asp Glu Thr Ala
                        100                 105                 110

Thr Ile Val Glu Phe Leu Asn Arg Trp Ile Thr Phe Cys Gln Ser Ile
                        115                 120                 125

Ile Ser Thr Leu Thr
                130

<210> SEQ ID NO 23
<211> LENGTH: 133
<212> TYPE: PRT
<213> ORGANISM: Artificial Sequence
<220> FEATURE:
<223> OTHER INFORMATION: Sequenc eof variants of IL-2 (3M, M61)

<400> SEQUENCE: 23
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
            35                  40                  45

Lys Ala Thr Glu Leu Lys His Leu Gln Cys Leu Glu Arg Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: Sequence of variants of IL-2 (3M, M72)

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 25
<211> LENGTH: 1851
<212> TYPE: DNA
<213> ORGANISM: Artificial Sequence
<220> FEATURE:
<223> OTHER INFORMATION: Sequence of nucleotiedes coding fusion protein
      (GI102-M45)

<400> SEQUENCE: 25
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120

-continued

```
tgcggccaca acgtttcagt ggaagaactg gcccagacca ggatctactg cagaaagaa       180 aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg       540 tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg gaagcggagg cggaggatct gctgagtcta agtatggccc tccttgtcct      780
ccatgtcctg ctccagaagc tgctggcgga ccctctgtgt tcctgttttcc tccaaagcct    840 aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc tagagagga acagttcaac tccacctaca gagtggtgtc cgtgctgacc      1020
gtgctgcacc aggattggct gaacggcaaa gagtacaagt gcaaggtgtc caacaagggc    1080
ctgccttcca gcatcgaaaa gaccatctcc aaggctaagg gccagcctag gaaccccag      1140 gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca acgtgttctc ctgctctgtg     1380
ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca actataagaa ccccaagctg     1560
accgccatgc tgaccgctaa gttcgccatg cccaagaagg ccaccgagct gaagcacctc    1620
cagtgcctgg aagaagaact gaagcccctg gaagaggtgc tgaatctggc ccagtccaag    1680
aacttccacc tgaggccacg ggacctgatc agcaacatca cgtgatcgt gctgaactg       1740 aagggctccg agacaacctt tatgtgcgag tacgccgacg agacagccac catcgtggaa     1800
tttctgaacc ggtggatcac cttctgccag agcatcatct ccacactgac c             1851
```

<210> SEQ ID NO 26
<211> LENGTH: 592
<212> TYPE: PRT
<213> ORGANISM: Artificial Sequence
<220> FEATURE:
<223> OTHER INFORMATION: Sequence of fusion protein (GI102-M45)

<400> SEQUENCE: 26

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60
```

```
Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                 85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480
```

```
Gln Met Ile Leu Asn Gly Ile Asn Asn Tyr Lys Asn Pro Lys Leu Thr
                485                 490                 495
Ala Met Leu Thr Ala Lys Phe Ala Met Pro Lys Lys Ala Thr Glu Leu
            500                 505                 510
Lys His Leu Gln Cys Leu Glu Glu Leu Lys Pro Leu Glu Glu Val
        515                 520                 525
Leu Asn Leu Ala Gln Ser Lys Asn Phe His Leu Arg Pro Arg Asp Leu
        530                 535                 540
Ile Ser Asn Ile Asn Val Ile Val Leu Glu Leu Lys Gly Ser Glu Thr
545                 550                 555                 560
Thr Phe Met Cys Glu Tyr Ala Asp Glu Thr Ala Thr Ile Val Glu Phe
                565                 570                 575
Leu Asn Arg Trp Ile Thr Phe Cys Gln Ser Ile Ile Ser Thr Leu Thr
            580                 585                 590

<210> SEQ ID NO 27
<211> LENGTH: 1851
<212> TYPE: DNA
<213> ORGANISM: Artificial Sequence
<220> FEATURE:
<223> OTHER INFORMATION: Sequence of nucleotiedes coding fusion protein
      (GI102-M61)

<400> SEQUENCE: 27
atggatgcta tgctgagagg cctgtgttgc gtgctgctgc tgtgtggcgc tgtgttcgtg       60
tctccttctc acgctgtgat ccacgtgacc aaagaagtga agaggtcgc cacactgtcc      120 tgcggccaca acgtttcagt ggaagaactg gcccagacca ggatctactg cagaaagaa      180 aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga ggacgcctt caagcgcgag       360 cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg       540 tctcaggacc ccgaaaccga gctgtacgct gtgtcctcca gctggactt caacatgacc      600 accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg aagcggagg cggaggatct gctgagtcta gtatgggccc tccttgtcct      780
ccatgtcctg ctccagaagc tgctggcgga ccctctgtgt tcctgttccc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc tagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg gccagcctag gaaccccag     1140 gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca cgtgttctc ctgctctgtg     1380 ctgcacgagg ccctgcacaa tcactacacc cagaagtccc tgtctctgtc tcttggaggt     1440
```

-continued

```
ggtggcggtt ctgcccctac cagctcctct accaagaaaa cccagctcca gttggagcat    1500
ctgctgctgg acctccagat gattctgaac gggatcaaca actataagaa ccccaagctg    1560
accgccatgc tgaccgctaa gttctacatg cccaagaagg ccaccgagct gaagcacctc    1620
cagtgcctgg aaagggaact gaagcccctg gaagaggtgc tgaatctggc ccagtccaag    1680
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac c             1851
```

<210> SEQ ID NO 28
<211> LENGTH: 592
<212> TYPE: PRT
<213> ORGANISM: Artificial Sequence
<220> FEATURE:
<223> OTHER INFORMATION: Sequence of fusion protein (GI102-M61)

<400> SEQUENCE: 28

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285
```

| | | | | | | | | | | | |
|---|---|---|---|---|---|---|---|---|---|---|---|
|Gly|Val|Glu|Val|His|Asn|Ala|Lys|Thr|Lys|Pro|Arg|Glu|Glu|Phe|
| |290| | | |295| | | |300| | |

Gly Val Glu Val His Asn Ala Lys Thr Lys Pro Arg Glu Glu Phe
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Gln Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
                435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
                500                 505                 510

Lys His Leu Gln Cys Leu Glu Arg Glu Leu Lys Pro Leu Glu Glu Val
            515                 520                 525

Leu Asn Leu Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
                580                 585                 590

<210> SEQ ID NO 29
<211> LENGTH: 1857
<212> TYPE: DNA
<213> ORGANISM: Artificial Sequence
<220> FEATURE:
<223> OTHER INFORMATION: Sequence of nucleotiedes coding fusion protein
      (GI102-M72)

<400> SEQUENCE: 29
atggatgcta tgctgagagg cctgtgttgc gtgctgctgc tgtgtggcgc tgtgttcgtg     60
tctccttctc acgctgtgat ccacgtgacc aaagaagtga agaggtcgc cacactgtcc    120 tgcggccaca acgtttcagt ggaagaactg gcccagacca ggatctactg gcagaaagaa    180
aagaaaatgg tgctgaccat gatgtccggc gacatgaaca tctggcctga gtacaagaac    240
cggaccatct tcgacatcac caacaacctg tccatcgtga ttctggccct gaggccttct    300
gatgagggca cctatgagtg cgtggtgctg aagtacgaga aggacgcctt caagcgcgag    360

```
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg aagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc tagagagga acagttcaac tccacctaca gagtggtgtc cgtgctgacc    1020
gtgctgcacc aggattggct gaacggcaaa gagtacaagt gcaaggtgtc caacaagggc    1080
ctgccttcca gcatcgaaaa gaccatctcc aaggctaagg gccagcctag gaaccccag    1140 gtttacaccc tgcctccaag ccaagaggaa atgaccaaga accaggtgtc cctgacctgc    1200
ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctagatgg caagagggca acgtgttctc ctgctctgtg    1380
ctgcacgagg ccctgcacaa tcactacacc cagaagtccc tgtctctgtc tcttggaggt    1440
ggtggcggtt ctgcccctac cagctcctct accaagaaaa cccagctcca gttggagcat    1500
ctgctgctgg acctccagat gattctgaac gggatcaaca actataagaa ccccaagctg    1560
accgccatgc tgaccgctaa gttctacatg cccaagaagg ccaccgagct gaagcacctc    1620
cagtgcctgg aagaagaact gaagcccctg gaagaggtgc tgaatggggc ccagtccaag    1680
aacttccacc tgaggccacg ggacctgatc agcaacatca cgtgatcgt gctggaactg    1740 aagggctccg agacaacctt tatgtgcgag tacgccgacg agacagccac catcgtggaa    1800
tttctgaacc ggtggatcac cttctgccag agcatcatct ccacactgac ctgatga      1857
```

<210> SEQ ID NO 30
<211> LENGTH: 592
<212> TYPE: PRT
<213> ORGANISM: Artificial Sequence
<220> FEATURE:
<223> OTHER INFORMATION: Sequence of fusion protein (GI102-M72)

<400> SEQUENCE: 30

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95
```

```
Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
        130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
```

```
          515                 520                 525
Leu Asn Gly Ala Gln Ser Lys Asn Phe His Leu Arg Pro Arg Asp Leu
        530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ser Thr Leu Thr
                580                 585                 590
```

<210> SEQ ID NO 31
<211> LENGTH: 1851
<212> TYPE: DNA
<213> ORGANISM: Artificial Sequence
<220> FEATURE:
<223> OTHER INFORMATION: Sequence of nucleotiedes coding fusion protein (GI101w)

<400> SEQUENCE: 31

| | | | | | |
|---|---|---|---|---|---|
| atggatgcta | tgctgagagg | cctgtgttgc | gtgctgctgc | tgtgtggcgc | tgtgttcgtg | 60 |
| tctccttctc | acgctgtgat | ccacgtgacc | aaagaagtga | agaggtcgc | cacactgtcc | 120 |
| tgcggccaca | acgtttcagt | ggaagaactg | gcccagacca | ggatctactg | cagaaagaa | 180 |
| aagaaaatgg | tgctgaccat | gatgtccggc | gacatgaaca | tctggcctga | gtacaagaac | 240 |
| cggaccatct | tcgacatcac | caacaacctg | tccatcgtga | ttctggccct | gaggccttct | 300 |
| gatgagggca | cctatgagtg | cgtggtgctg | aagtacgaga | aggacgcctt | caagcgcgag | 360 |
| cacctggctg | aagtgacact | gtccgtgaag | gccgactttc | ccacccttc | catctccgac | 420 |
| ttcgagatcc | ctacctccaa | catccggcgg | atcatctgtt | ctacctctgg | cggctttcct | 480 |
| gagcctcacc | tgtcttggct | ggaaaacggc | gaggaactga | acgccatcaa | caccaccgtg | 540 |
| tctcaggacc | ccgaaaccga | gctgtacgct | gtgtcctcca | agctggactt | caacatgacc | 600 |
| accaaccaca | gcttcatgtg | cctgattaag | tacggccacc | tgagagtgaa | ccagaccttc | 660 |
| aactggaaca | ccaccaagca | agagcacttc | cctgacaatg | gatctggcgg | cggaggttct | 720 |
| ggcggaggtg | gaagcggagg | cggaggatct | gctgagtcta | agtatggccc | tccttgtcct | 780 |
| ccatgtcctg | ctccagaagc | tgctggcgga | ccctctgtgt | tcctgtttcc | tccaaagcct | 840 |
| aaggaccagc | tcatgatctc | tcggacaccc | gaagtgacct | gcgtggtggt | ggatgtgtct | 900 |
| caagaggacc | ctgaggtgca | gttcaattgg | tacgtggacg | gcgtggaagt | gcacaacgcc | 960 |
| aagaccaagc | ctagagagga | acagttcaac | tccacctaca | gagtggtgtc | cgtgctgacc | 1020 |
| gtgctgcacc | aggattggct | gaacggcaaa | gagtacaagt | gcaaggtgtc | caacaagggc | 1080 |
| ctgccttcca | gcatcgaaaa | gaccatctcc | aaggctaagg | gccagcctag | ggaaccccag | 1140 |
| gtttacaccc | tgcctccaag | ccaagaggaa | atgaccaaga | accaggtgtc | cctgacctgc | 1200 |
| ctggtcaagg | gcttctaccc | ttccgacatt | gccgtggaat | gggagtccaa | tggccagcct | 1260 |
| gagaacaact | acaagaccac | acctcctgtg | ctggactccg | acggctcctt | ctttctgtac | 1320 |
| tctcgcctga | ccgtggacaa | gtctagatgg | caagagggca | acgtgttctc | ctgctctgtg | 1380 |
| ctgcacgagg | ccctgcacaa | tcactacacc | cagaagtccc | tgtctctgtc | tcttggaggt | 1440 |
| ggtggcggtt | ctgccccta c| cagctcctct | accaagaaaa | cccagctcca | gttggagcat | 1500 |
| ctgctgctgg | acctccagat | gattctgaac | gggatcaaca | actataagaa | ccccaagctg | 1560 |
| acccgcatgc | tgacctttaa | gttctacatg | cccaagaagg | ccaccgagct | gaagcacctc | 1620 |

-continued

```
cagtgcctgg aagaagaact gaagccctg gaagaggtgc tgaatctggc ccagtccaag    1680
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac c              1851
```

<210> SEQ ID NO 32
<211> LENGTH: 592
<212> TYPE: PRT
<213> ORGANISM: Artificial Sequence
<220> FEATURE:
<223> OTHER INFORMATION: Sequence of fusion protein (GI101w)

<400> SEQUENCE: 32

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
```

```
                        325                 330                 335
Pro Ser Ser Ile Glu Lys Thr Ile Ser Lys Ala Lys Gly Gln Pro Arg
                340                 345                 350

Glu Pro Gln Val Tyr Thr Leu Pro Pro Ser Gln Glu Glu Met Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
                435                 440                 445

Leu Ser Leu Ser Leu Gly Gly Gly Gly Ser Ala Pro Thr Ser Ser
                450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
                500                 505                 510

Lys His Leu Gln Cys Leu Glu Glu Glu Leu Lys Pro Leu Glu Glu Val
                515                 520                 525

Leu Asn Leu Ala Gln Ser Lys Asn Phe His Leu Arg Pro Arg Asp Leu
                530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
                580                 585                 590
```

<210> SEQ ID NO 33
<211> LENGTH: 1848
<212> TYPE: DNA
<213> ORGANISM: Artificial Sequence
<220> FEATURE:
<223> OTHER INFORMATION: Sequence of nucleotiedes coding fusion protein (mGI102-M61)

<400> SEQUENCE: 33

```
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcaccctaa catcaccgag      420 tctggcaacc cttccgccga caccaagaga atcacctgtt cgcctctgg cggcttccct      480 aagcctcggt tctcttggct ggaaaacggc agagagctgc ccggcatcaa taccaccatt     540
```

-continued

```
tctcaggacc cagagtccga gctgtacacc atctccagcc agctcgactt taacaccacc    600
agaaaccaca ccatcaagtg cctgattaag tacggcgacg cccacgtgtc cgaggacttt    660
acttgggaga aacctcctga ggaccctcct gactctggat ctggcggcgg aggttctggc    720
ggaggtggaa gcggaggcgg aggatctgct gagtctaagt atggccctcc ttgtcctcca    780
tgtcctgctc cagaagctgc tggcggaccc tctgtgttcc tgtttcctcc aaagcctaag    840
gaccagctca tgatctctcg gacccctgaa gtgacctgcg tggtggtgga tgtgtctcaa    900
gaggaccctg aggtgcagtt caattggtac gtggacggcg tggaagtgca aacgccaag     960
accaagccta gaggaacag gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga accccaggtt    1140
tacaccctgc ctccaagcca agaggaaatg accaagaacc aggtgtccct gacctgcctg    1200
gtcaagggct tctacccttc cgacattgcc gtgaatggg agtccaatgg ccagcctgag    1260
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtctct ggaggtggt    1440
ggcggttctg cccctacctc cagctctacc aagaaaaccc agctccagtt ggagcatctg    1500
ctgctggacc tccagatgat cctgaatggc atcaacaatt acaagaaccc caagctgacc    1560
gccatgctga ccgctaagtt ctacatgccc aagaaggcca ccgagctgaa gcacttgcag    1620
tgcctggaaa gggaactgaa gccctggaa gaagtgctga atctggccca gtccaagaac    1680
ttccacctga ggcctaggga cctgatctcc aacatcaacg tgatcgtgct ggaactgaaa    1740
ggctccgaga caaccttcat gtgcgagtac gccgacgaga cagccaccat cgtggaattt    1800
ctgaaccggt ggatcacctt ctgccagagc atcatctcca cactgacc                1848
```

<210> SEQ ID NO 34
<211> LENGTH: 616
<212> TYPE: PRT
<213> ORGANISM: Artificial Sequence
<220> FEATURE:
<223> OTHER INFORMATION: Sequence of fusion protein (mGI102-M61)

<400> SEQUENCE: 34

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
```

-continued

```
                130                 135                 140
Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
                180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
        210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
                260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
        370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
        450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
                500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Arg
530                 535                 540

Glu Leu Lys Pro Leu Glu Glu Val Leu Asn Leu Ala Gln Ser Lys Asn
545                 550                 555                 560
```

```
Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615

<210> SEQ ID NO 35
<211> LENGTH: 153
<212> TYPE: PRT
<213> ORGANISM: Homo sapiens
<220> FEATURE:
<223> OTHER INFORMATION: wild type hIL-2

<400> SEQUENCE: 35

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
        100                 105                 110

Val Leu Glu Leu Lys Gly Ser Glu Thr Thr Phe Met Cys Glu Tyr Ala
    115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 36
<211> LENGTH: 158
<212> TYPE: PRT
<213> ORGANISM: Homo sapiens
<220> FEATURE:
<223> OTHER INFORMATION: IL-2 with signal sequence

<400> SEQUENCE: 36

Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
            20                  25                  30

Lys Lys Thr Gln Leu Gln Leu Glu His Leu Leu Leu Asp Leu Gln Met
        35                  40                  45

Ile Leu Asn Gly Ile Asn Asn Tyr Lys Asn Pro Lys Leu Thr Arg Met
    50                  55                  60

Leu Thr Phe Lys Phe Tyr Met Pro Lys Ala Thr Glu Leu Lys His
65                  70                  75                  80

Leu Gln Cys Leu Glu Glu Glu Leu Lys Pro Leu Glu Glu Val Leu Asn
```

```
                    85                  90                  95
Leu Ala Gln Ser Lys Asn Phe His Leu Arg Pro Arg Asp Leu Ile Ser
                100                 105                 110

Asn Ile Asn Val Ile Val Leu Glu Leu Lys Gly Ser Glu Thr Thr Phe
            115                 120                 125

Met Cys Glu Tyr Ala Asp Glu Thr Ala Thr Ile Val Glu Phe Leu Asn
        130                 135                 140

Arg Trp Ile Thr Phe Cys Gln Ser Ile Ile Ser Thr Leu Thr
145                 150                 155

<210> SEQ ID NO 37
<211> LENGTH: 474
<212> TYPE: DNA
<213> ORGANISM: Artificial Sequence
<220> FEATURE:
<223> OTHER INFORMATION: Sequence of nucleotide sequence coding IL-2
      with signal sequence

<400> SEQUENCE: 37
atggatgcta tgctgagagg cctgtgttgc gtgctgctgc tgtgtggcgc tgtgttcgtg      60
tctccttctc acgctgcccc taccagctcc tctaccaaga aaacccagct ccagttggag     120
catctgctgc tggacctcca gatgattctg aacgggatca caactataa gaaccccaag      180 ctgacccgca tgctgacctt taagttctac atgcccaaga aggccaccga gctgaagcac     240
ctccagtgcc tggaagaaga actgaagccc tggaagagg tgctgaatct ggcccagtcc      300
aagaacttcc acctgaggcc acgggacctg atcagcaaca tcaacgtgat cgtgctggaa     360
ctgaagggct ccgagacaac ctttatgtgc gagtacgccg acgagacagc caccatcgtg     420
gaatttctga accggtggat caccttctgc cagagcatca tctccacact gacc           474

<210> SEQ ID NO 38
<211> LENGTH: 591
<212> TYPE: PRT
<213> ORGANISM: Artificial Sequence
<220> FEATURE:
<223> OTHER INFORMATION: Sequence of mGI-101

<400> SEQUENCE: 38

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
    50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
                100                 105                 110

Ile Thr Glu Ser Gly Asn Pro Ser Ala Asp Thr Lys Arg Ile Thr Cys
            115                 120                 125

Phe Ala Ser Gly Gly Phe Pro Lys Pro Arg Phe Ser Trp Leu Glu Asn
        130                 135                 140

Gly Arg Glu Leu Pro Gly Ile Asn Thr Thr Ile Ser Gln Asp Pro Glu
```

```
                145                 150                 155                 160
Ser Glu Leu Tyr Thr Ile Ser Ser Gln Leu Asp Phe Asn Thr Thr Arg
                    165                 170                 175

Asn His Thr Ile Lys Cys Leu Ile Lys Tyr Gly Asp Ala His Val Ser
                    180                 185                 190

Glu Asp Phe Thr Trp Glu Lys Pro Glu Asp Pro Pro Asp Ser Gly
                195                 200                 205

Ser Gly Gly Gly Gly Ser Gly Gly Gly Ser Gly Gly Gly Ser
    210                 215                 220

Ala Glu Ser Lys Tyr Gly Pro Pro Cys Pro Pro Cys Pro Ala Pro Glu
225                 230                 235                 240

Ala Ala Gly Gly Pro Ser Val Phe Leu Phe Pro Pro Lys Pro Lys Asp
                    245                 250                 255

Gln Leu Met Ile Ser Arg Thr Pro Glu Val Thr Cys Val Val Val Asp
                260                 265                 270

Val Ser Gln Glu Asp Pro Glu Val Gln Phe Asn Trp Tyr Val Asp Gly
                275                 280                 285

Val Glu Val His Asn Ala Lys Thr Lys Pro Arg Glu Glu Gln Phe Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                    325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                    405                 410                 415

Leu Thr Val Asp Lys Ser Arg Trp Gln Glu Gly Asn Val Phe Ser Cys
                    420                 425                 430

Ser Val Leu His Glu Ala Leu His Asn His Tyr Thr Gln Lys Ser Leu
                435                 440                 445

Ser Leu Ser Leu Gly Gly Gly Gly Ser Ala Pro Thr Ser Ser Ser
    450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Ala
                    485                 490                 495

Met Leu Thr Ala Lys Phe Tyr Met Pro Lys Lys Ala Thr Glu Leu Lys
                500                 505                 510

His Leu Gln Cys Leu Glu Glu Glu Leu Lys Pro Leu Glu Glu Val Leu
                515                 520                 525

Asn Leu Ala Gln Ser Lys Asn Phe His Leu Arg Pro Arg Asp Leu Ile
                530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575
```

```
Asn Arg Trp Ile Thr Phe Cys Gln Ser Ile Ile Ser Thr Leu Thr
            580                 585                 590

<210> SEQ ID NO 39
<211> LENGTH: 120
<212> TYPE: PRT
<213> ORGANISM: Artificial Sequence
<220> FEATURE:
<223> OTHER INFORMATION: Sequence of TIGIT ECD

<400> SEQUENCE: 39

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120
```

PHARMACEUTICAL COMPOSITION FOR CANCER TREATMENT COMPRISING FUSION PROTEIN INCLUDING IL-2 PROTEIN AND CD80 PROTEIN AND ANTICANCER DRUG

CROSS REFERENCE TO RELATED APPLICATIONS

This application is a National Stage of International Application No. PCT/KR2021/003375 filed Mar. 18, 2021, claiming priority based on Korean Patent Application No. 10-2020-0033233 filed Mar. 18, 2020 and Korean Patent Application No. 10-2021-0020708 filed Feb. 16, 2021.

INCORPORATION BY REFERENCE OF SEQUENCE LISTING

The content of the electronically submitted sequence listing, file name: Sequence Listing As Filed.txt; size: 99,611 bytes; and date of creation: Sep. 14, 2022, filed herewith, is incorporated herein by reference in its entirety.

TECHNICAL FIELD

The present invention relates to a pharmaceutical composition for treating cancer, comprising, as active ingredients, a fusion protein comprising an IL-2 protein and a CD80 protein, and an anticancer agent.

BACKGROUND ART

Interleukin 2 (IL-2), also called T-cell growth factor (TCGF), is a globular glycoprotein that plays a central role in lymphocyte production, survival, and homeostasis. IL-2 has a protein size of 15.5 kDa to 16 kDa and consists of 133 amino acids. IL-2 mediates various immune actions by binding to an IL-2 receptor composed of three distinct subunits.

In addition, IL-2 is synthesized mainly by activated T cells, in particular by CD4+ helper T cells. IL-2 stimulates proliferation and differentiation of T cells, and induces production of cytotoxic T lymphocytes (CTLs) and differentiation of peripheral blood lymphocytes into cytotoxic cells and lymphokine-activated killer cells (LAK cells).

Meanwhile, CD80, also known as B7-1, is a member of the B7 family of membrane-bound proteins that are involved in immune regulation by binding to its ligand by way of delivering costimulatory responses and coinhibitory responses. CD80 is a transmembrane protein expressed on the surface of T cells, B cells, dendritic cells, and monocytes. CD80 is known to bind CD28, CTLA-4 (CD152), and PD-L1 (programmed cell death ligand 1). CD80, CD86, CTLA-4, and CD28 are involved in a costimulatory-coinhibitory system. For example, they regulate activity of T cells and are involved in proliferation, differentiation, and survival thereof.

In addition, recently, immune checkpoint inhibitors such as KEYTRUDA® are in the spotlight. Immune checkpoint inhibitors are anticancer agents that help to attack cancer cells by activating the body's immune system. Until now, cancer therapy has focused on killing rapidly dividing cells that are characteristic of cancer cells, so it has side effects by acting on rapidly proliferating cells among normal cells as well as cancer cells. However, it is known that immune anticancer agents affect cancer cells by utilizing the immune system of cancer patients, so there are few typical side effects exhibited by existing anticancer agents. Anti-PD-1 antibodies, such as Keytruda, bind to a specific receptor (PD-1) on T cells and block the pathway by which cancer cells avoid the surveillance system of active T cells, thereby exhibiting anticancer effect through immune reactivation that allows T cells in the human body to attack cancer cells (KR 10-2018-0030580 A).

DETAILED DESCRIPTION OF INVENTION

Technical Problem

The present inventors have studied to develop IL-2 which is safe and effective. As a result, the present inventors have confirmed that a novel fusion protein, which comprises an IL-2 protein and a CD80 protein in one molecule, and an anticancer agent exhibit excellent anticancer effect, thereby completing the present invention.

Solution to Problem

In order to achieve the above object, in an aspect of the present invention, there is provided a pharmaceutical composition for treating cancer, comprising, as active ingredients, a fusion protein comprising an IL-2 protein and a CD80 protein, and an anticancer agent.

Effects of the Invention

A fusion protein comprising an IL-2 protein and a CD80 protein can not only activate immune cells owing to IL-2, but also effectively regulate Treg cells owing to CD80. In addition, it was confirmed that a synergistic effect appeared when administered in combination with an anticancer agent. Therefore, a pharmaceutical composition for treating cancer, comprising, as active ingredients, the fusion protein comprising an IL-2 protein and a CD80 protein, and an anticancer agent can be usefully employed for treatment of cancer disease.

BRIEF DESCRIPTION OF DRAWINGS

FIG. 35A illustrates proportions of CD8+ T cells and CD4+ T cells, FIG. 35B illustrates proliferation capacity of CD8+ T cells, and FIG. 35C illustrates a proportion of CD4+/FoxP3+ Treg cells.

FIG. 128 illustrates a survival rate of mice after mGI101 and DMXAA, a STING agonist, are administered in combination in mice transplanted with rodent-derived colorectal cancer cells (MC38).

FIG. 129 illustrates the degree of tumor growth of individual experimental animals after mGI101 and DMXAA, a STING agonist, are administered in combination in mice transplanted with rodent-derived colorectal cancer cells (MC38).

FIGS. 130 to 133 illustrate the degree of tumor growth of individual experimental animals for each experimental group after mGI101 and DMXAA, a STING agonist, are administered in combination in mice transplanted with rodent-derived colorectal cancer cells (MC38).

BEST MODE FOR CARRYING OUT THE INVENTION

Combination Therapy of Fusion Protein

Figure 1:
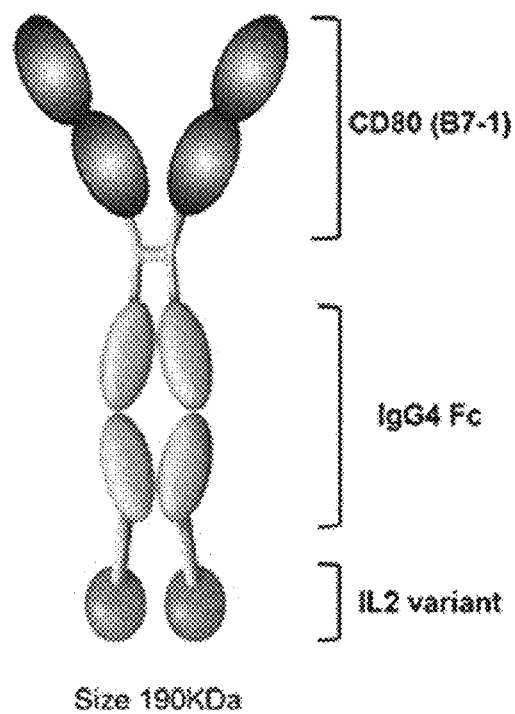
FIG. 1 illustrates a schematic diagram of an embodiment of a fusion protein dimer.
Figure 2:
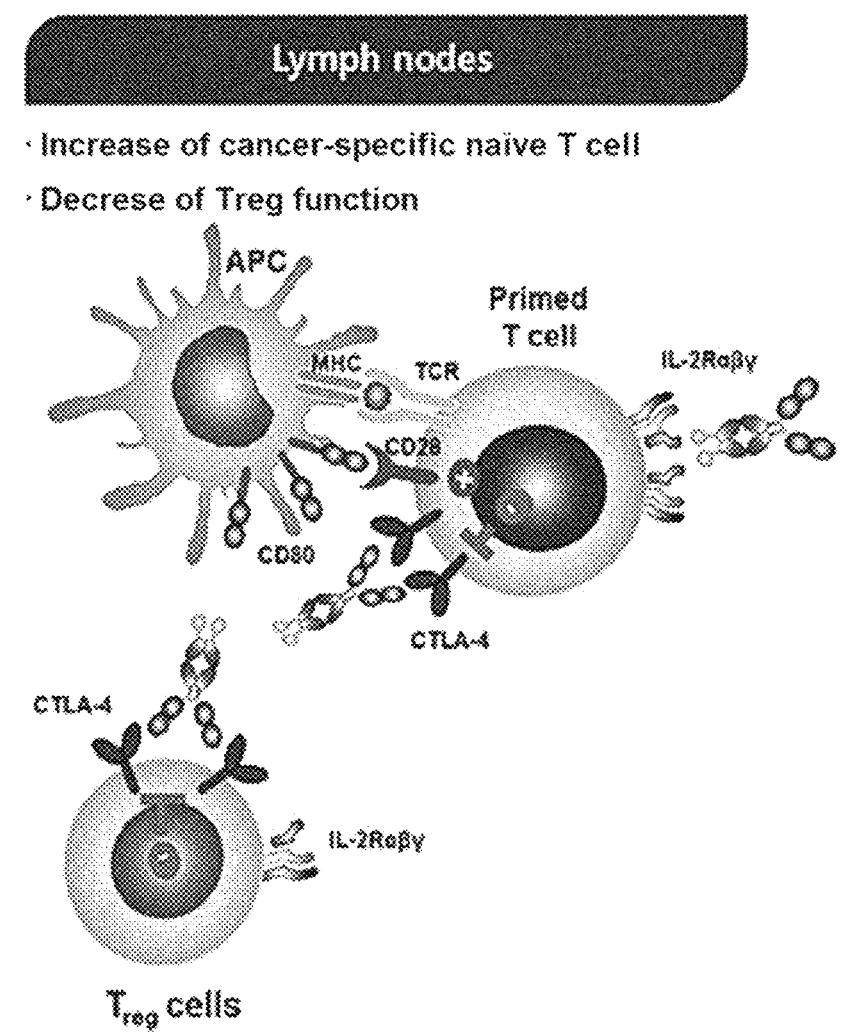
FIG. 2 illustrates a schematic diagram of a mechanism of action by which the fusion protein dimer exhibits in the lymph nodes.
Figure 3:
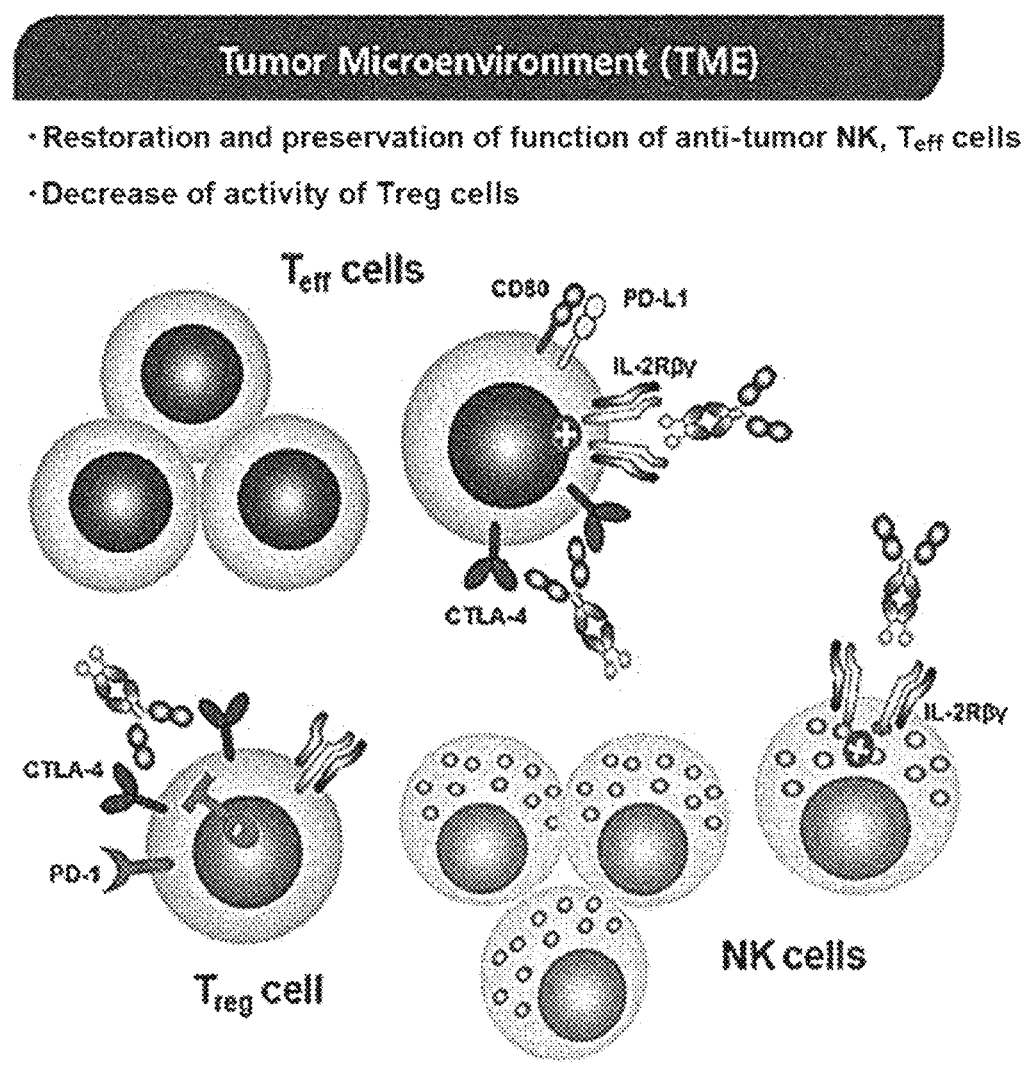
FIG. 3 illustrates a schematic diagram of a mechanism of action by which the fusion protein dimer exhibits in the tumor microenvironment.
Figure 4:
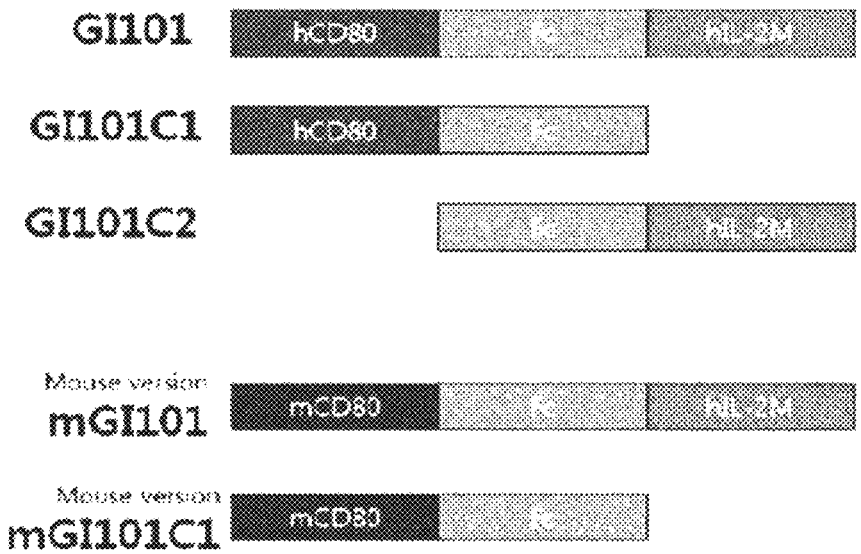
FIG. 4 illustrates a schematic view of the structure of the fusion protein. Here, each of GI101 and mGI101 is an embodiment of the fusion protein, and GI101C1, GI101C2, and mGI101C1 are comparative examples for comparison with activity of the fusion protein.
Figure 5:
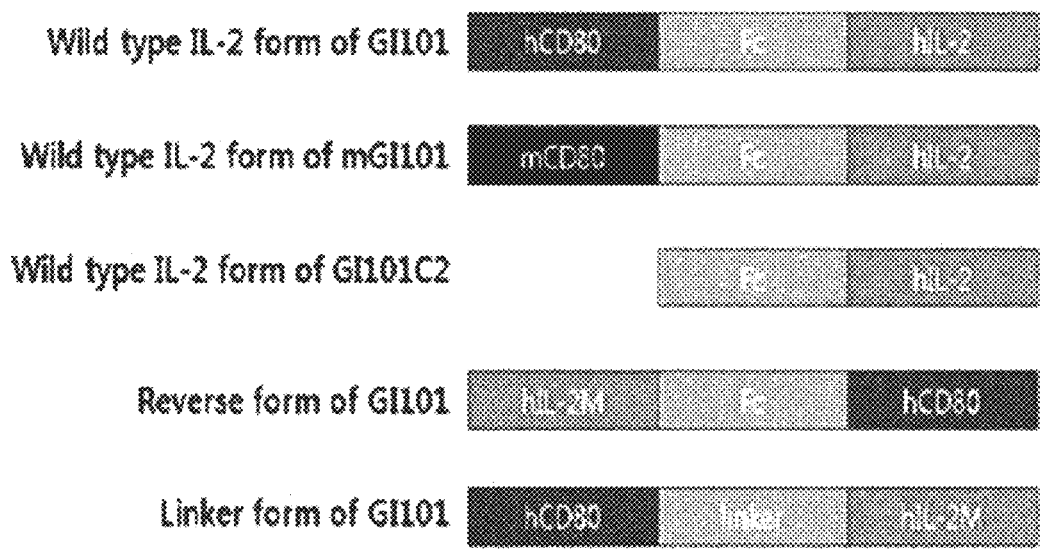
FIG. 5 illustrates various embodiments of the fusion protein. Human- and mouse-derived proteins may be combined to prepare a fusion protein. A CD80 protein and an IL-2 protein may be bound to each other via various linkers other than Fc.

In an aspect of the present invention, there is provided a pharmaceutical composition for preventing or treating cancer, comprising, as active ingredients, a fusion protein dimer comprising a CD80 protein or a fragment thereof, and an IL-2 protein or a variant thereof, and an anticancer agent.

Since the fusion protein dimer comprising an IL-2 protein and a CD80 protein increases the immune activity in the body, it may be used in combination with various anticancer treatment methods that have been conventionally used. Specifically, the conventional treatment method that can be used in combination may be selected from the group consisting of an anticancer chemotherapeutic agent for chemotherapy, a target anticancer agent, an anticancer virus, an antibody therapeutic agent, a cell therapeutic agent, an immune checkpoint inhibitor, and a combination thereof.

As used herein, the term "anticancer chemotherapeutic agent" is also referred to as an antineoplastic agent or a cytotoxic agent. It is a generic term for drugs that exhibit anticancer activity mainly by acting directly on DNA to block DNA replication, transcription and translation processes, or by interfering with the synthesis of nucleic acid precursors in the metabolic pathway, and by inhibiting cell division. The antineoplastic agent exhibits cytotoxicity by acting not only on tumor cells but also on normal cells. The anticancer chemotherapeutic agent may be used in maintenance therapy. In addition, as used herein, the term "maintenance therapy" refers to treatment of cancer with drugs after initial anticancer treatment, and refers to a treatment method performed to prevent or delay recurrence of cancer.

Specifically, an anticancer chemotherapeutic agent may be any one selected from the group consisting of an alkylating agent, a microtubule inhibitor, an anti-metabolite, and a topoisomerase inhibitor. The alkylating agent may be any one selected from the group consisting of Mechlorethamine, Cyclophosphamide, Ifosfamide, Melphalan, Chlorambucil, Thiotepa, Altretamine, Procarbazine, Busulfan, Streptozocin, Carmustine, Lomustine, Dacarbazine, Cisplatin, Carboplatin, and Oxaliplatin. The microtubule inhibitor may be any one selected from the group consisting of Docetaxel, Velban, Oncovin, and Navelbine. The anti-metabolite may be any one selected from the group consisting of Fluorouracil, Capecitabine, Cytarabine, Gemcitabine, Fludarabine, Methotrexate, Pemetrexed, and Mercaptopurine. The topoisomerase inhibitor may be any one selected from the group consisting of Hycamtin, Camptosar, Vepesid, Paclitaxel, Blenoxane, Adriamycin, and Cerubidine.

As used herein, the term "target anticancer agent" is a therapeutic agent that specifically kills cancer cells by blocking signals involved in the growth and development of cancer by targeting specific proteins or specific genetic changes that are frequently present only in cancer cells. It is classified into monoclonal antibodies that react outside the cell, and small molecule substances that act inside the cell. Monoclonal antibodies are anticancer agents that block cancer cell induction signals transmitted to the outside of cells, and act on initiation signals related to proliferation, death and the like; and small molecule substances act on complex signal transduction occurring inside the cells.

Specifically, proteins to be targeted may be EGFR, VEGFR, CD20, CD38, RNAK-L, BTK, Bcr-abl, PDGFR/FGFR family, MEK/RAF, HER2/Neu, Ubiquitin, JAK, ALK, PARP, TGFβR1, Proteasome, Bcl-2, C-Met, VR1, VR2, VR3, c-kit, AXL, RET, Braf, DNMT, CDK4/6, STING, and the like.

The target anticancer agent may be any one selected from the group consisting of Cetuximab, Trastuzumab, Pertuzumab, Axitinib, Lenvatinib, Bevacizumab, Ramucirumab, Aflibercept, Rituximab, Obinutuzumab, Daratumumab, Denosumab, Ibrutinib, Dasatinib, Nilotinib, Imatinib, Bosutinib, Galunisertib, Vactosertib, Nintedanib, Sunitinib, Sorafenib, Cabozantinib, Regorafenib, Masitinib, Semaxanib, Tivozanib, Vandetanib, Pazopanib, Trametinib, Dabrafenib, Trastuzumab, Afatinib, Lapatinib, Neratinib, Lenalidomide, Ixazomib, Ruxolitinib, Lestaurtinib, Pacritinib, Cobimethinib, Selumetinib, Trametinib, Binimetinib, Alectinib, Crizotinib, Venetoclax, Crizotinib, Cabozantinib, Bemcentinib, Gilteritinib, Selpercatinib, Pralsetinib, Vemurafenib, Olaparib, Talazoparib, Niraparib, Rucaparib, Azacitidine, Decitabine, Guadecitabine, Abemaciclib, Ribociclib, Palbociclib, CDNs, SB11285, and DMXAA.

As used herein, the term "epidermal growth factor receptor (EGFR)" is a cell membrane receptor that regulates cell growth, division, survival, and death. In various cancers, the expression of EGFR is increased in tumor tissues. It is known that tumor tissues with the increased EGFR are invasive, metastatic, and highly resistant to anticancer agents. The EGFR inhibitor may be a substance that inhibits the EGFR. In an embodiment, it may be Cetuximab, Trastuzumab, Pertuzumab, Gefitinib, Elotinib, or Panitumumab.

As used herein, the term "vascular endothelial growth factor receptor (VEGFR)" is a cell membrane receptor of a vascular endothelial growth factor that induces angiogenesis, and a VEGFR inhibitor inhibits the angiogenesis to suppress tumor growth and metastasis. In an embodiment, the VEGFR inhibitor may be Axitinib, Lenvatinib, Bevacizumab, Ramucirumab, or Aflibercept.

As used herein, the term "CD20 (B lymphocyte antigen CD20)" is a protein expressed on the surface of B cells and is used as a target protein for the treatment of B cell lymphoma. The CD20 target inhibitor may be Rituximab or Obinutuzumab.

As used herein, the term "CD38 (cluster of differentiation 38)" is a protein that regulates cell proliferation and death while acting as a signal transduction receptor in immune cells, and an inhibitor targeting it may be Daratumumab.

As used herein, the term "RNAK-L (Receptor activator of nuclear factor kappa-B ligand)" is a RANK receptor expressed on the surface of osteoclasts, and when it is activated by binding to its ligand, it acts to cause bone destruction. The RANK-L inhibitor is mainly used for cancer patients suffering from bone metastasis or osteoporosis, and it may be specifically Denosumab.

As used herein, the term "BTK (Bruton's tyrosine kinase)" is an enzyme involved in the proliferation of B cells and may develop into hematologic malignancy when overexpressed. In an embodiment, the BTK target inhibitor may be Ibrutinib.

As used herein, the term "Bcr-abl" is a fusion protein that is highly expressed in chronic myelogenous leukemia patients, and is known to induce abnormal proliferation of blood cells. Specifically, the inhibitor of the protein may be Dasatinib, Nilotinib, Imatinib, or Bosutinib.

As used herein, the term "tumor growth factor β receptor (TGFβR)" is a cell membrane receptor of a tumor growth factor, and regulates the growth, migration, differentiation, death and the like of epithelial cells and hematopoietic cells. The TGFβR target inhibitor includes, but is not limited to, Galunisertib, Vactosertib or the like.

As used herein, the term "PDGFR (platelet derived growth factor receptor)" is a cell membrane receptor of PDGF that is frequently expressed in cancer cells, and is known to regulate cancer growth, metastasis, and drug resistance by participating in angiogenesis. FGFR (Fibroblast growth factor receptor) is a receptor of fibroblast growth factor (FGF), and regulates various biological processes including cell growth, differentiation, migration, and the like. The FGFR gene is easily mutated, and these variants are commonly observed in breast cancer, uterine cancer, ovarian cancer, cervical cancer, and the like. The Inhibitor targeting PDGFR or FGFR may be Nintedanib, Sunitinib, Sorafenib, Cabozantinib, Lenvatinib, Regorafenib, Masitinib, Semaxanib, Tivozanib, Vandetanib, Axitinib, or Pazopanib.

As used herein, the term "MEK/RAF" is an intracellular signaling mediator involved in cell proliferation, cell cycle regulation, cell survival, angiogenesis, cell migration, and the like, and is overactivated in cancer cells. The inhibitor targeting MEK/RAF may be Trametinib or Dabrafenib.

As used herein, the term "HER-2/neu (human epidermal growth factor receptor 2) regulates cell proliferation through activation of PI3K/AkT. It is known that it is overexpressed in metastatic breast cancer, and ovarian cancer and the like, and induces resistance against anticancer agents. The Her2/neu target anticancer agent may be Trastuzumab, Afatinib, Lapatinib, or Neratinib.

As used herein, the term "ubiquitin" maintains cell homeostasis by binding to other proteins and inducing proteolysis (ubiquitin-proteasome system, UPS) by proteasome, which is a proteolytic enzyme. Abnormal expression or activity of the UPS is observed in various tumors, and its inhibitor exhibits anticancer activity. Specifically, the inhibitor targeting ubiquitin or proteasome may be Lenalidomide or Ixazomib.

As used herein, the term "JAK (Janus kinase)" is an upstream protein of STAT, which is a transcription factor that regulates cell proliferation, cell survival, cell migration, and immune response. A JAK inhibitor is known to decrease cell proliferation and induce cell death by inhibiting the activity of STAT. The JAK target inhibitor may be Ruxolitinib, Lestaurtinib, or Pacritinib.

As used herein, the term "MAP2K (Mitogen-activated protein kinase kinase)" is an intracellular signaling mediator involved in cell proliferation, cell cycle regulation, cell survival, angiogenesis, cell migration and the like by phosphorylating MAPK, and it is overactivated in cancer cells. The MAP2K target inhibitor may be Cobimethinib, Selumetinib, Trametinib, or Binimetinib.

As used herein, the term "ALK (Anaplastic lymphoma kinase)" is a signaling mediator that promotes cell proliferation, cell migration and angiogenesis and inhibits cell death; and it is overactivated in various cancer tissues. The ALK target inhibitor may be Alectinib or Crizotinib.

As used herein, the term "Bcl-2" is a protein that inhibits cell death, and it is overexpressed or overactivated in various cancer tissues. The inhibitor targeting Bcl-2 may be Venetoclax.

As used herein, the term "C-Met" is a receptor of hepatocyte growth factor (HGF), and activates signal transduction related to cell growth, formation, motility, survival, angiogenesis and the like. The C-Met target anticancer agent may be Crizotinib or Cabozantinib.

As used herein, the term "VR (vanilloid receptor)" is also known as TRPV (Transient receptor potential vanilloid), and exists in the form of VR1, VR2, VR3, VR4, VR5, and VR6. VR is known to regulate proliferation, death, migration, infiltration and angiogenesis of cancer cells at each stage in the process of cancer progression.

As used herein, the term "c-kit" is also known as CD117, and induces signal transduction that activates cell survival, proliferation and differentiation. c-kit is a proto-oncogene, and overexpression or mutation of its gene is related to the onset of cancer.

As used herein, the term "AXL (tyrosine-protein kinase receptor UFO)" is a tyrosine kinase receptor present on the cell surface, and mediates signal transduction involved in cell proliferation and survival. It is known to be involved in anticancer agent resistance in anticancer treatment. In an embodiment, the AXL target anticancer agent may be Bemcentinib or Gilteritinib.

As used herein, the term "RET (REarragned during transfection)" is a receptor that mediates signals involved in cell proliferation, cell death, and survival; and mutations in RET are known to be involved in cancer development. The RET target inhibitor may be Selpercatinib or Pralsetinib, but is not limited thereto.

As used herein, the term "Braf" is a MAPK signaling mediator involved in cell proliferation, cell cycle regulation, cell survival, angiogenesis, cell migration, and the like, and genetic mutations are observed in cancer cells. The inhibitor targeting Braf may be Vemurafenib.

As used herein, the term "PARP (Poly[ADP-ribose]polymerase)" is a protein that recognizes damaged DNA in the nucleus and is activated, and then activates a DNA repair-related protein. The PARP target inhibitor suppresses proliferation of cancer cells by inhibiting DNA repair of cancer cells. In an embodiment, the PARP target inhibitor may be Olaparib, Talazoparib, Niraparib, or Rucaparib.

As used herein, the term "DNA methyltransferase (DNMT)" is an enzyme that transfers a methyl group to DNA, and expression of a gene is inhibited through the above process. The DMNT target inhibitor exhibits anticancer activity by inhibiting hypermethylation of the cancer suppressor gene and inducing normal expression of the cancer suppressor gene. In an embodiment, the DNMT target inhibitor may be Azacitidine, Decitabine, or Guadecitabine.

As used herein, the term "CDK (cyclin dependent kinase) 4/6" is a protein that regulates the cell cycle and promotes cell growth, and is overactivated in the development and progression stages of various malignant tumors. The CDK4/6 target inhibitor exhibits anticancer activity by inhibiting cell cycle of cancer cells, inhibiting cell proliferation, and inducing cell death. The CDK4/6 target inhibitor may be Abemaciclib or Palbociclib.

As used herein, the term "STING (Stimulator of Interferon Genes)" is an in vivo sensor that recognizes DNA fragments derived from cancer cells, and activates immune cells in the body such as dendritic cells by stimulating interferon genes. The STING agonist exhibits an immune enhancing effect and a cancer angiogenesis inhibitory effect. For example, the STING agonist may be CDNs, SB11285, DMXAA, or the like.

As used herein, the term "anticancer virus therapeutic agent" is a therapeutic agent that kills cancer by inserting a specific gene targeting cancer cells into a virus that is capable of proliferation and has infectivity. The anticancer virus therapeutic agent may be Talimogenem or Laherparepvec.

As used herein, the term "antibody therapeutic agent" is a therapeutic agent that exhibits anticancer effect by using an antibody that recognizes a specific protein of cancer cells as an antigen. The antibody therapeutic agent may be Trastuzumab, Emtansine, Emtansine, Rituximab, Ibritumomab, Tositumomab, Brentuximab, Ofatumumab, Obinutuzumab, Necitumumab, Bevacizumab, Ramucirumab, Nivolumab, Pembrolizumab, Atezolizumab, Durvalumab, Ipilimumab, or the like.

As used herein, the term "immune cell therapeutic agent" is a therapeutic agent that exhibits anticancer effect by activating an immune response in the body using immune cells such as dendritic cells, natural killer cells, and T cells. The immune cell therapeutic agent is used after extracting and potentiating immune cells in the body or genetically engineering them to be reinjected into the body. The representative immune cell therapeutic agent includes T cell receptor-modified T cells (TCR-T), chimeric antigen receptor-modified T cells (CAR-T), and the like. Specifically, it may be Tisagenlecleucel or Axicabtagene Ciloleucel, but is not limited thereto.

As used herein, the term "immune checkpoint inhibitor" is a substance that inhibits the activity of an immune checkpoint protein that inhibits differentiation, proliferation, and activity of immune cells, and it is known to eliminate cancer cells by preventing them from exerting the function of evading the immune system. The immune checkpoint inhibitor may be any one selected from the group consisting of an anti-CTLA-4 antibody, an anti-PD-1 antibody, an anti-PD-L1 antibody, an anti-PD-L2 antibody, an anti-B7-H4 antibody, an anti-HVEM antibody, an anti-TIM3 antibody, an anti-GAL9 antibody, an anti-LAG3 antibody, an anti-VISTA antibody, an anti-KIR antibody, an anti-BTLA antibody, and an anti-TIGIT antibody. In an embodiment, the immune checkpoint inhibitor may be Ipilimumab, Pembrolizumab, Nivolumab, Cemiplimab, Atezolizumab, Avelumab, Duralumab and the like, but is not limited thereto.

As used herein, the term "ADC (antibody drug conjugate)" is a therapeutic agent that chemically binds an antibody and a cytotoxic drug to exhibit high anticancer effect through target delivery. It may be Gemtuzumab-Ozogamicin, Brentuximab-Vedotin, Trastuzumab-Emtansine, Inotuzumab-Ozogamicin, Eribulin-Mesylate, and the like.

The fusion protein dimer comprising an IL-2 protein and a CD80 protein may be used in combination with an anticancer vaccine or the like.

In addition, an anticancer agent may be used not only in combination with the anticancer agent described above, but also in combination with an anticancer vaccine or the like.

Preferably, the anticancer agent may be any one selected from the group consisting of Cisplatin, Oxaliplatin, ALTIMA, Axitinib (VR1,2,3, PDGFR, c-kit), Galunisertib (TGFβR1), Lenvatinib (VR1,2,3), Ramucirumab (VR2), Cabozatinib (c-Met, VR2, AXL, RET), Olaparib (PARP), Guadecitabine (DNMT), Docetaxel, Paclitaxel, Pemetrexed, Vemurafenib (Braf), Abemaciclib (CDK4/6), Cetuximab (EGFR), Durvalumab (PD-L1), Trastuzumab (Her2), DMXAA, NK cell, T cell, and Keytruda (PD-1).

In addition, the anticancer agent may include one or more anticancer agents. Specifically, the fusion protein dimer may be used commonly together with two anticancer agents. As an example, it may be an anticancer chemotherapeutic agent and a target anticancer agent; an anticancer chemotherapeutic agent and an anticancer virus; a target anticancer agent and an antibody therapeutic agent; an anticancer chemotherapeutic agent and a cell therapeutic agent; and an anticancer chemotherapeutic agent and an immune checkpoint inhibitor. In addition, it may be a target anticancer agent and an anticancer virus; a target anticancer agent and an antibody therapeutic agent; a target anticancer agent and a cell therapeutic agent; a target anticancer agent and an immune checkpoint inhibitor. In addition, it may be an anticancer virus and an antibody therapeutic agent; an anticancer virus and a cell therapeutic agent; and an anticancer virus and an immune checkpoint inhibitor. In addition, it may be an antibody therapeutic agent and a cell therapeutic agent; and an antibody therapeutic agent and an immune checkpoint inhibitor.

In addition, the fusion protein dimer may be used together with three anticancer agents. In addition to the two anticancer agents, a different anticancer agent may be further included and used.

In an embodiment, the anticancer agent may be an anticancer chemotherapeutic agent and a target anticancer agent; an anticancer chemotherapeutic agent and an immune checkpoint inhibitor; or an anticancer chemotherapeutic agent, a target anticancer agent and an immune checkpoint inhibitor.

Use of Fusion Protein Dimer in Anticancer Maintenance Therapy

In another aspect of the present invention, there is provided a composition for anticancer maintenance therapy, comprising, as an active ingredient, a fusion protein dimer comprising a CD80 protein or a fragment thereof and an IL-2 protein or a variant thereof.

As described above, "maintenance therapy" refers to treating cancer after initial anticancer treatment. In particular, it is a treatment method that increases the effect of cancer treatment by preventing or delaying the recurrence of cancer.

Here, it may further include at least one anticancer agent for maintenance therapy. Here, the anticancer agent is as described above.

Kit Comprising Fusion Protein Dimer

In another aspect of the present invention, there is provided a kit for preventing or treating cancer, comprising, as active ingredients, a fusion protein dimer comprising a CD80 protein or a fragment thereof and an IL-2 protein or a variant thereof, and an anticancer agent.

In another aspect of the present invention, there is provided a kit for anticancer maintenance therapy, comprising, as active ingredients, a fusion protein dimer comprising a CD80 protein or a fragment thereof and an IL-2 protein or a variant thereof, and an anticancer agent.

Fusion Protein Comprising IL-2 Protein and CD80 Protein

As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{st}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{st}$ amino acids in the amino acid sequence of SEQ ID NO: 10. In addition, in an embodiment, the IL-2 variant may be obtained by substitution of the 45$^{th}$ and 72$^{nd}$ amino acids in the amino acid sequence of SEQ ID NO: 10. In addition, in an embodiment, the IL-2 variant may be obtained by substitution of the 61$^{st}$ and 72$^{nd}$ amino acids in the amino acid sequence of SEQ ID NO: 10.

Furthermore, an IL-2 variant may be in a form in which three amino acids are substituted. Specifically, the IL-2 variant may be obtained by substitution of the 38$^{th}$, 42$^{nd}$, and 45$^{th}$ amino acids in the amino acid sequence of SEQ ID NO: 10. In addition, in an embodiment, the IL-2 variant may be obtained by substitution of the 38$^{th}$, 42$^{nd}$, and 61$^{st}$ amino acids in the amino acid sequence of SEQ ID NO: 10. In addition, in an embodiment, the IL-2 variant may be obtained by substitution of the 38$^{th}$, 42$^{nd}$, and 72$^{nd}$ amino acids in the amino acid sequence of SEQ ID NO: 10. In addition, in an embodiment, the IL-2 variant may be obtained by substitution of the 38$^{th}$, 45$^{th}$, and 61$^{st}$ amino acids in the amino acid sequence of SEQ ID NO: 10. In addition, in an embodiment, the IL-2 variant may be obtained by substitution of the 38$^{th}$, 45$^{th}$, and 72$^{nd}$ amino acids in the amino acid sequence of SEQ ID NO: 10. In addition, in an embodiment, the IL-2 variant may be obtained by substitution of the 38$^{th}$, 61$^{st}$ and 72$^{nd}$ amino acids in the amino acid sequence of SEQ ID NO: 10. In addition, in an embodiment, the IL-2 variant may be obtained by substitution of the 42$^{nd}$, 45$^{th}$, and 61$^{st}$ amino acids in the amino acid sequence of SEQ ID NO: 10. In addition, in an embodiment, the IL-2 variant may be obtained by substitution of the 42$^{nd}$, 45$^{th}$, and 72$^{nd}$ amino acids in the amino acid sequence of SEQ ID NO: 10. In addition, in an embodiment, the IL-2 variant may be obtained by substitution of the 45$^{th}$, 61$^{st}$ and 72$^{nd}$ amino acids in the amino acid sequence of SEQ ID NO: 10.

In addition, an IL-2 variant may be in a form in which four amino acids are substituted. Specifically, the IL-2 variant may be obtained by substitution of the 38$^{th}$, 42$^{nd}$, 45$^{th}$, and 61$^{st}$ amino acids in the amino acid sequence of SEQ ID NO: 10. In addition, in an embodiment, the IL-2 variant may be obtained by substitution of the 38$^{th}$, 42$^{nd}$, 45$^{th}$, and 72$^{nd}$ amino acids in the amino acid sequence of SEQ ID NO: 10. In addition, in an embodiment, the IL-2 variant may be obtained by substitution of the 38$^{th}$, 45$^{th}$, 61$^{st}$, and 72$^{nd}$ amino acids in the amino acid sequence of SEQ ID NO: 10. In addition, in an embodiment, the IL-2 variant may be obtained by substitution of the 38$^{th}$, 42$^{nd}$, 61$^{st}$, and 72$^{nd}$ amino acids in the amino acid sequence of SEQ ID NO: 10. In addition, in an embodiment, the IL-2 variant may be obtained by substitution of 42$^{nd}$, 45$^{th}$, 61$^{st}$, and 72$^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the 38$^{th}$, 42$^{nd}$, 45$^{th}$, 61$^{st}$, and 72$^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the 38$^{th}$ amino acid cannot be substituted with arginine, the 42$^{nd}$ amino acid cannot be substituted with phenylalanine, the 45$^{th}$ amino acid cannot be substituted with tyrosine, the 61$^{st}$ amino acid cannot be substituted with glutamic acid, and the 72$^{nd}$ amino acid cannot be substituted with leucine.

Regarding amino acid substitution for an IL-2 variant, in the amino acid sequence of SEQ ID NO: 10, the 38$^{th}$ amino acid, arginine, may be substituted with an amino acid other than arginine. Preferably, regarding amino acid substitution for an IL-2 variant, in the amino acid sequence of SEQ ID NO: 10, the 38$^{th}$ amino acid, arginine, may be substituted with alanine (R38A).

Regarding amino acid substitution for an IL-2 variant, in the amino acid sequence of SEQ ID NO: 10, the 42$^{nd}$ amino acid, phenylalanine, may be substituted with an amino acid other than phenylalanine. Preferably, regarding amino acid substitution for an IL-2 variant, in the amino acid sequence of SEQ ID NO: 10, the 42$^{nd}$ amino acid, phenylalanine, may be substituted with alanine (F42A).

Regarding amino acid substitution for an IL-2 variant, in the amino acid sequence of SEQ ID NO: 10, the 45$^{th}$ amino acid, tyrosine, may be substituted with an amino acid other than tyrosine. Preferably, regarding amino acid substitution for an IL-2 variant, in the amino acid sequence of SEQ ID NO: 10, the 45$^{th}$ amino acid, tyrosine, may be substituted with alanine (Y45A).

Regarding amino acid substitution for an IL-2 variant, in the amino acid sequence of SEQ ID NO: 10, the 61$^{st}$ amino acid, glutamic acid, may be substituted with an amino acid other than glutamic acid. Preferably, regarding amino acid substitution for an IL-2 variant, in the amino acid sequence of SEQ ID NO: 10, the 61$^{st}$ amino acid, glutamic acid, may be substituted with arginine (E61R).

Regarding amino acid substitution for an IL-2 variant, in the amino acid sequence of SEQ ID NO: 10, the 72$^{nd}$ amino acid, leucine, may be substituted with an amino acid other than leucine. Preferably, regarding amino acid substitution for an IL-2 variant, in the amino acid sequence of SEQ ID NO: 10, the 72$^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:

(a) R38A/F42A
(b) R38A/F42A/Y45A
(c) R38A/F42A/E61R
(d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Rα). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 is composed of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a cleaved form of CD80. In addition, the CD80 fragment may be an extracellular domain of CD80. An embodiment of the CD80 fragment may be obtained by elimination of the $1^{st}$ to $34^{th}$ amino acids from N-terminus which are a signal sequence of CD80. Specifically, an embodiment of the CD80 fragment may be a protein composed of the $35^{th}$ to $288^{th}$ amino acids in SEQ ID NO: 11. In addition, an embodiment of the CD80 fragment may be a protein composed of the $35^{th}$ to $242^{nd}$ amino acids in SEQ ID NO: 11. In addition, an embodiment of the CD80 fragment may be a protein composed of the $35^{th}$ to $232^{nd}$ amino acids in SEQ ID NO: 11. In addition, an embodiment of the CD80 fragment may be a protein composed of the $35^{th}$ to $139^{th}$ amino acids in SEQ ID NO: 11. In addition, an embodiment of the CD80 fragment may be a protein composed of the $142^{nd}$ to $242^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fc domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively. Linkage between N-terminus or C-terminus of the Fc domain and CD-80 or IL-2 may optionally be achieved by a linker peptide.

Specifically, a fusion protein may consist of the following structural formula (I) or (II):

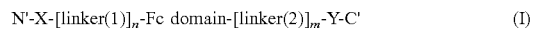

N'-X-[linker(1)]$_n$-Fc domain-[linker(2)]$_m$-Y-C'  (I)

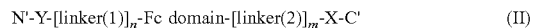

N'-Y-[linker(1)]$_n$-Fc domain-[linker(2)]$_m$-X-C'  (II)

Here, in the structural formulas (I) and (II),
N' is the N-terminus of the fusion protein,
C' is the C-terminus of the fusion protein, X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80. Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be $(G4S)_n$ (where n is an integer of 1 to 10). Here, in $(G4S)_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

Pharmaceutical Use

The pharmaceutical composition for treating or preventing cancer of the present invention, the composition comprising, as an active ingredient, a fusion protein comprising an IL-2 protein and a CD80 protein, and an anticancer agent may enhance efficacy for treating and/or preventing cancer.

The fusion protein comprising an IL-2 protein and a CD80 protein, or the fusion protein dimer where the two fusion proteins are attached is as described above.

The cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain tumor, neuroblastoma, retinoblastoma, head and neck cancer, salivary gland cancer, and lymphoma.

A preferred dose of the pharmaceutical composition varies depending on the patient's condition and body weight, severity of disease, form of drug, route and duration of administration and may be appropriately selected by those skilled in the art. In the pharmaceutical composition for treating or preventing cancer of the present invention, the active ingredient may be contained in any amount (effective amount) depending on application, dosage form, blending purpose, and the like, as long as the active ingredient can exhibit anticancer activity. A conventional effective amount thereof will be determined within a range of 0.001 wt % to 20.0 wt % by weight, based on the total weight of the composition. Here, the term "effective amount" refers to an amount of an active ingredient capable of inducing an anticancer effect. Such an effective amount can be experimentally determined within the scope of common knowledge of those skilled in the art.

As used herein, the term "treatment" may be used to mean both therapeutic and prophylactic treatment. Here, prophylaxis may be used to mean that a pathological condition or disease of an individual is alleviated or mitigated. In an embodiment, the term "treatment" includes both application or any form of administration for treating a disease in a mammal, including a human. In addition, the term includes inhibiting or slowing down a disease or disease progression; and includes meanings of restoring or repairing impaired or lost function so that a disease is partially or completely alleviated; stimulating inefficient processes; or alleviating a serious disease.

As used herein, the term "efficacy" refers to capacity that can be determined by one or parameters, for example, survival or disease-free survival over a certain period of time such as one year, five years, or ten years. In addition, the parameter may include inhibition of size of at least one tumor in an individual.

Pharmacokinetic parameters such as bioavailability and underlying parameters such as clearance rate may also affect efficacy. Thus, "enhanced efficacy" (for example, improvement in efficacy) may be due to enhanced pharmacokinetic parameters and improved efficacy, which may be measured by comparing clearance rate and tumor growth in test animals or human subjects, or by comparing parameters such as survival, recurrence, or disease-free survival.

As used herein, the term "therapeutically effective amount" or "pharmaceutically effective amount" refers to an amount of a compound or composition effective to prevent or treat the disease in question, which is sufficient to treat the disease at a reasonable benefit/risk ratio applicable to medical treatment and does not cause adverse effects. A level of the effective amount may be determined depending on factors including the patient's health condition, type and severity of disease, activity of drug, the patient's sensitivity to drug, mode of administration, time of administration, route of administration and excretion rate, duration of treatment, formulation or simultaneously used drugs, and other factors well known in the medical field. In an embodiment, the therapeutically effective amount means an amount of drug effective to treat cancer.

Here, the pharmaceutical composition may further comprise a pharmaceutically acceptable carrier. The pharmaceutically acceptable carrier may be any carrier as long as the carrier is a non-toxic substance suitable for delivery to a patient. Distilled water, alcohol, fat, wax, and inert solid may be contained as the carrier. A pharmaceutically acceptable adjuvant (buffer, dispersant) may also be contained in the pharmaceutical composition.

Specifically, by including a pharmaceutically acceptable carrier in addition to the active ingredient, the pharmaceutical composition may be prepared into a parenteral formulation depending on its route of administration using conventional methods known in the art. Here, the term "pharmaceutically acceptable" means that the carrier does not have more toxicity than the subject to be applied (prescribed) can adapt while not inhibiting activity of the active ingredient.

When the pharmaceutical composition is prepared into a parenteral formulation, it may be made into preparations in the form of injections, transdermal patches, nasal inhalants, or suppositories with suitable carriers according to methods known in the art. In a case of being made into injections, sterile water, ethanol, polyol such as glycerol or propylene glycol, or a mixture thereof may be used as a suitable carrier; and an isotonic solution, such as Ringer's solution, phosphate buffered saline (PBS) containing triethanol amine or sterile water for injection, and 5% dextrose, or the like may preferably be used. Formulation of pharmaceutical compositions is known in the art, and reference may specifically be made to Remington's Pharmaceutical Sciences (19th ed., 1995) and the like. This document is considered part of the present description.

A preferred dose of the pharmaceutical composition may range from 0.01 µg/kg to 10 g/kg, or 0.01 mg/kg to 1 g/kg, per day, depending on the patient's condition, body weight, sex, age, severity of the patient, and route of administration. The dose may be administered once a day or may be divided into several times a day. Such a dose should not be construed as limiting the scope of the present invention in any aspect.

Subjects to which the pharmaceutical composition can be applied (prescribed) are mammals and humans, with humans being particularly preferred. In addition to the active ingredient, the pharmaceutical composition of the present application may further contain any compound or natural extract, which has already been validated for safety and is known to have anticancer activity or a therapeutic effect on an infectious disease, so as to boost or reinforce anticancer activity.

Use of Composition Comprising Fusion Protein Dimer and Anticancer Agent

In another aspect of the present invention, there is provided a use of a composition for combination administration comprising a fusion protein dimer comprising a CD80 protein or a fragment thereof and an IL-2 protein or a variant thereof, and an anticancer agent for the treatment of cancer disease.

In another aspect of the present invention, there is provided a use of a composition for combination administration comprising a fusion protein dimer comprising an IL-2 protein and a CD80 protein, and an anticancer agent for enhancing the therapeutic effect of cancer disease.

In another aspect of the present invention, there is provided a use of a fusion protein dimer comprising a CD80 protein or a fragment thereof and an IL-2 protein or a variant thereof for maintenance therapy. Here, an anticancer agent may be further included.

In another aspect of the present invention, there is provided a method for treating cancer disease and/or a method for enhancing therapeutic effect, comprising a step of administering, to a subject, a fusion protein comprising an IL-2 protein and a CD80 protein or a fusion protein dimer in which the two fusion proteins are bound to each other, and an anticancer agent.

The subject may be a subject suffering from cancer. In addition, the subject may be a mammal, preferably a human. The fusion protein comprising an IL-2 protein and a CD80 protein or the fusion protein dimer in which the two fusion proteins are bound to each other is as described above.

Route of administration, dose, and frequency of administration of the fusion protein or the fusion protein dimer may vary depending on the patient's condition and the presence or absence of side effects, and thus the fusion protein or the fusion protein dimer may be administered to a subject in various ways and amounts. The optimal administration method, dose, and frequency of administration may be selected in an appropriate range by those skilled in the art. In addition, the fusion protein or the fusion protein dimer may be administered in combination with other drugs (for example, the above described anticancer agent) or physiologically active substances whose therapeutic effect is known with respect to a disease to be treated, or may be formulated in the form of combination preparations with other drugs.

Due to IL-2 activity, the fusion protein in an embodiment of the present invention can activate immune cells such as natural killer cells. Thus, the fusion protein can be effectively used for cancer disease. In particular, it was identified that as compared with the wild type, an IL-2 variant with two to five amino acid substitutions, in particular, an IL-2 variant that contains amino acid substitutions at two, three, four, or five positions among the positions selected from the group consisting of R38A, F42A, Y45A, E61R, and L72G in the amino acid sequence of SEQ ID NO: 10, has low binding ability for the IL-2 receptor alpha chain and thus exhibits improved characteristics with respect to pharmacological side effects of conventional IL-2. Thus, such an IL-2 variant, when used alone or in the form of a fusion protein, can decrease incidence of vascular (or capillary) leakage syndrome (VLS), which is a conventionally known problem of IL-2.

Pharmaceutical Composition Comprising, as Active Ingredients, IL-2 Protein or Variant Thereof, CD80 Protein or Variant Thereof, and Anticancer Agent In another aspect of the present invention, there is provided a composition for treating cancer, comprising, as active ingredients, IL-2 or a variant thereof, a CD80 protein or a variant thereof, and an anticancer agent.

Here, the IL-2 or variant thereof is as described above. In addition, the IL-2 or variant thereof may further include an immunoglobulin Fc region. Here, the IL-2 or variant thereof may bind to the N-terminus or C-terminus of the Fc region. In an embodiment, the IL-2 or variant thereof may bind to the C-terminus of the Fc region. In addition, as described above, the variant of IL-2 may be a form in which two amino acids are substituted or a form in which three amino acids are substituted. Here, the IL-2 or variant thereof may be directly bound to the Fc region, but may be bound through a peptide linker. Here, the peptide linker may be any one of the linkers described above.

In addition, the CD80 protein or variant thereof is as described above. In addition, the CD80 or variant thereof may further include an immunoglobulin Fc region. Here, the CD80 or variant thereof may bind to the N-terminus or C-terminus of the Fc region. Here, the CD80 may be in the form of a fragment, and may be a fragment of CD80 including a V domain. In an embodiment, the CD80 or variant may bind to the N-terminus of the Fc region. In addition, the variant of CD80 may be a variant in various forms as long as its activity is maintained.

In addition, the anticancer agent may be any one selected from various types of the anticancer agents described above.

MODE FOR CARRYING OUT THE INVENTION

Hereinafter, the present invention will be described in more detail by way of the following examples. However, the following examples are only for illustrating the present invention, and the scope of the present invention is not limited thereto.

I. Preparation of Fusion Protein

Preparation Example 1. Preparation of hCD80-Fc-IL-2 Variant (2M): GI101

In order to produce a fusion protein comprising a human CD80 fragment, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 8) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) having two amino acid substitutions, in this order, from the N-terminus. The polynucleotide was inserted into pcDNA3_4 vector. In addition, the vector was introduced into CHO cells (EXPI-CHO™) to express the fusion protein of SEQ ID NO: 9. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101".

Purification was carried out using chromatography containing Mab Select SuRe protein A resin. The fusion protein was bound thereto under a condition of 25 mM Tris, 25 mM NaCl, pH 7.4. Then, elution was performed with 100 mM NaCl and 100 mM acetic acid at pH 3. 20% 1 M Tris-HCl at pH 9 was placed in a collection tube, and then the fusion protein was collected. For the collected fusion protein, the buffer was exchanged through dialysis with PBS buffer for 16 hours.

Figure 6:
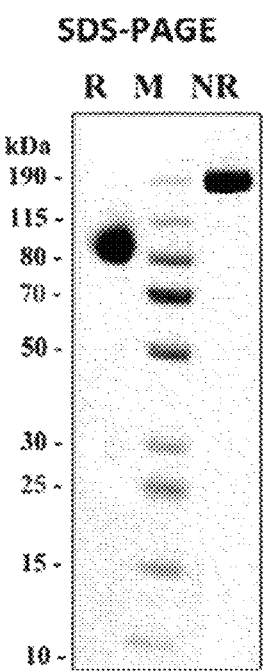
FIG. 6 illustrates a result obtained by identifying the obtained fusion protein dimer (GI101) with SDS-PAGE.
Figure 7:
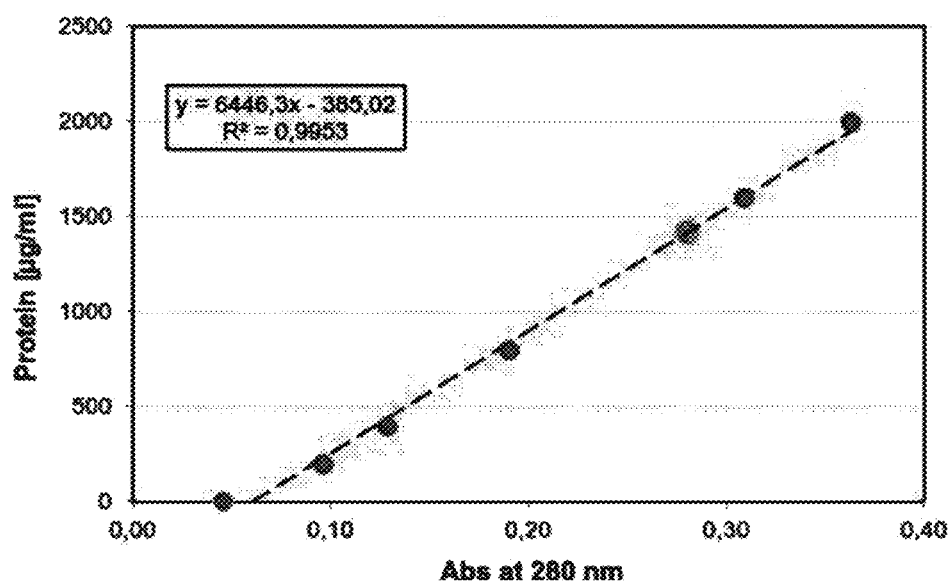
FIG. 7 illustrates amounts of the fusion protein (GI101) measured by absorbance.
Figure 8:
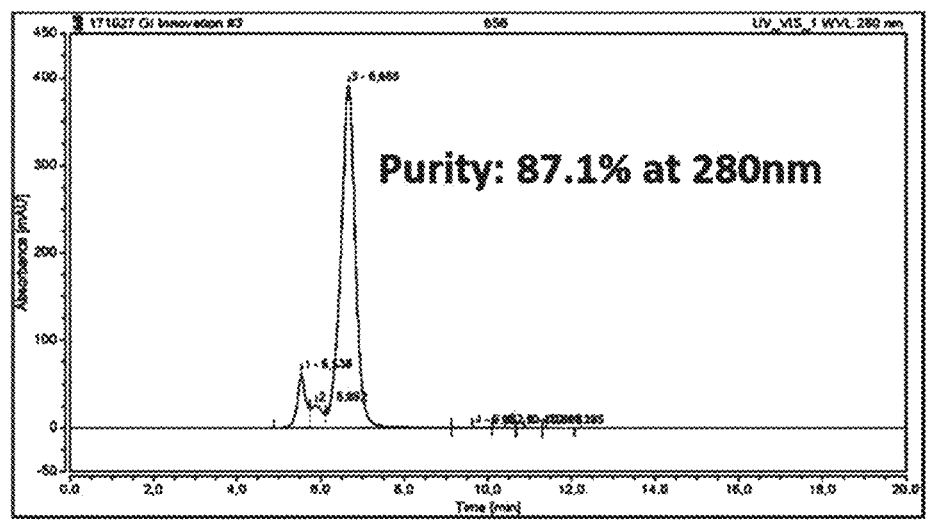
FIG. 8 illustrates a result obtained by analyzing the obtained fusion protein dimer (GI101) by size exclusion chromatography (SEC).

Thereafter, absorbance at 280 nm wavelength was measured, over time, with size exclusion chromatography using a TSKgel G3000SWXL column (TOSOH Bioscience), to obtain a highly concentrated fusion protein. Here, the isolated and purified fusion protein was subjected to SDS-PAGE under reduced (R) or non-reduced (NR) condition, and stained with Coomassie Blue to check its purity (FIG. 6). It was identified that the fusion protein was contained at a concentration of 2.78 mg/ml when detected with NanoDrop (FIG. 7). In addition, the results obtained by analysis using size exclusion chromatography are provided in FIG. 8.

Preparation Example 2. Preparation of mCD80-Fc-IL-2 Variant (2M): mGI101

In order to produce a fusion protein comprising a mouse CD80, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 14) which encodes a fusion protein that contains a signal peptide (SEQ ID NO: 1), a mCD80 (SEQ ID NO: 13), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (EXPI-CHO™) to express the fusion protein of SEQ ID NO: 15. After the vector was introduced, culture was performed for 7 days in an environment of 37° C., 125 rpm, and 8% $CO_2$ concentration. Then, the culture was harvested and the fusion protein was purified therefrom. The purified fusion protein was designated "mGI101".

Figure 9:
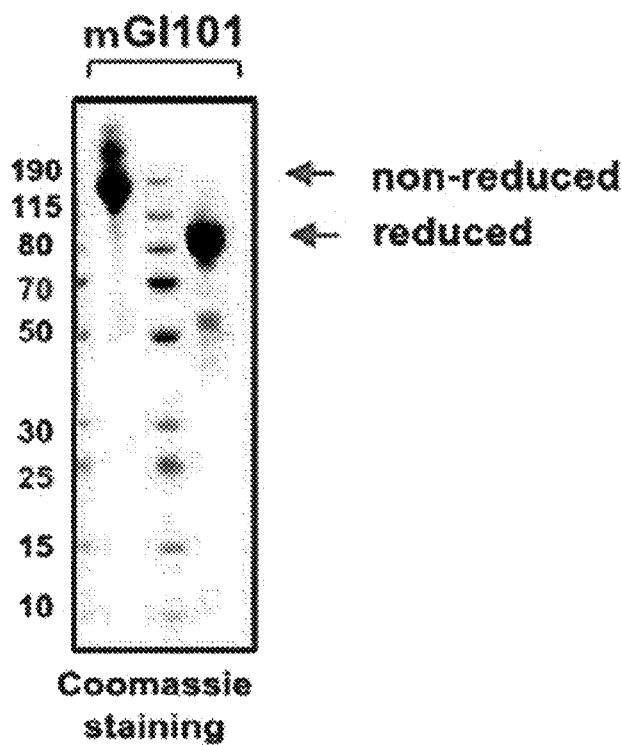
FIG. 9 illustrates a result obtained by identifying the obtained mGI101 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 9). It was found that the fusion protein was contained at a concentration of 1.95 mg/ml when detected by absorbance at 280 nm using NanoDrop.

Preparation Example 3. Preparation of hCD80-Fc: GI101C1

In order to produce a fusion protein comprising a human CD80 fragment and an Fc domain, a polynucleotide was synthesized through the Invitrogen GeneArt Gene Synthesis service of ThermoFisher Scientific. Specifically, the polynucleotide contains a nucleotide sequence (SEQ ID NO: 16) which encodes a fusion protein that contains a signal peptide (SEQ ID NO: 1), a CD80 fragment (SEQ ID NO: 2), an Ig hinge (SEQ ID NO: 3), and an Fc domain (SEQ ID NO: 4). The polynucleotide was inserted into pcDNA3_4 vector. In addition, the vector was introduced into CHO cells (EXPI-CHO™) to express the fusion protein of SEQ ID NO: 17. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101C1".

Figure 10:
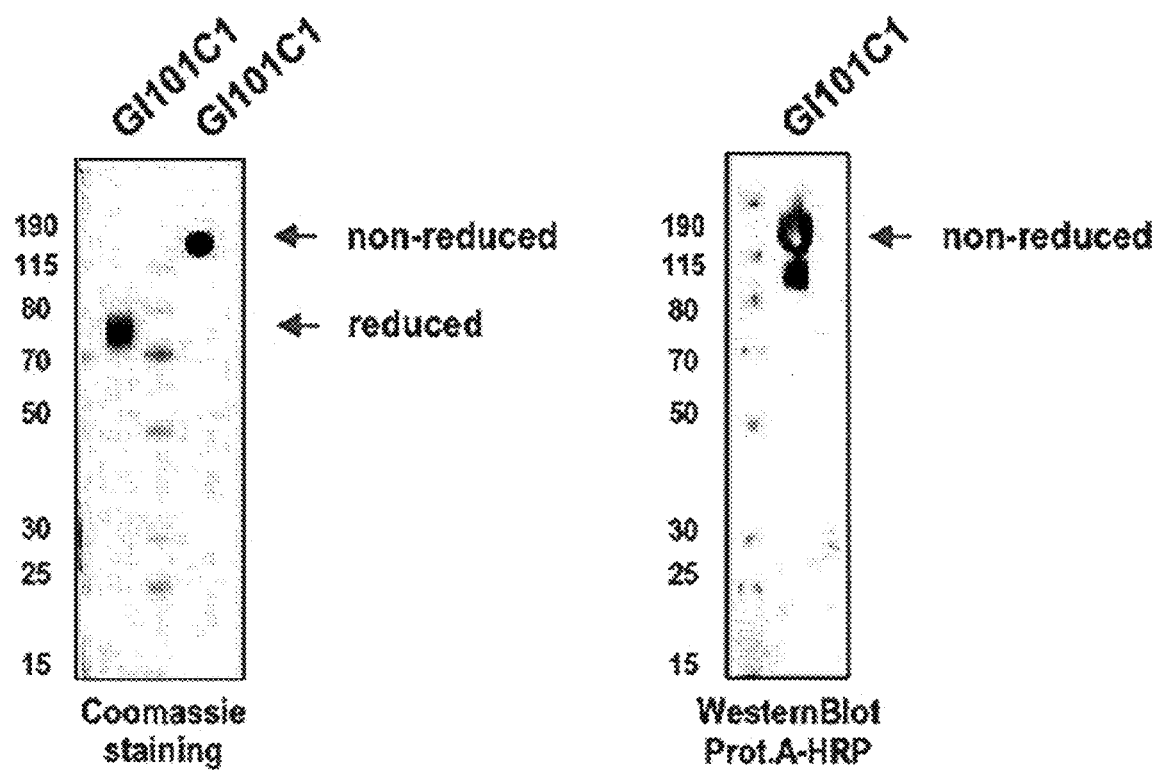
FIG. 10 illustrates a result obtained by identifying the obtained GI101C1 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 10). It was observed that the fusion protein was contained at a concentration of 3.61 mg/ml when detected by absorbance at 280 nm using NanoDrop.

Preparation Example 4. Preparation of Fc-IL-2 Variant (2M): GI101C2

In order to produce a fusion protein comprising an Fc domain and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 18)

which encodes a fusion protein that contains a signal peptide (SEQ ID NO: 1), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (EXPI-CHO™) to express the fusion protein of SEQ ID NO: 19. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101C2".

Figure 11:
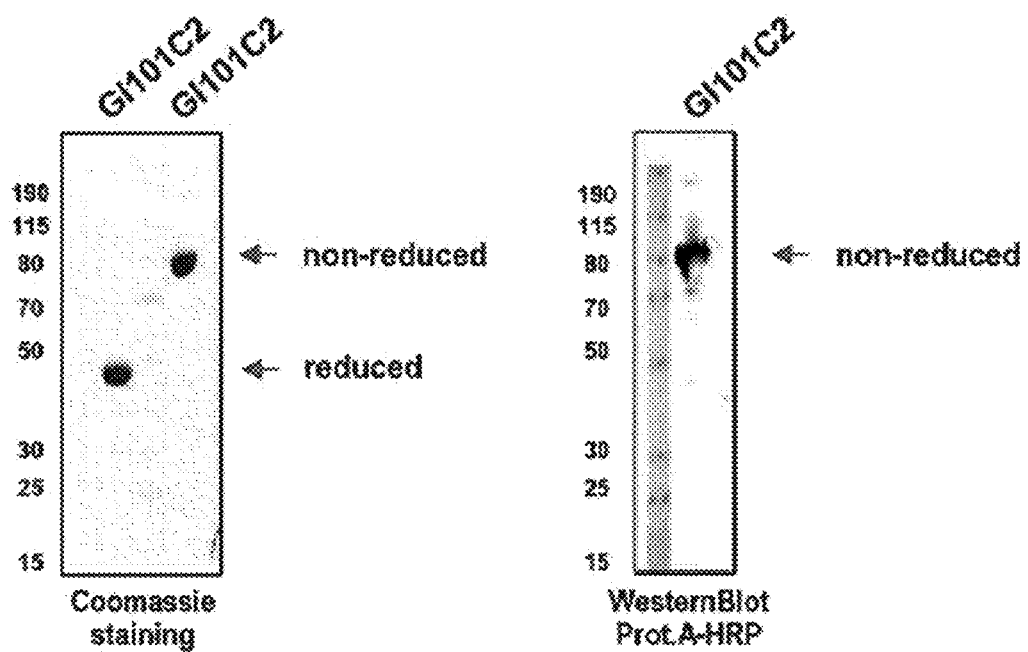
FIG. 11 illustrates a result obtained by identifying the obtained GI101C2 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 11). It was found that the fusion protein was contained at a concentration of 4.79 mg/ml when detected by absorbance at 280 nm using NanoDrop.

Preparation Example 5. Preparation of mCD80-Fc: mGI101C1

In order to produce a fusion protein comprising a mouse CD80 and an Fc domain, a polynucleotide was synthesized through the Invitrogen GeneArt Gene Synthesis service of ThermoFisher Scientific. Specifically, the polynucleotide contains a nucleotide sequence (SEQ ID NO: 20) which encodes a fusion protein that contains a signal peptide (SEQ ID NO: 1), a mouse CD80 (SEQ ID NO: 13), an Ig hinge (SEQ ID NO: 3), and an Fc domain (SEQ ID NO: 4), in this order, from the N-terminus. The polynucleotide was inserted into pcDNA3_4 vector. In addition, the vector was introduced into CHO cells (EXPI-CHO™) to express the fusion protein of SEQ ID NO: 21. After the vector was introduced, culture was performed for 7 days in an environment of 37° C., 125 rpm, and 8% $CO_2$ concentration. Then, the culture was harvested and the fusion protein was purified therefrom. The purified fusion protein was designated "mGI101C1".

Figure 12:
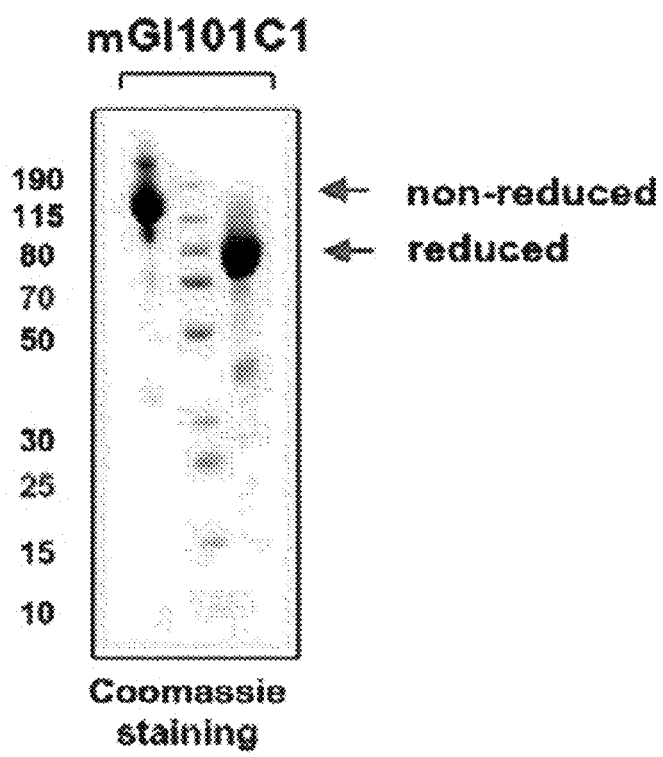
FIG. 12 illustrates a result obtained by identifying the obtained mGI101C1 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 12). It was observed that the fusion protein was contained at a concentration of 2.49 mg/ml when detected by absorbance at 280 nm using NanoDrop.

The fusion proteins prepared in Preparation Examples 1 to 5 are summarized in Table 1 below.

TABLE 1

| Item | N-terminus | Linker | C-terminus |
|---|---|---|---|
| Preparation Example 1 (GI101) | hCD80 fragment | Fc domain | hIL-2m |
| Preparation Example 2 (mGI101) | mCD80 fragment | Fc domain | hIL-2m |
| Preparation Example 3 (GI101C1) | CD80 fragment | Fc domain | — |
| Preparation Example 4 (GI101C2) | — | Fc domain | IL-2m |
| Preparation Example 5 (mGI101C1) | mCD80 fragment | Fc domain | — |

Preparation Example 6. Preparation of CD80-Fc-IL-2: GI101w

In order to produce a fusion protein comprising a human CD80 fragment, an Fc domain, and a human IL-2, a polynucleotide was synthesized through the Invitrogen GeneArt Gene Synthesis service of ThermoFisher Scientific. Specifically, the polynucleotide contais a nucleotide sequence (SEQ ID NO: 31) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and mature human IL-2 (SEQ ID NO: 10), in this order, from the N-terminus. The polynucleotide was inserted into pcDNA3_4 vector. In addition, the vector was introduced into CHO cells (EXPI-CHO™) to express the fusion protein of SEQ ID NO: 32. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101w". The purification and collection of the fusion protein were carried out in the same manner as in Preparation Example 1.

Preparation Example 7. Preparation of hCD80-Fc-IL-2 Variant (3M): GI102-M45

In order to produce a fusion protein comprising a human CD80 fragment, an Fc domain, and an IL-2 variant (3M) (R38A, F42A, and Y45A) (GI102-M45) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 25) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 22), in this order, from the N-terminus. The polynucleotide was inserted into pcDNA3_4 vector. In addition, the vector was introduced into CHO cells (EXPI-CHO™) to express the fusion protein of SEQ ID NO: 26. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI102-M45".

Figure 13:
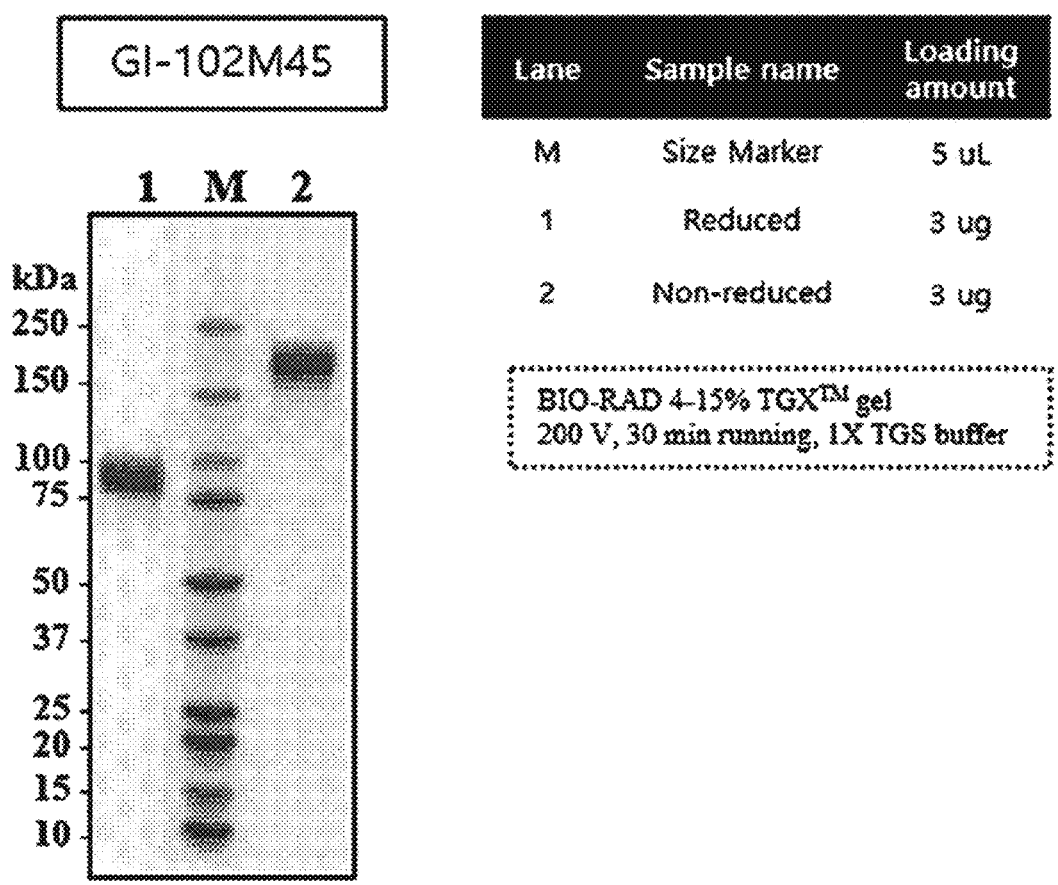
FIG. 13 illustrates a result obtained by identifying the obtained GI102-M45 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 13).

Preparation Example 8. Preparation of hCD80-Fc-IL-2 Variant (3M): GI102-M61

In order to produce a fusion protein comprising a human CD80 fragment, an Fc domain, and an IL-2 variant (3M) (R38A, F42A, and E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 27) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (EXPI-CHO™) to express the fusion protein of SEQ ID NO: 28. After the vector was introduced, culture was performed for 7 days in an environment of 37° C., 125 rpm, and 8% CO$_2$ concentration. Then, the culture was harvested and the fusion protein was purified therefrom. The purified fusion protein was designated "GI102-M61".

Figure 14:
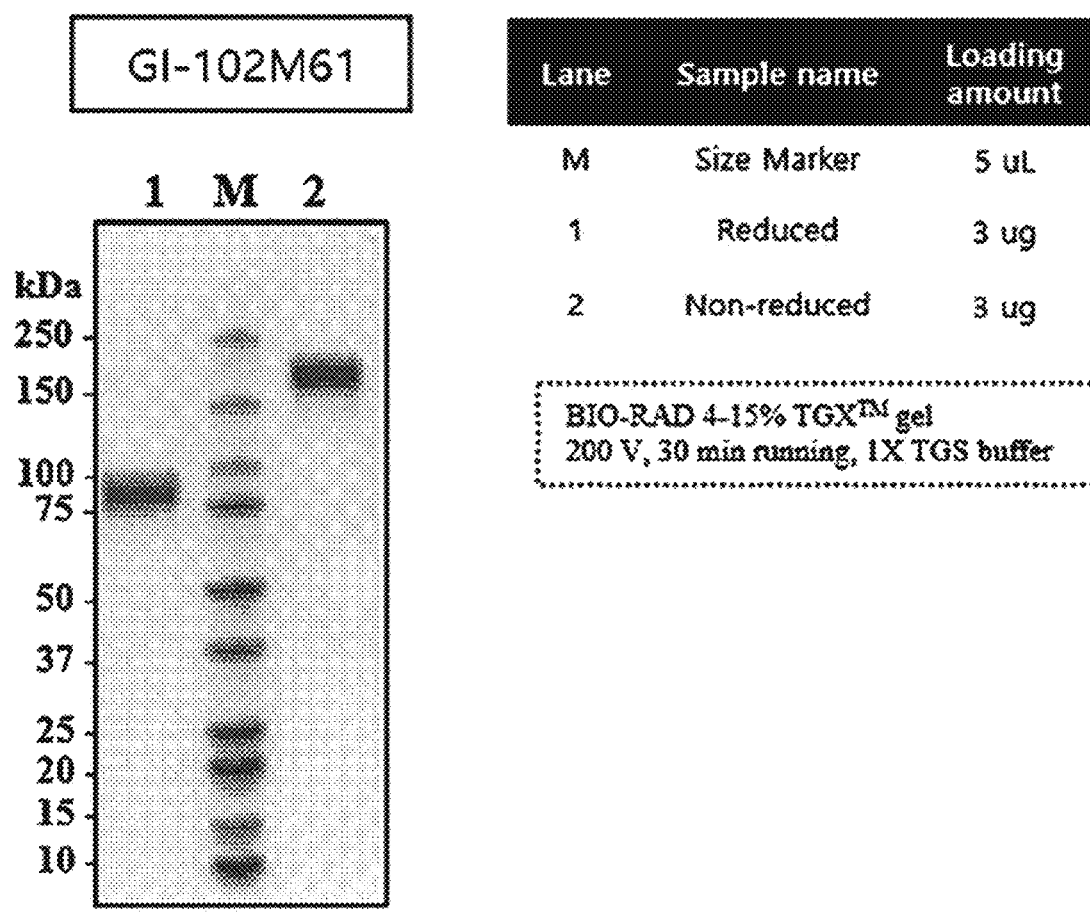
FIG. 14 illustrates a result obtained by identifying the obtained GI102-M61 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 14).

Preparation Example 9. Preparation of hCD80-Fc-IL-3M: GI102-M72

In order to produce a fusion protein comprising a human CD80 fragment, an Fc domain, and an IL-2 variant (3M) (R38A, F42A, and L72G) (GI102-M72) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 29) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 24), in this order, from the N-terminus. The polynucleotide was inserted into pcDNA3_4 vector. In addition, the vector was introduced into CHO cells (EXPI-CHO™) to express the fusion protein of SEQ ID NO: 30. After the vector was introduced, culture was performed for 7 days in an environment of 37° C., 125 rpm, and 8% CO$_2$ concentration. Then, the culture was harvested and the fusion protein was purified therefrom. The purified fusion protein was designated "GI102-M72".

Figure 15:
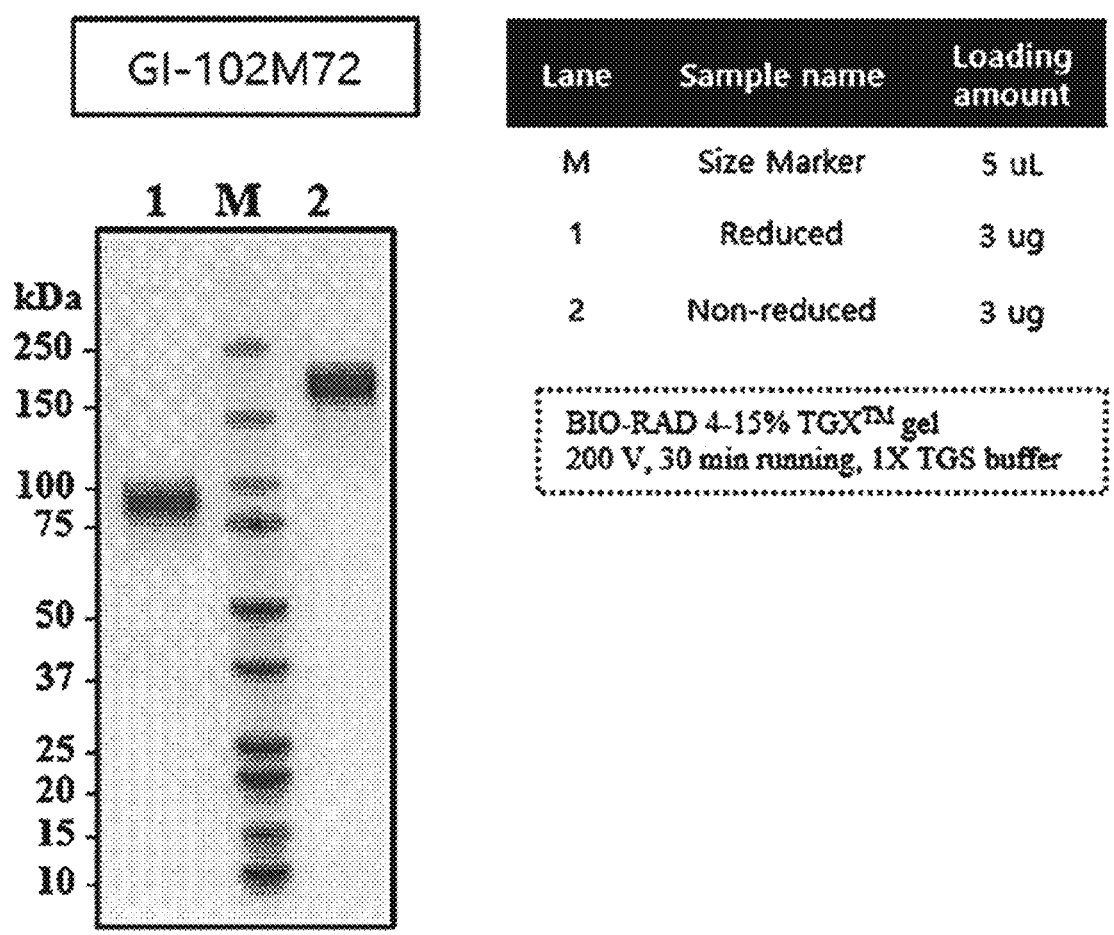
FIG. 15 illustrates a result obtained by identifying the obtained GI102-M72 fusion protein dimer with SDS-PAGE.

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 15).

Preparation Example 10. Preparation of mCD80-Fc-IL-3M: mGI102-M61

In order to produce a fusion protein comprising a mouse CD80 fragment, an Fc domain, and an IL-2 variant (3M) (R38A, F42A, and E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 33) which encodes a fusion protein that contains a signal peptide (SEQ ID NO: 1), a mCD80 fragment (SEQ ID NO: 13), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (EXPI-CHO™) to express the fusion protein of SEQ ID NO: 34. After the vector was introduced, culture was performed for 7 days in an environment of 37° C., 125 rpm, and 8% CO$_2$ concentration. Then, the culture was harvested and the fusion protein was purified therefrom. The purified fusion protein was designated "mGI102-M61".

The purification and collection of the fusion protein were carried out in the same manner as in Preparation Example 1.

II. Identification of Binding Affinity Between Fusion Protein and its Ligand

In order to identify the binding affinity between the fusion protein and its ligand, the binding affinity was measured using Octet RED 384.

Experimental Example 1. Identification of Binding Affinity Between hCTLA-4 and GI101

AR2G biosensor (Amine Reactive 2$^{nd}$ gen, ForteBio, Cat: 18-5092) was previously hydrated with 200 µl of distilled water in a 96-well microplate (GreinerBio-one, Cat: 655209). A ligand (CTLA-4, Human CTLA-4/CD152, His tag, Sino Biological, Cat: 11159-H08H) to be attached to the AR2G biosensor was diluted with 10 mM acetate buffer (pH 5, AR2G reagent Kit, ForteBio, Cat: 18-5095) to a concentration of 5 µg/ml. In addition, GI101 to be attached to the ligand was diluted with 1×AR2G kinetic buffer (AR2G reagent Kit, ForteBio, Cat: 18-5095) to a concentration of 1,000 nM, 500 nM, 250 nM, 125 nM, or 62.5 nM. Activation buffer was prepared by mixing 20 mM EDC and 10 mM s-NHS (AR2G reagent Kit, ForteBio, Cat: 18-5095) in distilled water. 80 µl of each reagent was placed in a 384-well microplate (GreinerBio-one, Cat: 781209) and the program was set up.

Figure 16:
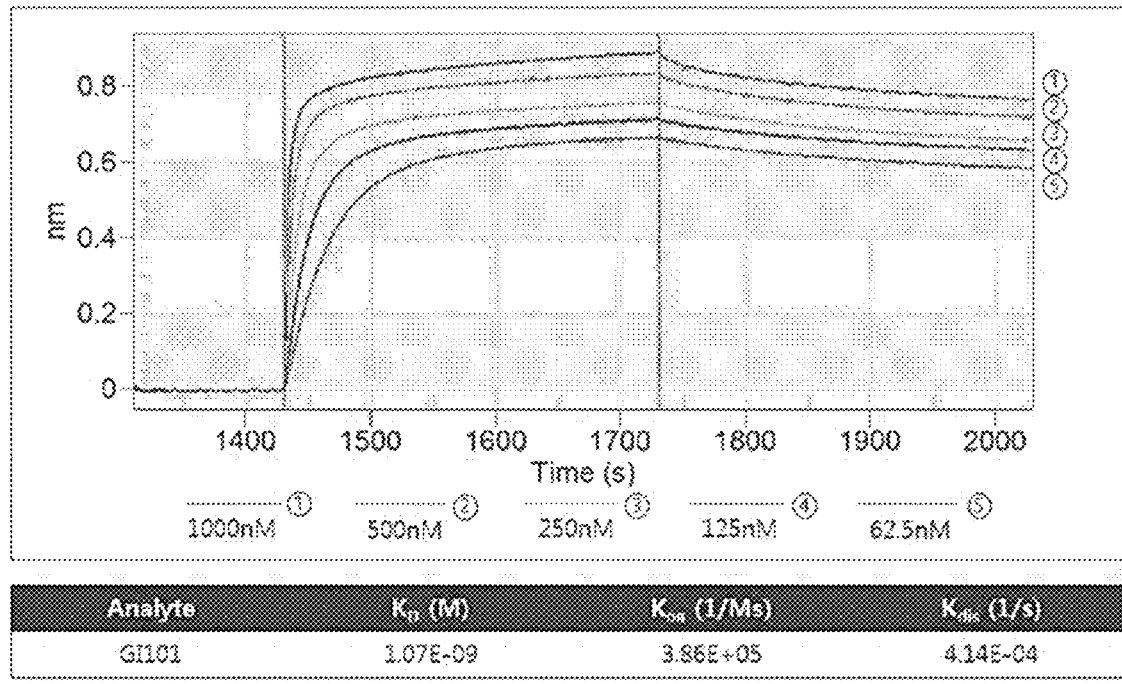
FIG. 16 illustrates binding affinity between hCTLA-4 and GI101.

As a result, the binding affinity between hCTLA-4 and GI101 was measured as illustrated in FIG. 16.

Experimental Example 2. Identification of Binding Affinity Between hPD-L1/GI101 and hPD-L1/PD-1

Ni-NTA (Nickel charged Tris-NTA, Ni-NTA Biosensors, ForteBio, 18-5101) was previously hydrated with 200 µl of 1×Ni-NTA kinetic buffer (10× Kinetics buffer, ForteBio, 18-1042) in a 96-well microplate. A ligand (Human PD-L1/B7-H1 protein, His-tag, Sino biological, Cat: 10084-H08H) to be attached to the Ni-NTA Biosensors was diluted with 1×Ni-NTA kinetic buffer to a concentration of 5 µg/ml. GI101 to be attached to the ligand was diluted with 1×Ni-NTA kinetic buffer to 1,000 nM, 500 nM, 250 nM, 125 nM, or 62.5 nM. In addition, human PD-1/PDCD1 (Human PD-1/PDCD1, Fc Tag, Sino Biological, Cat: 10377-H02H) to be attached to the ligand was diluted with 1×Ni-NTA kinetic buffer to a concentration of 2,000 nM, 1,000 nM, 500 nM, 250 nM, or 125 nM. Then, 80 µl of each reagent was placed in a 384-well microplate and the program was set up.

Figure 17:
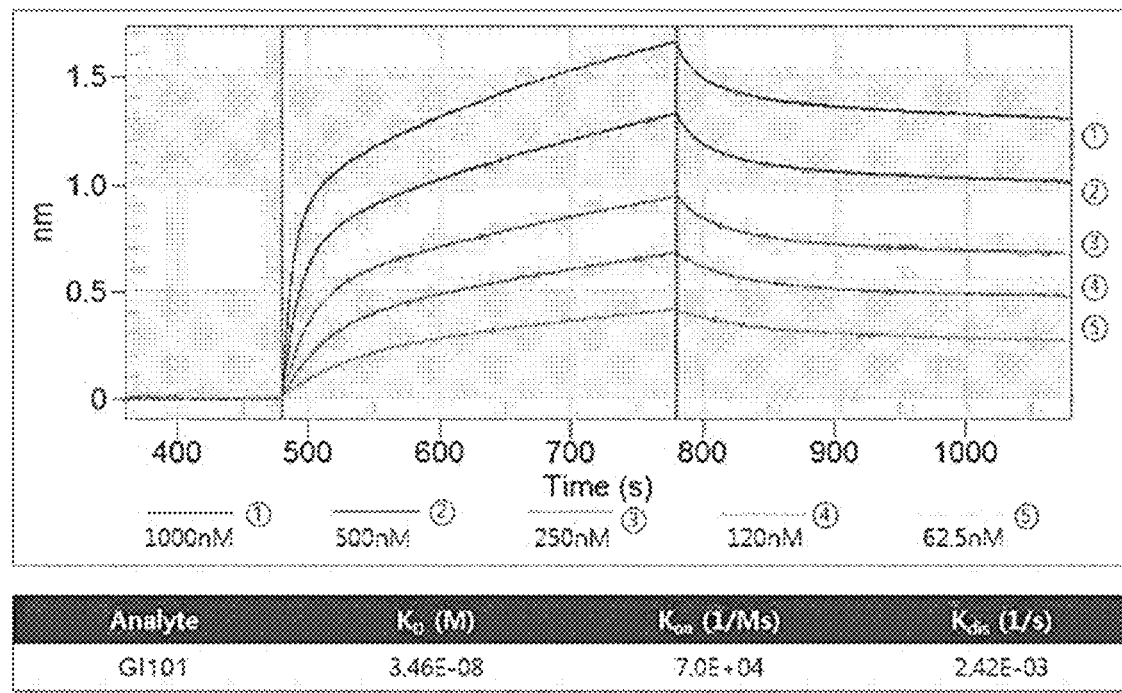
FIG. 17 illustrates binding affinity between hPD-L1 and GI101.
Figure 18:
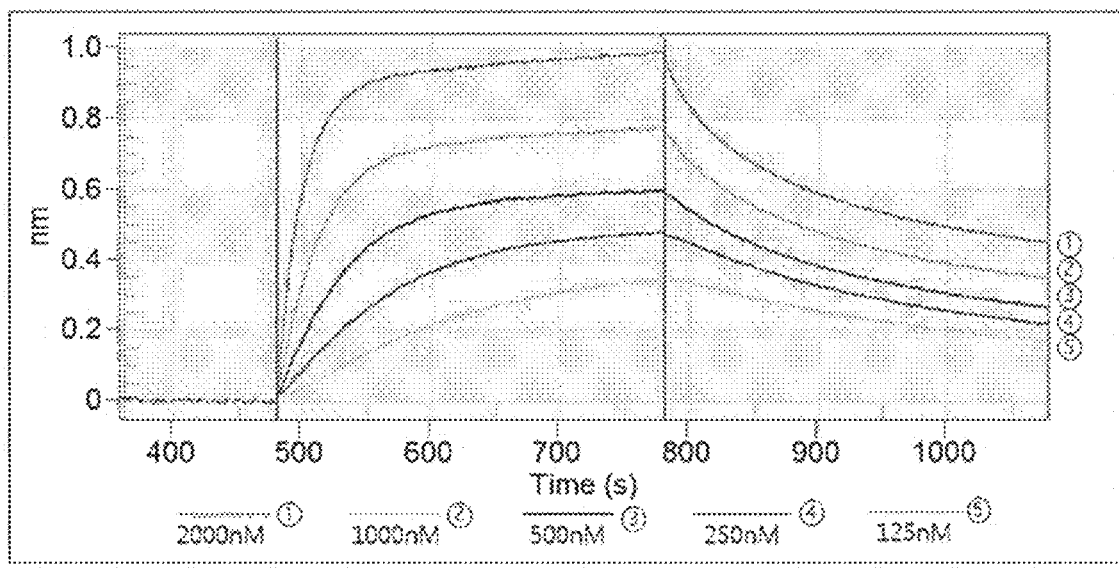
FIG. 18 illustrates binding affinity between hPD-L1 and hPD-1.

As a result, the binding affinity between hPD-L1 and GI101 was measured as illustrated in FIG. 17. In addition, the binding affinity between hPD-L1 and hPD-1 was measured as illustrated in FIG. 18.

Experimental Example 3. Identification of Binding Affinity Between mCTLA-4 and mGI101

The binding affinity between mCTLA-4 and mGI101 was identified in the same manner as in Experimental Example 1. Here, the equipment used is as follows: Biosensor: AR2G, Ligand: mCTLA-4 (Recombinant Mouse CTLA-4 Fc chimera, R&D Systems, Cat: 434-CT-200), Analyte: mGI101 (500 nM, 250 nM, 125 nM, 62.5 nM, 31.3 nM).

Figure 19:
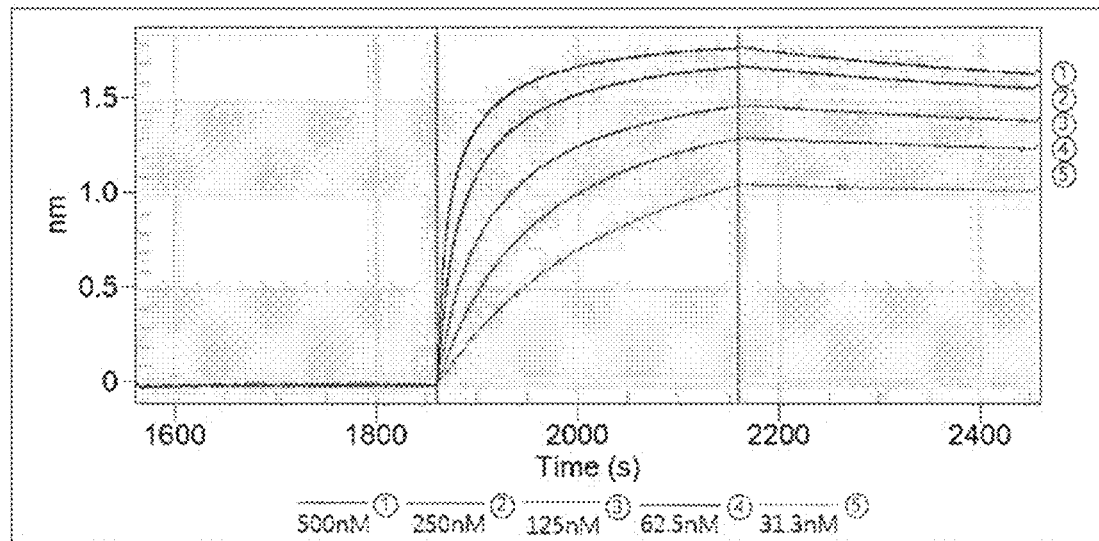
FIG. 19 illustrates binding affinity between mCTLA-4 and mGI101.

As a result, the binding affinity between mCTLA-4 and mGI101 was measured as illustrated in FIG. 19.

Experimental Example 4. Identification of Binding Affinity Between mPD-L1 and mGI101

The binding affinity between mPD-L1 and mGI101 was identified in the same manner as in Experimental Example 1. Here, the equipment used is as follows. Biosensor: AR2G, Ligand: mPD-L1 (Recombinant Mouse B7-H1/PD-L1 Fc chimera, R&D Systems, Cat: 434-CT-200), Analyte: mGI101 (500 nM, 250 nM, 125 nM, 62.5 nM, 31.3 nM).

Figure 20:
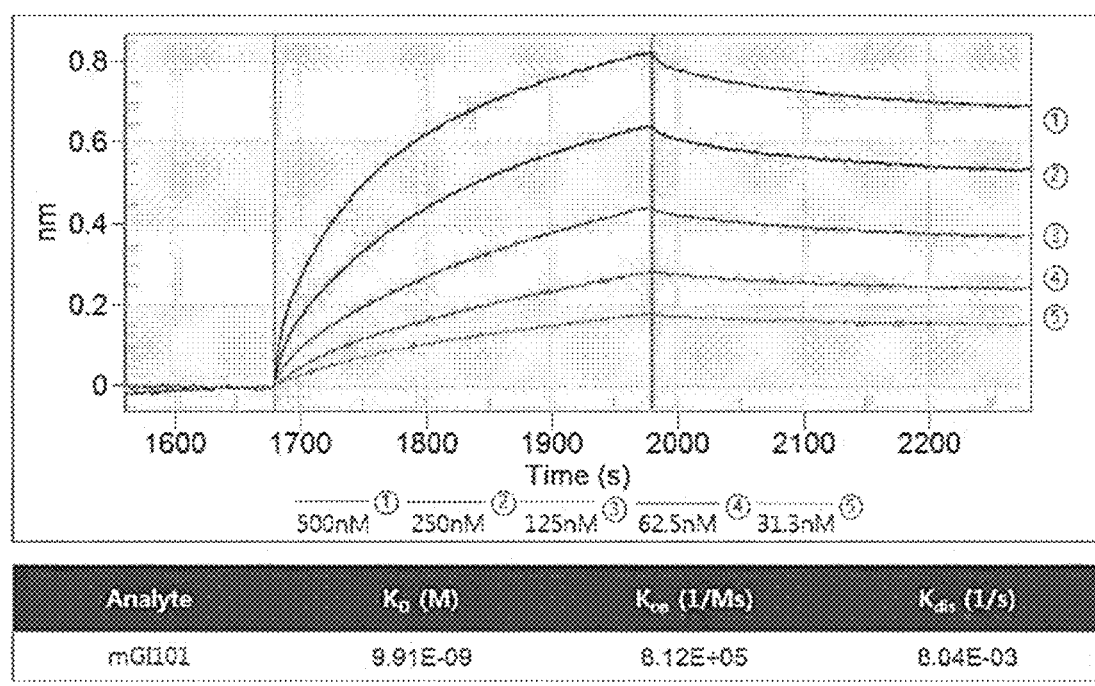
FIG. 20 illustrates binding affinity between mPD-L1 and mGI101.

As a result, the binding affinity between mPD-L1 and mGI101 was measured as illustrated in FIG. 20.

Experimental Example 5. Identification of Binding Ability of GI-101 (hCD80-Fc-hIL-2v) to CTLA-4

Binding kinetics measurements were performed using the Octet RED 384 instrument (ForteBio, Pall Life Science) with agitation at 30° C. and 1,000 rpm. The binding ability for CTLA-4 was measured using the Amine Reactive 2 generation (AR2G) biosensor chip, and the binding ability for PD-L1 was measured using the Nickel charged Tris-NTA (Ni-NTA) biosensor chip. The AR2G biosensor chip was activated with a combination of 400 mM EDC and 100 mM sulfo-NHS. Then, Human CTLA-4-His Tag (Sino Biological, Cat: 11159-H08H) was diluted with 10 mM acetate buffer (pH 5) to 5 µg/ml, and loaded on the AR2G biosensor chip for 300 seconds and fixed.

Figure 21:
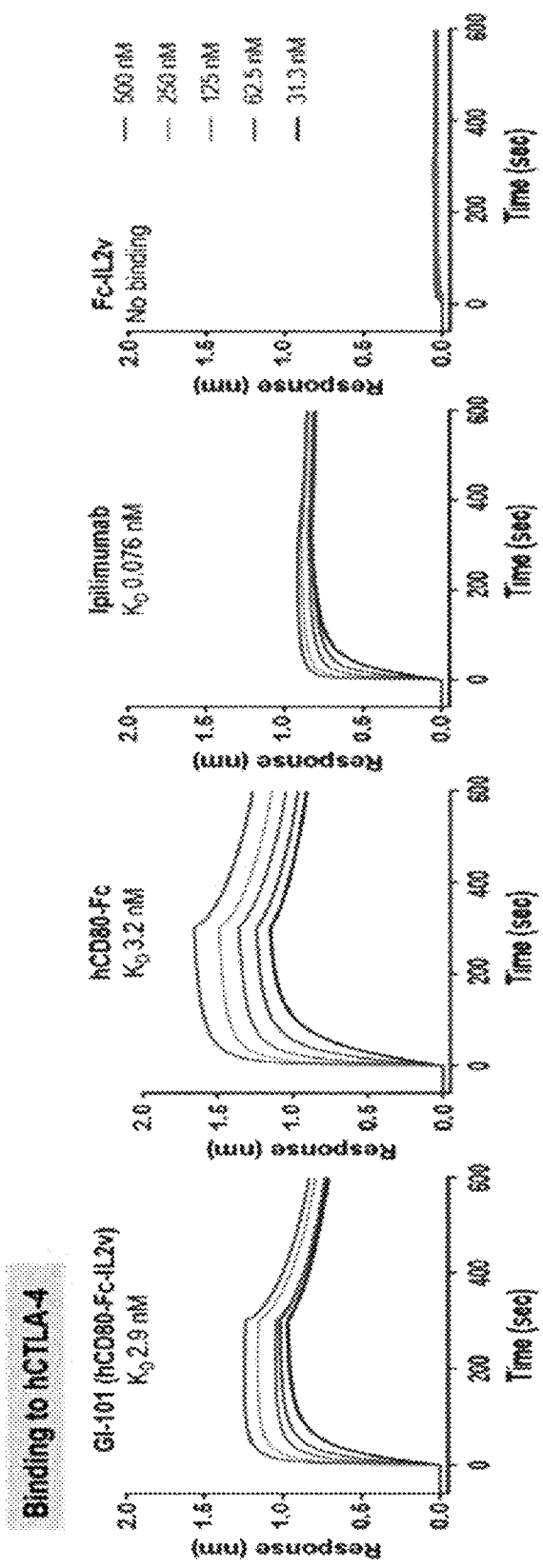
FIG. 21 illustrates a result obtained by identifying binding ability between GI101 (hCD80-Fc-hIL-2v) and CTLA-4. It was identified that GI101 (hCD80-Fc-hIL-2v) has high binding ability for CTLA-4.

Then, binding of CTLA-4 to GI-101 (hCD80-Fc-hIL-2v), GI-101C1 (hCD80-Fc), Ipilimumab (Bristol-Myers Squibb), and GI-101C2 (Fc-hIL-2v) at various concentrations was measured for 300 seconds and dissociation thereof was also measured for 300 seconds. Binding kinetics analysis was performed using Octet Data Analysis HT software ver. 10 provided by Pall Corporation. The results are illustrated in FIG. 21.

Experimental Example 6. Identification of Binding Affinity Between IL-2Rα or IL-2Rβ, and GI101

The binding ability for IL-2Rα was measured using the AR2G biosensor, and the binding ability for IL-2Rβ was measured using the Ni-NTA biosensors (Nickel charged Tris-NTA, Ni-NTA Biosensors, ForteBio, 18-5101).

A ligand (IL-2Rα-His Tag, Acro, Cat: ILA-H52H9) to be attached to the AR2G biosensor was diluted with 10 mM acetate buffer (pH 5, AR2G reagent Kit, ForteBio, Cat: 18-5095) to a concentration of 5 µg/ml. The AR2G biosensor was activated with a buffer prepared by mixing 400 mM EDC and 100 mM sulfo-NHS, and then the diluted ligand was loaded on the AR2G biosensor for 300 seconds and fixed.

Meanwhile, a ligand (IL-2Rβ-His Tag, Acro, Cat: CD2-H5221) to be attached to the Ni-NTA biosensor was diluted with 1×Ni-NTA kinetic buffer to a concentration of 5 µg/ml. The diluted ligand was loaded on the Ni-NTA biosensor for 600 seconds and fixed.

Figure 22:
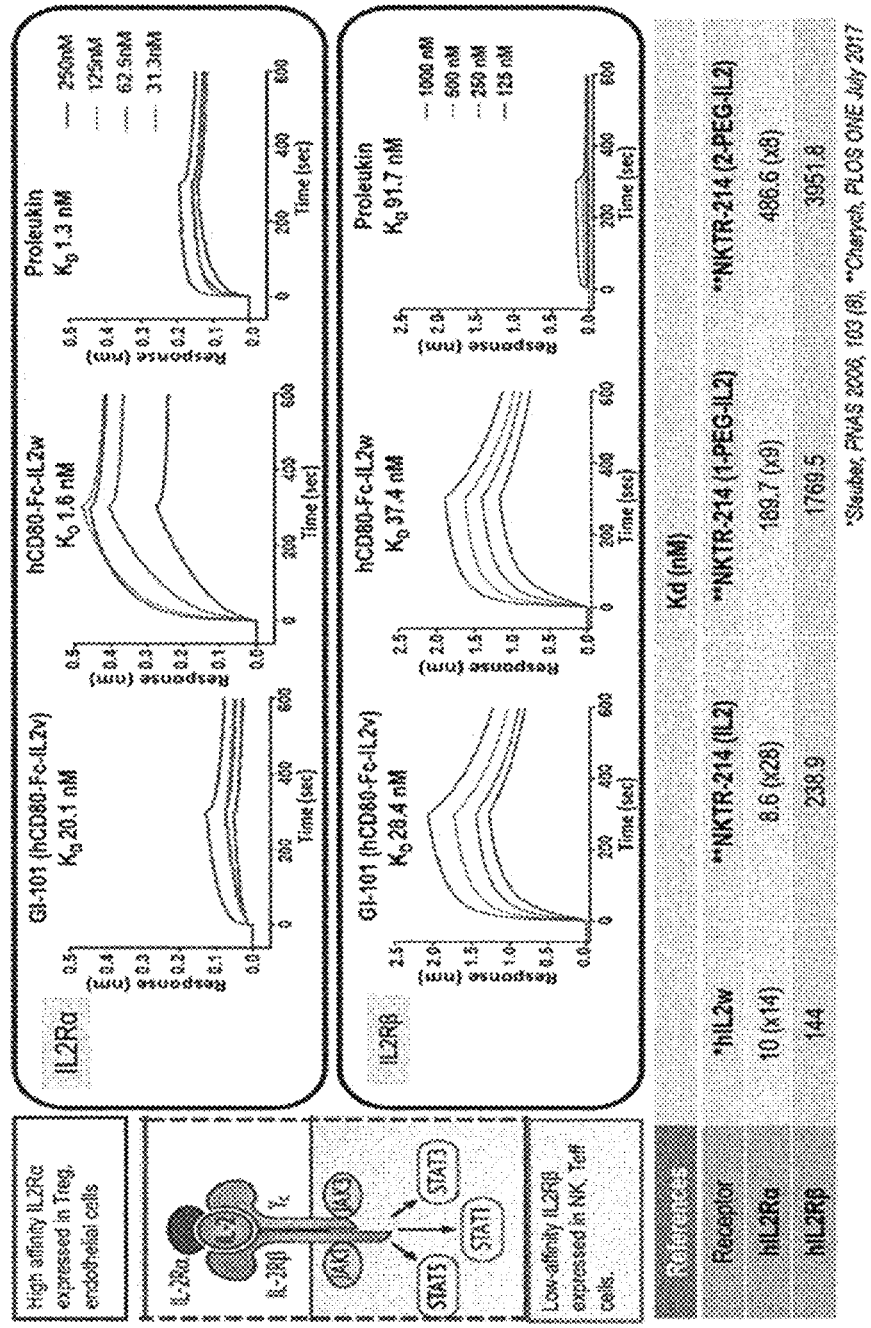
FIG. 22 illustrates a result obtained by identifying binding affinity between GI101, and IL-2Rα or IL-2Rβ.
Figure 23:
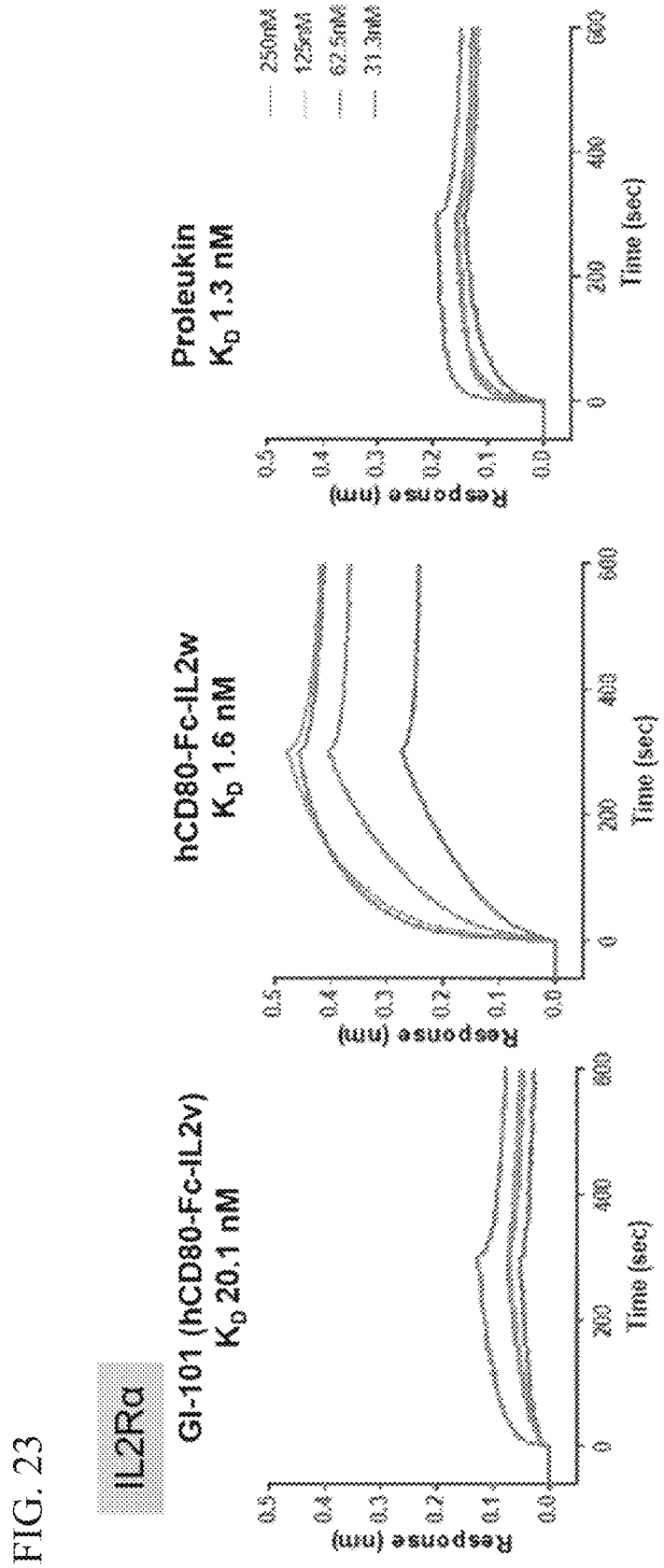
FIG. 23 illustrates a result obtained by identifying binding affinity between GI101 and IL-2Rα.
Figure 24:
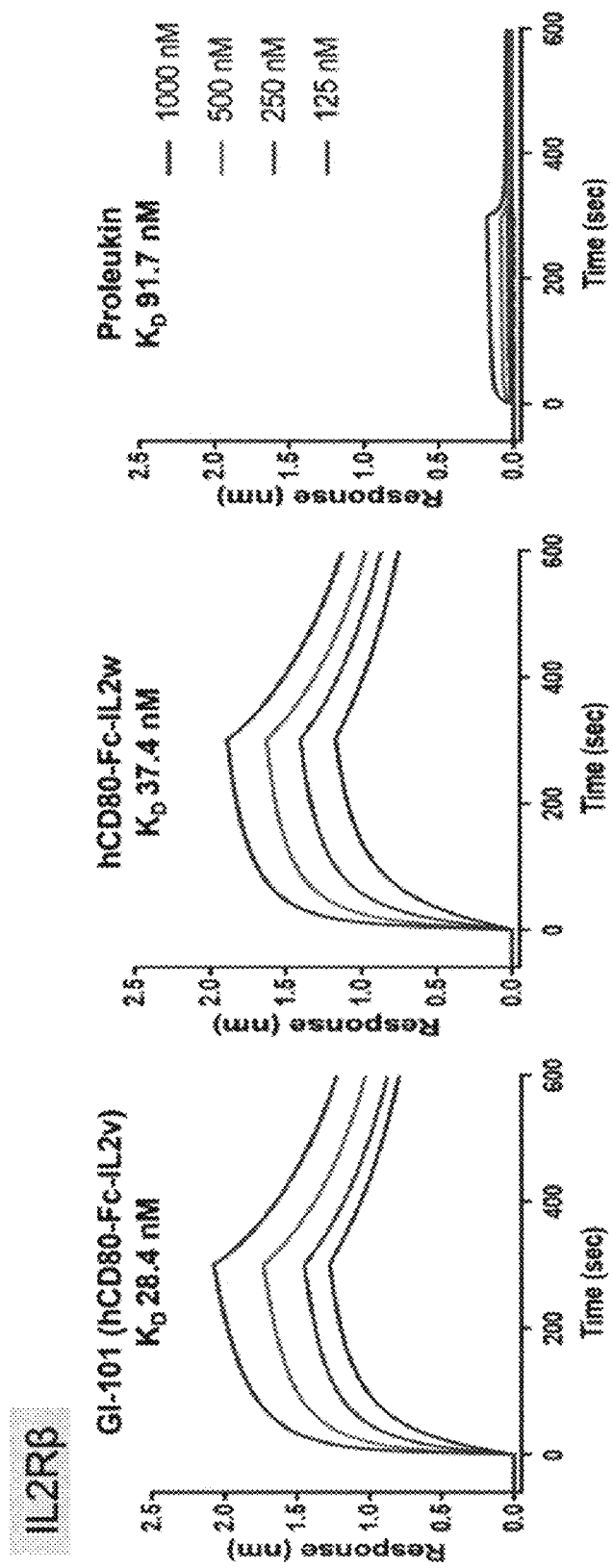
FIG. 24 illustrates a result obtained by identifying binding affinity between GI101 and IL-2Rβ.

Thereafter, GI101, GI101w, or Proleukin (Novartis, hIL-2), at various concentrations, to be attached to the ligand was loaded thereon for 300 seconds. Then, binding thereof was measured and dissociation thereof was also measured for 300 seconds. Binding kinetics analysis was performed using Octet Data Analysis HT software ver. 10 provided by Pall Corporation. The results are illustrated in FIGS. 22 to 24.

As a result, it was identified that GI101 has low binding ability for the IL-2 receptor IL-2Rα and high binding ability for IL-2Rβ, as compared with GI101w and Proleukin.

Experimental Example 7. Measurement of Binding Affinity Between Fusion Protein and Ligand In order to identify the binding affinity between the fusion protein and its ligand, the binding affinity was measured using Octet RED 384.

Experimental Example 7.1. Identification of Binding Affinity Between IL-2 Alpha Receptor, and GI101-M45, GI101-M61, or GI101-M72

AR2G biosensor (Amine Reactive 2$^{nd}$ gen, ForteBio, Cat: 18-5092) was previously hydrated with 200 µl of distilled water (DW) in a 96-well microplate (GreinerBio-one, Cat: 655209). A ligand (Human IL-2 R alpha protein, His Tag, Acro, ILA-H52H9) to be attached to the biosensor was diluted with 10 mM acetate buffer (pH 5) (AR2G reagent Kit, ForteBio, Cat: 18-5095) to a concentration of 5 µg/ml. An analyte (GI101-M45, GI101-M61, GI101-M72) to be attached to the ligand was diluted with 1×AR2G kinetic buffer (AR2G reagent Kit, ForteBio, Cat: 18-5095) to 500 nM, 250 nM, 125 nM, and 62.5 nM, respectively. Activation buffer was prepared by mixing 20 mM EDC and 10 mM s-NHS (AR2G reagent Kit, ForteBio, Cat: 18-5095) in DW. 80 µl of each reagent was placed in a 384-well microplate (GreinerBio-one, Cat: 781209) and the program was set up.

Figure 25:
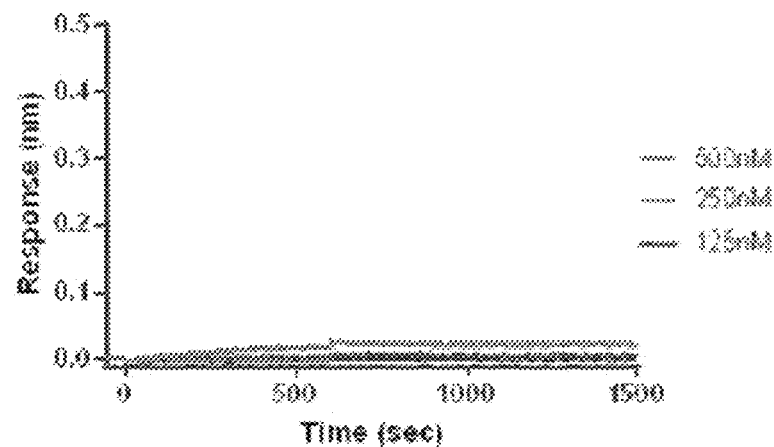
FIG. 25 illustrates binding affinity between IL-2Rα and GI102-M45.
Figure 26:
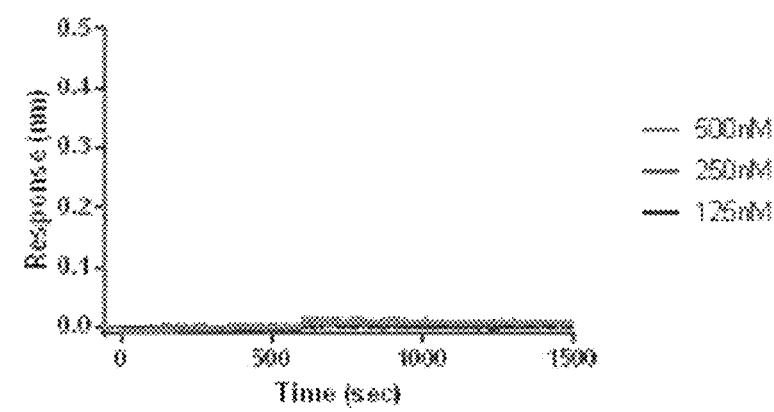
FIG. 26 illustrates binding affinity between IL-2Rα and GI102-M61.
Figure 27:
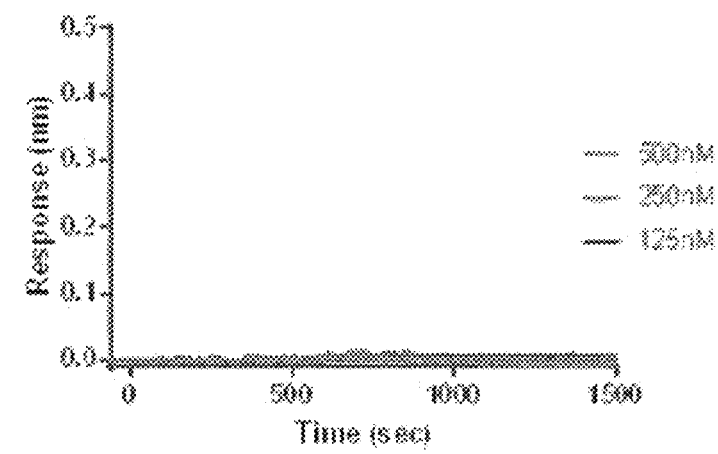
FIG. 27 illustrates binding affinity between IL-2Rα and GI102-M72.

As a result, the binding affinity between IL-2 alpha receptor and GI101-M45 is illustrated in FIG. 25. In addition, the binding affinity between IL-2 alpha receptor and GI101-M61 is illustrated in FIG. 26, and the binding affinity between IL-2 alpha receptor and GI101-M72 is illustrated in FIG. 27.

Experimental Example 7.2. Identification of Binding Affinity of GI102-M45, GI102-M61, and GI102-M72 to IL-2Rβ

Ni-NTA Biosensors were previously hydrated with 200 µl of 1×Ni-NTA kinetic buffer (10× Kinetics buffer, ForteBio, 18-1042) in a 96-well microplate. A ligand (Human IL-2 R beta protein, His-Tag, Acro, CD2-H5221) to be attached to the biosensor was diluted with 1×Ni-NTA kinetic buffer to a concentration of 2 µg/ml. GI102-M45, GI102-M61, or GI102-M72 to be attached to the ligand was diluted with 1×Ni-NTA kinetic buffer to a concentration of 500 nM, 250 nM, 125 nM, or 62.5 nM. 80 µl of each reagent was placed in a 384-well microplate and the program was set up.

Figure 28:
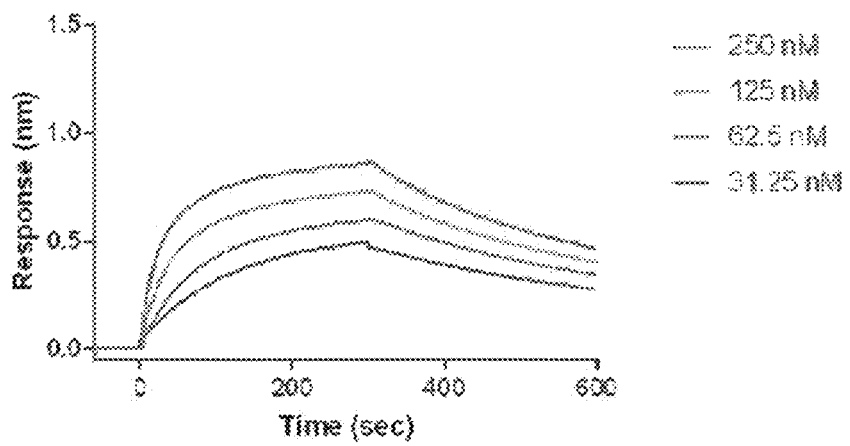
FIG. 28 illustrates binding affinity between IL-2Rβ and GI102-M45.
Figure 29:
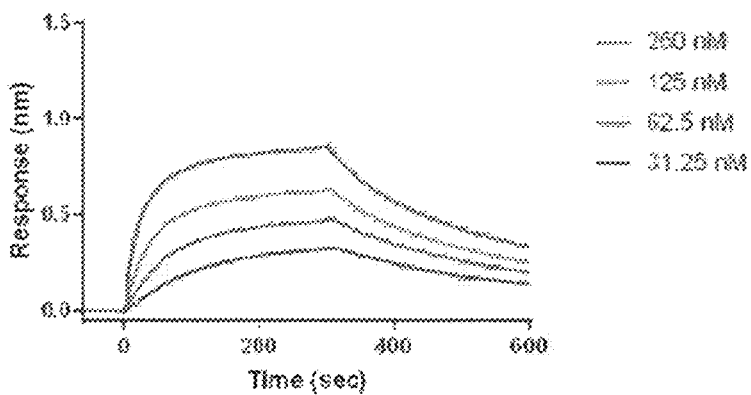
FIG. 29 illustrates binding affinity between IL-2Rβ and GI102-M61.
Figure 30:
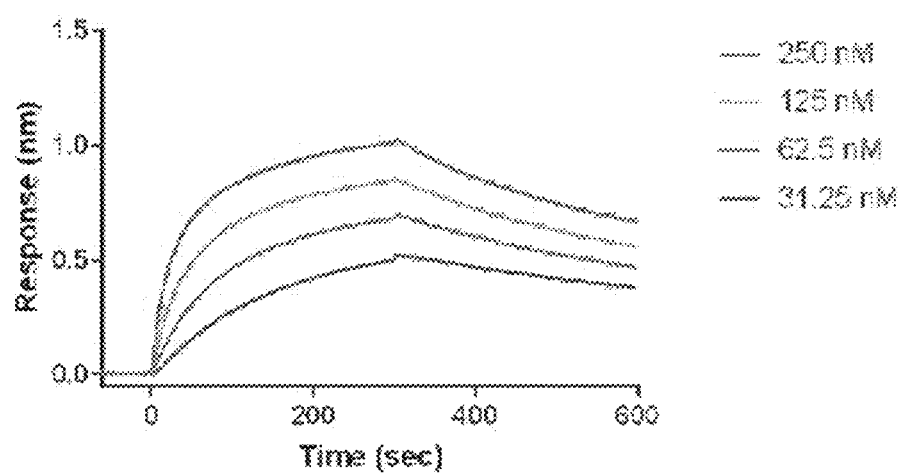
FIG. 30 illustrates binding affinity between IL-2Rβ and GI102-M72.

As a result, the binding affinity between IL-2Rβ and GI102-M45 was measured as illustrated in FIG. 28, and the binding affinity between IL-2Rβ and GI102-M61 was measured as illustrated in FIG. 29. In addition, the binding affinity between IL-2Rβ and GI102-M72 was measured as illustrated in FIG. 30.

III. Identification of Immune Activity of Fusion Protein

Experimental Example 8. Identification of IFN-γ Production Caused by Fusion Protein Experimental Example 8.1. Culture of CFSE-Labeled PBMCs Peripheral blood mononuclear cells (PBMCs) isolated from a human were labeled with carboxyfluorescein succinimidyl ester (CFSE) by being reacted with 1 µM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFSE-labeled PBMCs were resuspended in the culture medium (RPMI1640 medium containing 10% fetal bovine serum (FBS), 10 mM HEPES, 100 U/ml penicillin/streptomycin, 1 mM sodium pyruvate, 55 µM 2-mercaptoethanol, 1 mM non-essential amino acid, and 2 mM L-glutamine), and then added to a 96-well microplate at $1\times10^5$ cells per well. Treatment with 5 µg/ml of PHA (Lectin from *Phaseolus Vulgaris*, red kidney bean, Sigma-Aldrich, St. Louis, MO, USA, cat No. L1668-5MG), and GI101, GI101C1, GI101C2, or IL-2 (Aldesleukin; human recombinant IL-2, Novartis) was performed and incubation was performed in a 5% $CO_2$ incubator at 37° C. for 6 days.

Here, the treatment with GI101, GI101C1, GI101C2, and IL-2 was performed at a concentration of 1 nM, 10 nM, or 100 nM. The cells were analyzed by FACS, and human IFN-γ present in the culture medium was measured using an ELISA kit (Biolegend, San Diego, CA, USA, cat No. 430103).

Experimental Example 8.2. FACS Analysis

The cell pellets obtained by removing the supernatant were washed with FACS buffer (3% fetal bovine serum, 10 mM EDTA, 1 M HEPES, 100 unit/ml penicillin, streptomycin, 1 mM sodium pyruvate), and then reacted with Fc blocker (Biolegend, cat NO. 422302) at 4° C. for 5 minutes. Then, treatment with APC anti-CD3 Ab (Biolegend, cat NO. 300412) and PE anti-CD8a Ab (Biolegend, cat NO. 300908) was performed and reaction was allowed to proceed at 4° C. for 20 minutes. Then, the resultant was washed with FACS buffer. The cell pellets were resuspended in FACS buffer and then analyzed using BD LSR Fortessa (BD biosciences, San Diego, CA, USA) and FlowJo Software.

Experimental Example 8.3. Human IFN-γ ELISA

The amount of human IFN-γ secreted into the supernatant of each sample in which the cells had been cultured was measured using a human IFN-γ ELISA kit (Biolegend, cat No. 430103). Briefly, anti-human-IFN-γ antibodies were added to an ELISA plate, and reaction was allowed to proceed overnight at 4° C. so that these antibodies were coated thereon. Then, blocking was performed at room temperature for 1 hour with a PBS solution to which 1% BSA had been added. Washing with a washing buffer (0.05% Tween-20 in PBS) was performed, and then a standard solution and each sample were properly diluted and added thereto. Then, reaction was allowed to proceed at room temperature for 2 hours.

After the reaction was completed, the plate was washed and secondary antibodies (detection antibodies) were added thereto. Reaction was allowed to proceed at room temperature for 1 hour. Washing with a washing buffer was performed, and then an Avidin-HRP solution was added thereto. Reaction was allowed to proceed at room temperature for 30 minutes. A substrate solution was added thereto and color development reaction was induced in the dark at room temperature for 20 minutes. Finally, H2504 was added thereto to stop the color development reaction, and the absorbance at 450 nm was measured with Epoch Microplate Spectrophotometer (BioTek instruments, Winooski, VT, USA), and the concentration was calculated.

Figure 31:
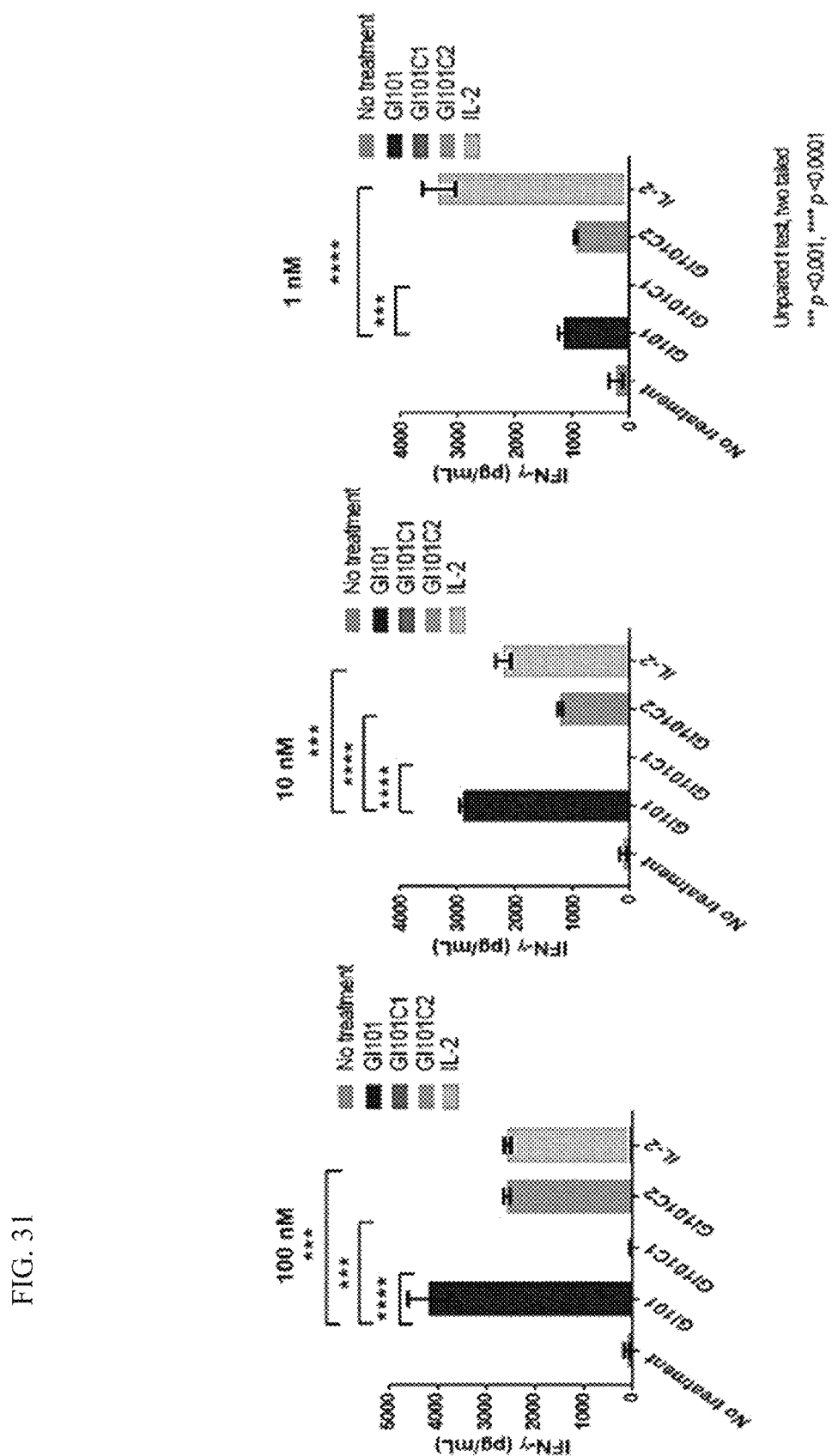
FIGS. 31 and 32 illustrate results obtained by measuring amounts of IFN-7 secreted from cells when the cells are treated and incubated with GI101, GI101C1, GI101C2, or IL-2 at respective concentrations.
Figure 32:
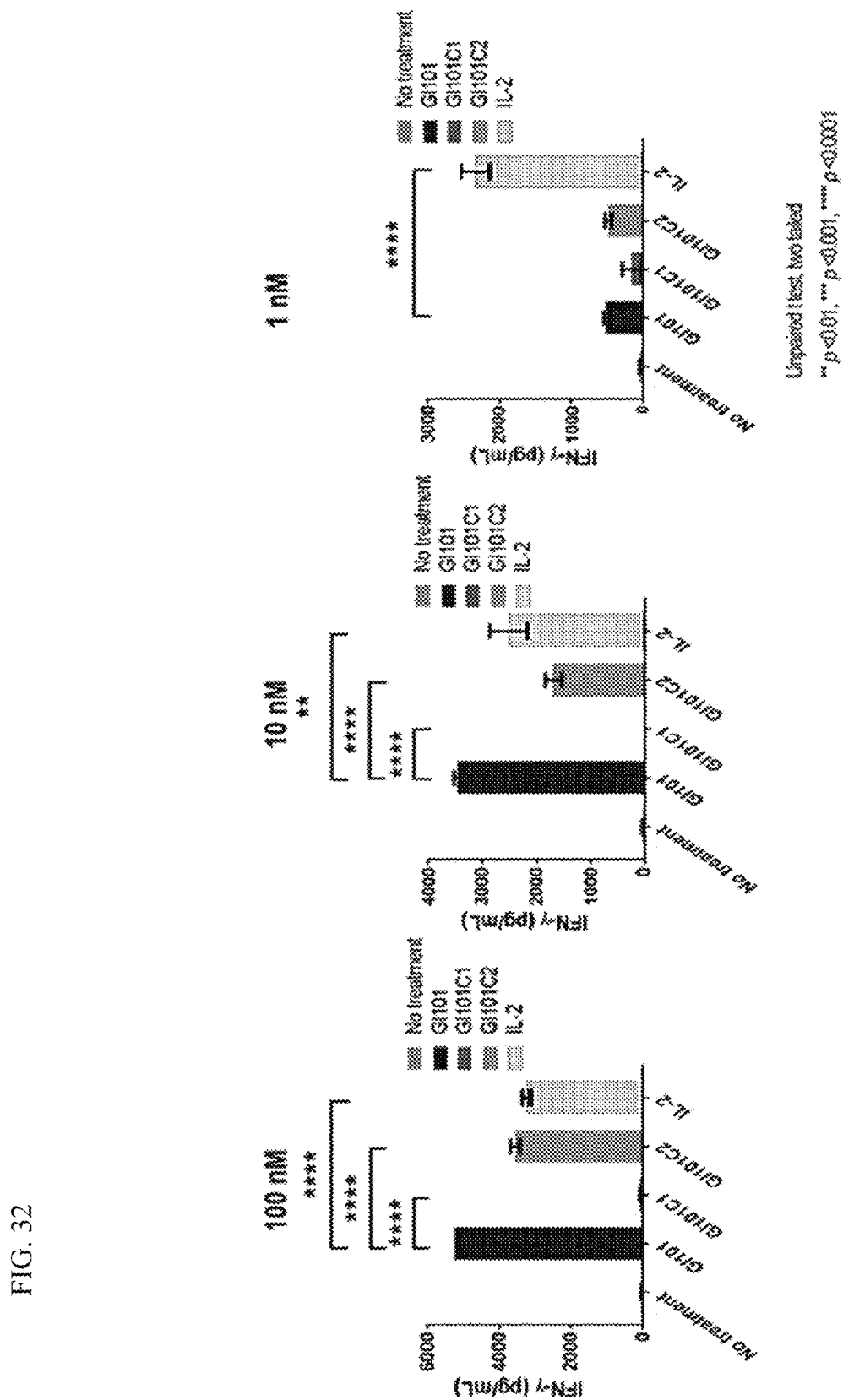

As a result, it was found that cells treated with GI101 exhibited a remarkable increase in IFN-γ secretion, as compared with cells treated with GI101C1, GI101C2, or IL-2 (FIGS. 31 and 32).

Experimental Example 9. Identification of Effect of GI101 on Proliferation of CD8+ T Cells Peripheral blood mononuclear cells (PBMCs) isolated from a human were labeled with CFSE by being reacted with 1 µM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFSE-labeled PBMCs were resuspended in the culture medium (RPMI1640 medium containing 10% fetal bovine serum, 10 mM HEPES, 100 U/ml penicillin/streptomycin, 1 mM sodium pyruvate, 55 µM 2-mercaptoethanol, 1 mM non-essential amino acid, and 2 mM L-glutamine), and then added to a 96-well microplate at $1\times10^5$ cells per well.

Thereafter, treatment with 1 µg/ml of anti-CD3ε antibody (Biolegend cat No. L1668-5MG), and GI101, GI101C1, GI101C2, or Proleukin (Novartis) was performed and incubation was performed in a 5% $CO_2$ incubator at 37° C. for 6 days. Here, the cells were treated with GI101, GI101C1, GI101C2, and IL-2 at a concentration of 100 nM. The incubated cells were examined for their degree of proliferation by measuring, with FACS analysis using APC-TCRαβ and PE-CD8α antibodies, a proportion of CD8+ T cells that had not been labeled with CFSE.

Figure 33:
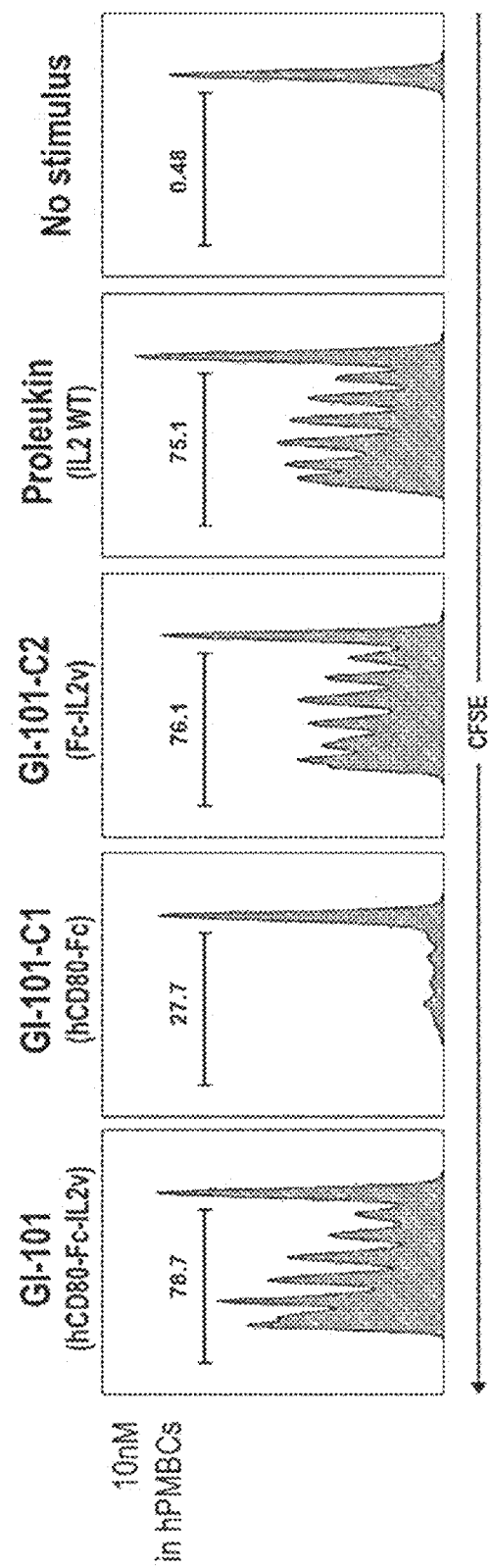
FIG. 33 illustrates results obtained by identifying effects of GI101, GI101C1, GI101C2, and IL-2 (Proleukin) on proliferation of CD8+ T cells.
Figure 34:
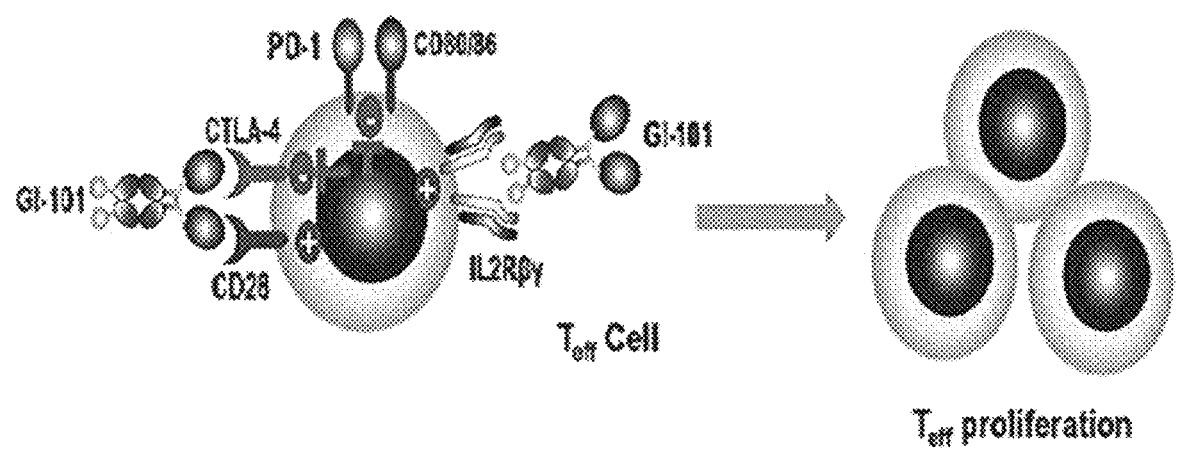
FIG. 34 illustrates a schematic diagram of a mechanism by which GI101 acts on effector T cells.

As a result, it was found that GI101 activated proliferation of CD8+ T cells in vitro to a to similar extent to the wild-type IL-2 Proleukin (FIGS. 33 and 34).

Experimental Example 10. Identification of Effect of GI101 and GI102 on Proliferation of CD8+ T Cells Human PBMCs were purchased from Allcells (Lot #3014928, USA). 1M CellTrace CFSE dye was used, which was reacted with the human PBMCs under a light-blocking condition at room temperature for 20 minutes. The cells were labeled with CFSE by being reacted with 1 µM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFSE-labeled PBMCs were resuspended in the culture medium (RPMI1640 medium containing 10% fetal bovine serum, 10 mM HEPES, 100 U/ml penicillin/streptomycin, 1 mM sodium pyruvate, 55 µM 2-mercaptoethanol, 1 mM non-essential amino acid, and 2 mM L-glutamine), and then added to a 96-well microplate at $1\times10^5$ cells per well.

Thereafter, the CFSE-labeled PBMCs were subjected to treatment with 1 µg/ml of anti-CD3ε antibody (OKT3, eBioscience, USA), and GI101, GI101C1, GI101C2, or Proleukin (Novartis), and incubation was performed in a 5% $CO_2$ incubator at 37° C. for 7 days. Here, the cells were subjected to treatment with GI101, GI101C1, GI101C2, and IL-2 at a concentration of 10 µM.

The incubated cells were examined for their degree of proliferation by measuring, with FACS analysis using anti-human CD4-PE antibody (BioLegend, USA), anti-human CD8-PE/Cy7 antibody (BioLegend, USA), and anti-human FoxP3-APC antibody (BioLegend, USA), a proportion of CD8+ T cells that had not been labeled with CFSE.

Figure 35:
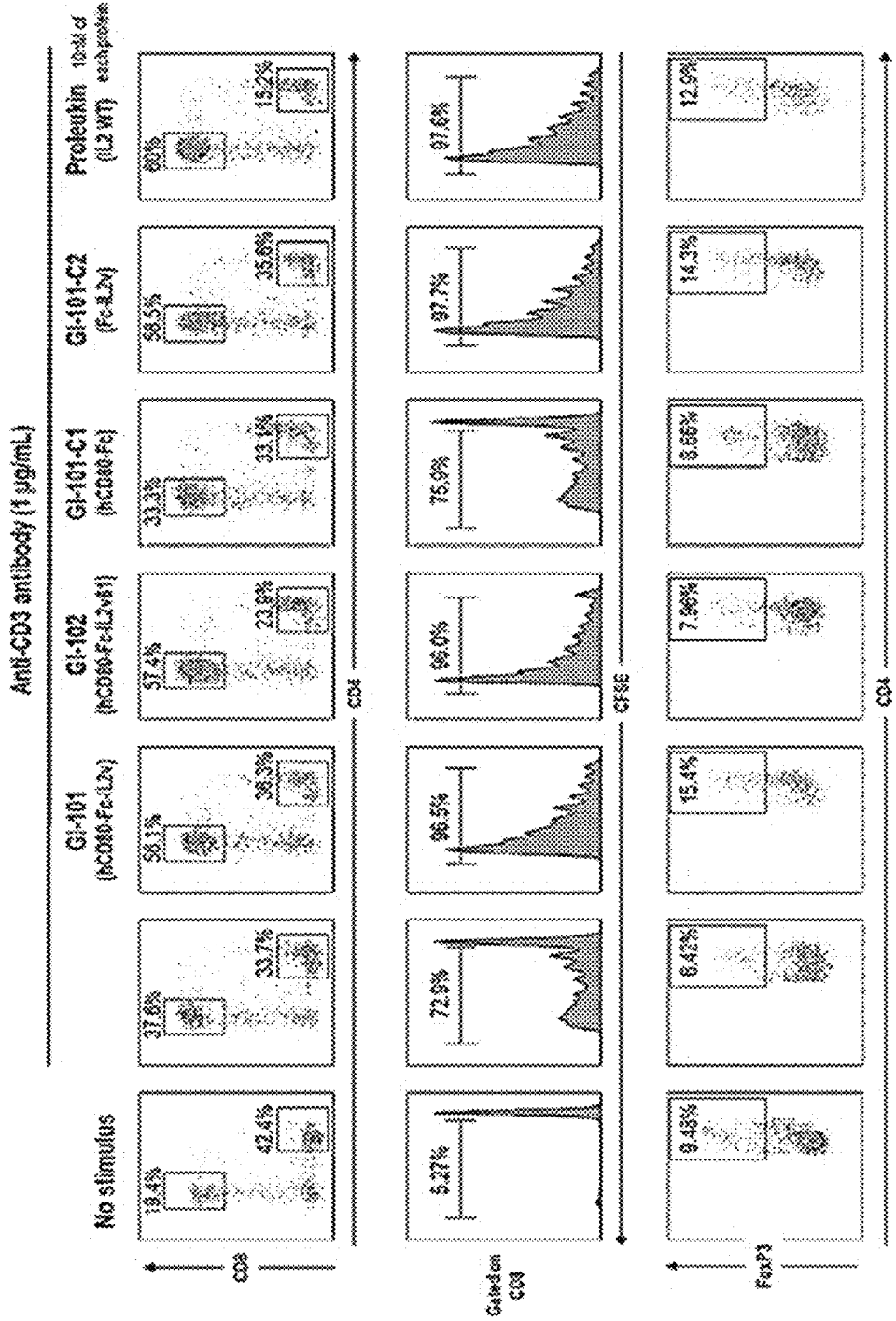
FIG. 35 illustrates results obtained by identifying effects of GI101 and GI102 on proliferation of CD8+ T cells and CD4+ T cells. Here.

As a result, the GI101, GI102 M61, GI101C2, and Proleukin treatment groups exhibited a significant increase in proportion of CD8+ T cells, as compared with the control (no stimulus), the anti-CD3 antibody alone treatment group, and the GI101C1 treatment group. In addition, as compared with the negative control (no stimulus) and the anti-CD3 antibody alone treatment group, the GI101, GI101C2, and Proleukin treatment groups exhibited a significant increase in proliferation of CD4+/FoxP3+ Treg cells, whereas the GI102 and GI101C1 treatment groups did not exhibit a significant increase in proliferation of CD4+/FoxP3+ Treg cells (FIG. 35).

Experimental Example 11. Identification of Effect of GI101 or GI101w on Proliferation of CD8+ T Cells and NK Cells 7-week-old C57BL/6 mice purchased from Orient Bio (Korea) were divided into 3 groups, each group including 3 mice, and PBS, GI101, or GI101w was injected intraperitoneally thereinto. Here, GI101 and GI101w were respectively prepared to be at 40.5 µg in 200 µl of PBS, and injected intraperitoneally thereinto. Five days after the injection, the spleens were removed from the mice of each group. The cells were isolated therefrom, and the total number of cells was measured using a hematocytometer. Splenocytes were examined for proportions of CD8+ T cells and NK cells therein, with FACS analysis using staining with APC-CD3ε antibody (Biolegend; 145-2C11), PE-NK1.1 antibody (Biolegend; PK136), and Pacific blue-CD8α antibody (BD; 53-6.7). As such, the numbers of CD8+ T cells and NK cells present in the spleen were calculated.

Figure 36:
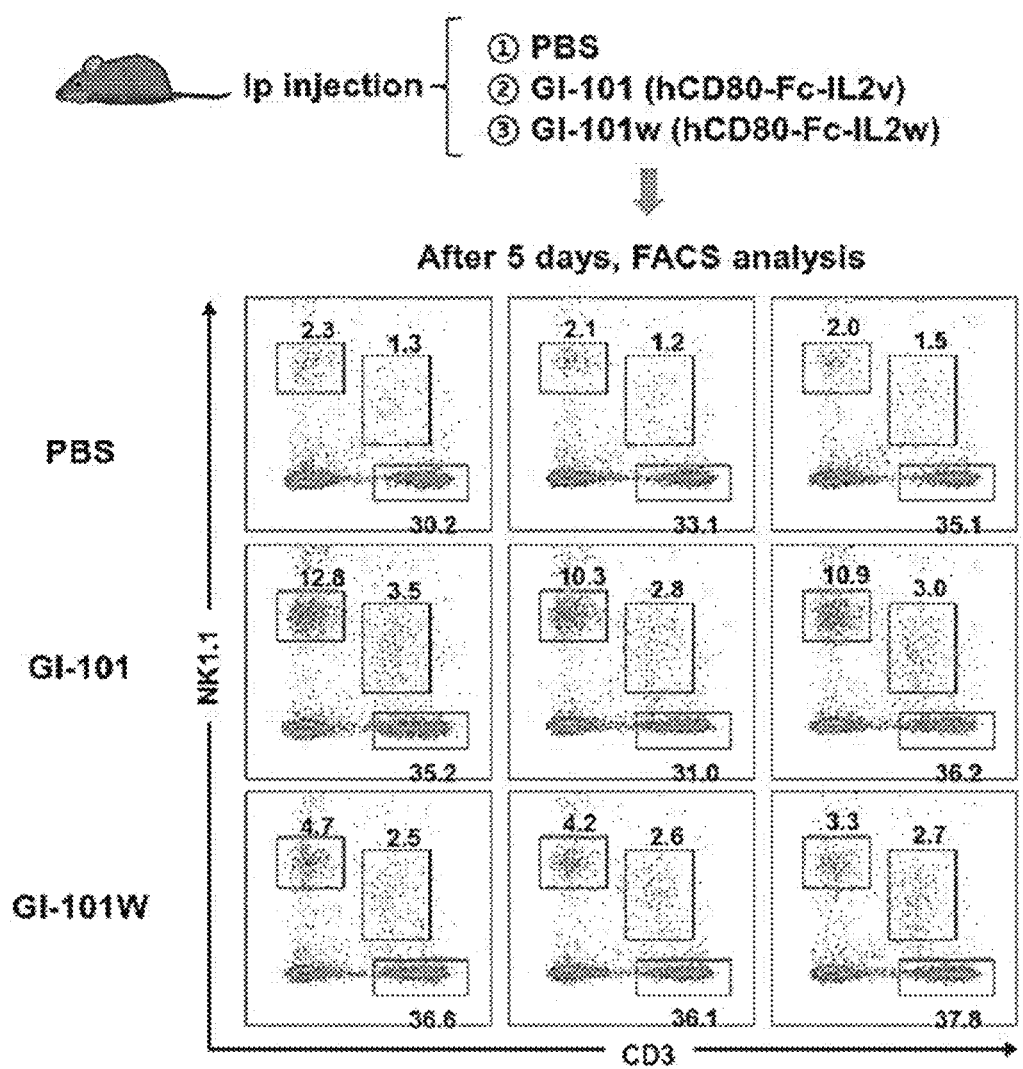
FIGS. 36 and 37 illustrate results obtained by identifying effects of GI101 and GI101w on proliferation of CD8+ T cells and NK cells.
Figure 37:
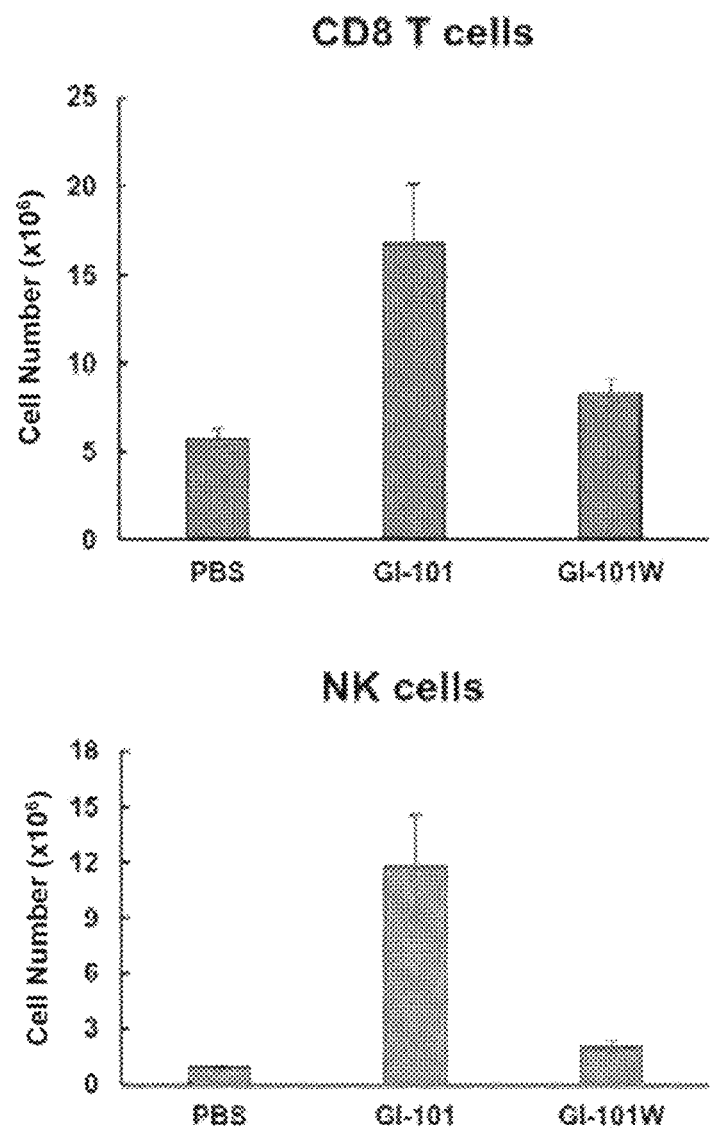

As a result, it was identified that GI101 activated proliferation of CD8+ T cells and NK cells in vivo as compared with GI101w (FIGS. 36 and 37).

Experimental Example 12. Identification of Effect of GI101 on Function of T Cells An experiment was performed using a CTLA-4 blockade bioassay kit (Promega cat No. JA4005). The experiment is briefly described as follows. CTLA-4 effector cells kept in liquid nitrogen were thawed in a 37° C. constant temperature water bath for 3 minutes, and 0.8 ml of CTLA-4 effector cells were mixed well with 3.2 ml of pre-warmed assay buffer (90% RPMI+10% fetal bovine serum). Then, the mixture was added to a 96-well white cell culture plate (SPL, cat No. 30196) at 25 µl per well. Then, 25 µl of GI101 at various concentrations was added thereto. For a negative control, 25 µl of assay buffer was added thereto. Then, the 96-well white cell culture plate was covered and placed at room temperature until aAPC/Raji cells were prepared.

aAPC/Raji cells kept in liquid nitrogen were thawed in a 37° C. constant temperature water bath for 3 minutes, and 0.8 ml of aAPC/Raji cells were mixed well with 3.2 ml of pre-warmed assay buffer. Then, 25 µl of the mixture was added to the plate at per well, and reaction was allowed to proceed in a 5% $CO_2$ incubator at 37° C. for 16 hours. After the reaction was completed, the resultant was allowed to stand at room temperature for 15 minutes, and then the Bio-Glo reagent was added thereto while taking care to avoid bubbles. The Bio-Glo reagent was also added to three of the outermost wells and the wells were used as blanks to correct the background signal. Reaction was allowed to proceed at room temperature for 10 minutes, and then luminescence was measured with Cytation 3 (BioTek instruments, Winooski, VT, USA). Final data analysis was performed by calculating RLU (GI101-background)/RLU (no treatment-background).

Figure 38:
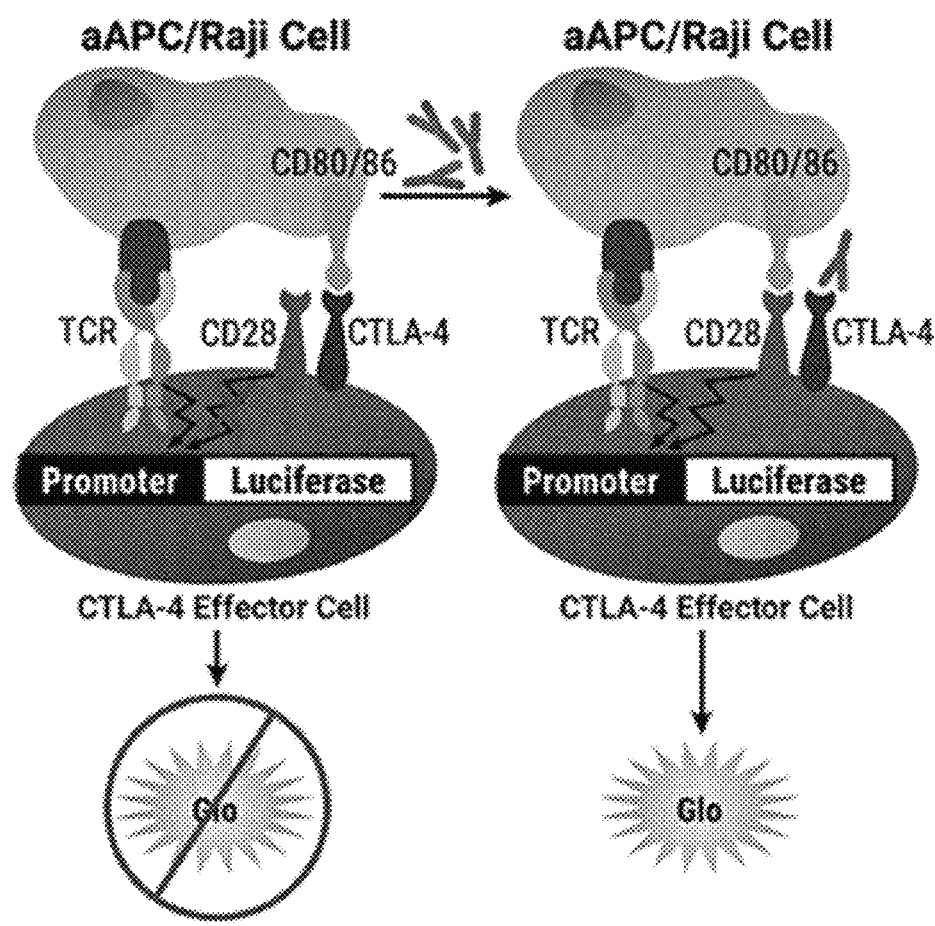
FIGS. 38 and 39 illustrate results obtained by identifying an effect of GI101 on effector T cells.
Figure 39:
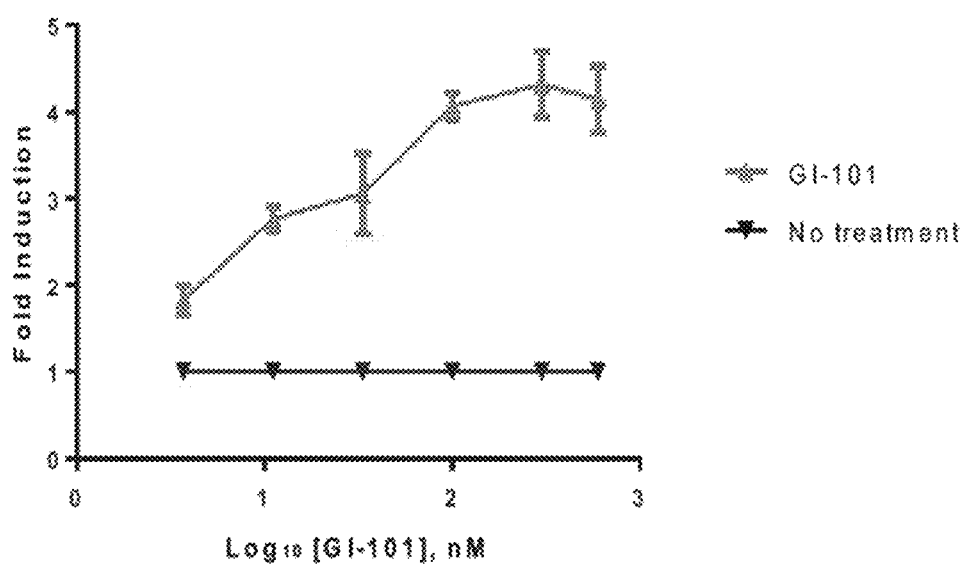

As a result, it was found that GI101 binds to CTLA-4 expressed on effector T cells, and activats the function of T cells rather than inhibiting the same (FIGS. 38 and 39).

Experimental Example 13. Identification of Effect of mGI101 and mGI102 on Immune Cells 7-week-old C57BL/6 mice purchased from Orient Bio (Korea) were divided into 3 groups, each group including 3 mice, and PBS, 3 mg/kg, 6 mg/kg, or 12 mg/kg of GI101, or 3 mg/kg, 6 mg/kg, or 12 mg/kg of mGI102 (mGI102-M61) was administered intravenously thereinto. On days 1, 3, 5, 7, and 14 after the injection, the spleen tissues were removed from the mice of each group. Thereafter, for the spleen tissue, the numbers of effector CD8+ T cells, NK cells, and Treg cells were calculated with FACS analysis using respective antibodies, and proportions of effector CD8+ T cells and NK cells with respect to Treg cells were respectively calculated. The information on the antibodies used in each cell analysis is as follows:

Effector CD8+ T cell: PB anti-mouse CD3ε antibody (Biolegend, #155612; KT3.1.1), FITC anti-mouse CD8α antibody (BD, #553031, 53-6.7), PE/Cy7 anti-mouse CD44 antibody (Biolegend, #103030; IM7), APC anti-mouse CD122 antibody (Biolegend, #123214; TM-β1)

NK cell: PB anti-mouse CD3ε antibody (Biolegend, #155612; KT3.1.1), PE anti-mouse NK-1.1 (Biolegend, #108708; PK136)

Treg cell: FITC anti-mouse CD3 antibody (Biolegend, #100204; 17A2), PB anti-mouse CD4 antibody (Biolegend, #100531; RM4-5), PE anti-mouse CD25 antibody (Biolegend, #102008; PC61), APC anti-mouse Foxp3 antibody (Invitrogen, #FJK-16s, 17-5773-82).

Figure 40:
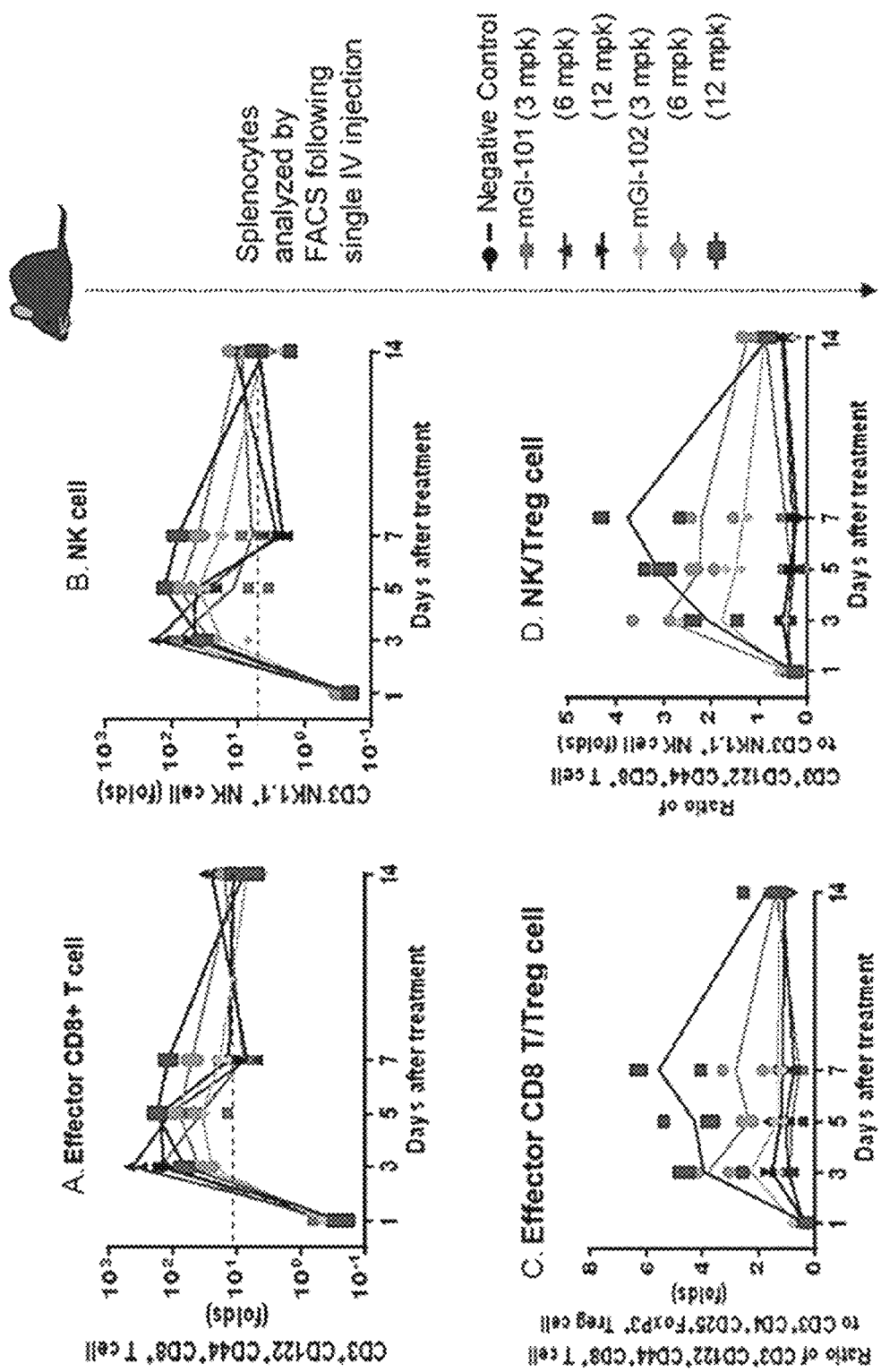
FIG. 40 illustrates a result obtained by identifying effects of mGI101 and mGI102-M61 on mouse immune cells.

As a result, the group having received mGI101 or mGI102 (mGI102-M61) exhibited a significant increase in numbers of CD8+ T cells and NK cells at the time points from the $3^{rd}$ to $14^{th}$ days after administration, as compared with the PBS administration group. In addition, it was found that the group having received mGI102 exhibited a significant increase in proportions of activated CD8+ T cells/Treg cells and NK cells/Treg cells at the time points from the $3^{rd}$ to $7^{th}$ days after administration, as compared with the PBS administration group (FIG. 40).

IV. Identification of Anticancer Effect of Fusion Protein

Experimental Example 14. Identification of Effect of GI101 on T Cell Activity Inhibition by Cancer Cells Expressing PD-L1 and CTLA-4

NCl-H292 cancer cell line expressing PD-L1 and CTLA-4 was cultured for 3 hours in a culture medium containing 10 µg/ml Mitomycin C (Sigma), and then Mitomycin C was removed by washing with the culture medium. Thereafter, $5\times10^4$ cells of the Mitomycin C-treated NCl-H292 cancer cell line were incubated with $1\times10^5$ cells of human PBMCs in a 96-well microplate. Here, treatment with 5 µg/ml of PHA (Sigma) was performed for T cell activity. In addition, GI101C1 and GI101 at a concentration of 50 nM were reacted with IgG1-Fc (Biolegend) or abatacept (=Orencia; Bristol-Myers Squibb) at a concentration of 50 nM for 30 minutes at 4° C., and then the resultant was used to treat the NCl-H292 cancer cells. After 3 days, the supernatant of the cell culture was collected and the amount of IFN-γ was quantified using an ELISA kit (Biolegend).

As a positive control, human PBMCs stimulated with PHA in the absence of the Mitomycin C-treated NCl-H292 cancer cell line were used; and as a negative control, human PBMCs stimulated with PHA in the presence of the Mitomycin C-treated NCl-H292 cancer cell line were used. An experimental method using the IFN-7 ELISA kit was carried out in the same manner as in Experimental Example 9.3.

Figure 41:
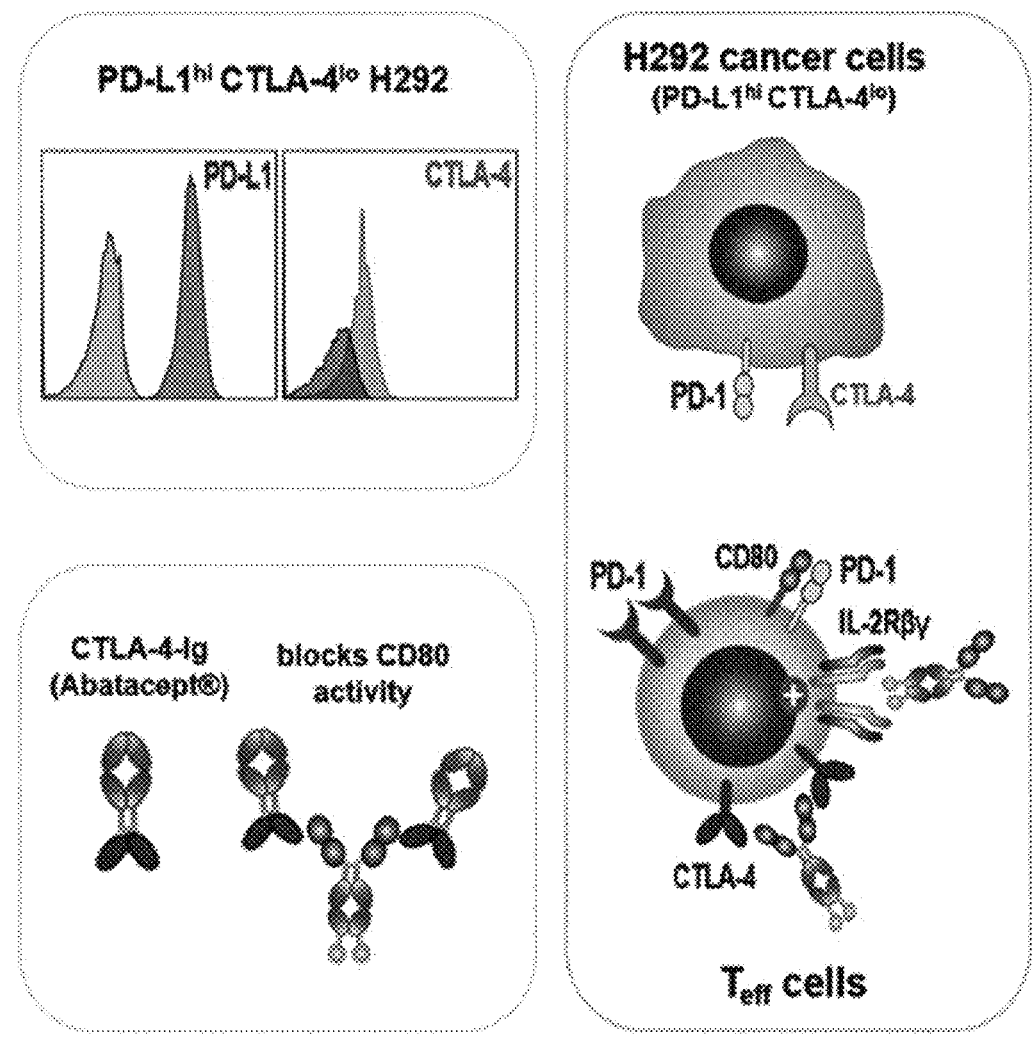
FIGS. 41 and 42 illustrate results obtained by identifying a T cell activity inhibitory effect of GI101 on cancer cells expressing PD-L1 and CTLA-4.
Figure 42:
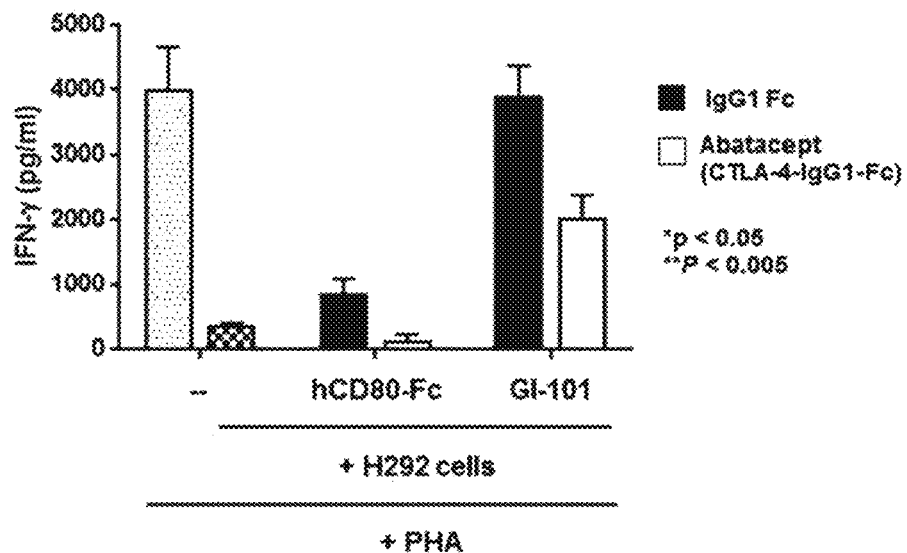

As a result, GI101 effectively activated the immune response that had been inhibited by the cancer cell line overexpressing PD-L1. In addition, it was identified that GI101 inhibited signaling of CTLA-4 expressed on effector T cells (FIGS. 41 and 42).

Experimental Example 15. Identification of Anticancer Effect of mGI101 in Mice Transplanted with Mouse-Derived Colorectal Cancer Cells BALB/c mice (female, 7-week-old) purchased from Orient Bio were subjected to an acclimation period of 7 days. Then, 5×10$^6$ cells of CT-26 cancer cell line (ATCC, USA) were mixed with 0.05 ml of MATRIGEL™ matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 mm$^3$ were selected, and then the selected mice were grouped evenly based on tumor size and body weight, each group including 10 mice. Thereafter, using a disposable syringe (31G, 1 ml), hIgG4 was administered at a dose of 6 mg/kg to a negative control. For experimental groups, mGI101 at a dose of 3 mg/kg, 6 mg/kg, or 12 mg/kg was administered intravenously thereto. A total of three administrations were given once every three days after the first administration. The tumor size was measured daily.

Figure 43:
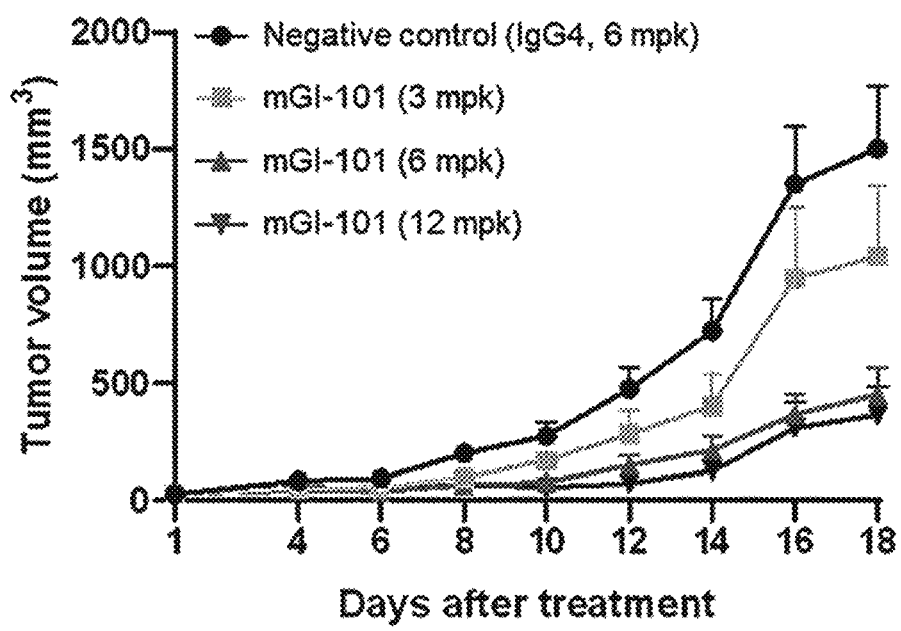
FIG. 43 illustrates a result obtained by identifying a tumor inhibitory effect of mGI101, depending on its dose, in mice transplanted with mouse-derived colorectal cancer cells (CT26).
Figure 44:
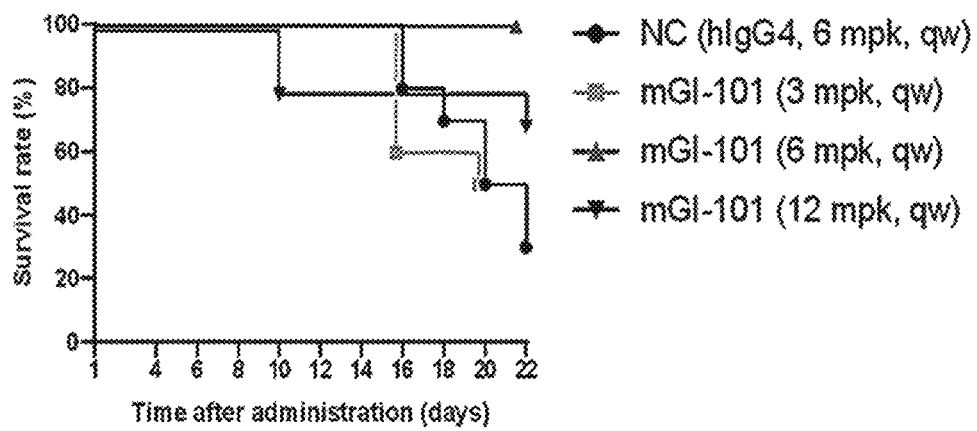
FIG. 44 illustrates results obtained by analyzing survival rate of mice, depending on the administration of mGI101, in mice transplanted with mouse-derived colorectal cancer cells (CT26).

As a result, it was found that the experimental group having received mGI101 at a dose of 6 mg/kg and 12 mg/kg exhibited significant tumor growth inhibition at some measurement time points and at the end of the test, as compared with the negative control (FIG. 43). In addition, as a result of measuring a survival rate, it was found that the experimental group having received mGI101 at a dose of 6 mg/kg exhibited significant improvement at some measurement time points and at the end of the test, as compared with the negative control (FIG. 44).

Experimental Example 16. Identification of Anticancer Effect of GI101 in Mice Transplanted with Mouse-Derived Colorectal Cancer Cells Experimental Example 16.1. Identification of Tumor Inhibitory Effect BALB/c mice (female, 7-week-old) purchased from Orient Bio were subjected to an acclimation period of 7 days. Then, 5×10$^6$ cells of CT-26 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group including 10 mice. Thereafter, using a disposable syringe (31G, 1 mL), no drug was administered to a negative control, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive controls. For experimental groups, GI101 at a dose of 0.1 mg/kg or 1 mg/kg was administered intravenously thereto. A total of three administrations were given once every three days after the first administration. The tumor size was measured daily.

Figure 45:
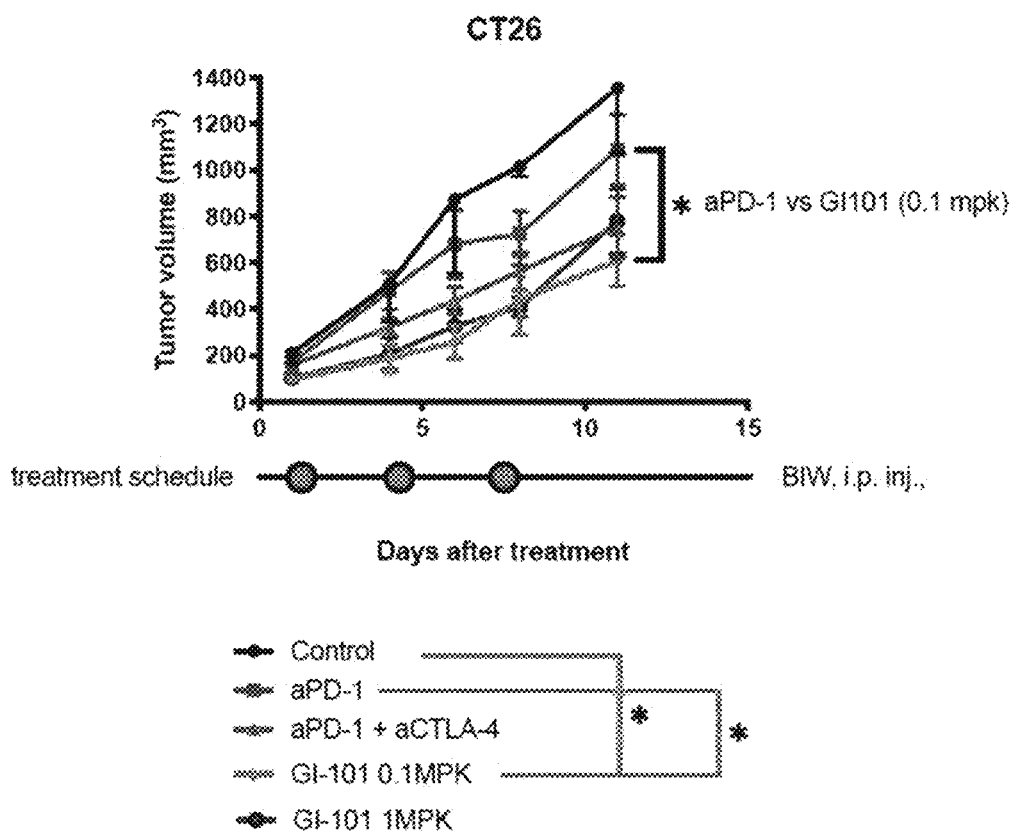
FIG. 45 illustrates a result obtained by identifying a tumor inhibitory effect of GI101 in mice transplanted with mouse-derived colorectal cancer cells (CT26).

As a result, in the mice transplanted with CT-26 cancer cell line, all groups having received anti-PD-1 antibody; anti-PD-1 antibody and anti-CTLA-4 antibody; or GI101 at a dose of 0.1 mg/kg or 1 mg/kg exhibited significant tumor growth inhibition, as compared with the negative control. In particular, the experimental group having received GI101 at a dose of 0.1 mg/kg exhibited a significant tumor inhibitory effect, as compared with the group having received an anti-PD-1 antibody (* p<0.05) (FIG. 45).

Experimental Example 16.2. Immune Cell Analysis in Cancer Tissue

The mice of each group in Experimental Example 16.1 were sacrificed when the tumor volume reached an average of 200 mm$^3$, and cancer tissues were collected. Thereafter, the cancer tissues were separated to a single-cell level to analyze immune cells therein, and then FACS analysis was performed on immune cells in the cancer tissues using the following antibodies: Anti-mouse-CD3 (Biolegend, Cat. No. 100320), Anti-mouse-CD4 (Biolegend, Cat. No. 100526), Anti-mouse-CD8 (Biolegend, Cat. No. 100750), Anti-mouse-FoxP3 (eBioscience, Cat. No. 12-5773-82), Anti-mouse-CD25 (Biolegend, Cat. No. 102049), Anti-mouse-CD44 (eBioscience, Cat. No. 61-0441-82), Anti-mouse-PD-1 (Biolegend, Cat. No. 135218), Anti-mouse-IFN-gamma (Biolegend, Cat. No. 505832), Anti-mouse-CD49b (Biolegend, Cat. No. 108906), Anti-mouse-H2 (Invitrogen, Cat. No. A15443), Anti-mouse-CD11c (Biolegend, Cat. No. 117343), Anti-mouse-CD80 (eBioscience, Cat. No. 47-4801-82), Anti-mouse-CD86 (Biolegend, Cat. No. 104729), Anti-mouse-F4/80 (eBioscience, Cat. No. 47-4801-82), and Anti-mouse-CD206 (eBioscience, Cat. No. 17-2061-80).

Figure 46:
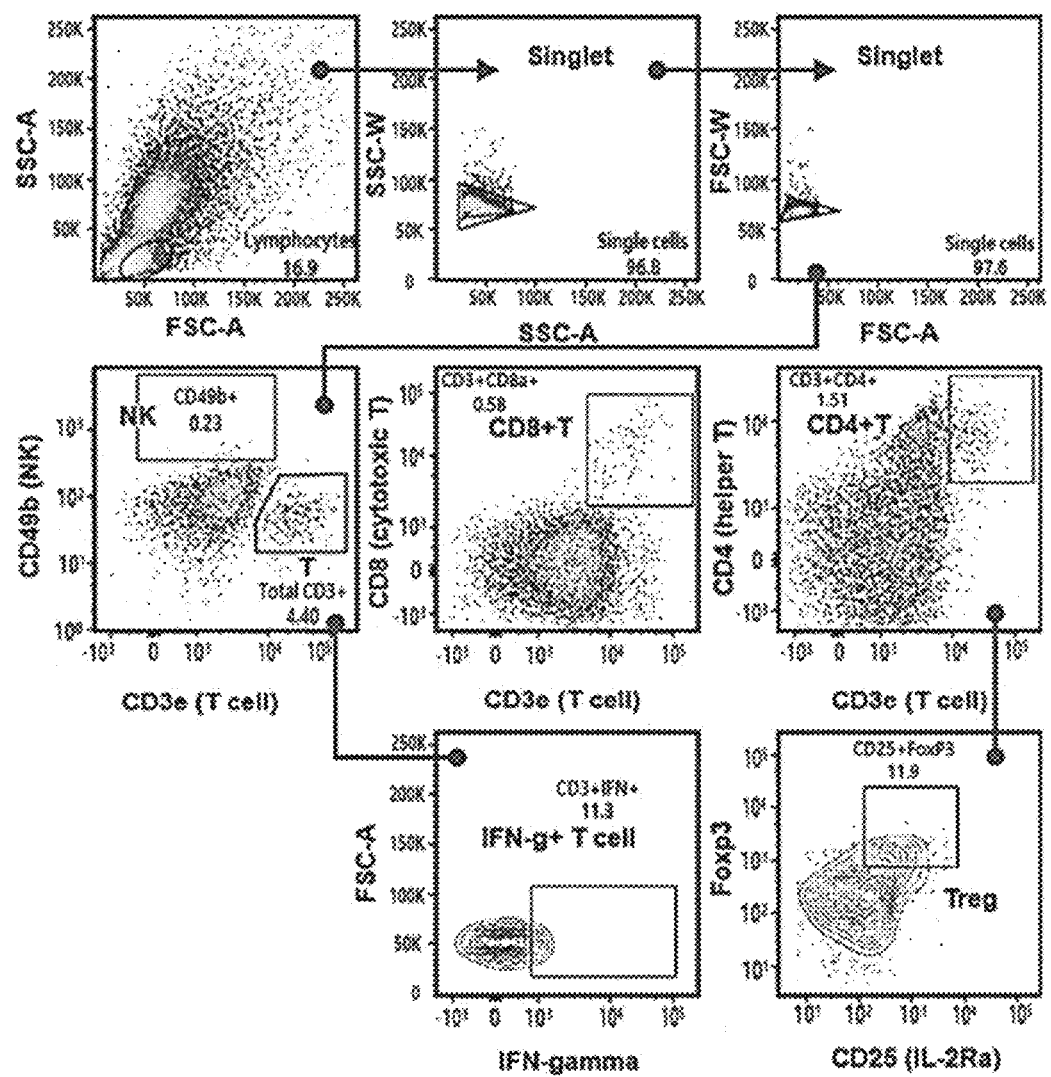
FIG. 46 illustrates results obtained by subjecting mice transplanted with mouse-derived colorectal cancer cells (CT26) to treatment with hIgG4, an anti-PD-1 antibody, or GI101, and then analyzing, with FACS, CD8+ T cells, IFN-7 T cells, CD4+ T cells, and Treg cells in cancer tissues.
Figure 47:
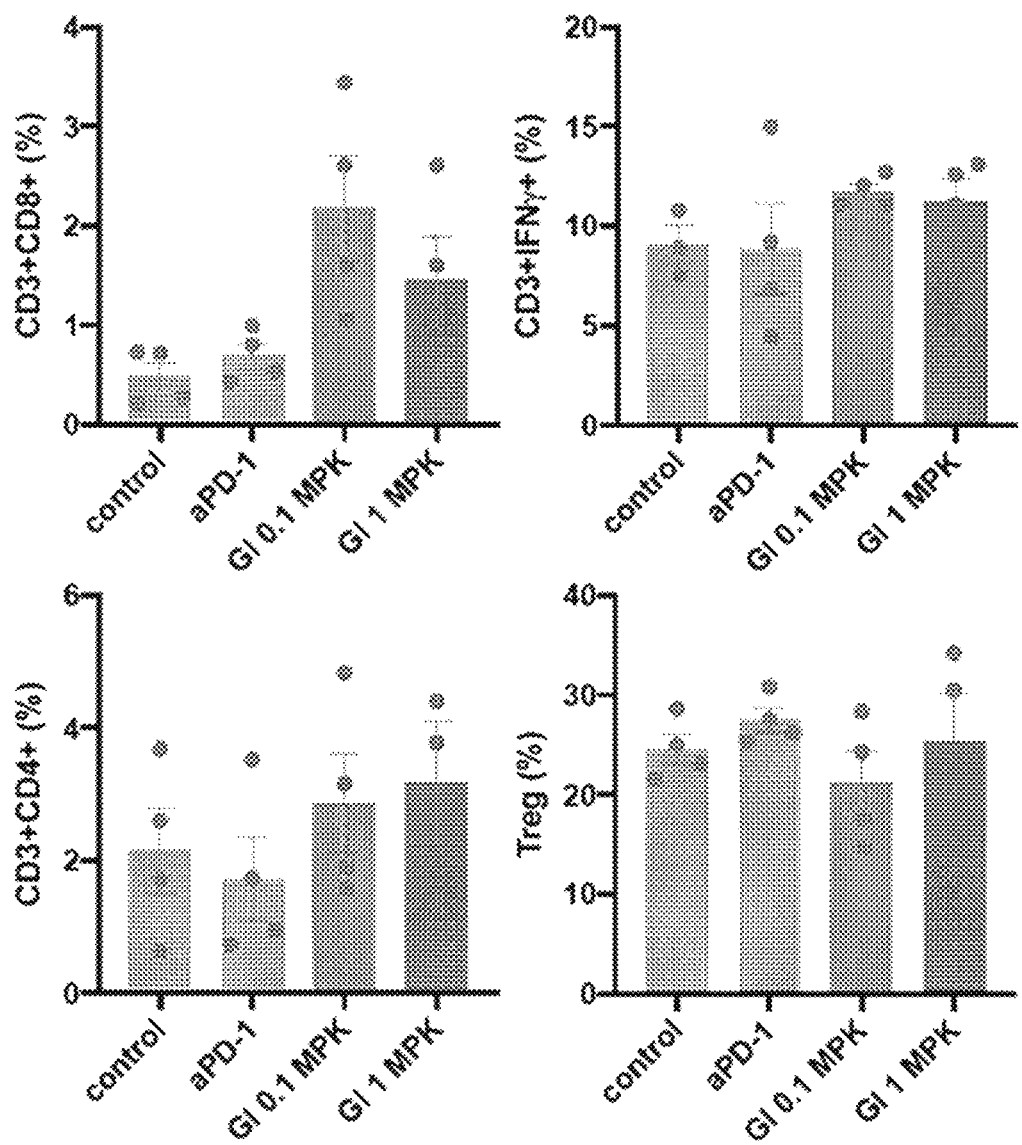
FIG. 47 graphically illustrates results obtained by subjecting mice transplanted with mouse-derived colorectal cancer cells (CT26) to treatment with hIgG4, an anti-PD-1 antibody, or GI101, and then analyzing, with FACS, CD8+ T cells, IFN-7 T cells, CD4+ T cells, and Treg cells in cancer tissues.
Figure 48:
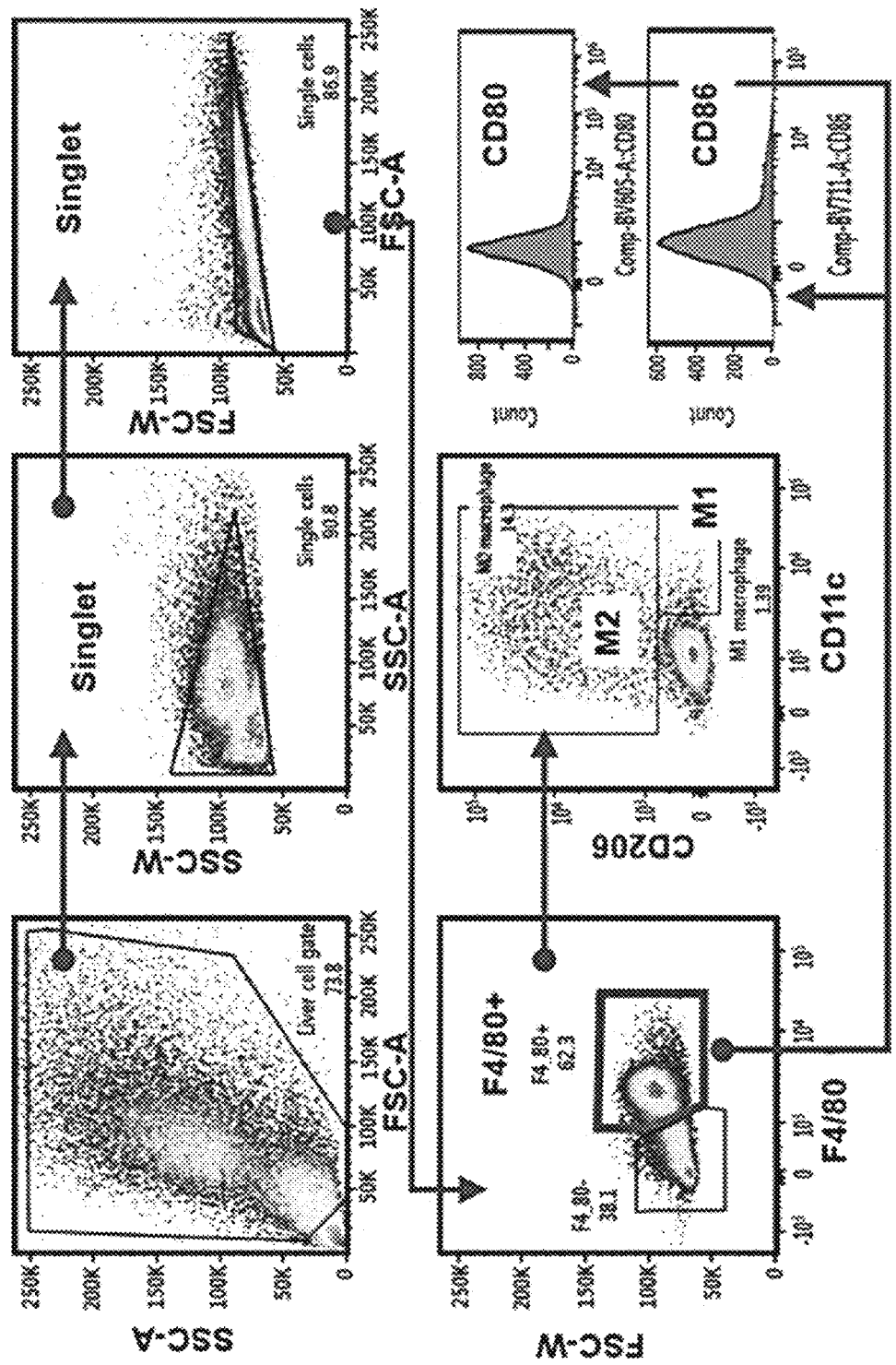
FIG. 48 illustrates results obtained by subjecting mice transplanted with mouse-derived colorectal cancer cells (CT26) to treatment with hIgG4, an anti-PD-1 antibody, or GI101, and then analyzing, with FACS, macrophages in cancer tissues.
Figure 49:
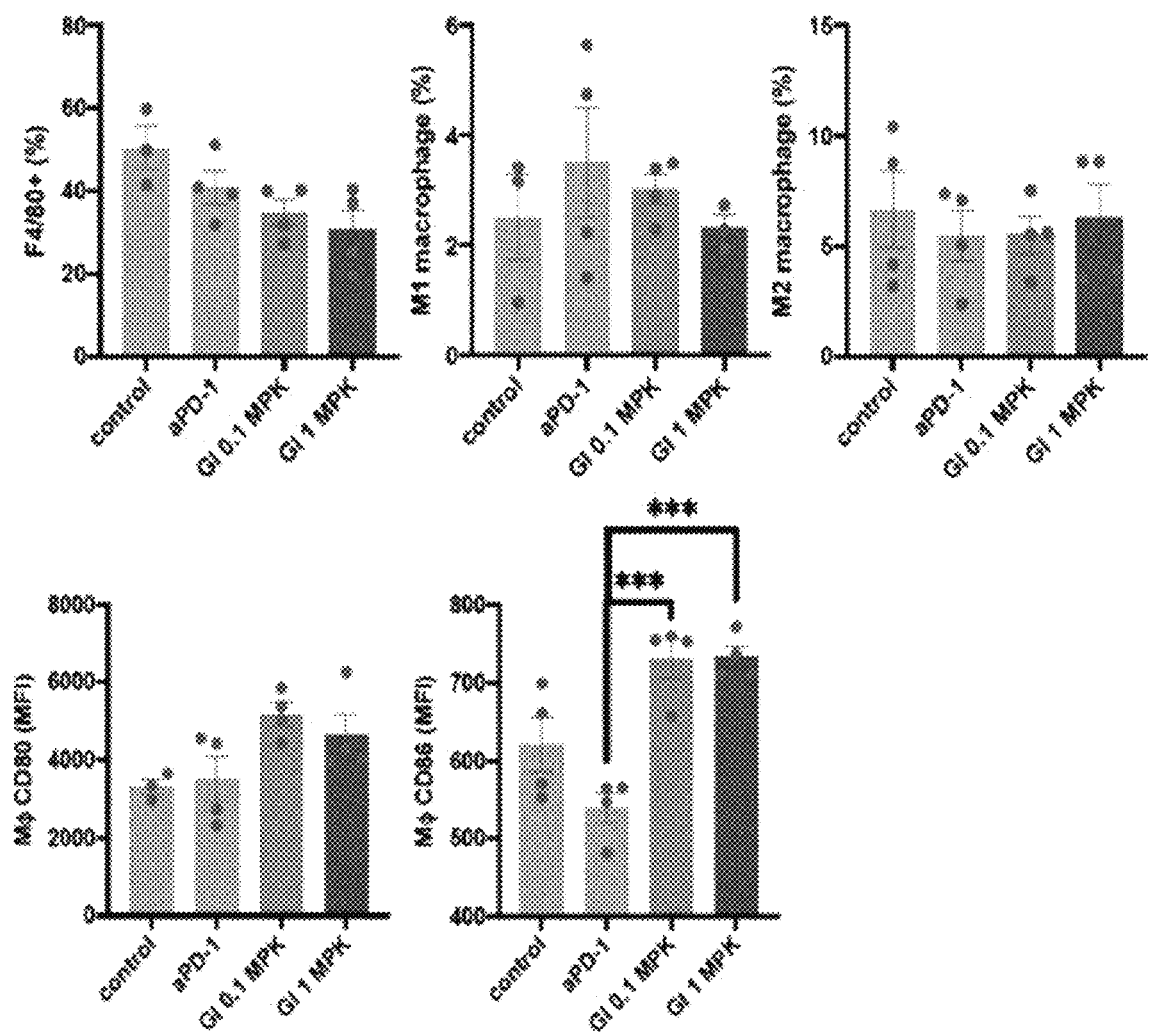
FIG. 49 graphically illustrates results obtained by subjecting mice transplanted with mouse-derived colorectal cancer cells (CT26) to treatment with hIgG4, an anti-PD-1 antibody, or GI101, and then analyzing, with FACS, macrophages in cancer tissues.
Figure 50:
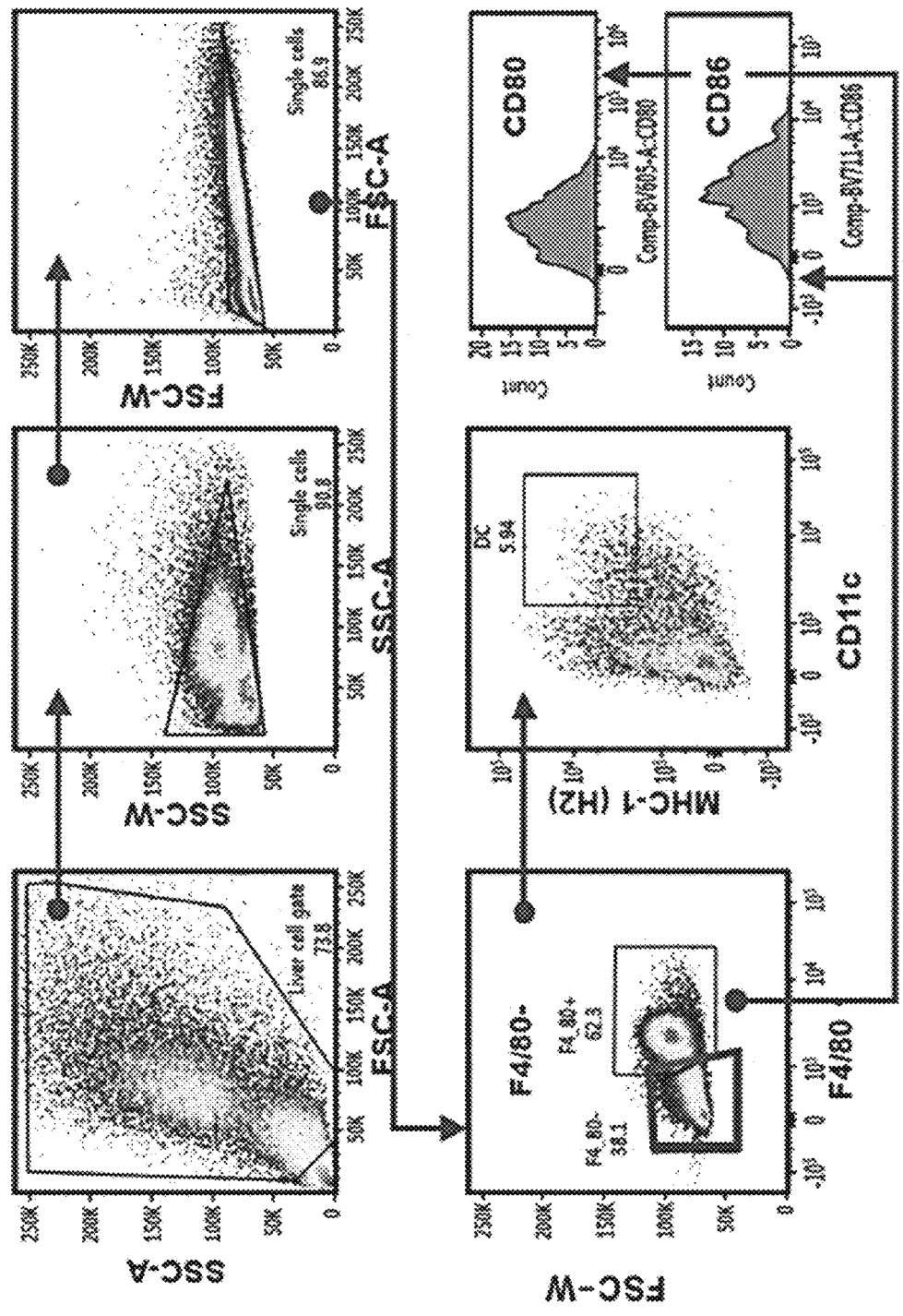
FIG. 50 illustrates results obtained by subjecting mice transplanted with mouse-derived colorectal cancer cells (CT26) to treatment with hIgG4, an anti-PD-1 antibody, or GI101, and then analyzing, with FACS, dendritic cells in cancer tissues.
Figure 51:
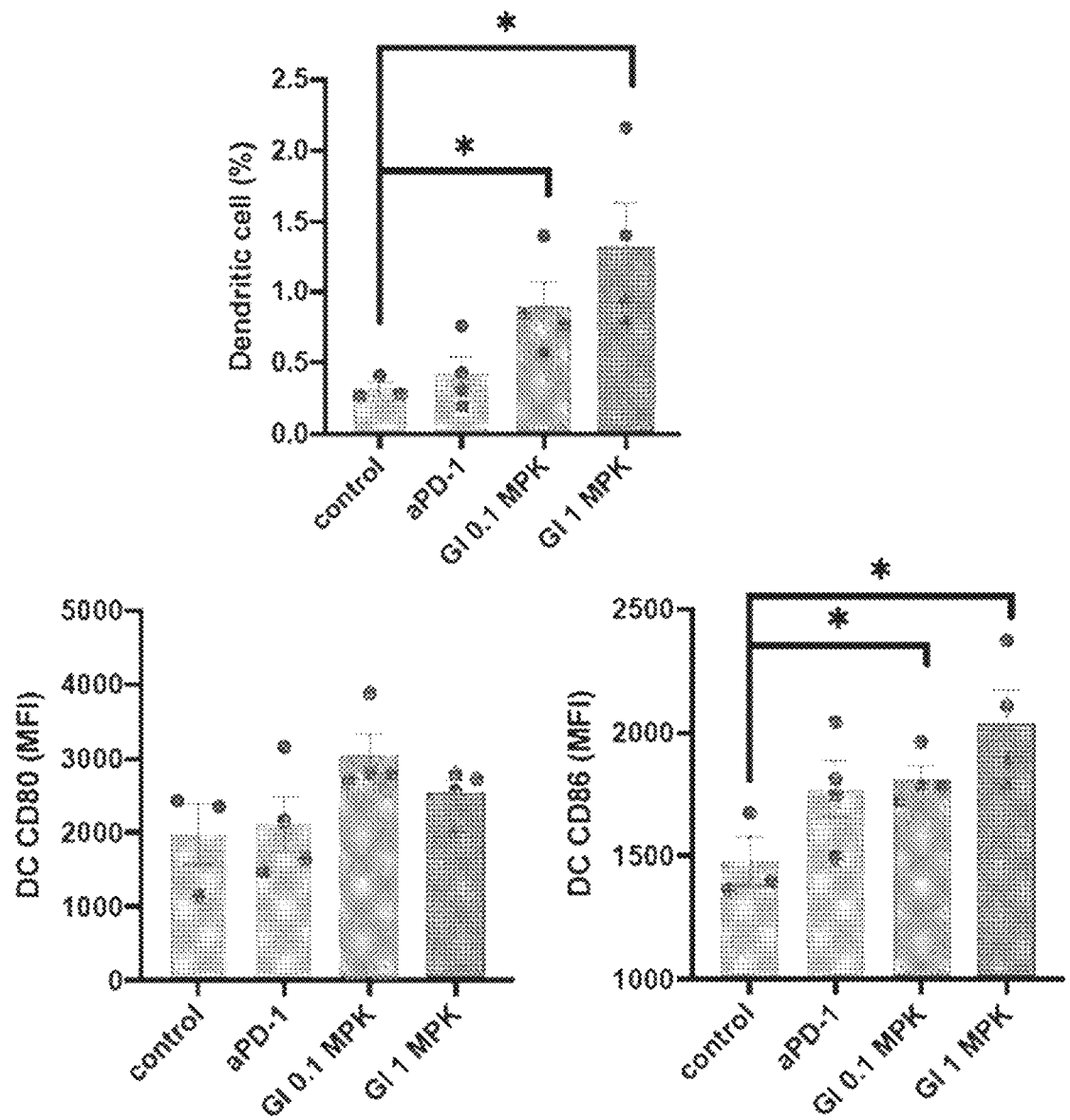
FIG. 51 graphically illustrates results obtained by subjecting mice transplanted with mouse-derived colorectal cancer cells (CT26) to treatment with hIgG4, an anti-PD-1 antibody, or GI101, and then analyzing, with FACS, dendritic cells in cancer tissues.

As a result, the experimental group having received GI101 at a dose of 0.1 mg/kg exhibited a significant increase in CD8+ T cells, as compared with the positive control having received anti-PD-1 antibody alone at a dose of 5 mg/kg (* p<0.05, FIGS. 46 and 47). Furthermore, all experimental groups having received GI101 exhibited a significantly increased level of expression of IFN-γ in T cells, as compared with the negative control (* p<0.05, FIGS. 46 and 47). In addition, the experimental group having received GI101 at a dose of 0.1 mg/kg exhibited an increase in M1 macrophages as compared with the negative control and the positive control having received anti-PD-1 antibody alone (FIGS. 48 and 49). In addition, all experimental groups having received GI101 exhibited an increased level of CD86 expression in macrophages and dendritic cells (* p<0.05, FIGS. 48 to 51).

Experimental Example 17. Identification of Anticancer Effect of GI101 in Mice Transplanted with Mouse-Derived Lung Cancer Cells Experimental Example 17.1. Identification of Tumor Inhibitory Effect C57BL/6 mice (female, 7-week-old) purchased from Orient Bio were subjected to an acclimation period of 7 days. Then, 5×10$^6$ cells of LL/2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group including 10 mice. Thereafter, using a disposable syringe (31G, 1 mL), no drug was administered to a negative control, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive controls. For experimental groups, GI101 at a dose of 0.1 mg/kg or 1 mg/kg was administered intravenously thereto. A total of three administrations were given once every three days after the first administration. The tumor size was measured daily.

Figure 52:
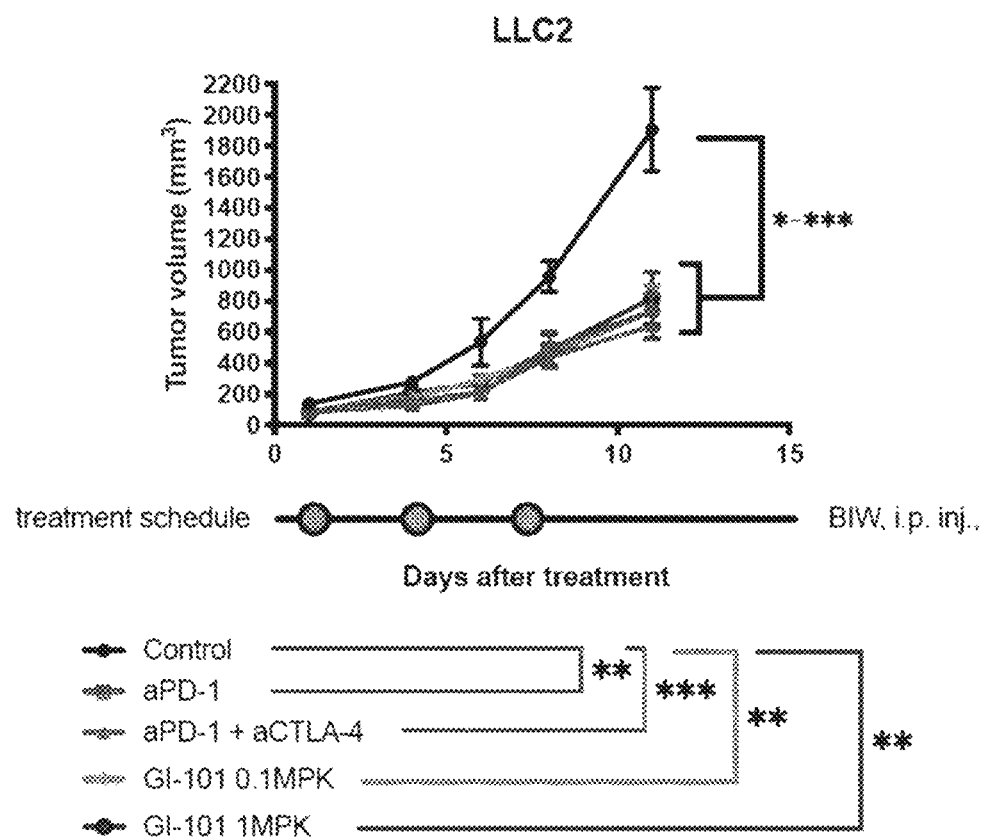
FIG. 52 illustrates a result obtained by identifying a tumor inhibitory effect of GI101 in mice transplanted with mouse-derived lung cancer cells (LL/2).

As a result, all experimental groups exhibited a significant tumor inhibitory effect, as compared with the negative control (* p<0.05) (FIG. 52).

Experimental Example 17.2. Immune Cell Analysis in Cancer Tissue

The mice of each group in Experimental Example 17.1. were sacrificed when the tumor volume reached an average of 200 mm$^3$, and cancer tissues were collected. Thereafter, FACS analysis was performed in the same manner as Experimental Example 16.2. to analyze immune cells in the cancer tissues.

Figure 53:
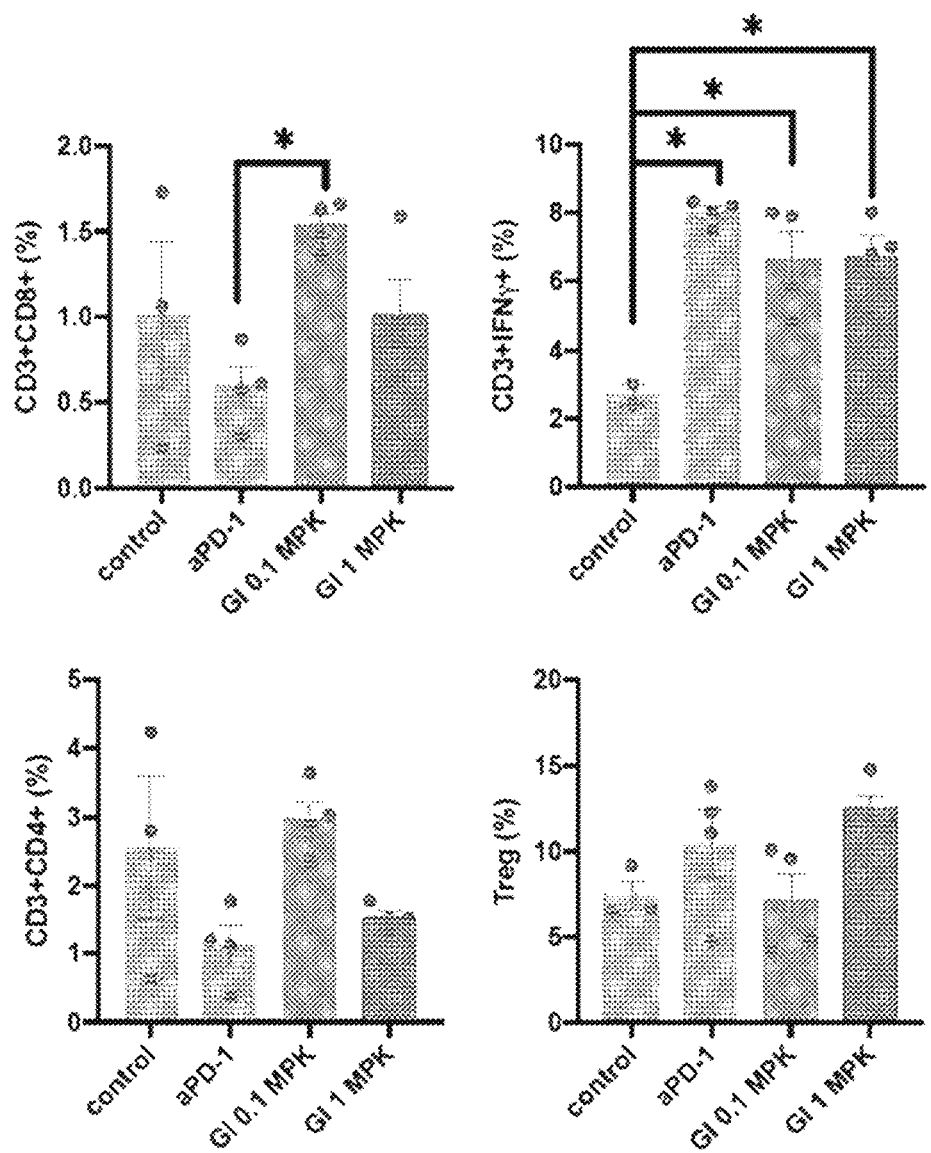
FIG. 53 graphically illustrates results obtained by subjecting mice transplanted with mouse-derived lung cancer cells (LL/2) to treatment with hIgG4, an anti-PD-1 antibody, or GI101, and then analyzing, with FACS, CD8+ T cells, IFN-7 T cells, CD4+ T cells, and Treg cells in cancer tissues.
Figure 54:
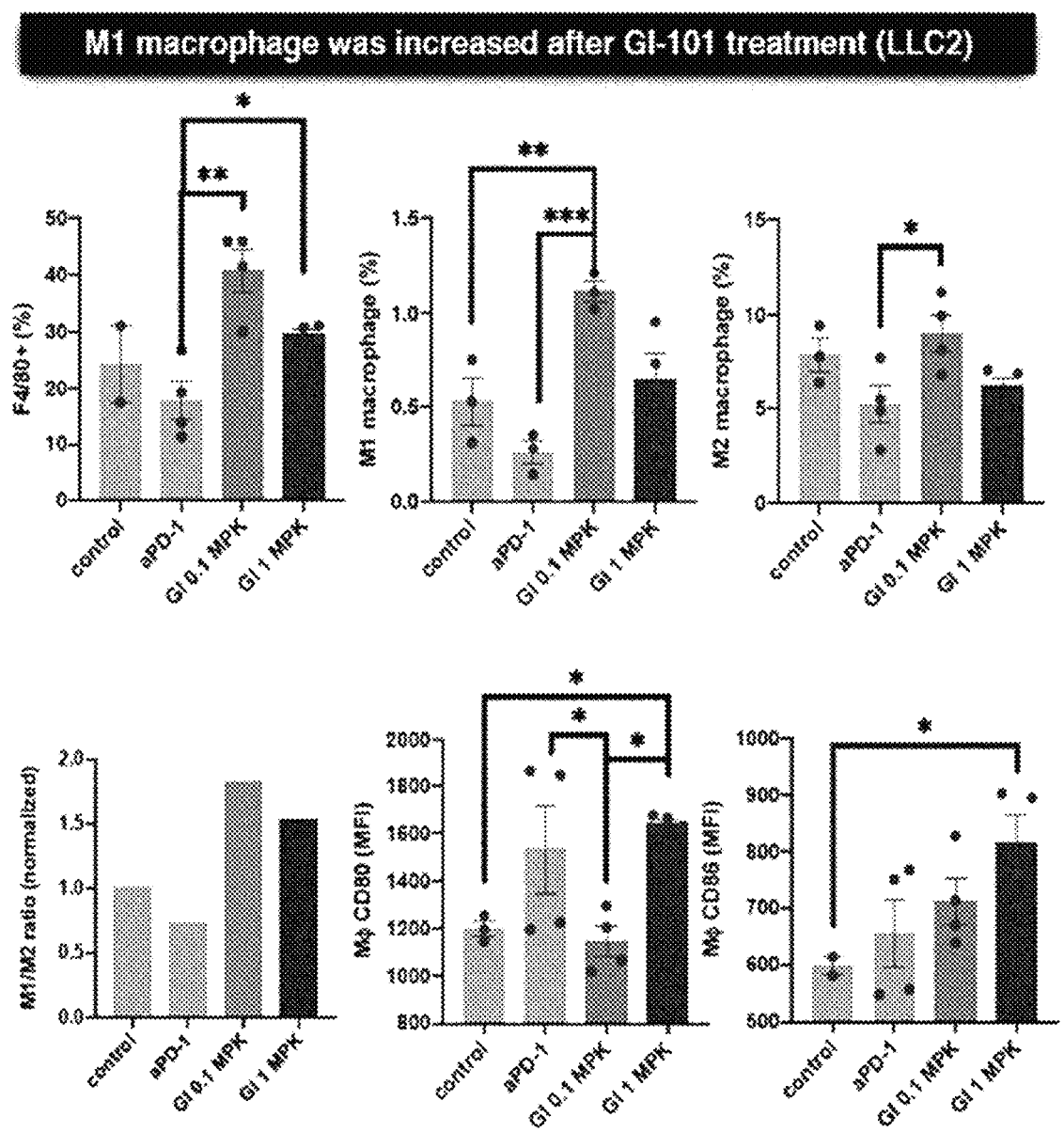
FIG. 54 graphically illustrates results obtained by subjecting mice transplanted with mouse-derived lung cancer cells (LL/2) to treatment with hIgG4, an anti-PD-1 antibody, or GI101, and then analyzing, with FACS, macrophages in cancer tissues.
Figure 55:
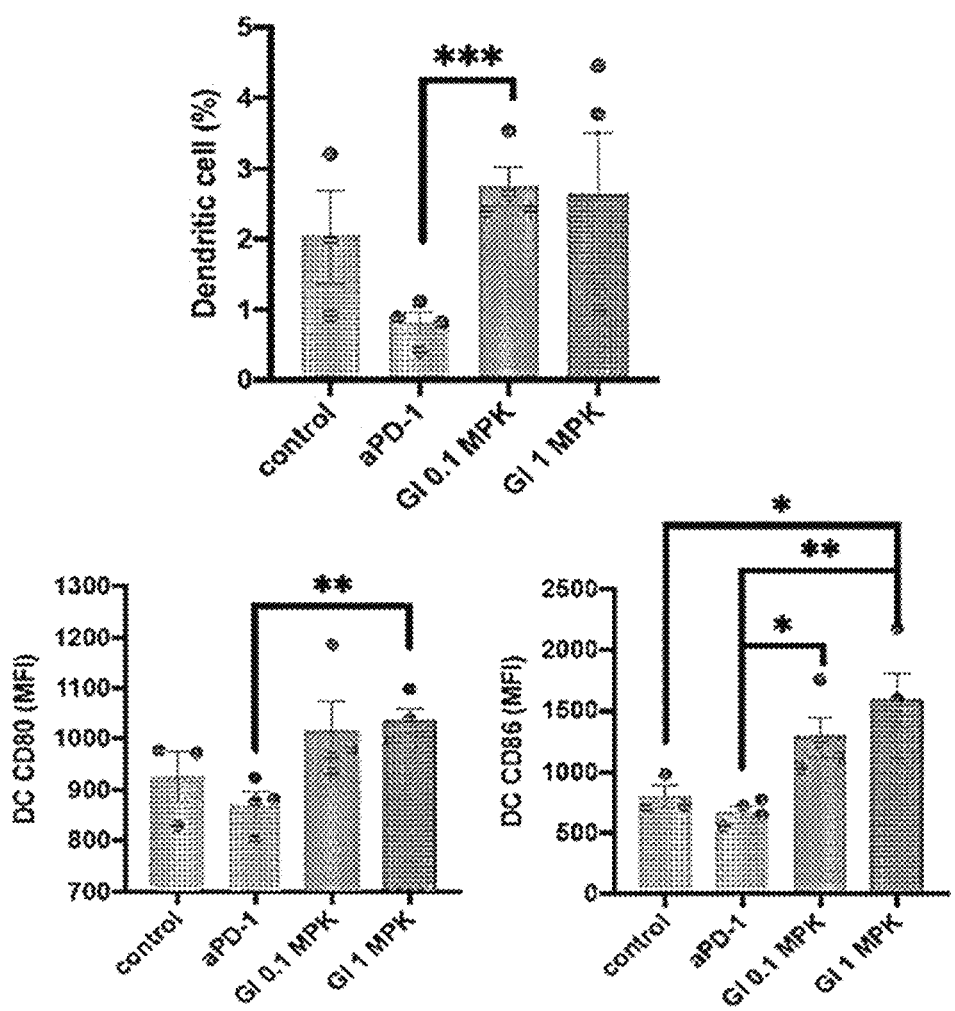
FIG. 55 graphically illustrates results obtained by subjecting mice transplanted with mouse-derived lung cancer cells (LL/2) to treatment with hIgG4, an anti-PD-1 antibody, or GI101, and then analyzing, with FACS, dendritic cells in cancer tissues.
Figure 59:
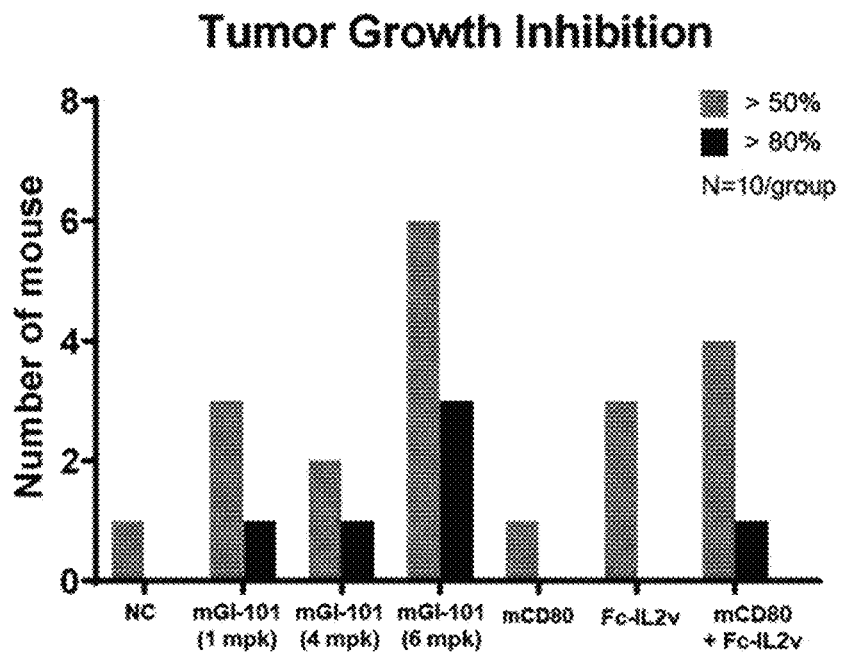
FIG. 59 illustrates tumor inhibition rate of mGI101 in mice transplanted with mouse-derived colorectal cancer cells (CT26).

As a result, the experimental group having received GI101 at a dose of 0.1 mg/kg exhibited a significant increase in CD8+ T cells, as compared with the positive control having received anti-PD-1 antibody alone (* p<0.05, FIG. 59). Furthermore, all experimental groups having received GI101 exhibited a significantly increased level of expression of IFN-γ, as compared with the negative control (* p<0.05, FIG. 59). In addition, all experimental groups having received GI101 exhibited an increased level of CD86 expression in macrophages and dendritic cells (* p<0.05, FIGS. 53 to 55).

Experimental Example 18. Identification of Anticancer Effect of mGI102-M61 in Mice Transplanted with Mouse-Derived Colorectal Cancer Cells BALB/c mice (female, 7-week-old) purchased from Orient Bio were subjected to an acclimation period of 7 days. Then, 5×10$^6$ cells of CT26 cancer cell line (ATCC, USA) were mixed with 0.05 ml of MATRIGEL™ matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 mm$^3$ were selected, and then the selected mice were grouped evenly based on tumor size and body weight, each group including 10 mice. Thereafter, using a disposable syringe (31G, 1 mL), hIgG4 was administered at a dose of 6 mg/kg to a negative control. For experimental groups, mGI102-M61 at a dose of 3 mg/kg, 6 mg/kg, or 12 mg/kg was administered intravenously thereto. A total of three administrations were given once every three days after the first administration. The tumor size was measured daily.

Figure 56:
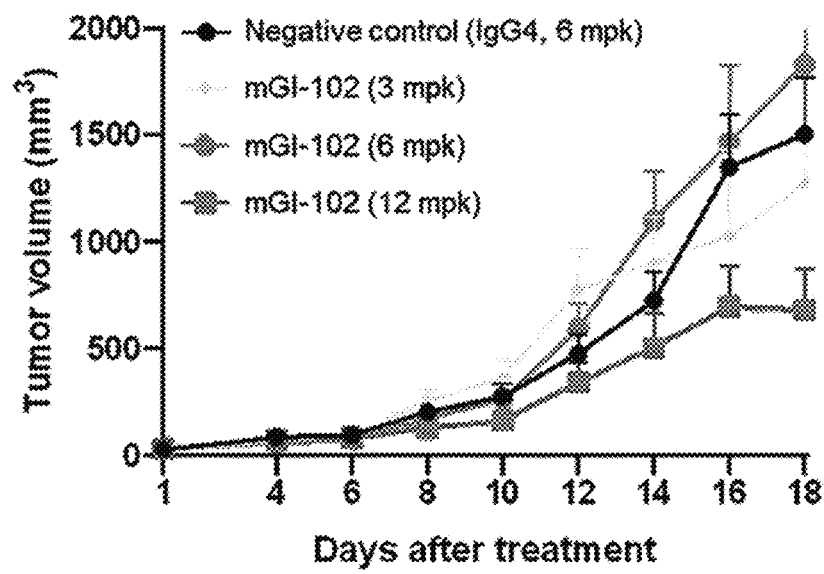
FIG. 56 illustrates a result obtained by identifying a tumor inhibitory effect of mGI102-M61 in mice transplanted with mouse-derived colorectal cancer cells (CT26).
Figure 57:
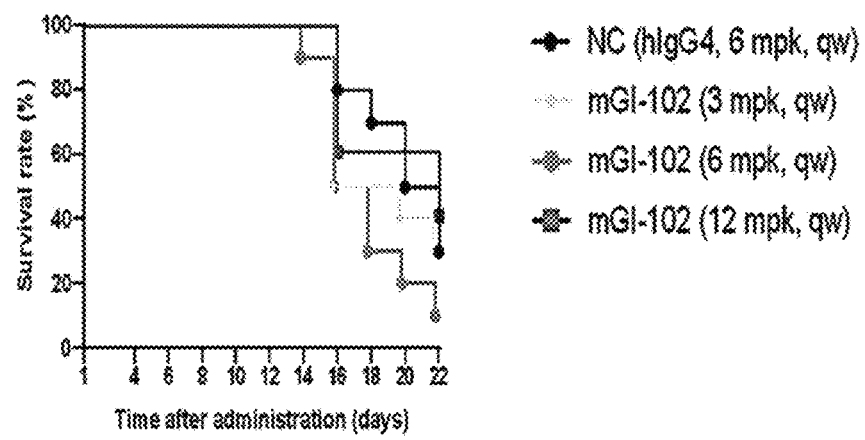
FIG. 57 illustrates results obtained by analyzing survival rate of mice, depending on the administration of mGI102-M61, in mice transplanted with mouse-derived colorectal cancer cells (CT26).

As a result, it was identified that the experimental group having received mGI102-M61 at a dose of 12 mg/kg exhibited significant tumor growth inhibition at some measurement time points and at the end of the test, as compared with the negative control (FIG. 56). In addition, as a result of measuring a survival rate, it was identified that the experimental group having received mGI102-M61 at a dose of 12 mg/kg exhibited significant improvement at some measurement time points and at the end of the test, as compared with the negative control (FIG. 57).

Experimental Example 19. Identification of Anticancer Effect of mGI101 in Mice Transplanted with Mouse-Derived Colorectal Cancer Cells BALB/c mice (female, 7-week-old) purchased from Orient Bio (Korea) were subjected to an acclimation period of 7 days. Then, 5×10$^6$ cells of CT-26 cancer cell line (ATCC, USA) were mixed with 0.05 ml of MATRIGEL™ matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 200 mm$^3$ to 250 mm$^3$ were selected, and then the selected mice were grouped evenly based on tumor size and body weight, each group including 10 mice.

Thereafter, using a disposable syringe (31G, 1 mL), hIgG4 was administered at a dose of 4 mg/kg to a negative control. For experimental groups, mGI101 at a dose of 1 mg/kg, 4 mg/kg, or 6 mg/kg was administered intravenously thereto. Additionally, groups having received mCD80 at 4.9 mg/kg or Fc-IL-2v (GI101C2) at 2.8 mg/kg were set as controls. In addition, a group having simultaneously received mCD80 at 4.9 mg/kg and Fc-IL-2v (GI101C2) at 2.8 mg/kg was set as a control.

In tumor volume measurement, it was identified that the group having received mGI101 at a dose of 6 mg/kg exhibited significant inhibition at some measurement time points and at the end of the test, as compared with the negative control. An excellent tumor growth inhibition rate was observed as compared with the group having received a combination of mCD80 and Fc-IL-2v (GI101C2) (FIGS. 58 and 59).

Figure 58:
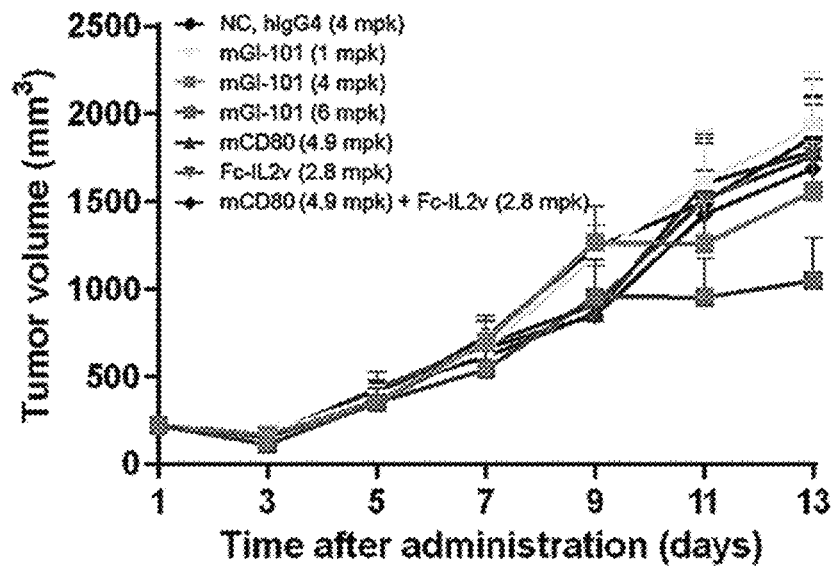
FIG. 58 illustrates a result obtained by identifying a tumor inhibitory effect of mGI101 in mice transplanted with mouse-derived colorectal cancer cells (CT26).

In conclusion, in the tumor growth-inhibitory efficacy test on BALB/c mice allotransplanted with CT-26, a BALB/c mouse-derived colorectal cancer cell line, it was demonstrated that the test substance mGI101 had tumor inhibitory efficacy under this test condition as compared with respective mCD80 and IL-2v single formulations; and it was identified that mGI101 exhibited excellent anticancer efficacy as compared with the group having received a combination of mCD80 and IL-2v (FIGS. 58 and 59). In particular, the group having received mGI101 at a dose of 6 mg/kg exhibited significant inhibition of tumor size, as compared with the negative control and the group having received a combination of mCD8 and Fc-IL2v (GI101C2).

V. Identification of Anticancer Effect According to Administration of Combination of Fusion Protein Dimer and Immune Checkpoint Inhibitor

Experimental Example 20. Identification of Anticancer Effect by Administration of Combination of GI101 and Anti-PD-1 Antibody in Mice Transplanted with Human-Derived Breast Cancer Cells This test was to evaluate the tumor growth inhibitory effect after intraperitoneal administration of GI101 as a test substance alone or in combination with Keytruda (Pembrolizumab, MSD), which is an anti-PD-1 antibody, as a positive control substance in a tumor model xenotransplanted with MDA-MB-231 cells, which are human-derived breast cancer cells, using a humanized mouse model prepared by xenotransplanting human PBMCs into NSGb2m mice.

The stock solution of the test substance, negative control substance, and positive control substance described in Table 2 was diluted by adding excipients according to each dose.

TABLE 2

| — | Test substance | Positive control substance | Negative control substance | Excipient |
|---|---|---|---|---|
| Substance name | GI101 | KEYTRUDA | hIgG4 | PBS |
| Appearance | clear liquid | clear liquid | clear liquid | clear liquid |
| Component | Fc fusion protein | anti-PD-1 antibody | — | — |
| pH | 7.5 | — | — | — |
| Storage condition | refrigerated storage (4° C.) | refrigerated storage (4° C.) | refrigerated storage (4° C.) | refrigerated storage (4° C.) |
| Precautions for handling | keep refrigerated until administration, and prepare and use on the day of administration | keep refrigerated until administration, and prepare and use on the day of administration | keep refrigerated until administration, and prepare and use on the day of administration | — |

Human-derived breast cancer cells, MDA-MB-231 (*Homo sapiens*, human mammary gland/breast; derived from metastatic site: pleural effusion), were purchased from the Korea cell line bank (Korea) and used for the test. The cell culture medium has a composition as shown in the table below. Fetal bovine serum (FBS, 16000-044, Thermofisher scientific, USA), penicillin-streptomycin; 10,000 units/ml penicillin and 10,000 µg/ml streptomycin (15140122, Thermofisher scientific, USA); and RPMI1640 (A1049101, Thermofisher scientific, USA) per 100 ml were mixed and used.

TABLE 3

| Name | Composition (ml) |
|---|---|
| FBS | 10 |
| Penicillin-Streptomycin | 1 |
| RPMI1640 | 89 |
| Total volume | 100 |

The cells to be used for the test were thawed, placed in a cell culture flask, and cultured in a 37° C., 5% $CO_2$ incubator (MCO-170M, Panasonic, Japan). The cells were suspended using Trypsin-EDTA (Cat. 25200-072, Thermofisher scientific, USA). The suspended cells were collected by centrifugation (125×g, 5 minutes) using a centrifuge, transferred to a new medium and a new flask, and passage cultured. The cultured cells were put to a centrifugation tube on the day of cell line transplantation and then collected. Thereafter, centrifugation (125×g, 5 minutes) was performed to discard the supernatant, and a cell suspension ($5 \times 10^6$ cells/0.05 ml) was prepare with PBS (Cat. LB 001-04, Welgene, KOREA) and stored on ice until inoculation. 8-week-old female NSGb2m (NOD.Cg-B2m$^{tm1Unc}$Prkdc$^{scid}$Il2rg$^{tm1Wjl}$/SzJ) mice were purchased from Joongang Bio (Korea) and used for the test. The body weight was measured the next day after the end of the quarantine and acclimation period, and then the human-derived PBMC cell suspension ($5 \times 10^6$ cells/0.2 ml) prepared for healthy animals was filled into a disposable syringe and administered to the caudal vein of the animals. General symptoms were observed once a day after cell transplantation.

MATRIGEL™ matrix phenol red-free (0.05 ml, 356237, BD, USA) was added to the prepared MDA-MB-231 cell suspension ($5 \times 10^6$ cells/0.05 ml) to prepared the solution, and the solution was filled into a disposable syringe, and transplantation of the solution was performed by subcutaneous administration at 0.1 ml/head in the right dorsal region of the animals transplanted with human PBMCs. General symptoms were observed once a day during the engraftment and growth period after cell line transplantation.

A certain period of time after the cell transplantation, the tumor volume was measured for animals with no abnormalities in the health condition of the animals, and 32 subjects were selected so that the average of each group reached 40 to 80 mm³. The selected animals were grouped into a total of 4 groups as evenly as possible based on tumor volume and body weight, each group including 8 animals.

As shown in Table 4, the test groups were configured. The test substance was administered to the animals using a disposable syringe (31G, 1 ml), and the administration frequency was 2 times/week, a total of 4 administrations were performed.

TABLE 4

| Group | | Dosage amount (mg/kg) | Dosage volume (ml/kg) | Number of animals |
|---|---|---|---|---|
| G1 | hIgG4 | 6 | 10 | 8 |
| G2 | GI101 | 6 | 10 | 8 |
| G3 | Keytruda | 5 | 10 | 8 |
| G7 | GI101 + Keytruda | 6 + 5 | 10 | 8 |

General symptoms such as appearance, behavior, and excrement were observed once a day during the observation period, and deceased animals were identified. Body weight was measured on the day of cell line transplantation, twice a week, and on the day of animal sacrifice. The major axis (maximum length, L) and minor axis (perpendicular width, W) of the tumor were measured using a caliper (Digital caliper, mitutoyo, Japan) three times a week during the observation period, and the tumor volume (TV) was calculated by substituting them into the following equations.

$$TV\ (mm^3) = (W^2 \times L)/2 \qquad [\text{Equation 1}]$$

$$\%\ TGI\ (\text{Tumor Growth Inhibition}) = (1 - (Ti - T0)/(Vi - V0)) \times 100 \qquad [\text{Equation 2}]$$

The tumor volume before administration of each subject was set as the value measured at the time of grouping.

Figure 60:
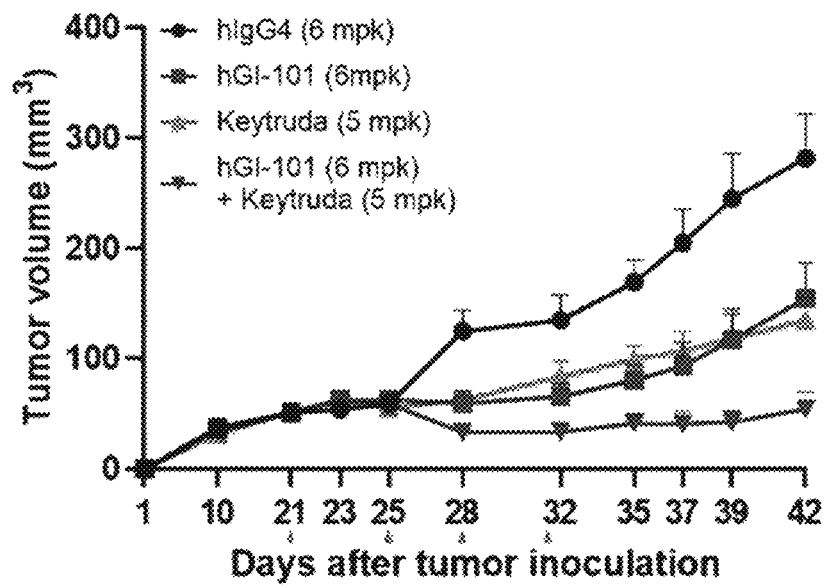
FIG. 60 illustrates a graph showing tumor growth when a combination of GI101 and Keytruda is used in mice transplanted with human-derived breast cancer cells (MDA-MB-231). The groups having received each of GI101 and Keytruda exhibited tumor growth inhibition as compared with the control (hIgG4). The group having received a combination of GI101 and Keytruda exhibited tumor growth inhibition as compared with the control. The group having received a combination of GI-101 and Keytruda exhibited tumor growth inhibition as compared with the group having received each of GI101 and Keytruda.

As a result of administering the drugs shown in Table 4 on days 21, 25, 28, and 31 after tumor transplantation, respectively, the group having received each of GI101 and Keytruda exhibited tumor growth inhibition as compared with the control (hIgG4). The group having received a combination of GI101 and Keytruda exhibited tumor growth inhibition as compared with the control. The group having received a combination of GI101 and Keytruda exhibited tumor growth inhibition as compared with the groups having received each of GI101 and Keytruda (FIG. 60).

Figure 61:
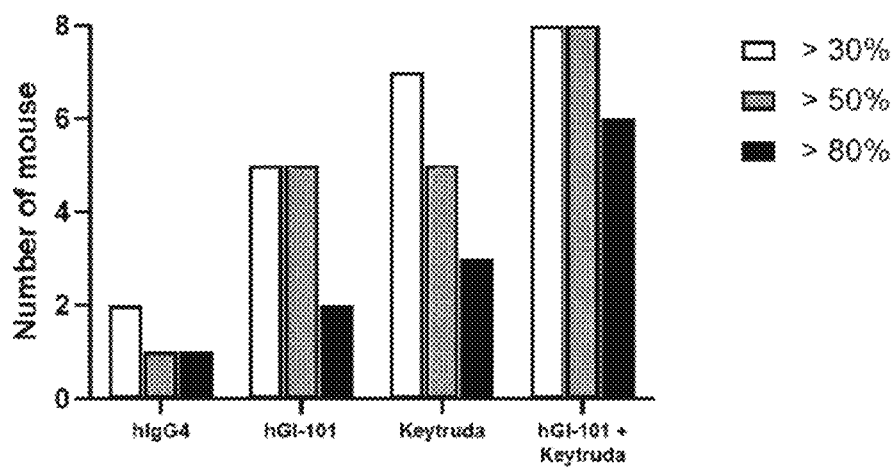
FIG. 61 illustrates a tumor growth inhibition rate when a combination of GI-101 and Keytruda is used in mice transplanted with human-derived breast cancer cells (MDA-MB-231). The groups having received IgG4 exhibited a tumor growth inhibition rate of 30% or more in 2 mice, 50% or more in 1 mouse, and 80% or more in 1 mouse. The group having received GI101 exhibited a tumor growth inhibition rate of 30% or more in 5 mice, 50% or more in 5 mice, and 80% or more in 2 mice. The group having received Keytruda exhibited a tumor growth inhibition rate of 30% or more in 7 mice, 50% or more in 5 mice, and 80% or more in 3 mice. The group having received a combination of GI101 and Keytruda exhibited a tumor growth inhibition rate of 30% or more in 8 mice, 50% or more in 8 mice, and 80% or more in 6 mice.
Figure 62:
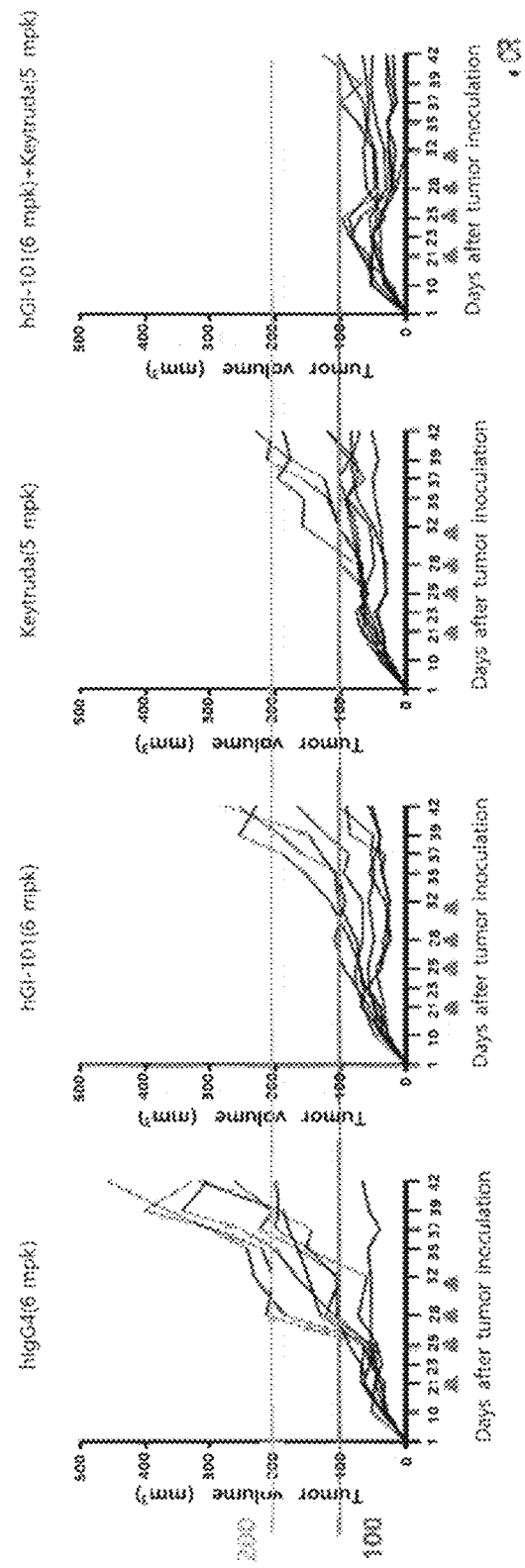
FIG. 62 illustrates the degree of tumor growth of individual experimental animals of each treatment group when a combination of GI101 and Keytruda is used in mice transplanted with human-derived breast cancer cells (MDA-MB-231).
Figure 63:
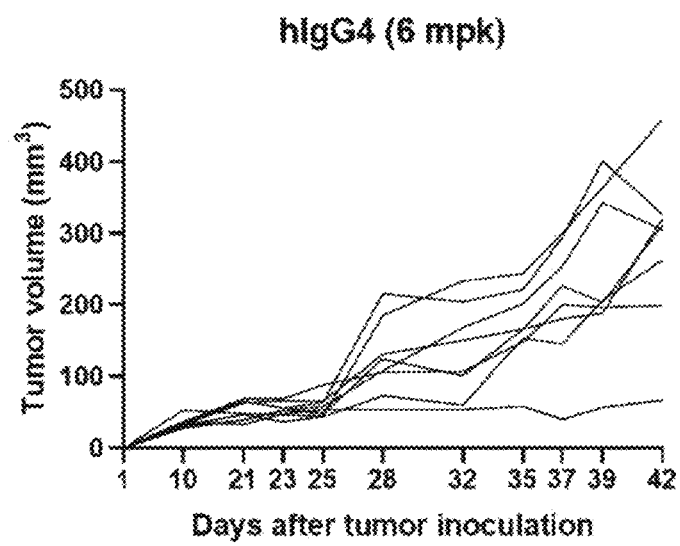
FIG. 63 illustrates the degree of tumor growth of individual experimental animals of the group having received hIgG4 in mice transplanted with human-derived breast cancer cells (MDA-MB-231).
Figure 64:
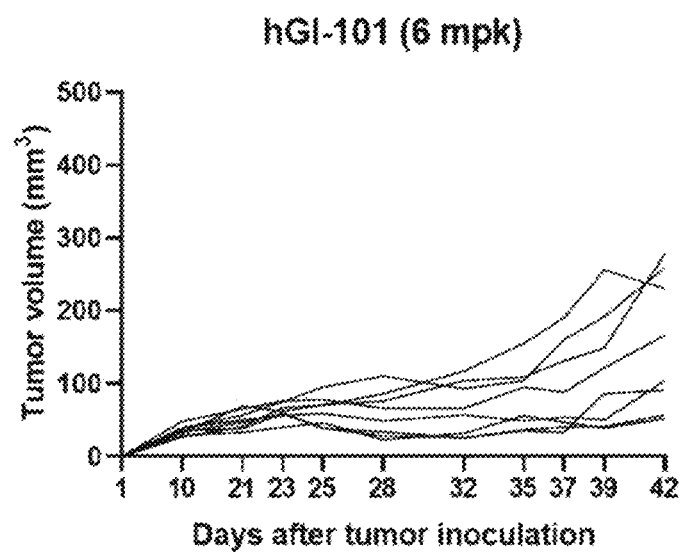
FIG. 64 illustrates the degree of tumor growth of individual experimental animals of the group having received GI101 in mice transplanted with human-derived breast cancer cells (MDA-MB-231).
Figure 65:
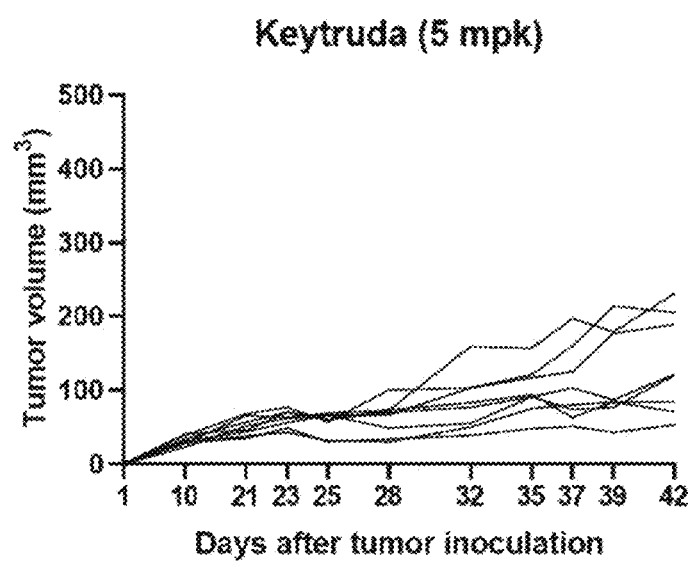
FIG. 65 illustrates the degree of tumor growth of individual experimental animals of the group having received Keytruda in mice transplanted with human-derived breast cancer cells (MDA-MB-231).
Figure 66:
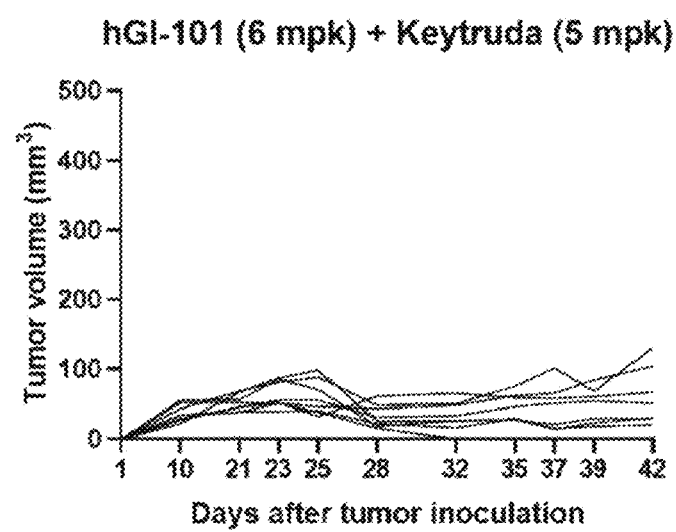
FIG. 66 illustrates the degree of tumor growth of individual experimental animals of the group having received a combination of GI101 and Keytruda in mice transplanted with human-derived breast cancer cells (MDA-MB-231).

As a result of calculating the tumor growth inhibition rate at the end of the experiment (after tumor transplantation, day 42) as compared with on day 1 of drug treatment (after tumor transplantation, day 21), the group having received hIgG4 exhibited the tumor growth inhibition rate of 30% or more in 2 mice, 50% or more in 1 mouse, and 80% or more in 1 mouse. In addition, the group having received GI101 exhibited the tumor growth inhibition rate of 30% or more in 5 mice, 50% or more in 5 mice, and 80% or more in 2 mice, and the group having received Keytruda exhibited the tumor growth inhibition rate of 30% or more in 7 mice, 50% or more in 5 mice, and 80% or more in 3 mice. In addition, the group having received a combination of GI101 and Keytruda exhibited the tumor growth inhibition rate of 30% or more in 8 mice, 50% or more in 8 mice, and 80% or more in 6 mice (FIG. 61).

In addition, the degree of tumor growth of individual experimental animals of each treatment group when a combination of GI101 and Keytruda is used in mice transplanted with human-derived breast cancer cells is shown in FIGS. 62 to 66.

Experimental Example 21. Identification of Anticancer Effect by Administration of Combination of mGI101 and Anti-PD-1 Antibody in Mice Transplanted with Mouse-Derived Colorectal Cancer Cells This test was to evaluate the tumor growth inhibitory effect after intraperitoneal administration of mGI101 as a test substance alone or in combination with an anti-PD-1 antibody as a positive control substance in a tumor model allotransplanted with MC38 into C57BL/6 mice.

Rodent-derived colorectal cancer cells, MC38, were purchased from Kerafast (USA) and used for the test. MC38 cells were cultured in RPMI1640 medium (Gibco) containing 10% fetal bovine serum (Gibco) and 1% antibiotic/antifungal agent (Gibco). The cultured cells were harvested using trypsin and then suspended in PBS. In order to establish an allotransplanted tumor model, $1 \times 10^6$ MC38 cells were subcutaneously injected into the right flank of C57BL/6 female mice (7-week-old).

The mice were randomly assigned based on tumor volume (30 mm$^3$), each group including 5 mice. The tumor grafts were identified about day 2 after cell inoculation. As shown in Table 5, the test groups were configured and the test substances were administered.

Clinical symptoms such as a disease and a behavioral change were observed once a day during the test period, and deceased animals were identified. At the end of the test period, the animals were sacrificed. The size of the MC38 solid cancer was measured using a tumor 3D scanner (TM900, Peria, Belgium). For each experimental group, the average loss and percentage change of body weight and the average tumor growth inhibition were calculated. The antitumor efficacy was evaluated as compared with the vehicle control. All statistical calculations were performed using Prism 8.0 (Graph Pad Software Inc, USA). The comparison of tumor volume measurements was made through one-way analysis of variance (at the end of this test) followed by Bonferroni's multiple comparison test. A p value of less than 0.05 was considered significant.

Figure 67:
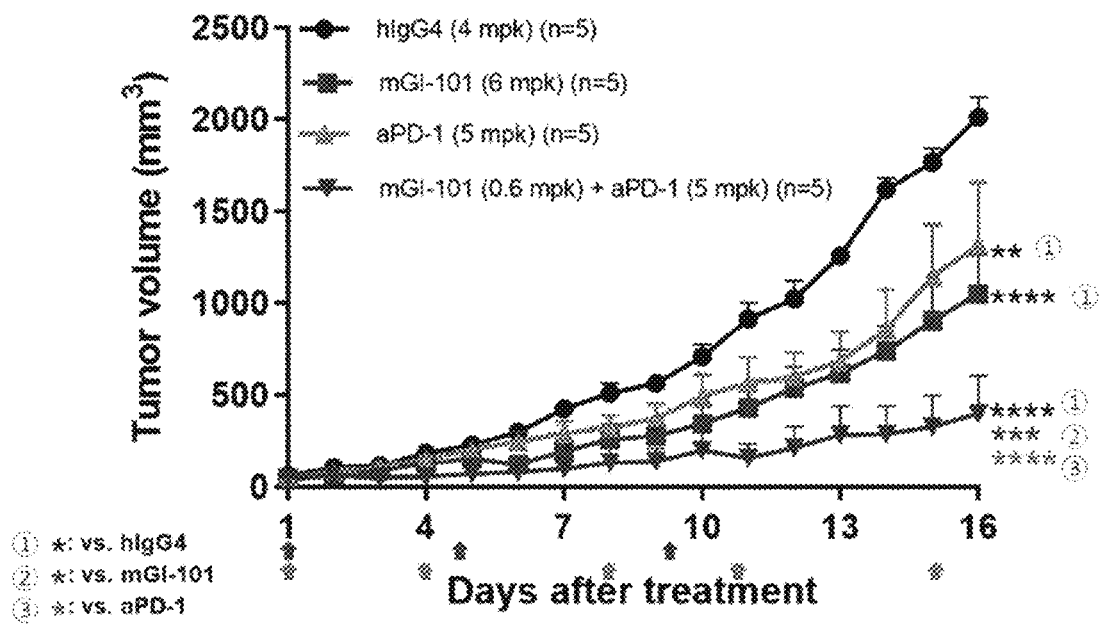
FIG. 67 illustrates a graph of tumor growth when mGI101 and an anti-PD-1 antibody are administered in combination in mice transplanted with rodent-derived colorectal cancer cells (MC38).
Figure 68:
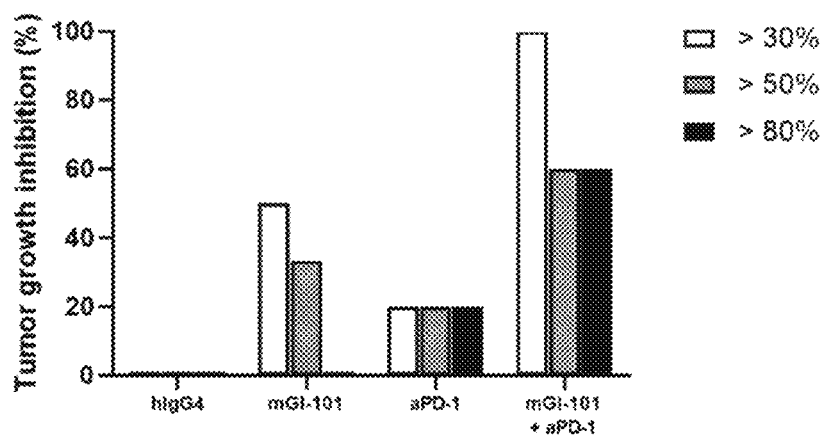
FIG. 68 illustrates a tumor growth inhibition rate when mGI101 and an anti-PD-1 antibody are administered in combination in mice transplanted with rodent-derived colorectal cancer cells (MC38).

All test animals maintained a healthy state without signs of pathological abnormalities after administration of mGI101 alone and with combination in an anti-PD-1 antibody. The results of combination therapy using mGI101 and/or an anti-PD-1 antibody against the MC38 tumor are shown in FIG. 67. The anticancer effect was observed in the group having received the drug as compared with the control, and the difference in tumor size was noticeable during the test period of 16 days. The MC38 tumor is known as a model responsive to an anti-PD-1 antibody in previous literature, and the anticancer effect was also observed in the group having received the anti-PD-1 antibody of this test (p>0.01). The anticancer effect was also shown in the group having received mGI101 (6 mpk) alone as well as the group having received the anti-PD-1 antibody (p>0.01). The group having received a combination of mGI101 (0.6 mpk)+anti-PD-1 (5 mpk) exhibited a remarkably excellent anticancer effect (p>0.0001).

Individual tumor sizes for each test group are shown in FIGS. 69 to 73. According to the results of individual tumor sizes, slight tumor regression was observed in some animals of the group having received the anti-PD-1 antibody. The group having received mGI101 (6 mpk) alone exhibited a more excellent tumor growth inhibitory effect as compared with the group having received the anti-PD-1 antibody. The tumor size was maintained at the same size from day 5 to day 7, but was regrown after day 7. The group having received the combination (GI101 (0.6 mpk)+an anti-PD-1 antibody (5 mpk)) exhibited a remarkably excellent tumor growth inhibition. In particular, two mice of the group having received the combination showed a complete remission (no tumor).

Figure 74:
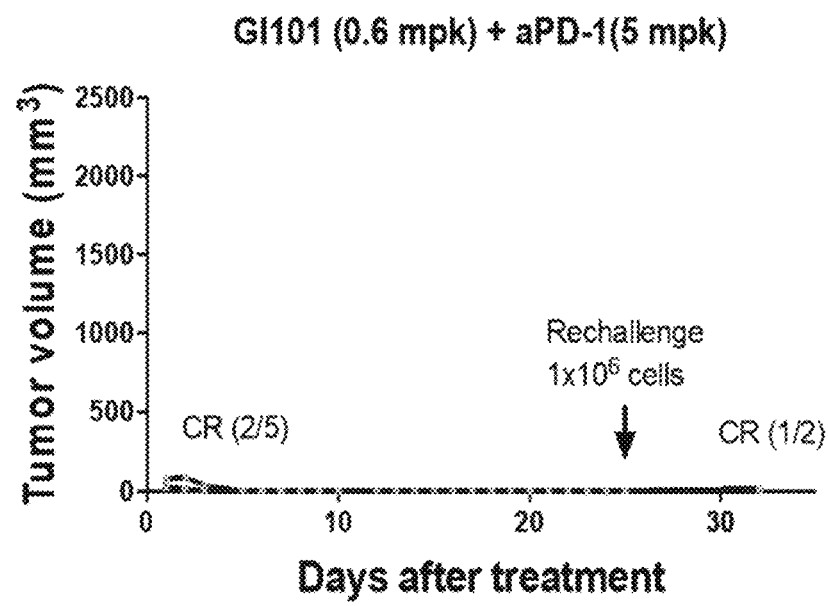
FIG. 74 illustrates the degree of tumor growth of individual experimental animals after reinjecting rodent-derived colorectal cancer cells into an experimental animal showing a complete remission, among the group having received a combination of mGI101 and an anti-PD-1 antibody in mice transplanted with rodent-derived colorectal cancer cells (MC38).

MC38 cells were reinjected into the left flank of two mice of the group having received the combination that showed a complete remission (the site opposite to the first injection site of cancer cells). These mice maintained an anti-PD-1 antibody administration (5 mpk, BIW) until day 32 (FIG. 74). A tumor with a small size (>30 mm$^3$) was observed in one of the two mice, but the tumor size did not grow any

TABLE 5

Figure 69:
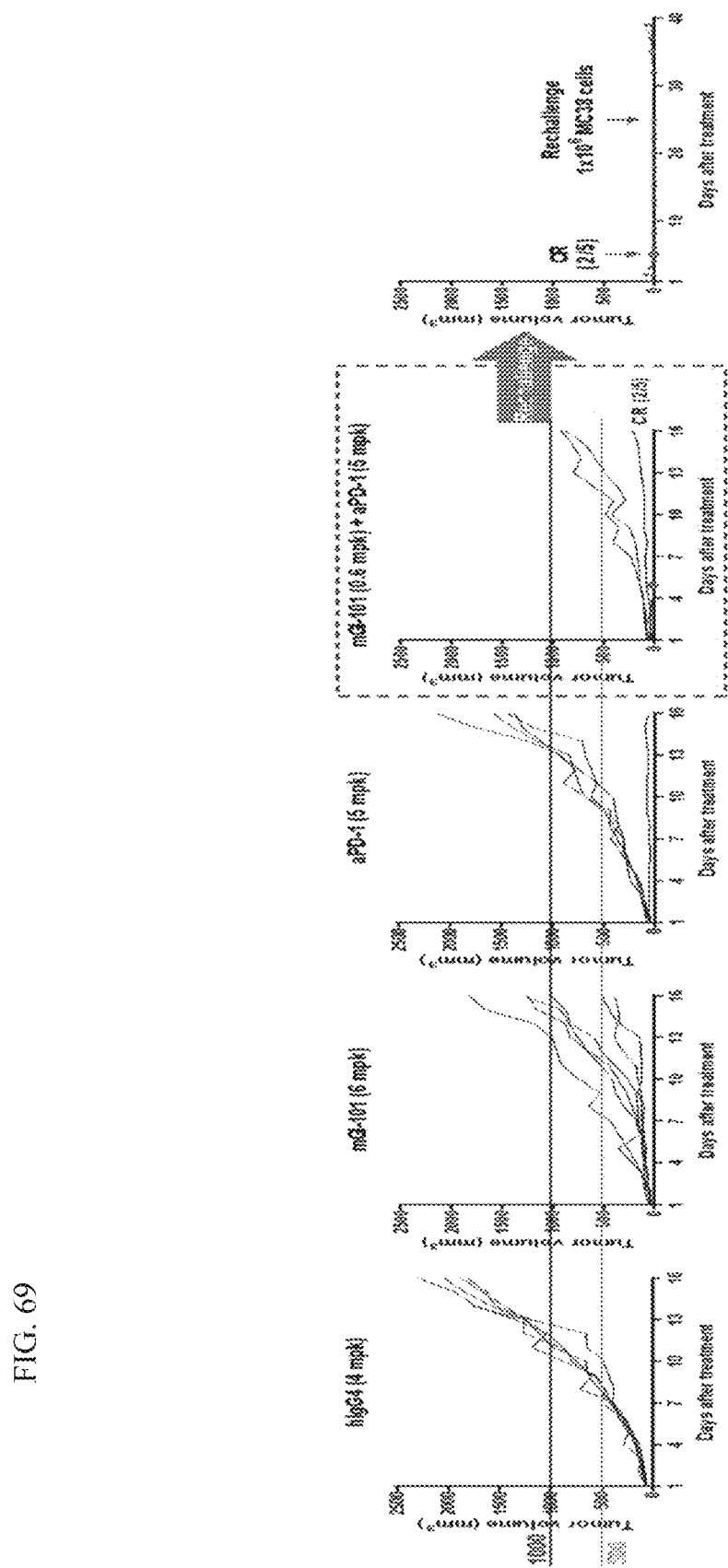
FIG. 69 illustrates the degree of tumor growth of individual experimental animals of each treatment group when mGI101 and an anti-PD-1 antibody are administered in combination in mice transplanted with rodent-derived colorectal cancer cells (MC38).
Figure 70:
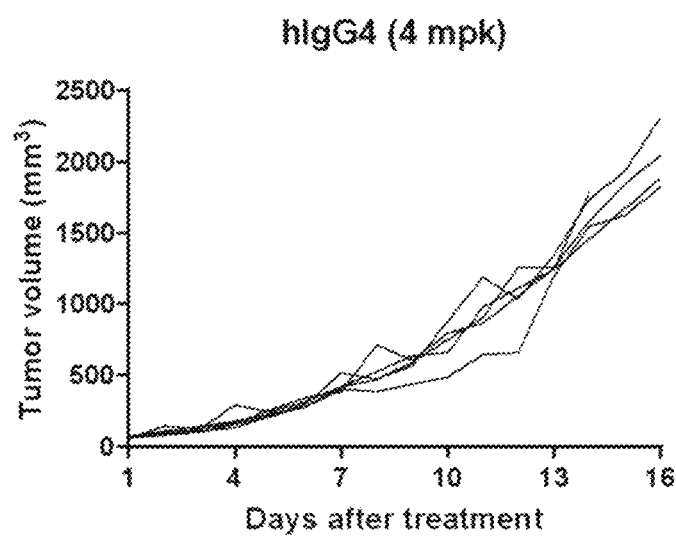
FIG. 70 illustrates the degree of tumor growth of individual experimental animals of the group having received hIgG4 in mice transplanted with rodent-derived colorectal cancer cells (MC38).
Figure 71:
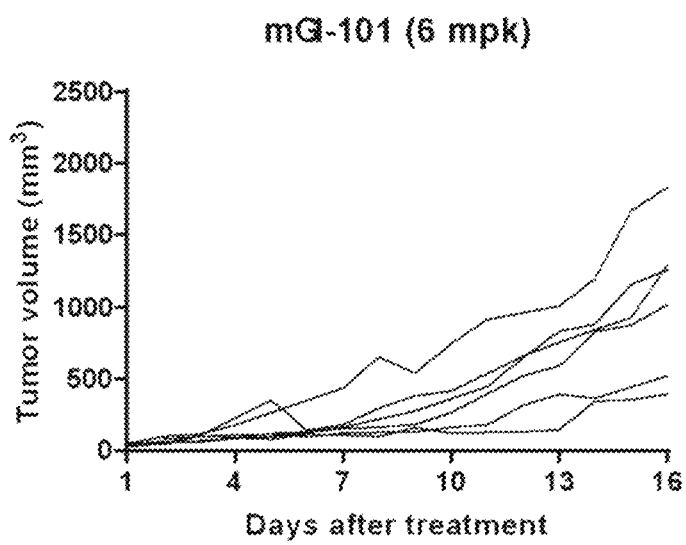
FIG. 71 illustrates the degree of tumor growth of individual experimental animals of the group having received mGI101 in mice transplanted with rodent-derived colorectal cancer cells (MC38).
Figure 72:
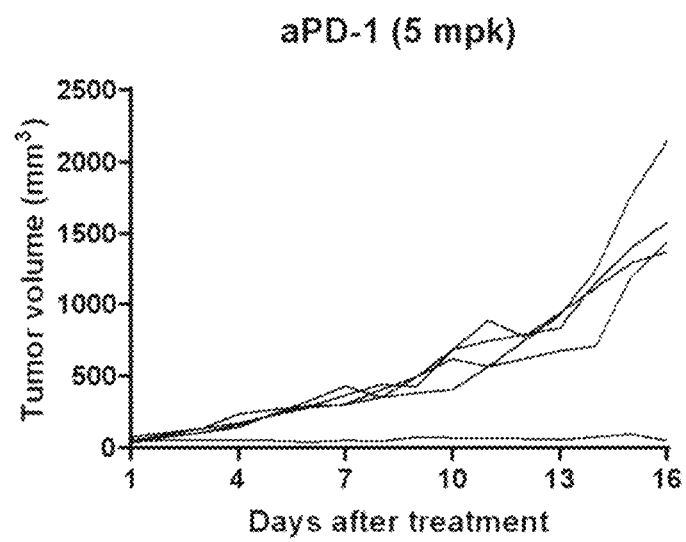
FIG. 72 illustrates the degree of tumor growth of individual experimental animals of the group having received an anti-PD-1 antibody in mice transplanted with rodent-derived colorectal cancer cells (MC38).
Figure 73:
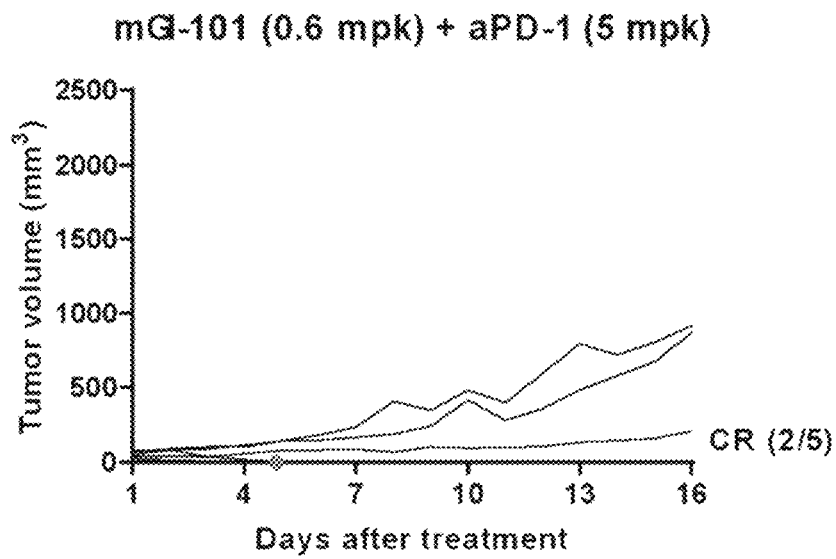
FIG. 73 illustrates the degree of tumor growth of individual experimental animals of the group having received a combination of mGI101 and an anti-PD-1 antibody in mice transplanted with rodent-derived colorectal cancer cells (MC38).

| | Experimental group | Route of administration, dosing cycle | Dosage amount | Number of animal |
|---|---|---|---|---|
| G1 | Vehicle control (hIgG4) | i.p. BIW × 16 days | 10 mg/kg | 5 |
| G2 | mGI101 | i.p. day 1, 5, 9 | 6 mg/kg | 6 |
| G3 | Anti-PD-1 antibody (cloneRMP1-14, InVivoMab) | i.p. BIW × 16 days | 5 mg/kg | 5 |
| G4 | mGI101 + anti-PD-1 antibody | i.p. day 1, 5, 9 (mGI101) i.p. BIW × 16 days (anti-PD-1 antibody) | 0.6 mg/kg 5 mg/kg | 5 | more until day 35 (FIG. 69). In another mouse, no tumor was observed after the tumor was reinjected (FIGS. 69 and 74).

In conclusion, as a result of testing the anti-tumor efficacy of mGI101 alone and in combination with an anti-PD-1 antibody in the MC38 allotransplanted tumor model, the most excellent anti-tumor efficacy was shown in the group having received the combination (GI101 (0.6 mpk)+anti-PD-1 (5 mpk)). Two of the experimental animals in the group having received the combination showed a complete remission, and the complete remission mice reinjected with MC38 showed a cancer resistance effect (Table 6).

TABLE 6

| Days After treatment | CR mouse | |
|---|---|---|
| | No. 1 Tumor Vol. (mm³) | No. 2 Tumor Vol. (mm³) |
| D1 | 78.2 | 23.6 |
| D2 | 84.5 | 13.5 |
| D3 | 36.3 | 0 |
| D4 | 0 | 0 |
| D5 | 0 | 0 |
| D6 | 0 | 0 |
| D7 | 0 | 0 |
| D8 | 0 | 0 |
| D9 | 0 | 0 |
| D10 | 0 | 0 |
| D11 | 0 | 0 |
| D12 | 0 | 0 |
| D13 | 0 | 0 |
| D14 | 0 | 0 |
| D15 | 0 | 0 |
| D16 | 0 | 0 |
| D17 | 0 | 0 |
| D18 | 0 | 0 |
| D19 | 0 | 0 |
| D20 | 0 | 0 |
| D21 | 0 | 0 |
| D22 | 0 | 0 |
| D23 | 0 | 0 |
| D24 | 0 | 0 |
| *D25 | 0 | 0 |
| D26 | 0 | 0 |
| D27 | 0 | 0 |
| D28 | 0 | 0 |
| D29 | 0 | 0 |
| D30 | 0 | 0 |
| D31 | 0 | 0 |
| D32 | 12.8 | 0 |

Experimental Example 22. Identification of Anticancer Effect by Administration of Combination of mGI101 and Anti-PD-L1 Antibody in Mice Transplanted with Mouse-Derived Colorectal Cancer Cells This test was to evaluate the tumor growth inhibitory effect after administration of mGI101 as a test substance alone or in combination with an anti-PD-L1 antibody (BioXcell, Cat #BE0101) as a positive control substance in a tumor model allotransplanted with CT26 cells (murine colon carcinoma cells) into BALB/c mice.

CT26 cells were cultured in RPMI1640 medium (Gibco) containing 10% fetal bovine serum (Gibco) and 1% antibiotic/antifungal agent (Gibco). The cultured cells were harvested using trypsin and then suspended in PBS. In order to establish an allotransplanted tumor model, $5 \times 10^5$ CT26 cells were subcutaneously injected into the right flank of BALB/c female mice (7-week-old).

The mice were randomly assigned based on tumor volume (50 to 120 mm³), each group including 4 mice. The tumor grafts were identified about day 2 after cell inoculation. As shown in Table 7, the test groups were configured and the test substances were administered.

TABLE 7

| Experimental group | | Route of administration, dosing cycle | Dosage amount | Number of animals |
|---|---|---|---|---|
| G1 | Vehicle control (PBS) | i.p. BIW × 9 days | — | 4 |
| G2 | mGI101 | i.v. QW × 9 days | 3 mg/kg | 4 |
| G3 | Anti-PD-L1 antibody (BioXcell, Cat# BE0101) | i.p. BIW × 9 days | 10 mg/kg | 4 |
| G4 | mGI101 + anti-PD-L1 antibody | i.v. QW × 9 days (mGI101) | 3 mg/kg | 4 |
| | | i.p. BIW × 9 days (anti-PD-L1 antibody) | 10 mg/kg | |

Clinical symptoms such as a disease and a behavioral change were observed once a day during the test period, and deceased animals were identified. At the end of the test period, the animals were sacrificed. The size of the CT26 solid cancer was measured using a tumor 3D scanner (TM900, Peria, Belgium). For each experimental group, the average loss and percentage change of body weight and the average tumor growth inhibition were calculated. The anti-tumor efficacy was evaluated as compared with the vehicle control. All statistical calculations were performed using Prism 8.0 (Graph Pad Software Inc, USA). The comparison of tumor volume measurements was made through one-way analysis of variance (at the end of this test) followed by Bonferroni's multiple comparison test. A p value of less than 0.05 was considered significant.

Figure 75:
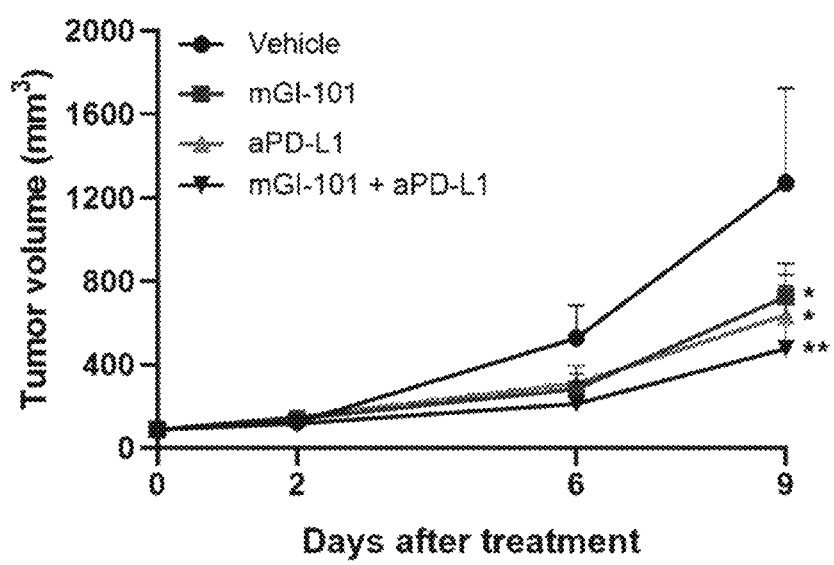
FIG. 75 illustrates a graph of tumor growth when mGI101 and an anti-PD-L1 antibody are administered in combination in mice transplanted with rodent-derived colorectal cancer cells (CT26).

As a result of testing the anti-tumor efficacy of mGI101 alone and in combination with an anti-PD-L1 antibody in the CT26 allotransplanted tumor model, the most excellent anti-tumor efficacy was shown in the group having received the combination (mGI101 (3 mpk)+anti-PD-L1 (10 mpk)) (FIG. 75).

Experimental Example 23. Identification of Anticancer Effect by Administration of Combination of mGI101 and Anti-TIGIT Antibody in Mice Transplanted with Mouse-Derived Colorectal Cancer Cells This test was to evaluate the tumor growth inhibitory effect after administration of mGI101 as a test substance alone or in combination with an anti-TIGIT antibody specifically binding to an extracellular domain (ECD) of TIGIT as a positive control substance in a tumor model allotransplanted with CT26 cells (murine colon carcinoma cells) into BALB/c mice.

CT26 cells were cultured in RPMI1640 medium (Gibco) containing 10% fetal bovine serum (Gibco) and 1% antibiotic/antifungal agent (Gibco). The cultured cells were harvested using trypsin and then suspended in PBS. In order to establish an allotransplanted tumor model, $5 \times 10^5$ CT26 cells were subcutaneously injected into the right flank of BALB/c female mice (7-week-old).

The mice were randomly assigned based on tumor volume (50 to 120 mm³), each group including 5 mice. The tumor grafts were identified about day 2 after cell inoculation. As shown in Table 8, the test groups were configured and the test substances were administered.

TABLE 8

| Experimental group | Route of administration, dosing cycle | Dsage amount | Number of animals |
|---|---|---|---|
| G1 | Vehicle control (PBS) | i.p. BIW × 9 days | — | 5 |
| G2 | mGI101 | i.v. QW × 9 days | 3 mg/kg | 5 |
| G3 | Anti-TIGIT antibody | i.p. BIW × 9 days | 20 mg/kg | 5 |
| G4 | mGI101 + anti-TIGIT antibody | i.v. QW × 9 days (mGI101) | 3 mg/kg | 5 |
| | | i.p. BIW × 9 days (anti-TIGIT antibody) | 20 mg/kg | |

Clinical symptoms such as a disease and a behavioral change were observed once a day during the test period, and deceased animals were identified. At the end of the test period, the animals were sacrificed. The size of the CT26 solid cancer was measured using a tumor 3D scanner (TM900, Peria, Belgium). For each experimental group, the average loss and percentage change of body weight and the average tumor growth inhibition were calculated. The anti-tumor efficacy was evaluated as compared with the vehicle control. All statistical calculations were performed using Prism 8.0 (Graph Pad Software Inc, USA). The comparison of tumor volume measurements was made through one-way analysis of variance (at the end of this test) followed by Bonferroni's multiple comparison test. A p value of less than 0.05 was considered significant.

Figure 76:
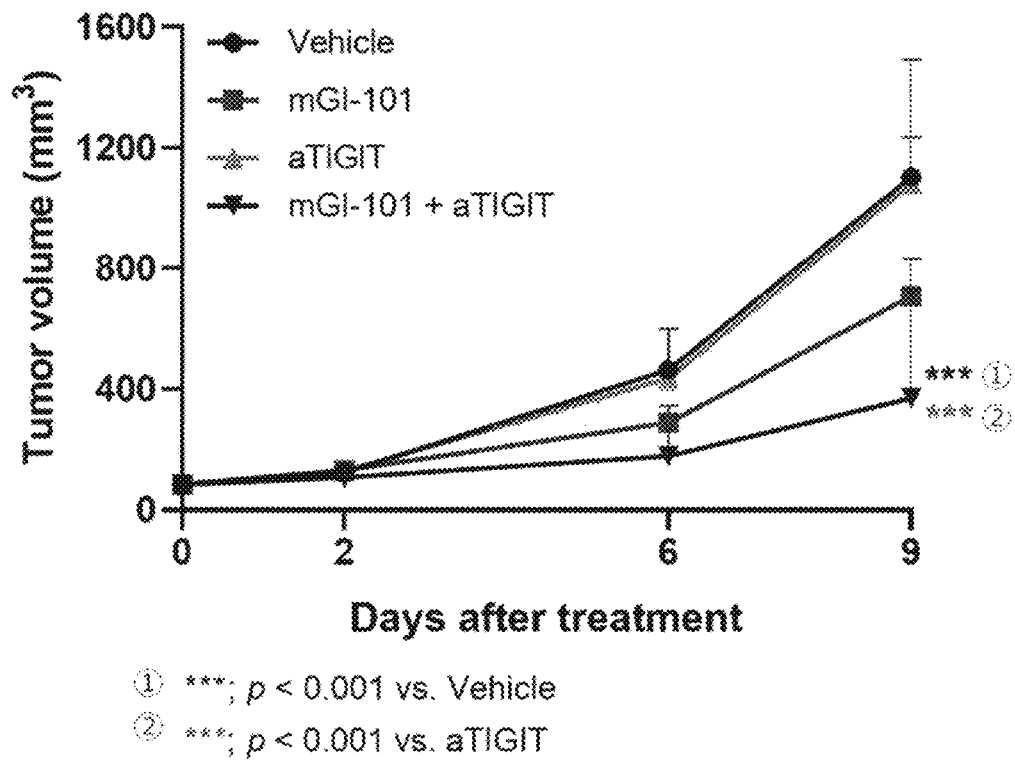
FIG. 76 illustrates a graph of tumor growth when mGI101 and an anti-TIGIT antibody are administered in combination in mice transplanted with rodent-derived colorectal cancer cells (CT26).

As a result of testing the anti-tumor efficacy of mGI101 alone and in combination with an anti-TIGIT antibody in the CT26 allotransplanted tumor model, the most excellent anti-tumor efficacy was shown in the group having received the combination (mGI101 (3 mpk)+anti-TIGIT (20 mpk)) (FIG. 76). No anti-tumor effect was observed in the group having received the anti-TIGIT antibody alone as compared with the control, but the group having received a combination with mGI101 exhibited a remarkably excellent anti-tumor effect as compared with the group having received mGI101 alone.

VI. Identification of Anticancer Effect According to Administration of Combination of Fusion Protein Dimer and TGF-βR Inhibitor

Experimental Example 24. Identification of Anticancer Effect by Administration of Combination of mGI-101 and TGF-βR Inhibitor (Galunisertib) in Mice Transplanted with Mouse-Derived Colorectal Cancer Cells This test was to evaluate the tumor growth inhibitory effect after administration of mGI-101 as a test substance alone or in combination with Galunisertib as a positive control substance in a tumor model allotransplanted with CT26 (mouse colon carcinoma) cells into mice.

The stock solution of the test substance, negative control substance, and positive control substance described in Table 9 was diluted by adding excipients according to each dose.

TABLE 9

| | Test substance | Positive control substance | Negative control substance |
|---|---|---|---|
| Substance name | mGI-101 | Galunisertib | hIgG4 |
| Appearance | clear liquid | clear liquid | clear liquid |
| Component | Fc fusion protein | TGF-β inhibitor | — |
| Excipient | histidine buffer (20 mM), pH 7.0, poloxamer 188 0.07 w/w %, arginine-HCl 15 mg/mL, sucrose 150 mg/mL | 1% CMC (carboxymethylcellulose)-Na | PBS |
| pH | 7.5 | — | — |
| Storage condition | refrigerated storage (4° C.) | refrigerated storage (4° C.) | refrigerated storage (4° C.) |
| Precautions for handling | keep refrigerated until administration, and prepare and use on the day of administration | keep refrigerated until administration, and prepare and use on the day of administration | keep refrigerated until administration, and prepare and use on the day of administration |

Mouse-derived colorectal cancer cells, CT26 (*Mus musculus*, Colon adenocarcinoma), were purchased from ATCC (USA) and used for the test. The cells to be used for the test were thawed, mixed with RPMI1640 (A1049101, Thermofisher scientific) medium containing 10% FBS (fetal bovine serum, Gibco, 10082-147), and then placed in a cell culture flask, and cultured in a 37° C., 5% $CO_2$ incubator. The cells were washed with PBS, and then the cells were isolated using Trypsin-EDTA (15090, Gibco), and centrifugation (125×g, 5 minutes) was performed to discard the supernatant, and then the cells were suspended in a new medium to obtain the cell suspension. The viability of the cells was identified, and then a cell line was prepared by diluting in a medium to a concentration of $5.0 \times 10^6$ cells/mL.

6-week-old male BALB/cAnHsd mice were purchased and used for the test. After the end of the acclimation period of 7 days, the cells were transplanted into healthy animals. The cell suspension ($5 \times 10^6$ cells/mL) was dispensed, and filled into a disposable syringe, and transplantation of the suspension was performed by subcutaneous administration at 0.1 mL/head in the right dorsal region of the animals. General symptoms were observed once a day during the engraftment and growth period after cell line transplantation.

After the inoculation of the cell line was performed, when the tumor size at the site to which the cell line was transplanted reached about 50 mm³, the tumor size of each group was distributed as uniformly as possible according to the tumor size.

As shown in Table 10, the test groups were configured. The test substance was administered orally or intraperitoneally, and administered for 3 weeks depending on the composition of the test group. In the case of oral administration, the animals were fixed with the cervical spine skin fixation method, and administered directly into the stomach using a sonde for oral administration. In the case of intraperitoneal administration, the animals were fixed with the cervical spine skin fixation method, and administered intraperitoneally using a syringe equipped with a 26 gauge needle. The administration rate was not to exceed 200 μl/min.

TABLE 10

| Group | Sex | Administered substance | Frequency of administration | Route of administration | Dosage amount (mg/kg/day) | Dosage volume (mL/kg/day) |
|---|---|---|---|---|---|---|
| G1 | M | Vehicle | 2 times/week | i.p. | — | 5 |
| G2 | M | mGI-101 | 2 times/week | i.p. | 3 | 5 |
| G3 | M | Galunisertib | 3 times/week | p.o. | 75 | 10 |
| G4 | M | mGI-101 | 2 times/week | i.p. | 3 | 5 |
|  |  | Galunisertib | 3 times/week | p.o. | 75 | 10 |

The type of general symptoms including death, the date of onset, and the severity of symptoms were observed once a day during the administration and observation period, and recorded for each subject. Body weight was measured on the day of grouping or on the day of start of administration of the test substance, and thereafter once a week.

The tumor size was measured three times a week for 3 weeks from the day of start of administration of the test substance. The major axis and minor axis of the tumor were measured using a caliper, and the tumor size (tumor volume, TV) was calculated using the following equations.

$$TV\ (mm^3) = (W^2 \times L)/2 \qquad \text{[Equation 1]}$$

The tumor growth inhibition rate was calculated using the tumor size measurement results. The tumor growth inhibition rate was calculated as follows.

$$\%\ TGI\ (\text{Tumor Growth Inhibition}) = (1-(Ti-T0)/(Vi-V0)) \times 100 \qquad \text{[Equation 2]}$$

As a result of measuring the tumor size, the tumor size levels of G2 and G4 on day 4 after the start of administration of the test substance were statistically significantly lower than that of G1 ($p<0.01$, $p<0.001$), and the tumor size levels of G2 and G4 on day 7 after the start of administration of the test substance were statistically significantly lower than that of G1 ($p<0.05$ or $p<0.01$).

Figure 77:
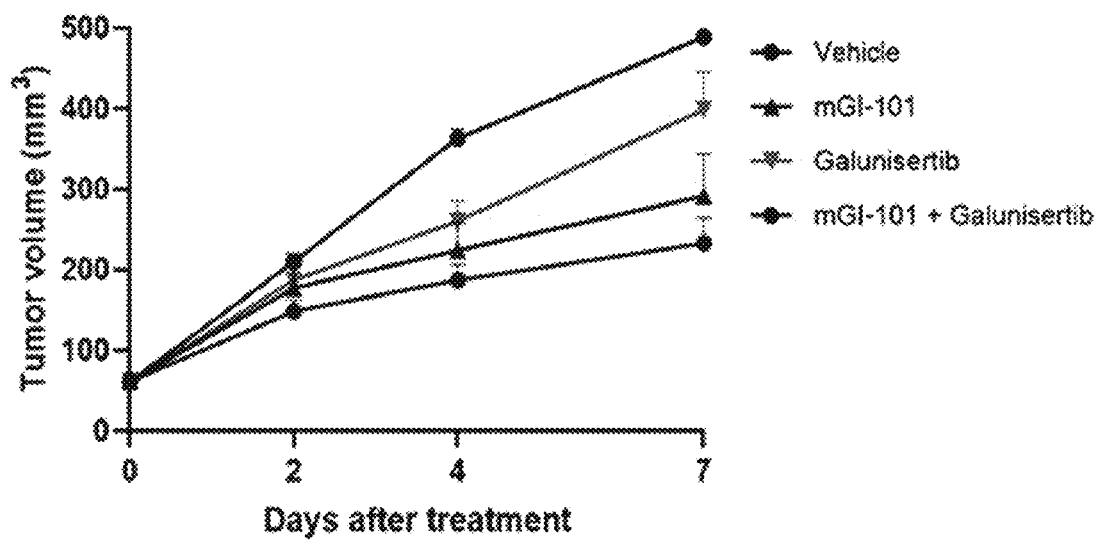
FIG. 77 illustrates a graph of tumor growth when mGI101 and Galunisertib, a TGF-βR inhibitor, are administered in combination in mice transplanted with rodent-derived colorectal cancer cells (CT26).
Figure 79:
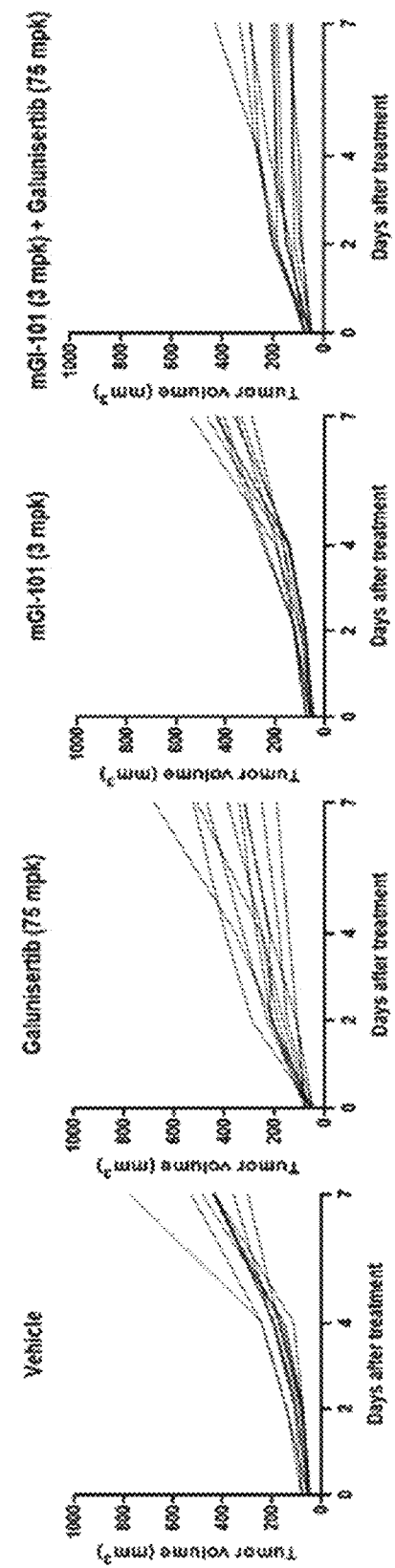
FIG. 79 illustrates the degree of tumor growth of individual experimental animals when mGI101, Galunisertib, a TGF-βR inhibitor, and a combination thereof are administered in mice transplanted with rodent-derived colorectal cancer cells (CT26).

From day 2 to day 7 after the start of administration of the test substance, the tumor size levels of G2 and G4 tended to be lower than that of G1. In addition, until day 7 after the start of administration of the test substance, the tumor size levels of G4 was lower than that of G2 or G3 (FIGS. 77 and 79).

TABLE 11

| | Tumor size | | | Unit: mm³ |
|---|---|---|---|---|
| | Experimental group | | | |
| Day | G1 | G2 | G3 | G4 |
| 0 | 61.97 ± 12.41 | 61.96 ± 11.81 | 61.98 ± 12.23 | 61.98 ± 12.16 |
| 2 | 210.34 ± 32.30 | 177.83 ± 78.22 | 187.20 ± 55.14 | 149.16 ± 43.02 |
| 4 | 363.47 ± 36.18 | 224.56 ± 105.31** | 260.69 ± 78.70 | 187.35 ± 60.13*** |
| 7 | 488.92 ± 81.97 | 291.81 ± 155.23 (9)* | 398.78 ± 146.30 | 232.95 ± 99.73** |
| N | 10 | 10 | 10 | 10 |

The results were expressed as mean ± standard deviation.
N: number of animals,
G1: Vehicle control IP,
G2: mGI-101 3 mg/kg IP,
G3: Galunisertib 75 mg/kg PO,
G4: mGI-101 3 mg/kg IP + Galunisertib 75 mg/kg PO
*//*A significant difference at $p < 0.001$/$p < 0.01$/$p < 0.05$ level compared to the G1

As a result of calculating the tumor growth inhibition rate, from day 4 to day 7 after the start of administration of the test substance, the tumor growth inhibition level of G2 was statistically significantly higher than that of G1. From day 2 to day 7 after the start of administration of the test substance, the tumor growth inhibition level of G4 was statistically significantly higher than that of G1. In addition, on day 7, the tumor growth inhibition level of G4 was statistically significantly higher than that of G3.

Figure 78:
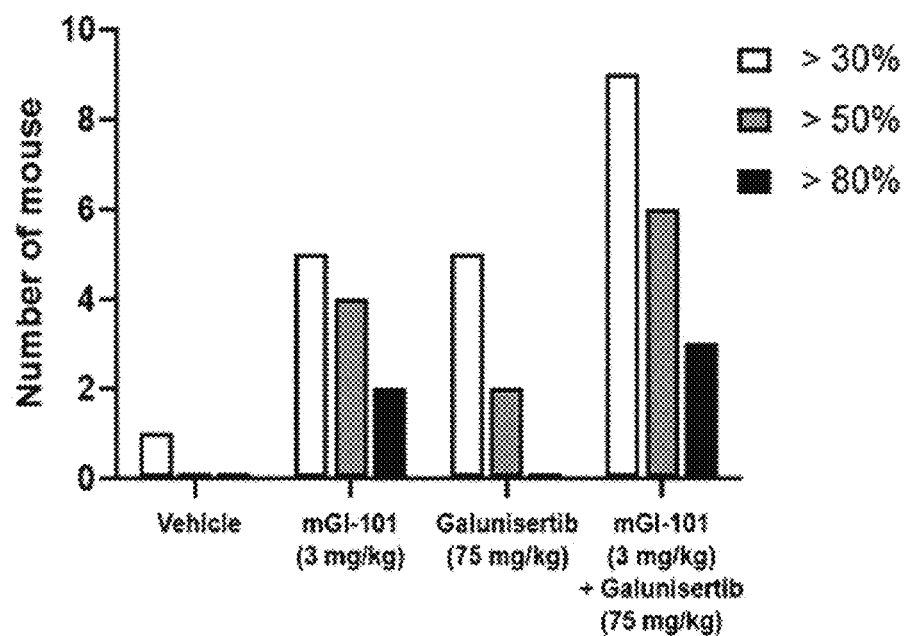
FIG. 78 illustrates a tumor growth inhibition rate when mGI101 and Galunisertib, a TGF-βR inhibitor, are administered in combination in mice transplanted with rodent-derived colorectal cancer cells (CT26).

At the end of the experiment, mice with the tumor growth inhibition rate of 30%, 50%, or 80% or more are as shown in FIG. 78.

TABLE 12

| | Tumor growth inhibition | | | Unit: % |
|---|---|---|---|---|
| | Experimental group | | | |
| Day | G1 | G2 | G3 | G4 |
| 2 | 0.00 ± 20.74 | 21.91 ± 53.41 | 15.60 ± 38.26 | 41.24 ± 25.98* |
| 4 | 0.00 ± 10.50 | 46.07 ± 35.1** | 34.09 ± 27.14 | 58.42 ± 17.88*** |
| 7 | 0.00 ± 19.21 | 46.48 ± 36.39 (9)** | 21.12 ± 34.98 | 59.96 ± 21.45***,$ |
| N | 10 | 10 | 10 | 10 |

The results were expressed as mean ± standard deviation.
N: number of animals,
G1: Vehicle control IP,
G2: mGI-101 3 mg/kg IP,
G3: Galunisertib 75 mg/kg PO,
G4: mGI-101 3 mg/kg IP + Galunisertib 75 mg/kg PO
*//*A significant difference at $p < 0.001/p < 0.01/p < 0.05$ level compared to the G1
$A significant difference at $p < 0.05$ level compared to the G3

Experimental Example 25. Identification of Anticancer Effect by Combination of mGI-101 and TGF-βR Inhibitor (Vactosertib) in Breast Cancer Cell Line This experiment was to evaluate the effect of killing cancer cells by treating MDA-MB-231 cells (human breast cancer cells) with the test substance GI-101 alone or in combination with the TGF-beta signal inhibitor Vactosertib substance in an in vitro environment.

MDA-MB-231 cells were purchased from the Korea cell line bank and cultured in RPMI1640 medium (Gibco) containing 10% FBS (Gibco) and 1% antibiotic/antifungal agent (Gibco). For use in cancer cell killing test, the cells were harvested using trypsin (Gibco), and then suspended in RPMI1640 medium, and then dead cells and debris were removed using Ficoll (GE Healthcare Life Sciences) solution. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was made into a suspension of $2\times10^5$ cells/mL with FBS-free RPMI1640 medium. The cancer cell suspension was stained at 37° C. for 1 hour using CELLTRACKER™ Deep Red Dye (Thermo) in order to track proliferation or inhibition of the proliferation of cancer cells. After staining, it was centrifuged at 1300 rpm for 5 minutes, and then it was washed with FBS-free RPMI1640 medium, and then suspended in RPMI1640 medium containing 5% human AB serum (Sigma) to a concentration of $2\times10^5$ cells/mL. The cancer cell suspension was added to each well of a 96-well microplate (Corning) by 50 μl ($1\times10^4$ cells), and then stabilized in an incubator (37° C., 5% $CO_2$) for 1 hour.

Human peripheral blood mononuclear cells (PBMCs) were used in order to identify the effect of killing cancer cells by GI-101. The human PBMCs were purchased from Zen-Bio, and the PBMCs stored frozen were placed in a 37° C. water bath, and thawed as quickly as possible, and then transferred to RPMI1640 medium (Gibco) containing 10% FBS (Gibco) and 1% antibiotic/antifungal agent (Gibco), and centrifuged at 1300 rpm for 5 minutes. The separated cell layer was suspended in RPMI1640 medium, and then dead cells and debris were removed using Ficoll (GE Healthcare Life Sciences) solution in the same manner as the cancer cell line. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was suspended in RPMI1640 medium containing 5% human AB serum (Sigma) to a concentration of $5\times10^5$ cells/mL. The PBMC suspension was dispensed 50 μl into each well of a 96-well microplate (Corning) in which cancer cell line has been dispensed, depending on the conditions.

In order to identify the effect of killing the cells, a CytoTox Green reagent (INCUCYTE™ CytoTox Green, Satorius) that binds to the DNA of cells to be killed was prepared in 1 μl per 1 mL of RPMI1640 medium containing 5% human AB serum (Sigma). The prepared medium was used for dilution of the test substance, and the effect of killing the cells could be quantitatively identified by staining the cells to be killed when the test substance was co-cultured with cancer cell lines and PBMCs.

Vactosertib power was dissolved in DMSO (Sigma) to a concentration of 48.4 mM, and diluted using RPMI1640 medium containing a CytoTox Green reagent, and then used in the experiment at a final concentration of 12.1 nM (50 μL) per well of a 96-well microplate.

GI-101 was diluted by ⅓ using RPMI1640 medium containing a CytoTox Green reagent, and then used in the experiment at final concentrations of 0.4 nM, 1.2 nM, 3.7 nM, 11.1 nM, 33.3 nM, and 100 nM by 50 μl per well of a 96-well microplate.

The prepared test substance was placed in each well of a 96-well microplate in which cancer cell lines and PBMCs were dispensed depending on the conditions, and cultured in an incubator (37° C., 5% $CO_2$) for 24 hours, and the proliferation or death of cancer cells was observed through the real-time cell imaging analysis equipment IncuCyte S3

(Satorious). The death of cancer cells was quantified by the integrated intensity of the cells stained in green with a CytoTox Green reagent.

As a result, it was identified that the group having received a combination of GI-101 and Vactosertib exhibited the excellent effect of killing cancer cells as compared with the group having received each drug alone.

VII. Identification of Anticancer Effect According to Administration of Combination of Fusion Protein Dimer and VEGFR Inhibitor

Experimental Example 26. Identification of Anticancer Effect by Administration of Combination of mGI-101 and VEGFR Inhibitor (Axitinib)

This test was to evaluate the tumor growth inhibitory effect after administration of mGI-101 as a test substance alone or in combination with Axitinib as a positive control substance in a tumor model allotransplanted with CT26 cells (mouse colon carcinoma) or LL2 cells (mouse lung carcinoma) into mice.

The stock solution of the test substance, negative control substance, and positive control substance described in Table 13 was diluted by adding excipients according to each dose.

TABLE 13

| — | Test substance | Positive control substance | Negative control substance |
|---|---|---|---|
| Substance name | mGI-101 | Axitinib | hIgG4 |
| Appearance | clear liquid | clear liquid | clear liquid |
| Component | Fc fusion protein | VEGFR inhibitor | — |
| Excipient | histidine buffer (20 mM), pH 7.0, poloxamer 188 0.07 w/w %, arginine-HCl 15 mg/mL, sucrose 150 mg/mL | 0.5% CMC (carboxymethylcellulose) | PBS |
| pH | 7.5 | — | — |
| Storage condition | refrigerated storage (4° C.) | refrigerated storage (4° C.) | refrigerated storage (4° C.) |
| Precautions for handling | keep refrigerated until administration, and prepare and use on the day of administration | keep refrigerated until administration, and prepare and use on the day of administration | keep refrigerated until administration, and prepare and use on the day of administration |

Mouse-derived colorectal cancer cells, CT26 (*Mus musculus*, Colon adenocarcinoma), and mouse-derived lung cancer cells, LL/2 (*Mus musculus*, Lung adenocarcinoma), were purchased from ATCC (USA) and used for the test. The cells to be used for the test were thawed, mixed with RPMI1640 (A1049101, Thermofisher scientific) medium containing 10% FBS (fetal bovine serum, Gibco, 10082-147), and then placed in a cell culture flask, and cultured in a 37° C., 5% $CO_2$ incubator. The cells were washed with PBS, and then the cells were isolated using Trypsin-EDTA (15090, Gibco), and centrifugation (125×g, 5 minutes) was performed to discard the supernatant, and then the cells were suspended in a new medium to obtain the cell suspension. The viability of the cells was identified, and then a cell line was prepared by diluting in a medium to a concentration of $5.0 \times 10^6$ cells/mL.

6-week-old male BALB/cAnHsd mice or C57BL/6NHsd mice were purchased and used for the test. After the end of the acclimation period of 7 days, the cells were transplanted into healthy animals. The cell suspension ($5 \times 10^6$ cells/mL) was dispensed, and filled into a disposable syringe, and transplantation of the suspension was performed by subcutaneous administration at 0.1 mL/head in the right dorsal region of the animals. General symptoms were observed once a day during the engraftment and growth period after cell line transplantation.

After the inoculation of the cell line was performed, when the tumor size at the site to which the cell line was transplanted reached about 50 $mm^3$, the tumor size of each group was distributed as uniformly as possible according to the ranked tumor size.

As shown in Table 14, the test groups were configured. The test substance was administered orally or intraperitoneally, and administered for 3 weeks depending on the composition of the test group. In the case of oral administration, the animals were fixed with the cervical spine skin fixation method, and administered directly into the stomach using a sonde for oral administration. In the case of intraperitoneal administration, the animals were fixed with the cervical spine skin fixation method, and administered intraperitoneally using a syringe equipped with a 26 gauge needle. The administration rate was not to exceed 200 μl/min.

TABLE 14

| Group | Sex | Administered substance | Frequency of administration | Route of administration | Dosage amount (mg/kg/day) | Dosage volume (mL/kg/day) |
|---|---|---|---|---|---|---|
| G1 | M | Vehicle | 2 times/week | IP | 3 | 5 |
| G2 | M | mGI-101 | 2 times/week | IP | 3 | 5 |
| G3 | M | Axitinib | 3 times/week | PO | 30 | 10 |
| G4 | M | mGI-101 | 2 times/week | IP | 3 | 5 |
| | | Axitinib | 3 times/week | PO | 30 | 10 |

The tumor size was measured in the same manner as described in Experimental Example 24.

Experimental Example 26.1. Mouse Tumor Model Allotrasplanted with Colorectal Cancer (CT26)

Syngeneic model was prepared by subcutaneously transplanting the CT26 cell line into Balb/c mice, and then the test substance was administered to evaluate the anticancer effect.

Figure 80:
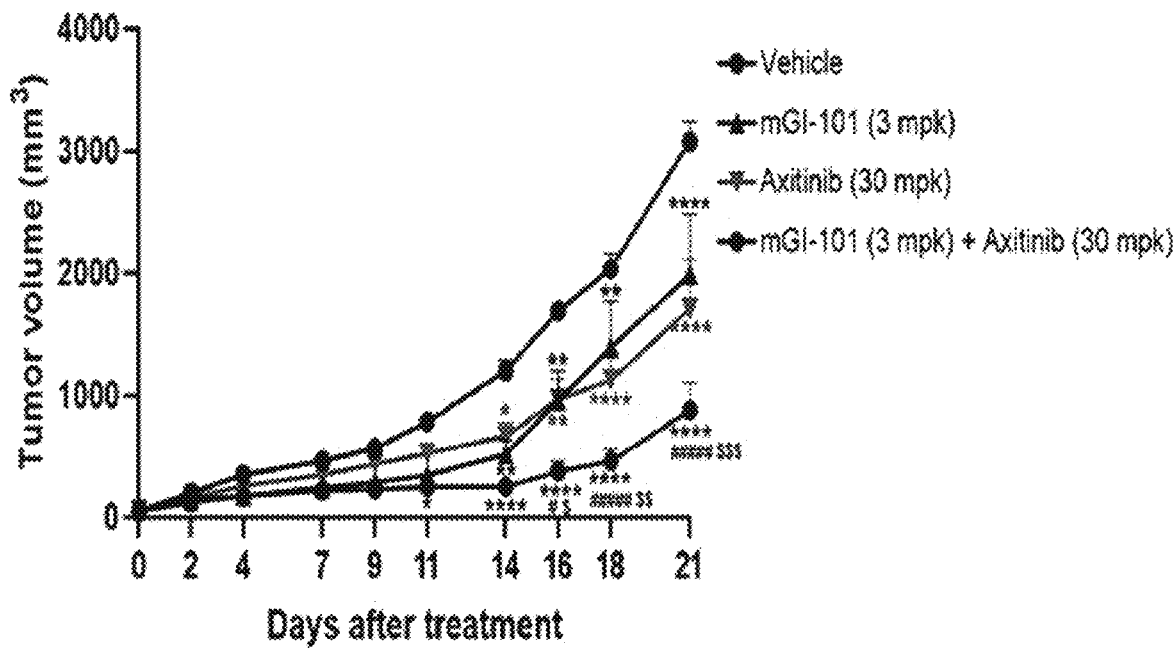
FIG. 80 illustrates a graph of tumor growth when mGI101 and Axitinib, a VEGFR inhibitor, are administered in combination in mice transplanted with rodent-derived colorectal cancer cells (CT26).
Figure 82:
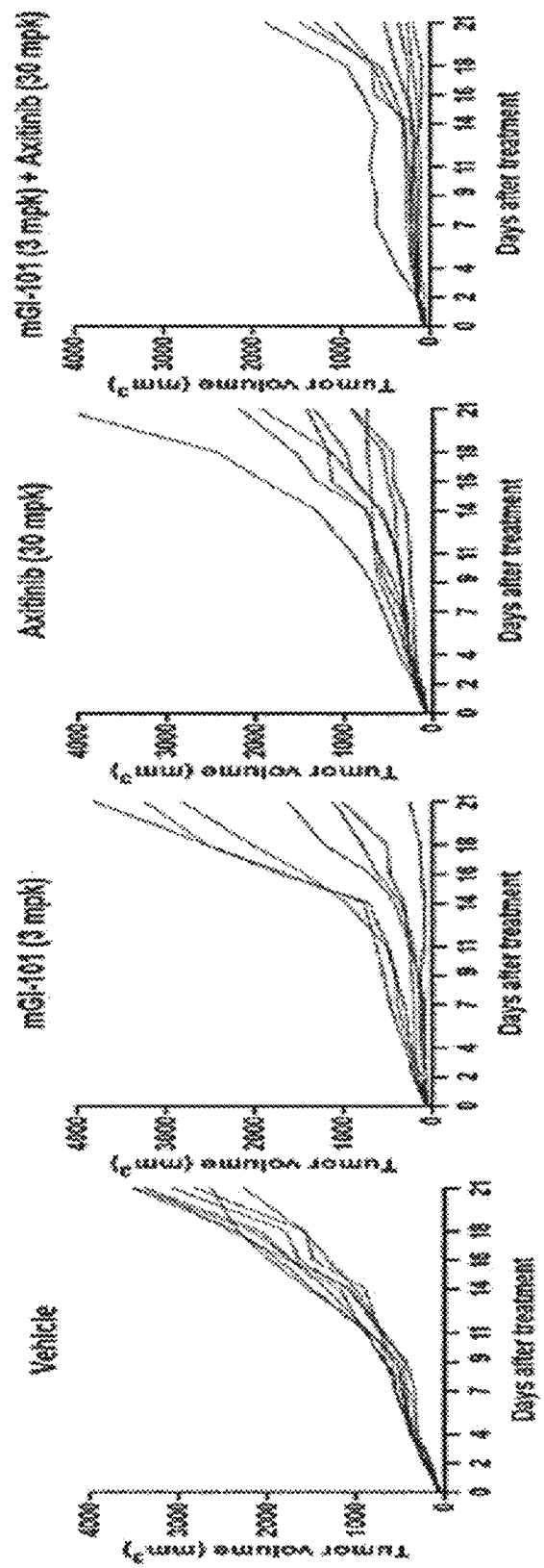
FIG. 82 illustrates the degree of tumor growth of individual experimental animals when mGI101 and Axitinib, a VEGFR inhibitor, are administered in combination in mice transplanted with rodent-derived colorectal cancer cells (CT26).

As a result of measuring the tumor size, the tumor size level of G4 on day 18 and day 21 after the start of administration of the test substance was statistically significantly lower than that of G1 and G2 ($p<0.001$, $p<0.01$, or $p<0.05$). The tumor size level of G4 on day 21 after the start of administration of the test substance was statistically significantly lower than that of G3 ($p<0.01$). In addition, the tumor size level of G3 on day 21 after the start of administration of the test substance was statistically significantly lower than that of G1 and G2 ($p<0.001$, $p<0.01$) (FIGS. 80 and 82).

TABLE 15

| | Tumor size | | | Unit: mm$^3$ |
|---|---|---|---|---|
| | Experimental group | | | |
| Day | G1 | G2 | G3 | G4 |
| 0 | 59.15 ± 11.65 | 63.53 ± 11.56 | 61.67 ± 12.58 | 59.58 ± 11.14 |
| 2 | 205.25 ± 31.92 | 148.98 ± 55.26 | 169.28 ± 32.19 | 127.90 ± 24.99 |
| 5 | 354.24 ± 32.53 | 186.53 ± 76.61 | 261.76 ± 61.86 | 178.53 ± 84.43 |
| 7 | 468.75 ± 75.04 | 249.93 ± 149.08 | 354.05 ± 104.90 | 224.92 ± 158.21 |
| 9 | 573.13 ± 101.41 | 290.71 ± 165.17 | 442.98 ± 148.70 | 235.75 ± 158.35 |
| 12 | 789.72 ± 88.58 | 352.46 ± 195.64 | 529.85 ± 206.76 | 254.91 ± 176.31* |
| 14 | 1206.38 ± 229.96 | 520.04 ± 307.47** | 671.72 ± 303.14* | 254.76 ± 159.31**** |
| 16 | 1693.18 ± 210.83 | 962.28 ± 634.90** | 970.72 ± 475.99** | 381.38 ± 235.37****,#,$ |
| 19 | 2037.27 ± 341.20 | 1395.48 ± 982.61** | 1129.12 ± 639.16**** | 465.02 ± 285.88****,####,$$ |
| 21 | 3082.01 ± 462.37 | 1987.45 ± 1320.62**** | 1710.57 ± 1133.79**** | 880.10 ± 632.96****,####,$$ |
| N | 8 | 8 | 8 | 8 |

The results were expressed as mean ± standard deviation.
N: number of animals,
G1: Vehicle control IP,
G2: mGI-101 3 mg/kg IP,
G3: Axitinib 30 mg/kg PO,
G4: mGI-101 3 mg/kg IP + Axitinib 30 mg/kg PO
**//*A significant difference at $p < 0.0001$/$p < 0.01$/$p < 0.05$ level compared to the Vehicle
/#A significant difference at $p < 0.0001$/$p < 0.05$ level compared to the mGI-101
$$$/$$/$A significant difference at $p < 0.001$/$p < 0.01$/$p < 0.05$ level compared to the Axitinib As a result of calculating the tumor growth inhibition rate, from day 2 to day 21 after the start of administration of the test substance, the tumor growth inhibition levels of G2 and G4 were statistically significantly higher than that of G1 ($p<0.0001$, $p<0.001$, $p<0.01$ or $p<0.05$), and from day 9 to day 14 after the start of administration of the test substance, the tumor growth inhibition level of G4 was statistically significantly higher than that of G3 ($p<0.05$). In addition, on day 19 after the start of administration of the test substance, the tumor growth inhibition level of G4 was statistically significantly higher than that of G2 ($p<0.05$).

Figure 81:
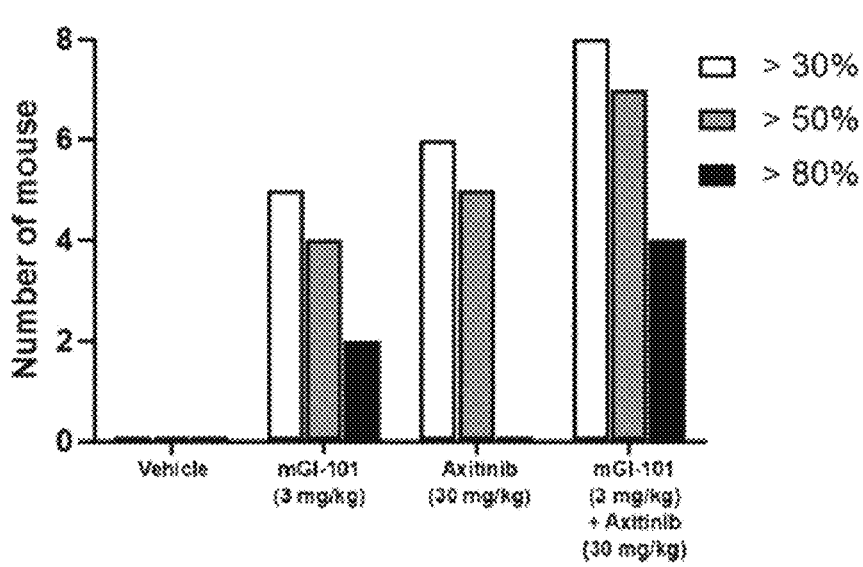
FIG. 81 illustrates a tumor growth inhibition rate when mGI101 and Axitinib, a VEGFR inhibitor, are administered in combination in mice transplanted with rodent-derived colorectal cancer cells (CT26).

At the end of the experiment, mice with the tumor growth inhibition rate of 30%, 50%, or 80% or more are as shown in FIG. 81.

TABLE 16

| | Tumor growth inhibition | | | Unit: % |
|---|---|---|---|---|
| | Experimental group | | | |
| Day | G1 | G2 | G3 | G4 |
| 2 | 0.00 ± 22.76 | 41.51 ± 36.11* | 26.34 ± 20.47 | 53.24 ± 19.71*** |
| 5 | 0.00 ± 10.69 | 58.32 ± 24.95*** | 32.19 ± 18.64 | 59.69 ± 29.99*** |
| 7 | 0.00 ± 19.60 | 62.12 ± 38.89**** | 28.62 ± 24.35 | 59.63 ± 39.68*** |
| 9 | 0.00 ± 20.29 | 62.87 ± 34.95**** | 25.81 ± 27.77 | 65.72 ± 31.54****,#,$ |
| 12 | 0.00 ± 11.98 | 66.48 ± 29.50**** | 35.92 ± 27.44 | 73.26 ± 24.71****,$ |
| 14 | 0.00 ± 20.33 | 65.87 ± 29.12**** | 46.82 ± 25.79** | 82.99 ± 14.19****,$ |
| 16 | 0.00 ± 13.20 | 52.36 ± 41.33** | 44.37 ± 28.66** | 80.31 ± 14.77**** |
| 19 | 0.00 ± 17.31 | 41.48 ± 52.17* | 46.04 ± 31.96** | 79.50 ± 14.72****,# |

TABLE 16-continued

| | Tumor growth inhibition | | | Unit: % |
|---|---|---|---|---|
| | | Experimental group | | |
| Day | G1 | G2 | G3 | G4 |
| 21 | 0.00 ± 15.45 | 44.57 ± 46.55** | 45.45 ± 37.30** | 72.86 ± 21.07**** |
| N | 8 | 8 | 8 | 8 |

The results were expressed as mean ± standard deviation.

N: number of animals,

G1: Vehicle control IP,

G2: mGI-101 3 mg/kg IP,

G3: Axitinib 30 mg/kg PO,

G4: mGI-101 3 mg/kg IP + Axitinib 30 mg/kg PO

**/*/**/*A significant difference at p < 0.0001/p < 0.001/p < 0.01/p < 0.05 level compared to the Vehicle

A significant difference at p < 0.05 level compared to the mGI-101 3 mg/kg $A significant difference at p < 0.05 level compared to the mGI-101 3 mg/kg + Axitinib 30 mg/kg Experimental Example 26.2. Mouse Tumor Model Allotrasplanted Lung Cancer (LL/2)

Syngeneic model was prepared by subcutaneously transplanting the LL/2 cell line into C57BL/6 mice, and then the test substance was administered to evaluate the anticancer effect.

As a result of measuring the tumor size, G3 and G4 maintained a lower tumor size level than that of G1 until the end of the test. In addition, the tumor size level of G4 during the entire test period was the lowest level among all test groups, and the tumor size level of G4 on day 19 after the start of administration of the test substance was statistically significantly lower than that of G1 ($p<0.05$) and G2 ($p<0.01$).

Figure 83:
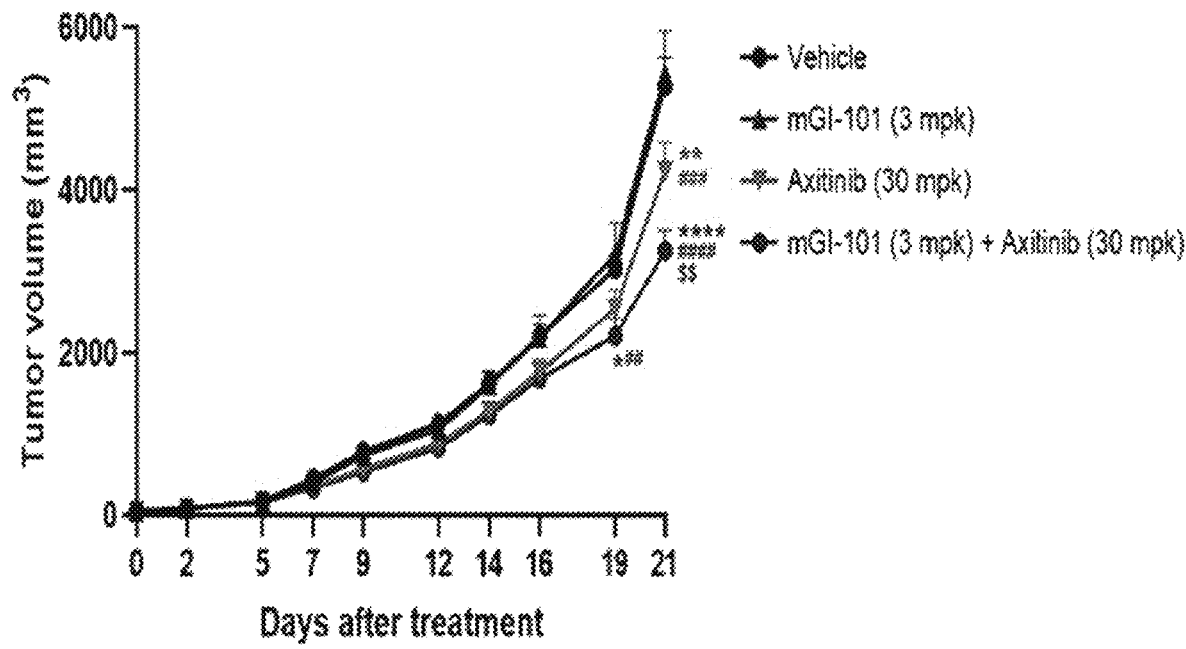
FIG. 83 illustrates a graph of tumor growth when mGI101 and Axitinib, a VEGFR inhibitor, are administered in combination in mice transplanted with rodent-derived lung cancer cells (LL/2).
Figure 85:
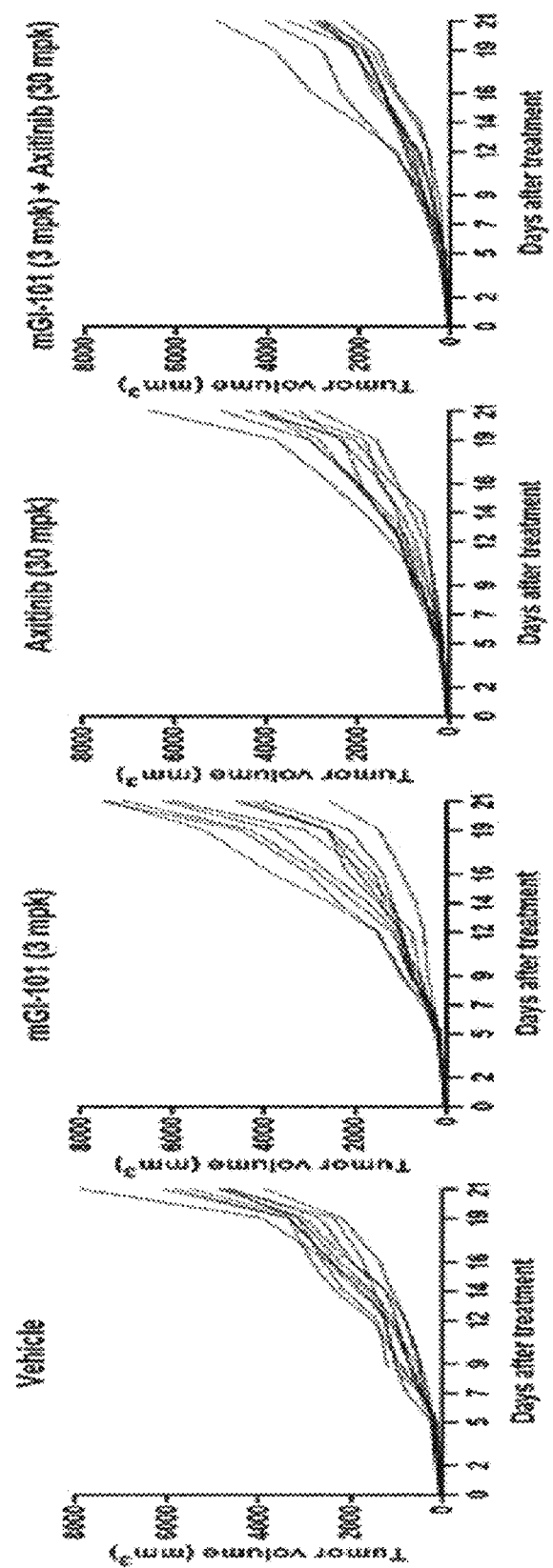
FIG. 85 illustrates the degree of tumor growth of individual experimental animals when mGI101 and Axitinib, a VEGFR inhibitor, are administered in combination in mice transplanted with rodent-derived lung cancer cells (LL/2).

The tumor size level of G4 on day 21 after the start of administration of the test substance was statistically significantly lower than that of all groups of G1 ($p<0.0001$), G2 ($p<0.0001$), and G3 ($p<0.01$). In addition, the tumor size level of G3 on day 21 after the start of administration of the test substance was statistically significantly lower than that of G1 ($p<0.01$) and G2 ($p<0.001$) (FIGS. 83 and 85).

TABLE 17

| | Tumor size | | | Unit: mm³ |
|---|---|---|---|---|
| | | Experimental group | | |
| Day | G1 | G2 | G3 | G4 |
| 0 | 55.75 ± 12.29 | 55.70 ± 11.48 | 55.77 ± 11.25 | 55.73 ± 9.99 |
| 2 | 96.34 ± 25.87 | 99.18 ± 19.96 | 88.73 ± 21.26 | 98.80 ± 24.93 |
| 5 | 181.94 ± 40.25 | 179.58 ± 39.71 | 179.31 ± 52.62 | 179.21 ± 58.26 |
| 7 | 460.71 ± 126.65 | 409.37 ± 72.98 | 362.30 ± 97.92 | 341.77 ± 91.55 |
| 9 | 791.60 ± 247.83 | 749.00 ± 174.47 | 584.17 ± 172.94 | 544.37 ± 155.89 |
| 12 | 1141.58 ± 236.27 | 1066.72 ± 307.18 | 892.90 ± 256.88 | 841.86 ± 267.92 |
| 14 | 1637.35 ± 402.07 | 1608.00 ± 572.50 | 1292.27 ± 385.43 | 1242.66 ± 424.70 |
| 16 | 2219.74 ± 442.05 | 2200.03 ± 850.12 | 1775.26 ± 462.50 (9) | 1693.31 ± 579.80 |
| 19 | 3044.87 ± 518.05 | 3223.87 ± 1191.11 | 2551.08 ± 695.31 (9) | 2215.02 ± 667.76*,## |
| 21 | 5285.56 ± 1120.41 | 5431.08 ± 1673.60 | 4236.33 ± 1060.18 (9)**,## | 3255.38 ± 819.52****,####,$$ |
| N | 10 | 10 | 10 | 10 |

The results were expressed as mean ± standard deviation.

N: number of animals,

G1: Vehicle control IP,

G2: mGI-101 3 mg/kg IP,

G3: Axitinib 30 mg/kg PO,

G4: mGI-101 3 mg/kg IP + Axitinib 30 mg/kg PO

****/*A significant difference at p < 0.0001/p < 0.05 level compared to the Vehicle

/##A significant difference at p < 0.0001/p < 0.01 level compared to the mGI-101 3 mg/kg $$A significant difference at p < 0.01 level compared to the mGI-101 3 mg/kg + Axitinib 30 mg/kg As a result of calculating the tumor growth inhibition rate, the tumor growth inhibition level of G4 on day 19 and day 21 after the start of administration of the test substance was statistically significantly higher than that of G2 ($p<0.01$, $p<0.05$), and the tumor growth inhibition level of G4 on day 21 after the start of administration of the test substance was statistically significantly higher than that of G1 ($p<0.05$). The lowest tumor size level was observed in G4, and the tumor growth inhibition rate also tended to be highest.

Figure 84:
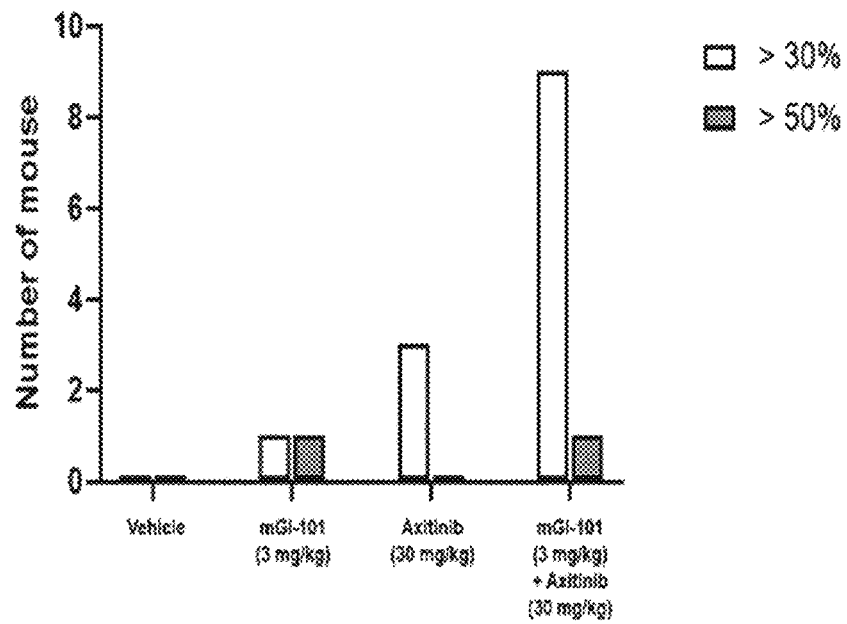
FIG. 84 illustrates a tumor growth inhibition rate when mGI101 and Axitinib, a VEGFR inhibitor, are administered in combination in mice transplanted with rodent-derived lung cancer cells (LL/2).

At the end of the experiment, mice with the tumor growth inhibition rate of 30%, 50%, or 80% or more are as shown in FIG. 84.

TABLE 18

Tumor growth inhibition      Unit: %

| Day | Experimental group | | | |
|---|---|---|---|---|
| | G1 | G2 | G3 | G4 |
| 2 | 0.00 ± 46.91 | −7.12 ± 34.31 | 18.79 ± 28.38 | −6.12 ± 53.19 |
| 5 | 0.00 ± 26.04 | 1.83 ± 27.19 | 2.10 ± 36.27 | 2.15 ± 43.77 |
| 7 | 0.00 ± 29.89 | 12.67 ± 19.15 | 24.30 ± 23.63 | 29.36 ± 21.69* |
| 9 | 0.00 ± 33.79 | 5.78 ± 24.08 | 28.19 ± 23.46 | 33.59 ± 20.83 |
| 12 | 0.00 ± 21.78 | 6.89 ± 28.47 | 22.90 ± 23.42 | 27.60 ± 24.47 |
| 14 | 0.00 ± 25.38 | 1.85 ± 36.39 | 21.82 ± 24.12 | 24.95 ± 26.67 |
| 16 | 0.00 ± 20.30 | 0.91 ± 39.37 | 20.58 ± 21.15 (9) | 24.33 ± 26.59 |
| 19 | 0.00 ± 17.10 | −5.99 ± 39.91 | 16.55 ± 23.06 (9) | 27.76 ± 22.20[#] |
| 21 | 0.00 ± 21.32 | −2.78 ± 32.04 | 20.08 ± 20.18 (9) | 38.82 ± 15.63*,[##] |
| N | 10 | 10 | 10 | 10 |

The results were expressed as mean ± standard deviation.
N: number of animals,
G1: Vehicle control IP,
G2: mGI-101 3 mg/kg IP,
G3: Axitinib 30 mg/kg PO,
G4: mGI-101 3 mg/kg IP + Axitinib 30 mg/kg PO
*A significant difference at $p < 0.05$ level compared to the Vehicle
[##/#]A significant difference at $p < 0.01$/$p < 0.05$ level compared to the mGI-101 3 mg/kg Experimental Example 27. Identification of Anticancer Effect by Administration of Combination of mGI-101 and VEGFR Inhibitor (Lenvatinib)

Experimental Example 27.1. Identification of Anticancer Effect by Administration of Combination of mGI-101 and Lenvatinib in Mice Transplanted with Mouse-Derived Colorectal Cancer Cells This experiment was to evaluate the tumor growth inhibitory effect after administration of mGI-101 as a test substance alone or in combination with Lenvatinib substance in a tumor model allotransplanted with CT26 cells (murine colon carcinoma cells) into BALB/c mice.

CT26 cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco) and then suspended in PBS. In order to establish an allotransplanted tumor model, $1\times10^6$ CT26 cells were subcutaneously injected into the right flank of BALB/c female mice (7-week-old). General symptoms were observed once a day during the engraftment and growth period after cell line transplantation.

A certain period of time after the cell transplantation, the tumor volume was measured for animals with no abnormalities in the health condition of the animals, and the mice were assigned so that the average tumor volume of each group was less than 70-100 mm³, each group including 10 mice. As shown in Table 19, the test groups were configured and the test substances were administered.

In the case of Lenvatinib powder, the dose was calculated and weighed, and it was prepared to the dose concentration using a 0.5% methyl cellulose excipient. In order to minimize the loss of the test substance, the doses for 3 or 4 days were weighed, and prepared using the excipient on the day of administration and injected.

TABLE 19

| Experimental group | | Route of administration | Dosing cycle | Dosage amount | Number of animals |
|---|---|---|---|---|---|
| G1 | Vehicle control (PBS) | i.v. | QW (once/week) | — mg/kg | 10 |
| G2 | mGI-101 | i.v. | QW (once/week) | 3 mg/kg | 10 |
| G3 | Lenvatinib | p.o. | daily | 3 mg/kg | 10 |
| G4 | mGI-101 + Lenvatinib | i.v. + p.o. | mGI-101: QW (once/week), Lenvatinib: daily | 3 mg/kg + 3 mg/kg | 10 |

Clinical symptoms such as a disease and a behavioral change were observed once a day during the test period, and deceased animals were identified, and the mice were sacrificed when the tumor size reached a size of 4,000 mm³. The size of the CT26 solid cancer was measured twice a week during the observation period, and the major axis (maximum length, L) and minor axis (perpendicular width, W) of the tumor were measured using a caliper (Digital caliper, Mitutoyo, Japan), and the tumor volume (TV) and the tumor growth inhibition rate (TGI) were calculated by substituting them into the following equations.

$$TV\ (mm^3) = (W^2 \times L)/2 \quad \text{[Equation 1]}$$

$$\%\ TGI\ (\text{Tumor Growth Inhibition}) = (1-(Ti-T0)/(Vi-V0)) \times 100 \quad \text{[Equation 2]}$$

The tumor volume before administration of each subject was set as the value measured at the time of grouping.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 86:
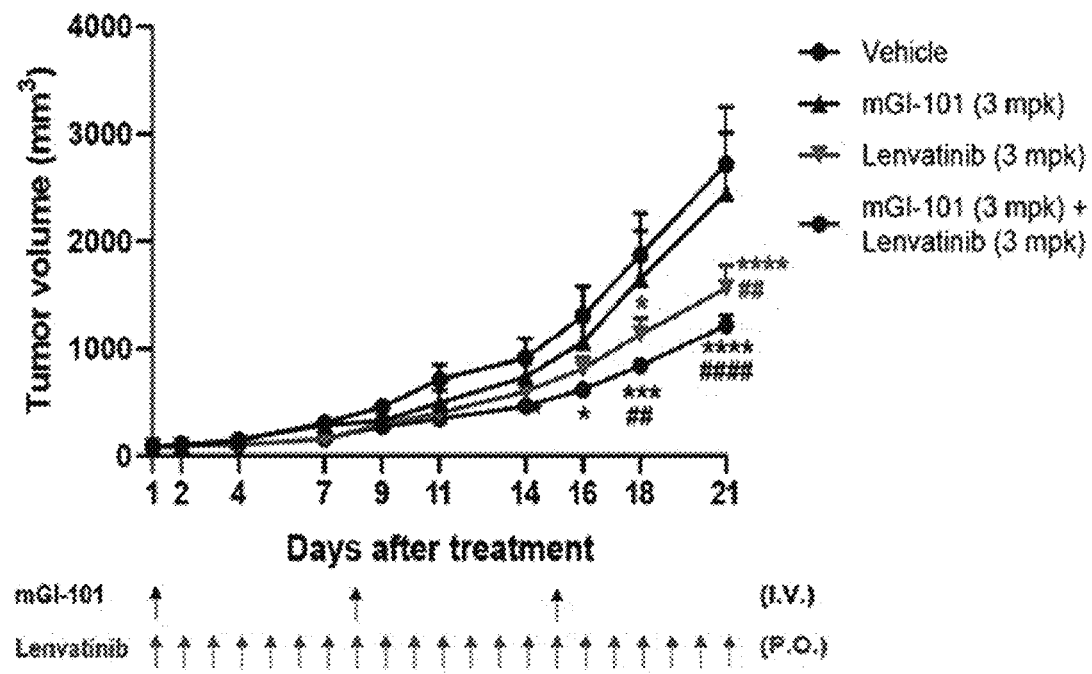
FIG. 86 illustrates a graph of tumor growth when mGI101 and Lenvatinib, a VEGFR inhibitor, are administered in combination in mice transplanted with rodent-derived colorectal cancer cells (CT26).

The results of tumor size upon administration of mGI-101 alone or in combination with Lenvatinib substance against the CT26 tumor are shown in FIG. 86. As a result of measuring the tumor size, as compared with the control, the statistically significant anticancer effect was observed in the group having received Lenvatinib alone and the group having received a combination of mGI-101+Lenvatinib. The tumor size level of the group having received Lenvatinib alone on day 18 and day 21 after the start of administration of the test substance was statistically significantly lower than that of the control (p<0.5, p<0.1). The tumor size level of the group having received a combination of mGI-101+Lenvatinib on day 16, day 18, and day 21 after the start of administration of the test substance was statistically significantly lower than that of the control (p<0.5, p<0.001, p<0.0001), and was statistically significantly lower than that of the group having received mGI-101 alone on day 18 and day 21 (p<0.01, p<0.0001).

Figure 88:
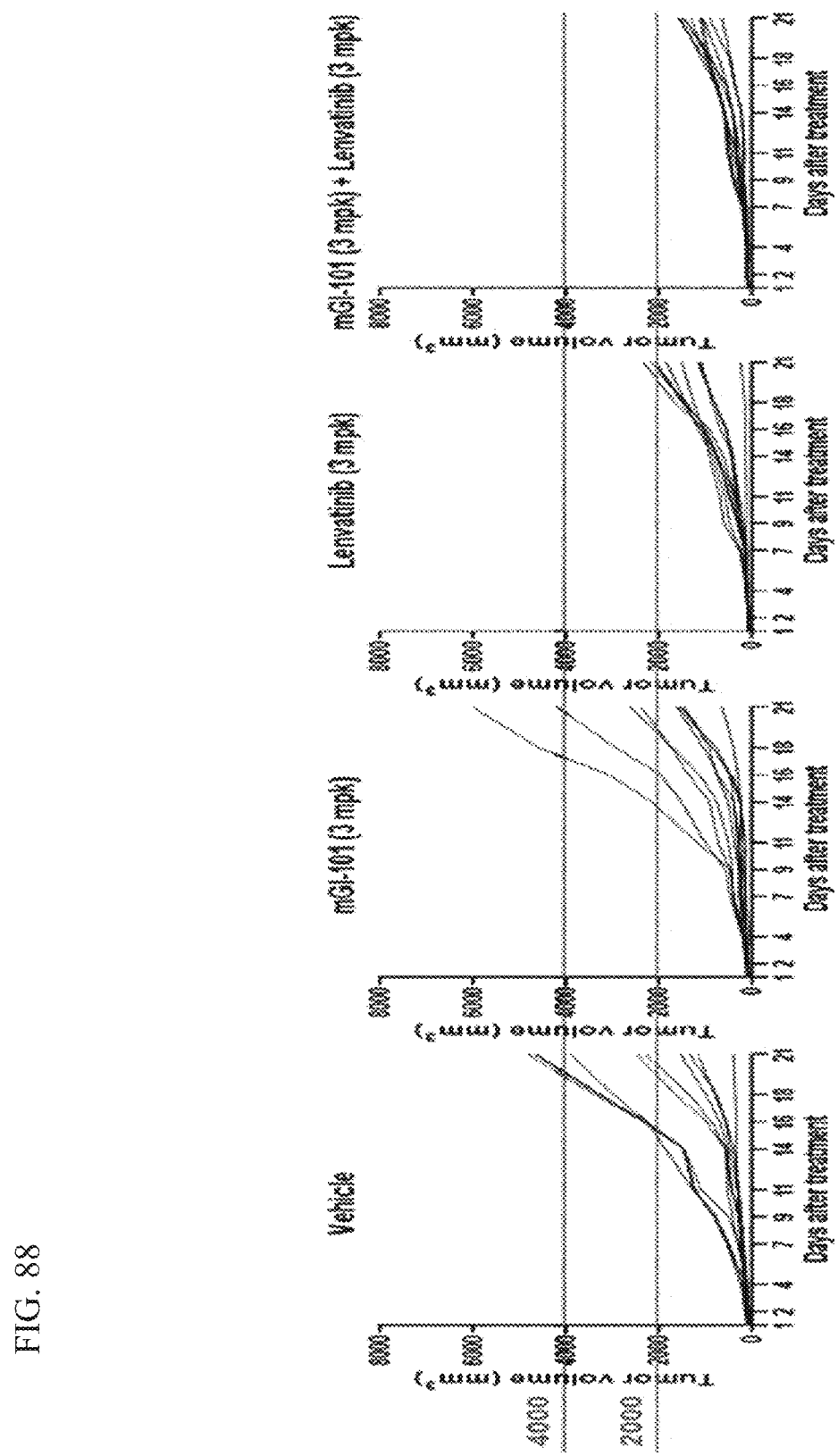
FIG. 88 illustrates the degree of tumor growth of individual experimental animals when mGI101 and Lenvatinib, a VEGFR inhibitor, are administered in combination in mice transplanted with rodent-derived colorectal cancer cells (CT26).

Individual tumor sizes for each test group are shown in FIG. 88. According to the results of individual tumor sizes, the group having received a combination of mGI-101+Lenvatinib exhibited an excellent tumor growth inhibitory effect as compared with the group having received mGI-101 alone.

Figure 87:
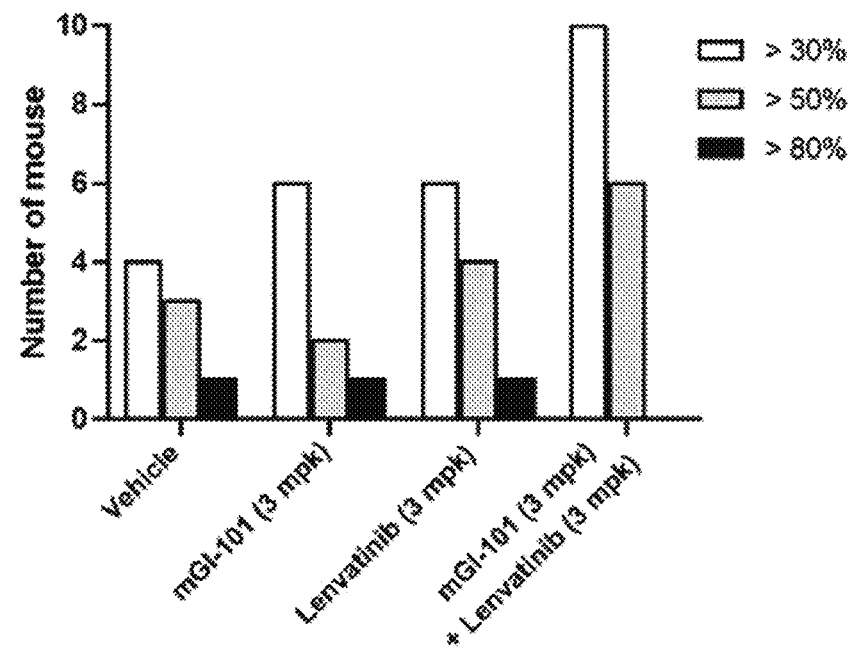
FIG. 87 illustrates a tumor growth inhibition rate when mGI101 and Lenvatinib, a VEGFR inhibitor, are administered in combination in mice transplanted with rodent-derived colorectal cancer cells (CT26).

At the end of the experiment, mice with the tumor growth inhibition rate of 30%, 50%, or 80% or more are as shown in FIG. 87. The vehicle control exhibited a tumor growth inhibition rate of 30% or more in 4 mice, 50% or more in 3 mice, and 80% or more in 1 mouse. The group having received mGI-101 alone exhibited a tumor growth inhibition rate of 30% or more in 6 mice, 50% or more in 2 mice, and 80% or more in 1 mouse. The group having received Lenvatinib alone exhibited a tumor growth inhibition rate of 30% or more in 6 mice, 50% or more in 4 mice, and 80% or more in 1 mouse. The group having received a combination of mGI-101+Lenvatinib exhibited a tumor growth inhibition rate of 30% or more in 10 mice, 50% or more in 6 mice, and 80% or more in no mouse.

Experimental Example 27.2. Identification of Anticancer Effect by Administration of Combination of mGI-101 and Lenvatinib in Mice Transplanted with Mouse-Derived Renal Cancer Cell Line This experiment was to evaluate the tumor growth inhibitory effect after administration of mGI-101 as a test substance alone or in combination with Lenvatinib substance in a tumor model allotransplanted with Renca cells (mouse renal cancer cells) into BALB/c mice.

Renca cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco) and then suspended in PBS. In order to establish an allotransplanted tumor model, $5 \times 10^6$ Renca cells were subcutaneously injected into the back of BALB/c female mice (8-week-old). General symptoms were observed once a day during the engraftment and growth period after cell line transplantation.

A certain period of time after cell inoculation of the tumor grafts of the mice, the tumor volume was measured for animals with no abnormalities in the health condition of the animals, and the mice were randomly selected and assigned, each group including 10 mice. As shown in Table 20, the test groups were configured and the test substances were administered.

TABLE 20

| Experimental group | Route of administration | Dosing cycle | Dosage amount | Number of animals |
|---|---|---|---|---|
| G1 Vehicle control (PBS) | i.p. | QW (once/week) | — mg/kg | 10 |
| G2 mGI-101 | i.p. | BIW (2 times/week) | 3 mg/kg | 10 |
| G3 Lenvatinib | p.o. | daily | 3 mg/kg | 10 |
| G4 mGI-101 + Lenvatinib | i.p. + p.o. | mGI-101: BIW (2 times/week), Lenvatinib: daily | 3 mg/kg + 3 mg/kg | 10 |

The death of the mouse, the type of general symptoms, the date of onset, and the severity of symptoms were observed once a day during the test period, and recorded for each subject. The size of the Renca solid cancer was measured twice a week during the observation period, and the major axis (maximum length, L) and minor axis (perpendicular width, W) of the tumor were measured using a vernier caliper, and the tumor volume (TV) and the tumor growth inhibition rate (TGI) were calculated by substituting them into the following equations.

$$TV\ (mm^3) = (W^2 \times L)/2 \quad \text{[Equation 1]}$$

$$\%\ TGI\ (\text{Tumor Growth Inhibition}) = (1-(Ti-T0)/(Vi-V0)) \times 100 \quad \text{[Equation 2]}$$

The tumor volume before administration of each subject was set as the value measured at the time of grouping, and the anti-tumor efficacy was evaluated as compared with the vehicle control.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 89:
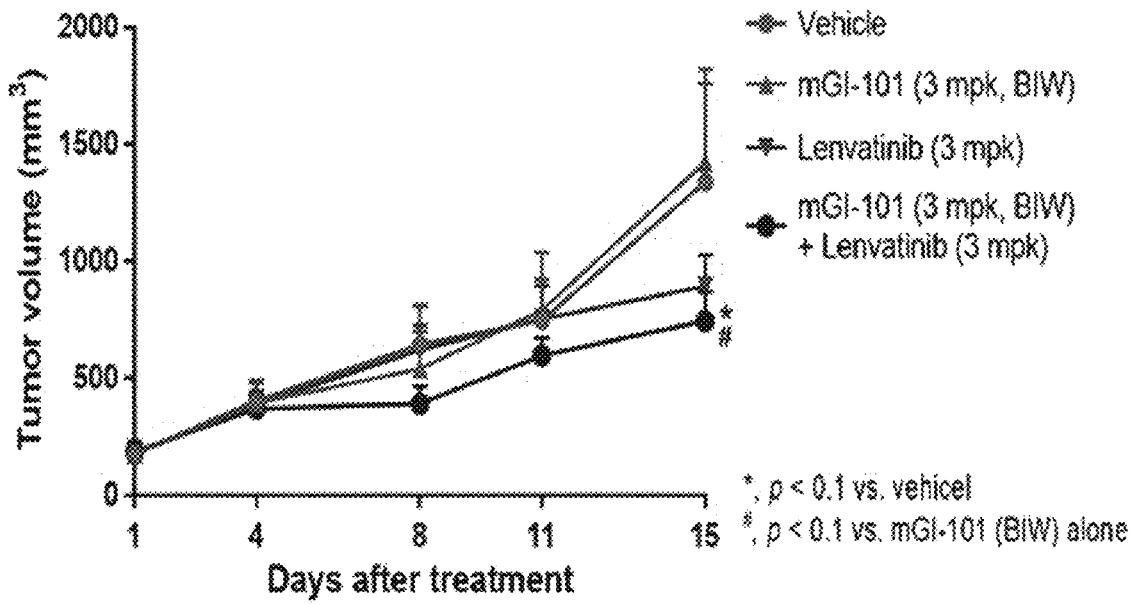
FIG. 89 illustrates a graph of tumor growth when mGI101 and Lenvatinib, a VEGFR inhibitor, are administered in combination in mice transplanted with rodent-derived renal cancer cells (Renca).

The results of tumor size upon administration of mGI-101 alone or in combination with Lenvatinib substance against the Renca tumor are shown in FIG. 89. As a result of measuring the tumor size, the tumor size of the group having received a combination of mGI-101 (BIW)+Lenvatinib on day 15 after the start of administration of the test substance was statistically significantly lower than that of vehicle control and the group having received mGI-101 (BIW) alone ($p<0.05$).

Figure 91:
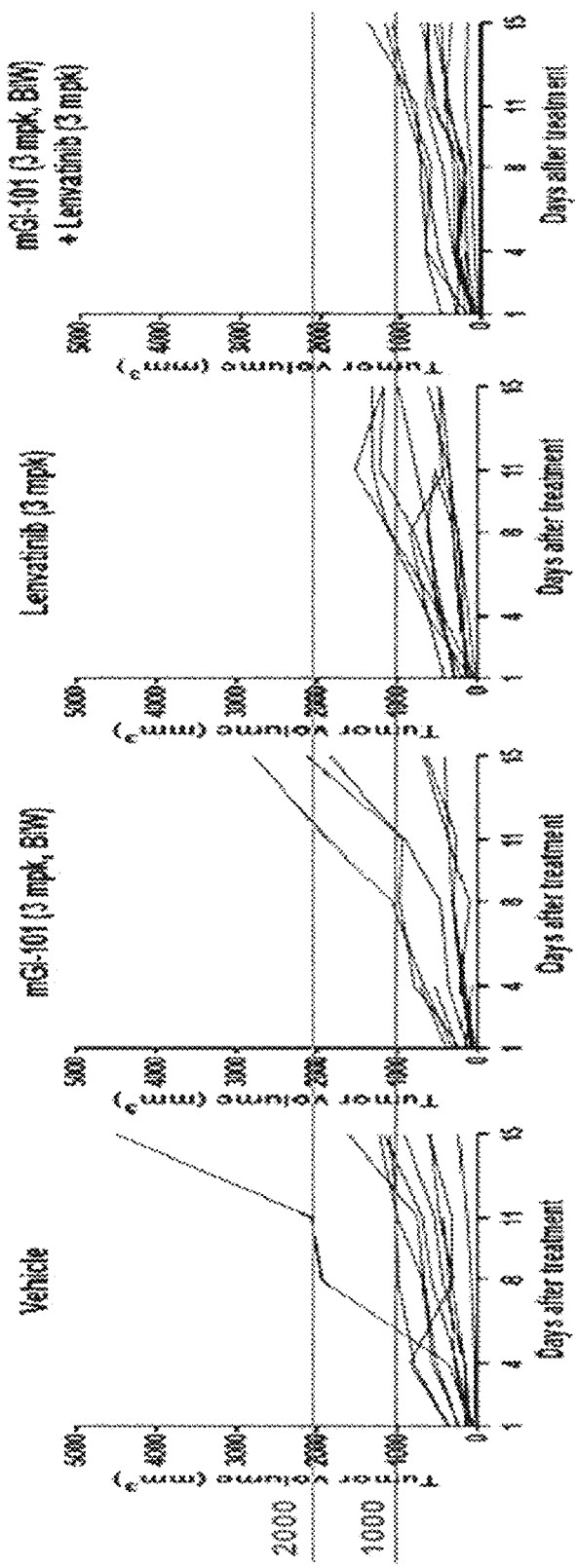
FIG. 91 illustrates the degree of tumor growth of individual experimental animals when mGI101 and Lenvatinib, a VEGFR inhibitor, are administered in combination in mice transplanted with rodent-derived renal cancer cells (Renca).

Individual tumor sizes for each test group are shown in FIG. 91. According to the results of individual tumor sizes, the group having received a combination of mGI-101 (BIW)+Lenvatinib exhibited an excellent tumor growth inhibitory effect.

Figure 90:
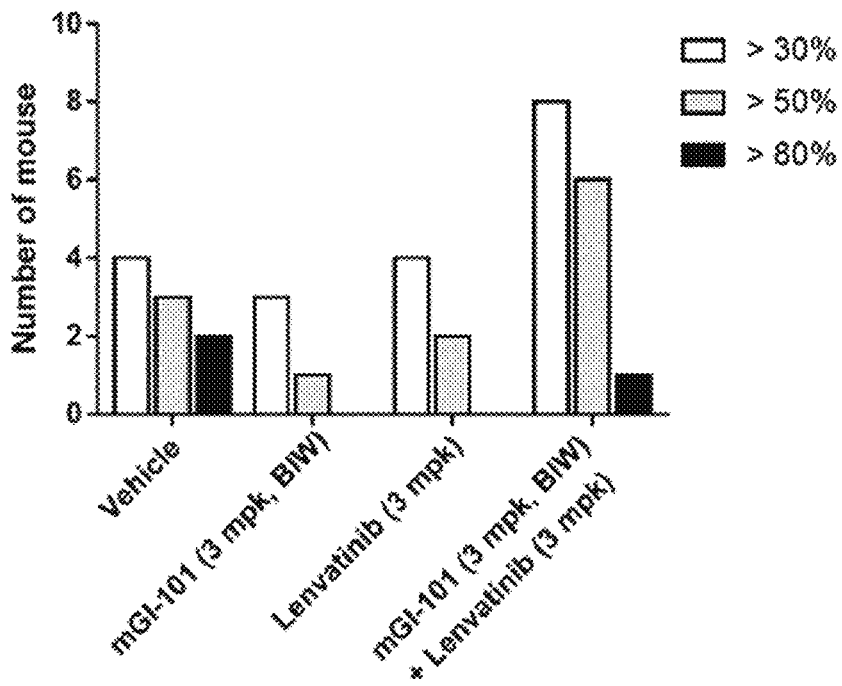
FIG. 90 illustrates a tumor growth inhibition rate when mGI101 and Lenvatinib, a VEGFR inhibitor, are administered in combination in mice transplanted with rodent-derived renal cancer cells (Renca).

FIG. 90 illustrates a tumor growth inhibition rate when mGI-101 and Lenvatinib are administered in combination in mice transplanted with Renca. The vehicle control exhibited a tumor growth inhibition rate of 30% or more in 4 mice, 50% or more in 3 mice, and 80% or more in 2 mice. The group having received mGI-101 alone once a week exhibited a tumor growth inhibition rate of 30% or more in 5 mice, 50% or more in 2 mice, and 80% or more in 1 mouse. The group having received mGI-101 alone twice a week exhibited a tumor growth inhibition rate of 30% or more in 3 mice, 50% or more in 1 mouse, and 80% or more in no mouse. The group having received Lenvatinib alone exhibited a tumor growth inhibition rate of 30% or more in 4 mice, 50% or more in 2 mice, and 80% or more in no mouse. The group having received a combination of mGI-101 (BIW)+Lenvatinib exhibited a tumor growth inhibition rate of 30% or more in 8 mice, 50% or more in 6 mice, and 80% or more in 1 mouse.

VIII. Identification of Anticancer Effect According to Administration of Combination of Fusion Protein Dimer and EGFR Inhibitor

Experimental Example 28. Identification of Anticancer Effect of Combination of mGI-101 and EGFR Inhibitor (Cetuximab)

This experiment was to evaluate the effect of killing cancer cells by treating HCT116 cells (human colon cancer cells) with the test substance GI-101 alone or in combination with Cetuximab substance in an in vitro environment.

HCT116 cells were purchased from the Korea cell line bank and cultured in McCoy's 5A medium (ATCC) containing 10% FBS (Gibco) and 1% antibiotic/antifungal agent (Gibco). For use in cancer cell killing test, the cells were harvested using trypsin (Gibco), and then suspended in McCoy's 5A medium, and then dead cells and debris were removed using Ficoll (GE Healthcare Life Sciences) solution. The cells suspended in McCoy's 5A medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was made into a suspension of $2\times10^5$ cells/mL with FBS-free RPMI1640 medium. The cancer cell suspension was stained at 37° C. for 1 hour using CELLTRACKER™ Deep Red Dye (Thermo) in order to track proliferation of cancer cells or inhibition of the proliferation. After staining, it was centrifuged at 1300 rpm for 5 minutes, and then it was washed with FBS-free RPMI1640 medium, and then suspended in RPMI1640 medium containing 5% human AB serum (Sigma) to a concentration of $2\times10^5$ cells/mL. The cancer cell suspension was added to each well of a 96-well microplate (Corning) by 50 μL ($1\times10^4$ cells), and then stabilized in an incubator (37° C., 5% $CO_2$) for 1 hour.

In order to identify the effect of killing cancer cells through antibody-dependent cellular cytotoxicity (ADCC) by the test substance, natural killer cells (NK cells) were isolated from human peripheral blood mononuclear cells (PBMCs) using a CD56+CD16+NK cell isolation kit (Miltenyi Biotec) and used. In isolated NK cells, dead cells and debris were removed using Ficoll (GE Healthcare Life Sciences) solution in the same manner as the cancer cell line. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was suspended in RPMI1640 medium containing 5% human AB serum (Sigma) to a concentration of $2\times10^5$ cells/mL. The PBMC suspension was dispensed 50 μl into each well of a 96-well microplate (Corning) in which cancer cell line has been dispensed, depending on the conditions.

In order to identify the effect of killing the cells, a CytoTox Green reagent (INCUCYTE™ CytoTox Green, Satorius) that binds to the DNA of cells to be killed was prepared in 1 μl per 1 mL of RPMI1640 medium containing 5% human AB serum (Sigma). The prepared medium was used for dilution of the test substance, and the effect of killing the cells could be quantitatively identified by staining the cells to be killed when the test substance was co-cultured with cancer cell lines and PBMCs.

Cetuximab was diluted using RPMI1640 medium containing a CytoTox Green reagent, and then used in the experiment at a final concentration of 68.6 nM (50 μl) per well of a 96-well microplate. GI-101 was diluted by ⅓ using RPMI1640 medium containing a CytoTox Green reagent, and then used in the experiment at a final concentration 100 nM by 50 μl per well of a 96-well microplate.

The prepared test substance was placed in each well of a 96-well microplate in which cancer cell lines and PBMCs were dispensed depending on the conditions, and cultured in an incubator (37° C., 5% $CO_2$) for 24 hours, and the proliferation or death of cancer cells was observed through the real-time cell imaging analysis equipment IncuCyte S3 (Satorious). The death of cancer cells was quantified by the integrated intensity of the cells stained in green with a CytoTox Green reagent.

Figure 92:
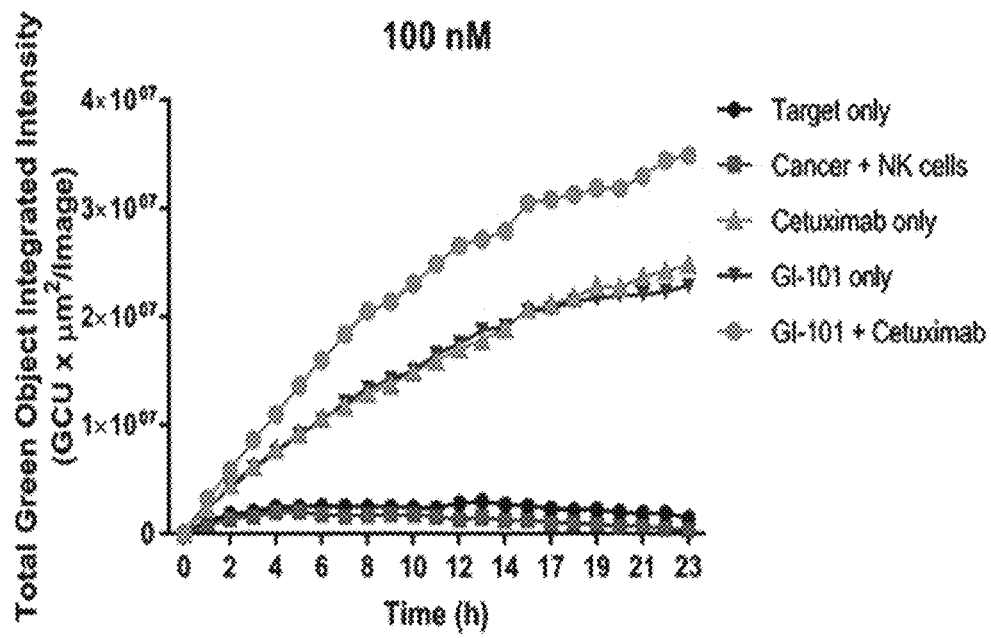
FIG. 92 illustrates the effect of killing cancer cell line when mGI101, Cetuximab as an EGFR inhibitor, and a combination thereof are administered in human-derived colorectal cancer cell line (HCT116).
Figure 93:
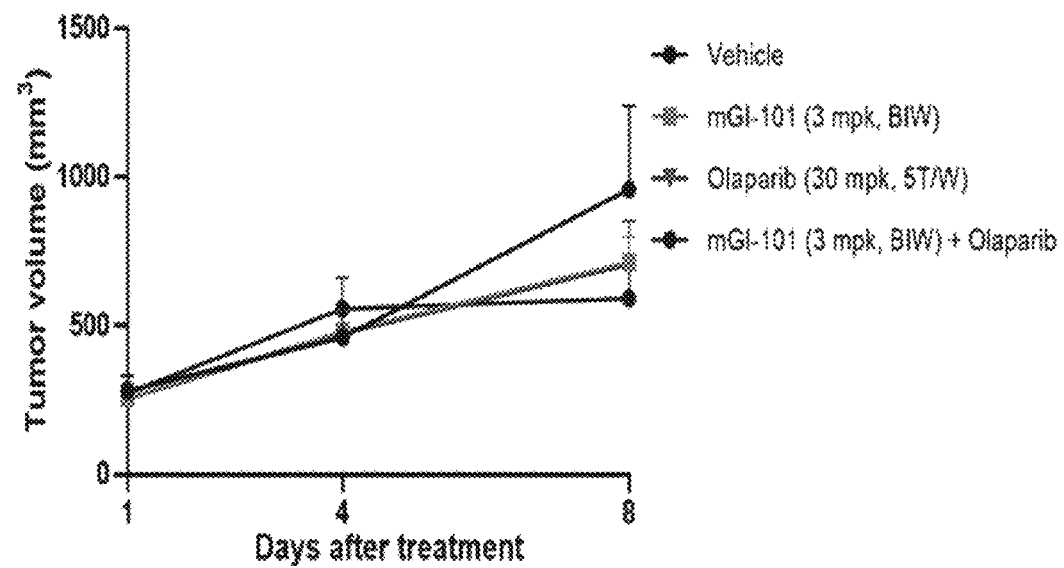
FIG. 93 illustrates a graph of tumor growth when mGI101 and Olaparib, a PARP inhibitor, are administered in combination in mice transplanted with rodent-derived breast cancer cells (4T1).

FIG. 92 illustrates the degree of killing cancer cells measured when the cancer cells were treated with GI-101 at a concentration of 100 nM. All groups having received GI-101 alone, Cetuximab alone, and a combination of GI-101+Cetuximab exhibited a high level of killing cancer cells, and the group having received a combination of GI-101+Cetuximab exhibited the most excellent effect of killing cancer cells.

IX. Identification of Anticancer Effect According to Administration of Combination of Fusion Protein Dimer and PARP Inhibitor

Experimental Example 29. Identification of Anticancer Effect by Administration of Combination of mGI-101 and PARP Inhibitor (Olaparib)

This experiment was to evaluate the tumor growth inhibitory effect after administration of mGI-101 as a test substance alone or in combination with Olaparib, a PARP inhibitor, in a tumor model allotransplanted with 4T1 cells (mouse breast cancer cells) into BALB/c mice.

4T1 cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco) and then suspended in PBS. In order to establish an allotransplanted tumor model, $1\times10^5$ of 4T1 cells were subcutaneously injected into the back of BALB/c female mice (8-week-old). General symptoms were observed once a day during the engraftment and growth period after cell line transplantation.

A certain period of time after cell inoculation of the tumor grafts of the mice, the tumor volume was measured for animals with no abnormalities in the health condition of the animals, and the mice were randomly selected and assigned, each group including 11 mice. As shown in Table 21, the test groups were configured and the test substances were administered.

Clinical symptoms such as a disease and a behavioral change were observed once a day during the test period, and deceased animals were identified, and the mice were sacrificed when the tumor size reached a size of 4,000 mm³. The size of the 4T1 solid cancer was measured twice a week during the observation period, and the major axis (maximum length, L) and minor axis (perpendicular width, W) of the tumor were measured using a caliper (Digital caliper, Mitutoyo, Japan), and the tumor volume (TV) and the tumor growth inhibition rate (TGI) were calculated by substituting them into the following equations.

$$TV\ (mm^3) = (W^2 \times L)/2 \quad \text{[Equation 1]}$$

$$\%\ TGI\ (\text{Tumor Growth Inhibition}) = (1 - (Ti - T0)/(Vi - V0)) \times 100 \quad \text{[Equation 2]}$$

The tumor volume before administration of each subject was set as the value measured at the time of grouping, and the anti-tumor efficacy was evaluated as compared with the vehicle control.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 94:
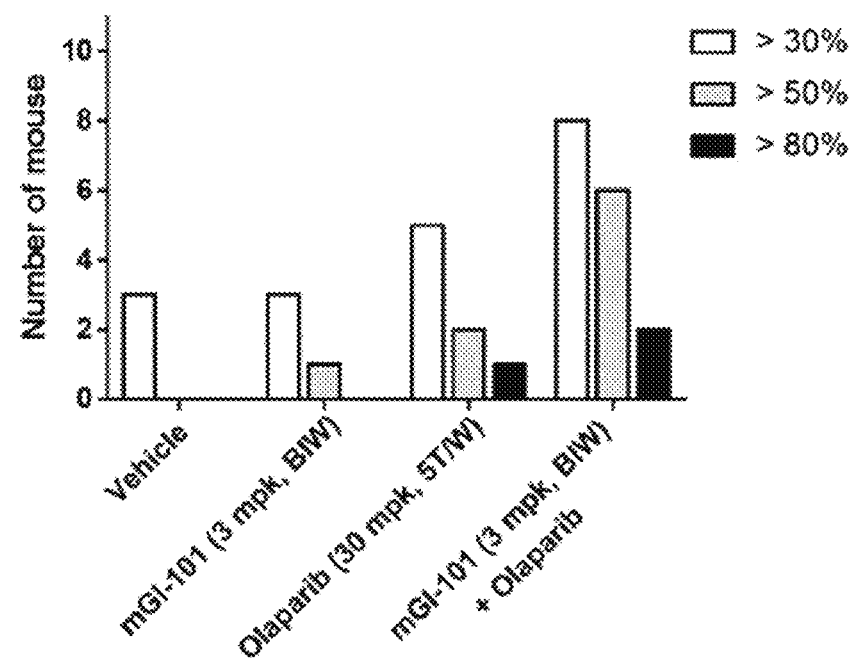
FIG. 94 illustrates a tumor growth inhibition rate when mGI101 and Olaparib, a PARP inhibitor, are administered in combination in mice transplanted with rodent-derived breast cancer cells (4T1).
Figure 95:
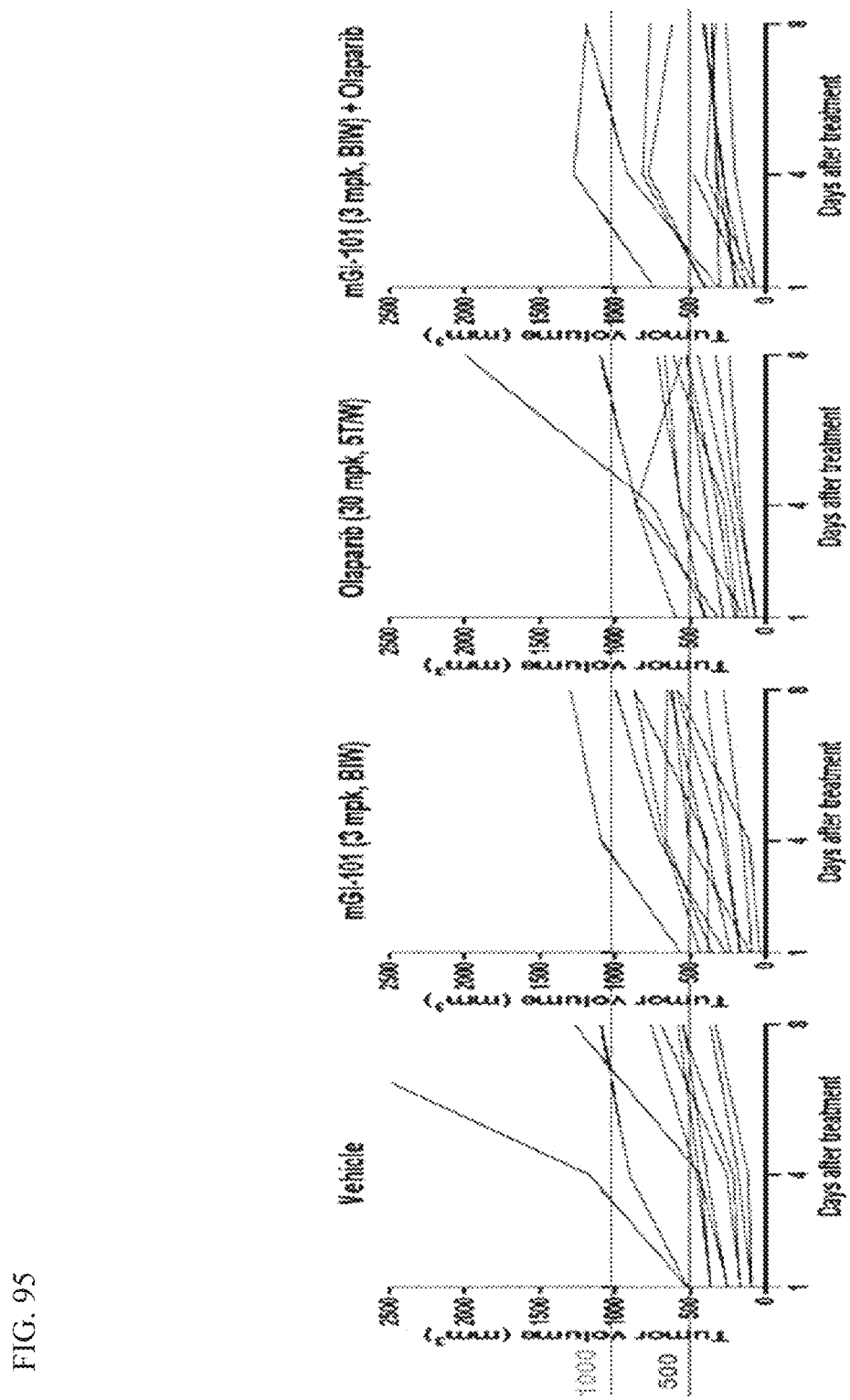
FIG. 95 illustrates the degree of tumor growth of individual experimental animals when mGI101 and Olaparib, a PARP inhibitor, are administered in combination in mice transplanted with rodent-derived breast cancer cells (4T1).
Figure 96:
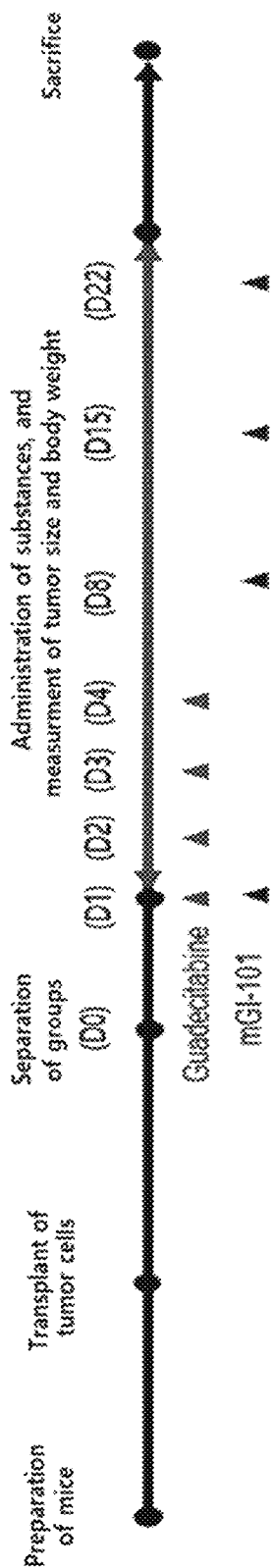
FIG. 96 is a schematic diagram of an experimental schedule for the administration of mGI101 and Guadecitabine, a DNA methyltransferase inhibitor, in combination in mice transplanted with rodent-derived colorectal cancer cells (CT26).

The results of tumor size upon administration of mGI-101 alone or in combination with Olaparib substance against the 4T1 tumor are shown in FIG. 94. As a result of measuring the tumor size, the anticancer effect was observed in the group having received the drug as compared with the control, and according to the results of tumor size levels, the group having received mGI-101 alone and in combination with Olaparib substance exhibited an excellent tumor growth inhibitory effect as compared with the group having received mGI-101 alone.

Experimental Example 30. Identification of Anticancer Effect by Administration of Combination of mGI-101 and PARP Inhibitor (Talazoparib)

This experiment was to evaluate the effect of killing cancer cells by treating MDA-MB-231 cells (human breast cancer cells) with the test substance GI-101 alone or in combination with the PARP inhibitor Talazoparib substance in an in vitro environment.

MDA-MB-231 cells were purchased from the Korea cell line bank and cultured in RPMI1640 medium (Gibco) containing 10% FBS (Gibco) and 1% antibiotic/antifungal agent (Gibco). For use in cancer cell killing test, the cells were harvested using trypsin (Gibco), and then suspended in RPMI1640 medium, and then dead cells and debris were removed using Ficoll (GE Healthcare Life Sciences) solution. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was made into a suspension of $2\times10^5$ cells/mL with FBS-free RPMI1640 medium. The cancer cell suspension was stained at 37° C. for 1 hour using CELLTRACKER™ Deep Red Dye (Thermo) in order to track proliferation of cancer cells or inhibition of the proliferation. After staining, it was centrifuged at 1300 rpm for 5 minutes, and then it was washed with FBS-free RPMI1640 medium, and then suspended in RPMI1640 medium containing 5% human AB serum (Sigma) to a concentration of $2\times10^5$ cells/mL. The cancer cell suspension was added to each well of a 96-well microplate (Corning) by 50 µl ($1\times10^4$ cells), and then stabilized in an incubator (37° C., 5% CO₂) for 1 hour.

Human peripheral blood mononuclear cells (PBMCs) were used in order to identify the effect of killing cancer cells by GI-101. The human PBMCs were purchased from Zen-Bio, and the PBMCs stored frozen were placed in a 37° C. water bath, and thawed as quickly as possible, and then

TABLE 21

| Experimental group | Route of administration | Dosing cycle | Dosage amount | Number of animals |
| --- | --- | --- | --- | --- |
| G1 Vehicle control (PBS) | i.p. | QW (once/week) | — mg/kg | 11 |
| G2 mGI-101 | i.p. | BIW (2 times/week) | 3 mg/kg | 11 |
| G3 Olaparib | P.O. | 5 times/week | 30 mg/kg | 11 |
| G4 mGI-101 + Olaparib | i.p. + P.O. | mGI-101: BIW (2 times/week), Olaparib: 5 times/week | 3 mg/kg + 30 mg/kg | 11 | transferred to RPMI1640 medium (Gibco) containing 10% FBS (Gibco) and 1% antibiotic/antifungal agent (Gibco), and centrifuged at 1300 rpm for 5 minutes. The separated cell layer was suspended in RPMI1640 medium, and then dead cells and debris were removed using Ficoll (GE Healthcare Life Sciences) solution in the same manner as the cancer cell line. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was suspended in RPMI1640 medium containing 5% human AB serum (Sigma) to a concentration of $5 \times 10^5$ cells/mL. The PBMC suspension was dispensed 50 μl into each well of a 96-well microplate (Corning) in which cancer cell line has been dispensed, depending on the conditions.

In order to identify the effect of killing the cells, a CytoTox Green reagent (INCUCYTE™ CytoTox Green, Satorius) that binds to the DNA of cells to be killed was prepared in 1 μl per 1 mL of RPMI1640 medium containing 5% human AB serum (Sigma). The prepared medium was used for dilution of the test substance, and the effect of killing the cells could be quantitatively identified by staining the cells to be killed when the test substance was co-cultured with cancer cell lines and PBMCs.

Talazoparib test substance was diluted using RPMI1640 medium containing a CytoTox Green reagent, and then used in the experiment at a final concentration of 0.57 nM (50 μl) per well of a 96-well microplate. GI-101 was diluted by ⅓ using RPMI1640 medium containing a CytoTox Green reagent, and then used in the experiment at final concentrations of 0.4 nM, 1.2 nM, 3.7 nM, 11.1 nM, 33.3 nM, and 100 nM by 50 μl per well of a 96-well microplate.

The prepared test substance was placed in each well of a 96-well microplate in which cancer cell lines and PBMCs were dispensed depending on the conditions, and cultured in an incubator (37° C., 5% $CO_2$) for 24 hours, and the proliferation or death of cancer cells was observed through the real-time cell imaging analysis equipment IncuCyte S3 (Satorious). The death of cancer cells was quantified by the integrated intensity of the cells stained in green with a CytoTox Green reagent.

As a result, it was identified that the group having received a combination of GO-101 and Talazoparib exhibited the excellent effect of killing cancer cells as compared with the group having received each drug alone.

X. Identification of Anticancer Effect According to Administration of Combination of Fusion Protein Dimer and DNA Methyltransferase Inhibitor

Experimental Example 31. Identification of Anticancer Effect by Administration of Combination of mGI-101 and Guadecitabine in Mice Transplanted with Mouse-Derived Colorectal Cancer Cells This experiment was to evaluate the tumor growth inhibitory effect after administration of mGI-101 as a test substance alone or in combination with Guadecitabine substance that inhibits DNA methylation in a tumor model allotransplanted with CT26 cells (murine colon carcinoma cells) into BALB/c mice.

Figure 97:
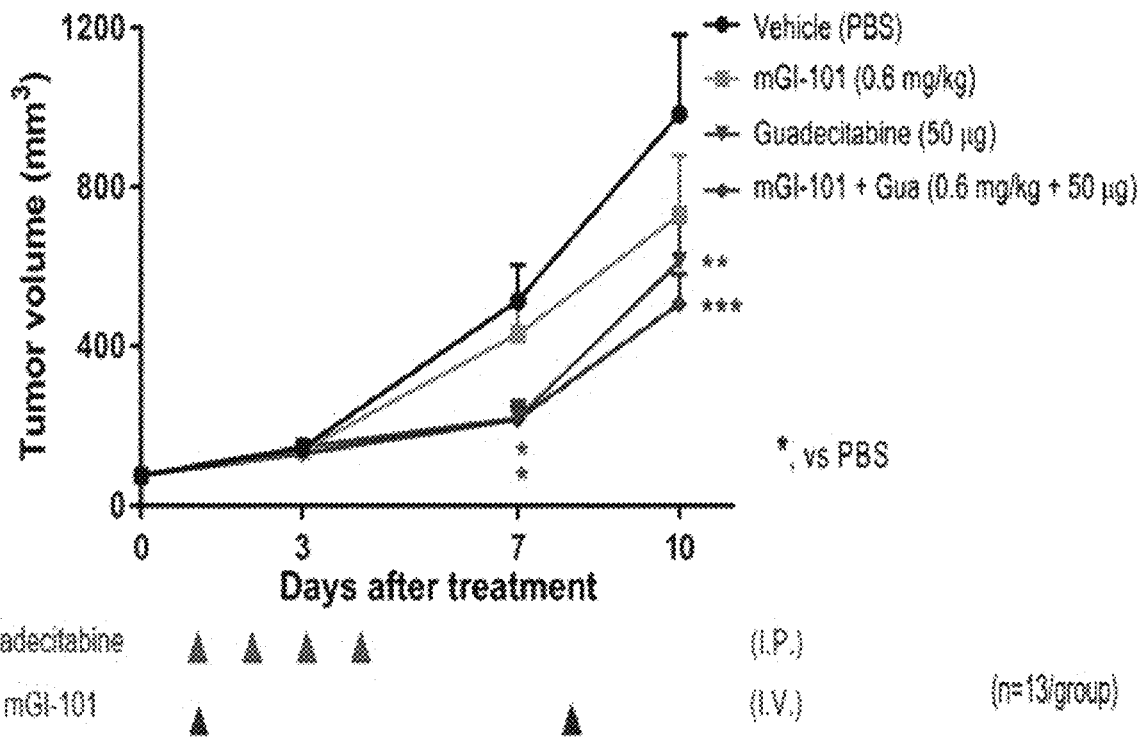
FIG. 97 illustrates a graph of tumor growth when mGI101 (0.6 mpk) and Guadecitabine, a DNA methyltransferase inhibitor, are administered in combination in mice transplanted with rodent-derived colorectal cancer cells (CT26).
Figure 98:
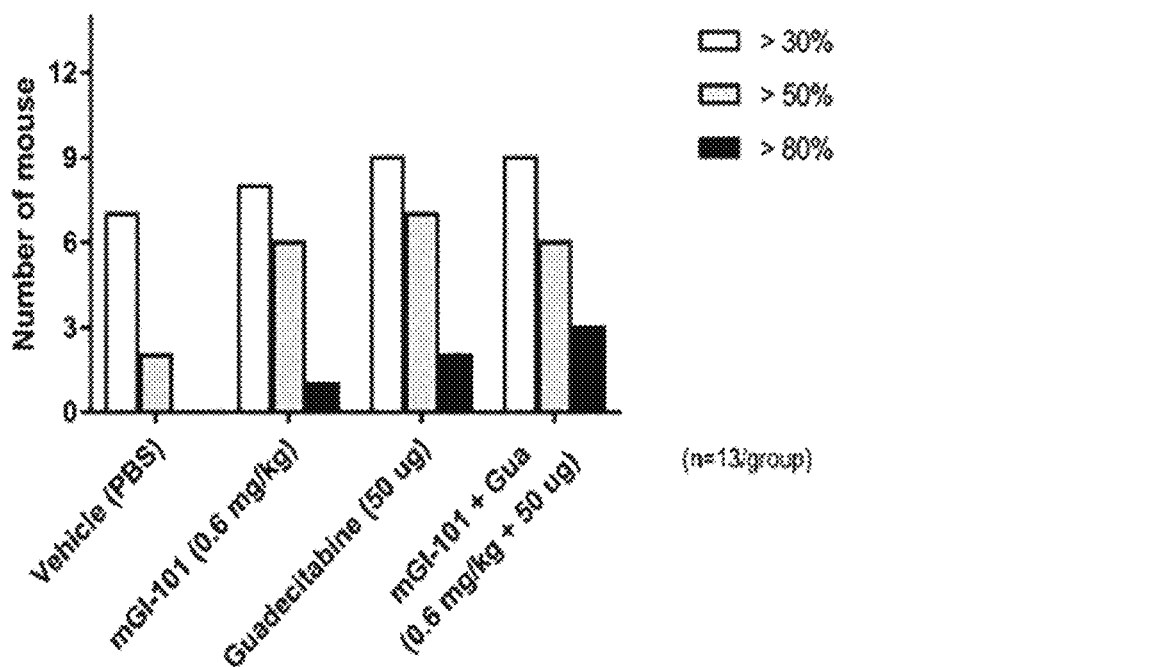
FIG. 98 illustrates a tumor growth inhibition rate when mGI101 (0.6 mpk) and Guadecitabine, a DNA methyltransferase inhibitor, are administered in combination in mice transplanted with rodent-derived colorectal cancer cells (CT26).

CT26 cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco) and then suspended in PBS. In order to establish an allotransplanted tumor model, $5 \times 10^5$ of CT26 cells were subcutaneously injected into the right flank of BALB/c female mice (8-week-old) (FIG. 97).

The tumor grafts of the mice were identified about day 7 after cell inoculation, and the mice were randomly assigned based on tumor volume (50-120 mm$^3$), each group including 13 mice. As shown in Table 22, the test groups were configured and the test substances were administered.

TABLE 22

| | Experimental group | Route of administration | Dosing cycle | Dosage amount | Number of animals |
|---|---|---|---|---|---|
| G1 | Vehicle control (PBS) | i.p. | QW (once/week) | — mg/kg | 13 |
| G2 | mGI-101 | i.v. | QW (once/week) | 0.6 mg/kg | 13 |
| G3 | mGI-101 | i.v. | QW (once/week) | 3 mg/kg | 13 |
| G4 | Guadecitabine | i.p. | total 4 times, 4 consecutive days | 50 μg | 13 |
| G5 | mGI-101 + Guadecitabine | i.v. + i.p. | mGI-101: QW (once/week), | 0.6 mg/kg + 50 μg | 13 |
| G6 | mGI-101 + Guadecitabine | i.v. + i.p. | Guadecitabine: total 4 times, 4 consecutive days | 3 mg/kg + 50 ng | 13 |

Clinical symptoms such as a disease and a behavioral change were observed once a day during the test period, and deceased animals were identified, and the mice were sacrificed when the tumor size reached a size of 4,000 mm$^3$. The size of the CT26 solid cancer was measured using a tumor 3D scanner (TM900, Peria, Belgium). For each experimental group, the average loss and percentage change of body weight and the average tumor growth inhibition were calculated. The anti-tumor efficacy was evaluated as compared with the vehicle control. All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 100:
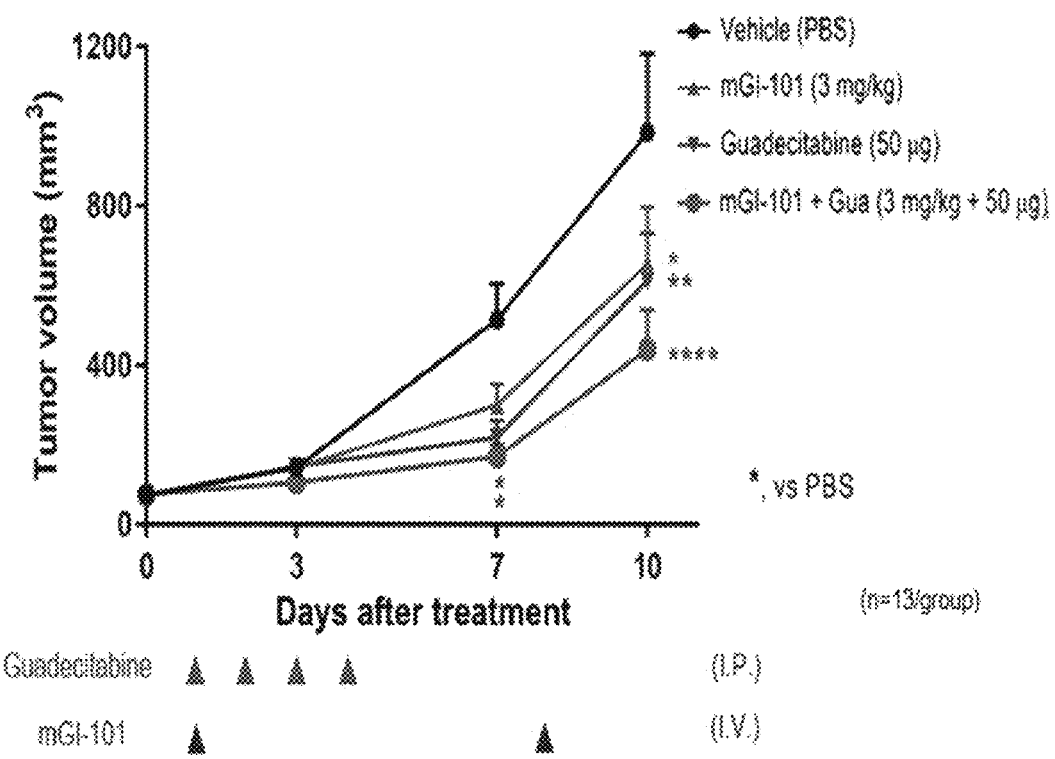
FIG. 100 illustrates a graph of tumor growth when mGI101 (3 mpk) and Guadecitabine, a DNA methyltransferase inhibitor, are administered in combination in mice transplanted with rodent-derived colorectal cancer cells (CT26).

The results of tumor size upon administration of mGI-101 alone or in combination with Guadecitabine substance against the CT26 tumor are shown in FIGS. 97 and 100. As a result of measuring the tumor size, the anticancer effect was observed in the group having received the drug as compared with the control, and the group having received a combination of mGI-101 and Guadecitabine exhibited a more excellent tumor growth inhibitory effect as compared with the group having received mGI-101 alone. The tumor size of the group having received a combination of mGI-101 (3 mg/kg)+Guadecitabine on day 7 after the start of administration of the test substance was statistically significantly lower than that of the control ($p<0.05$). On day 10 after the start of administration of the test substance, the tumor size level of the group having received mGI-101 (0.6 mg/kg) alone tended to be lower than that of the control, and the tumor size level of the group having received mGI-101 (3 mg/kg) alone was statistically significantly lower than that of the control ($p<0.05$). The tumor size levels of the group having received a combination of mGI-101 (0.6 mg/kg)+Guadecitabine and the group having received a combination of mGI-101 (3 mg/kg)+Guadecitabine were statistically significantly lower than that of the control ($p<0.01$, $p<0.001$).

Figure 99:
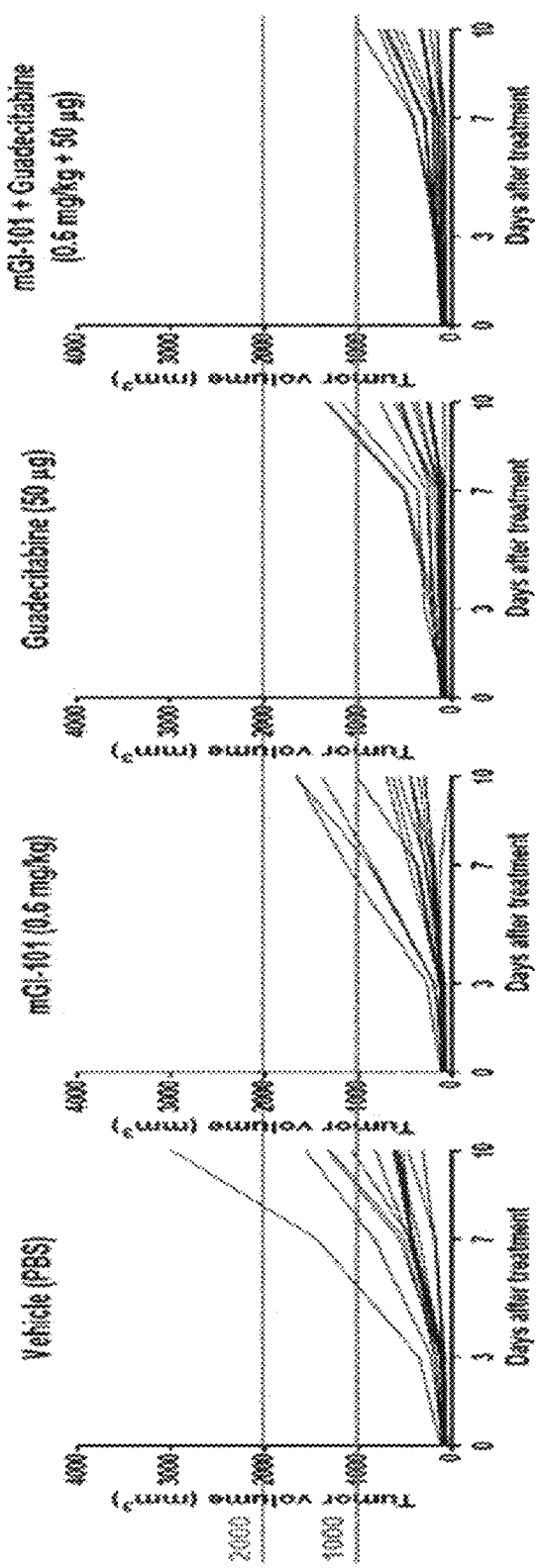
FIG. 99 illustrates the degree of tumor growth of individual experimental animals when mGI101 (0.6 mpk) and Guadecitabine, a DNA methyltransferase inhibitor, are administered in combination in mice transplanted with rodent-derived colorectal cancer cells (CT26).
Figure 102:
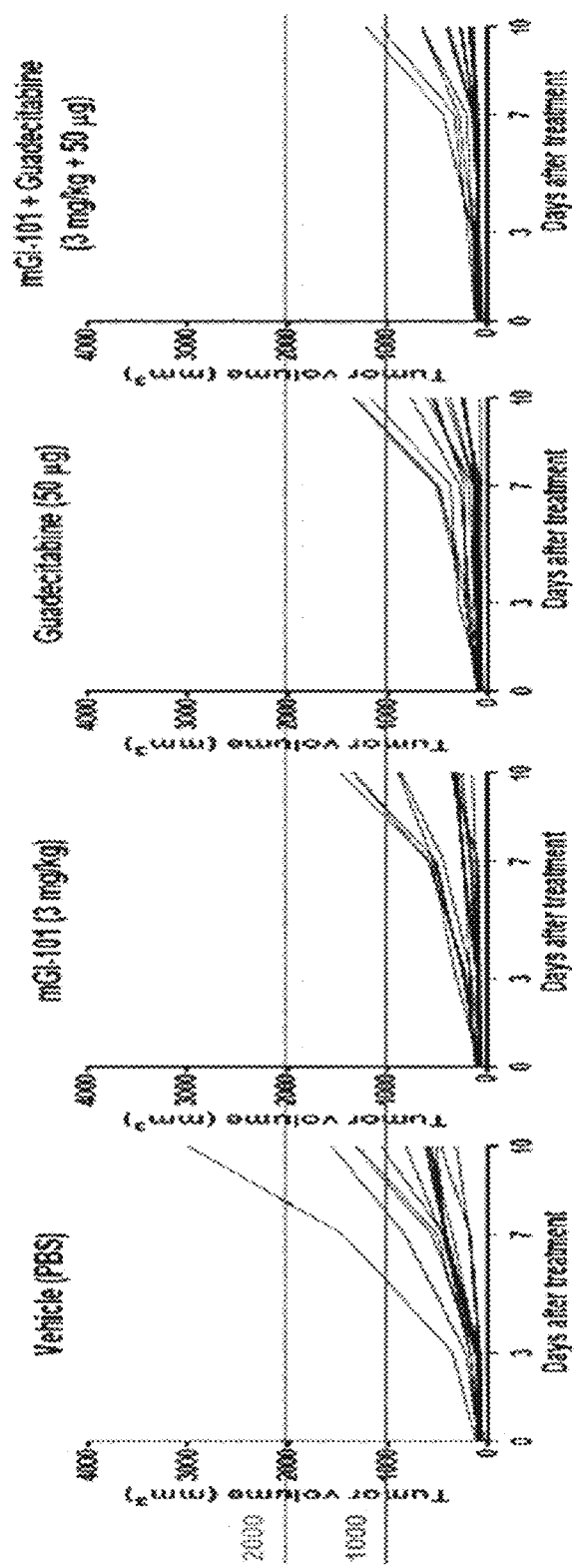
FIG. 102 illustrates the degree of tumor growth of individual experimental animals when mGI101 (3 mpk) and Guadecitabine, a DNA methyltransferase inhibitor, are administered in combination in mice transplanted with rodent-derived colorectal cancer cells (CT26).

Individual tumor sizes for each test group are shown in FIGS. 99 and 102. According to the results of individual tumor sizes, the group having received mGI-101 alone also exhibited the tumor growth inhibitory effect, and the group having received a combination mGI-101 and Guadecitabine substance exhibited the most excellent tumor growth inhibitory effect.

Figure 101:
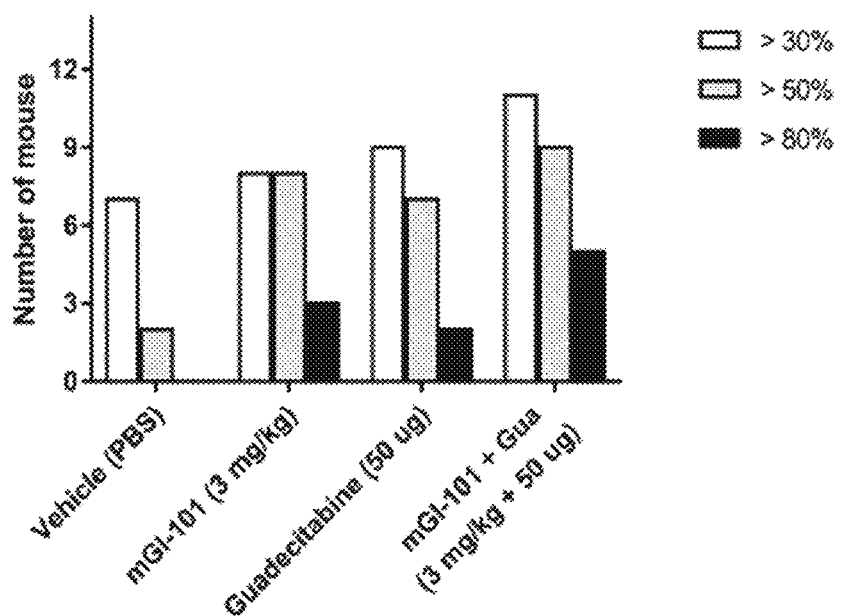
FIG. 101 illustrates a tumor growth inhibition rate when mGI101 (3 mpk) and Guadecitabine, a DNA methyltransferase inhibitor, are administered in combination in mice transplanted with rodent-derived colorectal cancer cells (CT26).

At the end of the experiment, mice with the tumor growth inhibition rate of 30%, 50%, or 80% or more are as shown in FIGS. 99 and 101. It was identified that subjects with the tumor growth inhibition rate of 30%, 50%, 80% or more were the most in the group having received a combination of mGI-101 (3 mg/kg)+Guadecitabine.

XI. Identification of Anticancer Effect According to Administration of Combination of Fusion Protein Dimer and Anticancer Chemotherapeutic Agent (Antineoplastic or Cytotoxic Agent)

Experimental Example 32. Identification of Anticancer Effect by Administration of Combination of mGI-101, Anti-PD-L1 Antibody, and Docetaxel in Mice Transplanted with Mouse-Derived Breast Cancer Cells This experiment was to evaluate the anticancer efficacy according to administration of the test substance mGI-101 alone or in combination with Docetaxel (Selleck Chemicals, cat. no. S1148) and the anti-PD-L1 antibody (BioXcell, cat. no. BE0101) in a tumor model allotransplanted with 4T1 cells (mouse breast cancer cells) into BALB/c mice.

4T1 cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco), and then a cell suspension was prepare with PBS and stored on ice until injected into mice. In order to establish an allotransplanted tumor model, after identifying the location of the second mammary fat pad from the upper right of the ventral region of BALB/c female mice (8-week-old), 4T1 cell line prepared inside the mammary fat pad was injected at $4\times10^4$ cells/40 μl/head.

A certain period of time after cell inoculation of the tumor grafts of the mice, the tumor volume was measured for animals with no abnormalities in the health condition of the animals, and the subjects were selected so that the average of each group reached less than 70-100 mm$^3$, and the selected animals were assigned as evenly as possible based on tumor volume and body weight, each group including 10 animals. As shown in Table 23, the test groups were configured and the test substances were administered.

Docetaxel was dissolved in 100% DMSO, and then the volume was adjusted with 5% of DMSO, 30% of PEG300, 5% of Tween 80, and 60% of distilled water for injection (DMSO PEG300: Tween 80: distilled water for injection=5%: 30%: 5%: 60% (v:v:v:v)) and prepared.

The Anti-PD-L1 antibody was prepared and administered using 1×PBS in consideration of dosage amount and volume.

TABLE 23

| Experimental group | | Route of administration | Dosing cycle | Dosage amount | Number of animals |
|---|---|---|---|---|---|
| G1 | Vehicle control (PBS) | i.p. | QW (once/week) | — mg/kg | 10 |
| G2 | mGI-101 + aPD-L1 | i.p. + i.p. | mGI-101: QW (once/week), | 3 mg/kg + 10 mg/kg | 10 |
| G3 | Docetaxel | i.p. | aPD-Ll: QW (once/week) | 15 mg/kg | 10 |
| G4 | Docetaxel + mGI-101 + aPD-Ll | i.p. + i.p. + i.p. | Docetaxel: QW (once/week), | 15 mg/kg + 3 mg/kg + 10 mg/kg | 10 |

Clinical symptoms such as a disease and a behavioral change were observed once a day during the test period, and deceased animals were identified, and the mice were sacrificed when the tumor size reached a size of 4,000 mm$^3$. The size of the 4T1 solid cancer was measured twice a week during the observation period, and the major axis (maximum length, L) and minor axis (perpendicular width, W) of the tumor were measured using a caliper (Digital caliper, Mitutoyo, Japan), and the tumor volume (TV) and the tumor growth inhibition rate (TGI) were calculated by substituting them into the following equations.

$$TV\ (mm^3)=(W^2 \times L)/2 \quad [\text{Equation 1}]$$

$$\%\ TGI\ (\text{Tumor Growth Inhibition})=(1-(Ti-T0)/(Vi-V0))\times 100 \quad [\text{Equation 2}]$$

The tumor volume before administration of each subject was set as the value measured at the time of grouping, and the anti-tumor efficacy was evaluated as compared with the vehicle control.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 103:
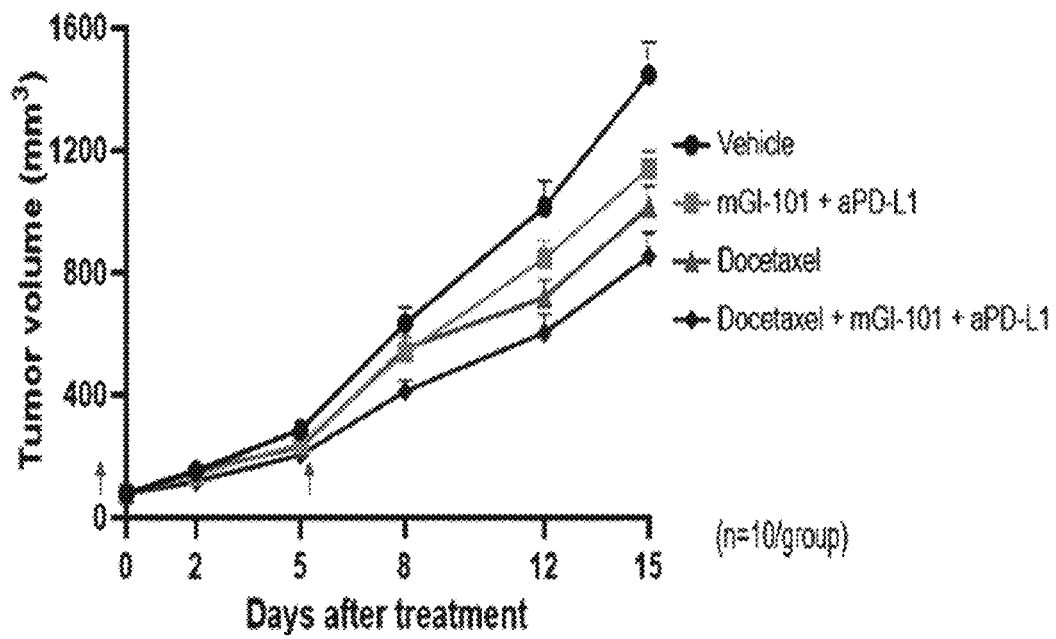
FIG. 103 illustrates a graph of tumor growth when mGI101, Docetaxel, and an anti-PD-L1 antibody are administered in combination in mice transplanted with rodent-derived breast cancer cells (4T1).

After administration of mGI-101 alone or in combination with Docetaxel and anti-PD-L1 antibody to mice transplanted with mouse-derived breast cancer cells, the results of measuring the tumor size are shown in FIG. 103. As a result of measuring the tumor size, on day 14 after the start of administration of the test substance, as compared with the control, the statistically significant anticancer effect was observed in the group having received Docetaxel and the group having received a combination of Docetaxel+mGI-101+aPD-L1 ($p<0.05$, $p<0.01$).

Figure 105:
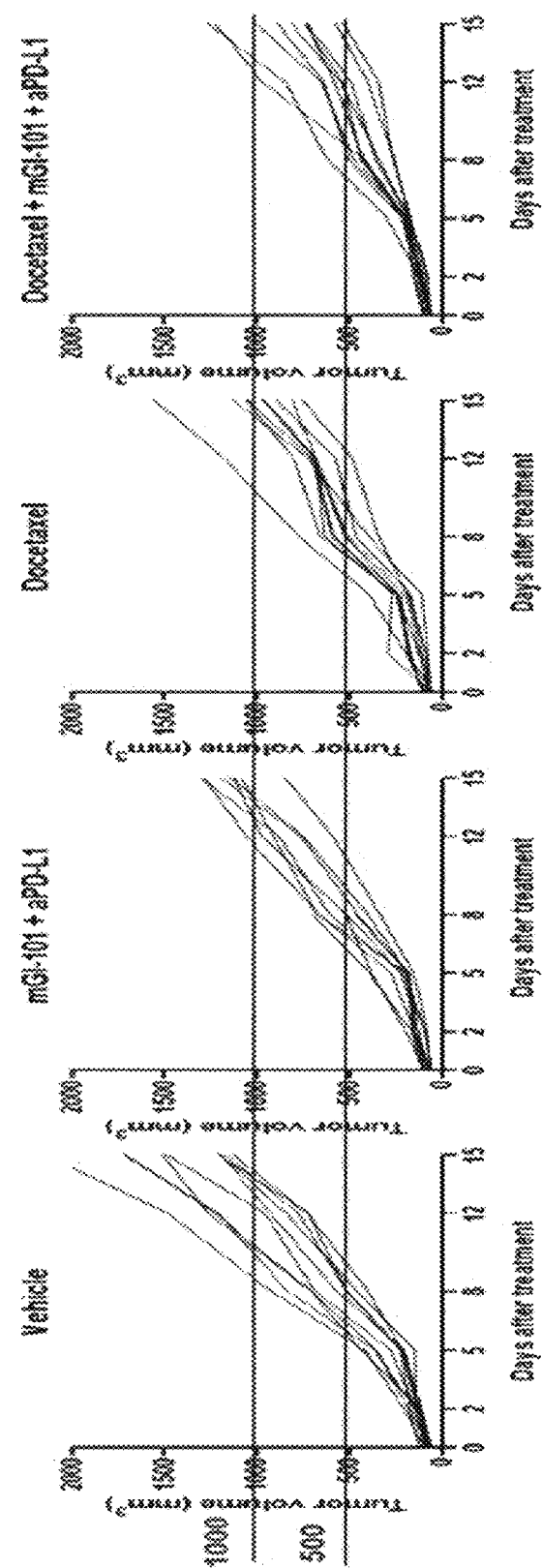
FIG. 105 illustrates the degree of tumor growth of individual experimental animals when mGI101, Docetaxel, and an anti-PD-L1 antibody are administered in combination in mice transplanted with rodent-derived breast cancer cells (4T1).

Individual tumor sizes for each test group are shown in FIG. 105.

Figure 104:
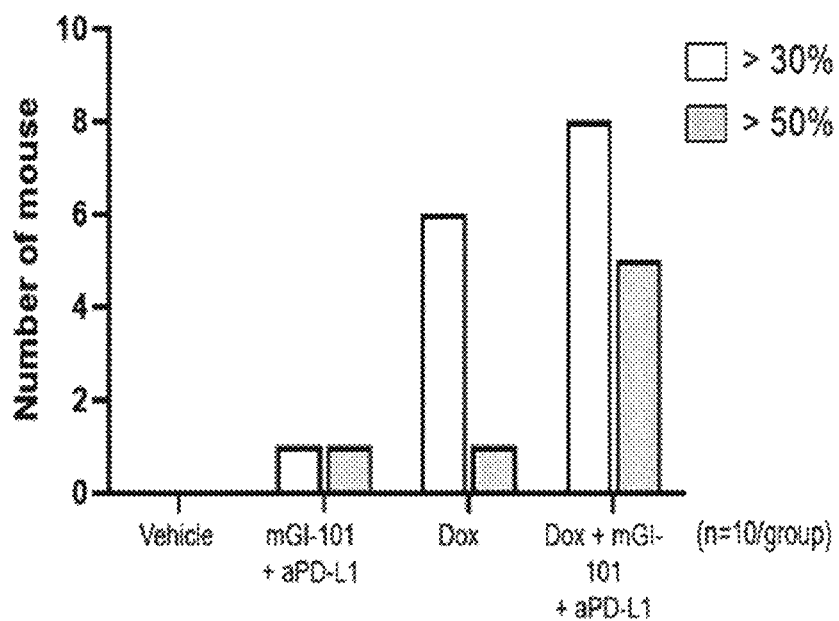
FIG. 104 illustrates a tumor growth inhibition rate when mGI101, Docetaxel, and an anti-PD-L1 antibody are administered in combination in mice transplanted with rodent-derived breast cancer cells (4T1).

FIG. 104 illustrates a tumor growth inhibition rate when mGI-101 is administered alone or in combination with Docetaxel and an anti-PD-L1 antibody in mice transplanted with 4T1 at the end of the test. The vehicle control exhibited a tumor growth inhibition rate of 30% or more, 50% or more in no mouse. The group having received a combination of mGI-101+aPD-L1 exhibited a tumor growth inhibition rate of 30% or more in 1 mouse, and 50% or more in no mouse. The group having received Docetaxel exhibited a tumor growth inhibition rate of 30% or more in 5 mice, and 50% or more in 1 mouse. The group having received a combination of Docetaxel+mGI-101+aPD-L1 exhibited a tumor growth inhibition rate of 30% or more in 6 mice, and 50% or more in 2 mice.

Experimental Example 33. Identification of Anticancer Effect by Administration of Combination of mGI-101 and Paclitaxel in Mice Transplanted with Mouse-Derived Breast Cancer Cells This experiment was to evaluate the tumor growth inhibitory effect after administration of mGI-101 as a test substance alone or in combination with Paclitaxel substance in a tumor model allotransplanted with EMT6 cells (mouse breast cancer cells) into BALB/c mice.

EMT6 cells were purchased from ATCC (USA) and cultured in Waymouth MB 751/1 medium (WELGENE) containing 10% FBS (Gibco) and 1% antibiotic/antifungal agent (Gibco). The cultured cells were harvested using trypsin (Gibco), and then a high-concentration cell suspension ($2\times10^6$ cells/0.4 mL) for 10 mice was prepare with PBS and stored on ice until injected into mice. In order to establish an allotransplanted tumor model, the skin was incised slightly away from the $4^{th}$ nipple position from the upper right of the ventral region of BALB/c female mice (7-week-old), and the location of mammary fat pad at the incised site was identified, and then EMT6 cell line prepared inside the mammary fat pad was injected at $2\times10^5$ cells/40 uL/head.

Figure 106:
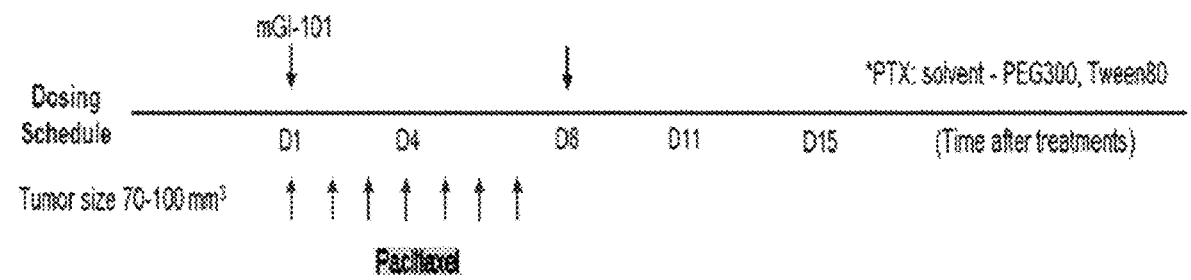
FIG. 106 is a schematic diagram of an experimental schedule for the administration of mGI101 and Paclitaxel in combination in mice transplanted with rodent-derived breast cancer cells (EMT6).

A certain period of time after cell inoculation of the tumor grafts of the mice, the tumor volume was measured for animals with no abnormalities in the health condition of the animals, and the subjects were selected so that the average of each group reached less than 70-100 mm³, and the selected animals were assigned as evenly as possible based on tumor volume and body weight, each group including 10 animals. As shown in Table 24 and FIG. 106, the test groups were configured and the test substances were administered.

TABLE 24

| Experimental group | | Route of administration | Dosing cycle | Dosage amount | Number of animals |
|---|---|---|---|---|---|
| G1 | Vehicle control (PBS) | i.v. | QW (once/week) | — mg/kg | 10 |
| G2 | mGI-101 | i.v. | QW (once/week) | 3 mg/kg | 10 |
| G3 | Paclitaxel (PTX) | i.p. | total 7 times, 7 consecutive days | 10 mg/kg | 10 |
| G4 | mGI-101 + Paclitaxel | i.v. + i.p. (once/week) + total 7 times, 7 consecutive days | QW mg/kg | 3 mg/kg + 10 | 10 |

Clinical symptoms such as a disease and a behavioral change were observed once a day during the test period, and deceased animals were identified, and the mice were sacrificed when the tumor size reached a size of 4,000 mm³. The size of the EMT6 solid cancer was measured twice a week during the observation period, and the major axis (maximum length, L) and minor axis (perpendicular width, W) of the tumor were measured using a caliper (Digital caliper, Mitutoyo, Japan), and the tumor volume (TV) and the tumor growth inhibition rate (TGI) were calculated by substituting them into the following equations.

TV (mm³)=($W^2 \times L$)/2 [Equation 1]

% TGI (Tumor Growth Inhibition)=(1−($Ti-T0$)/($Vi-V0$))×100 [Equation 2]

The tumor volume before administration of each subject was set as the value measured at the time of grouping, and the anti-tumor efficacy was evaluated as compared with the vehicle control.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 107:
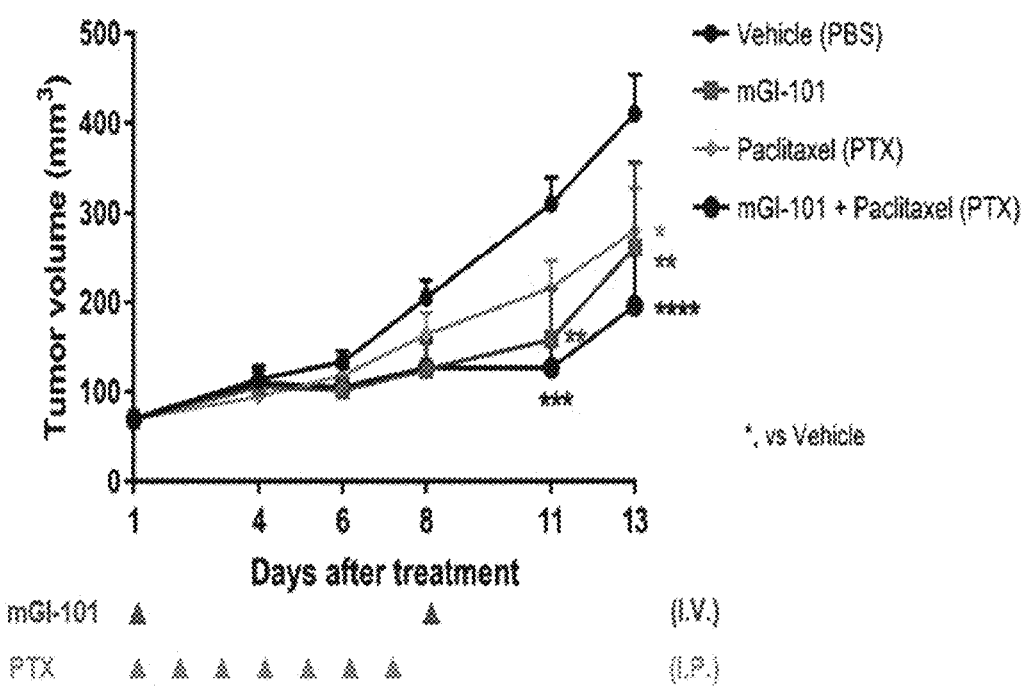
FIG. 107 illustrates a graph of tumor growth when mGI101 and Paclitaxel are administered in combination in mice transplanted with rodent-derived breast cancer cells (EMT6).

The results of tumor size upon administration of mGI-101 alone or in combination with Paclitaxel substance against the EMT6 tumor are shown in FIG. 107. As a result of measuring the tumor size, the anticancer effect was observed in the group having received the drug as compared with the control, and the tumor size level of the group having received mGI-101 alone and in combination with Paclitaxel substance on day 11 after the start of administration of the substance was statistically significantly lower than that of the control ($p<0.01$, $p<0.001$). The tumor size of all the group having received Paclitaxel, the group having received mGI-101 alone, and the group having received a combination of mGI-101 and Paclitaxel substance on day 13 after the start of administration of the substance was statistically significantly lower than that of the control (p<0.05, p<0.01, p<0.0001).

Figure 109:
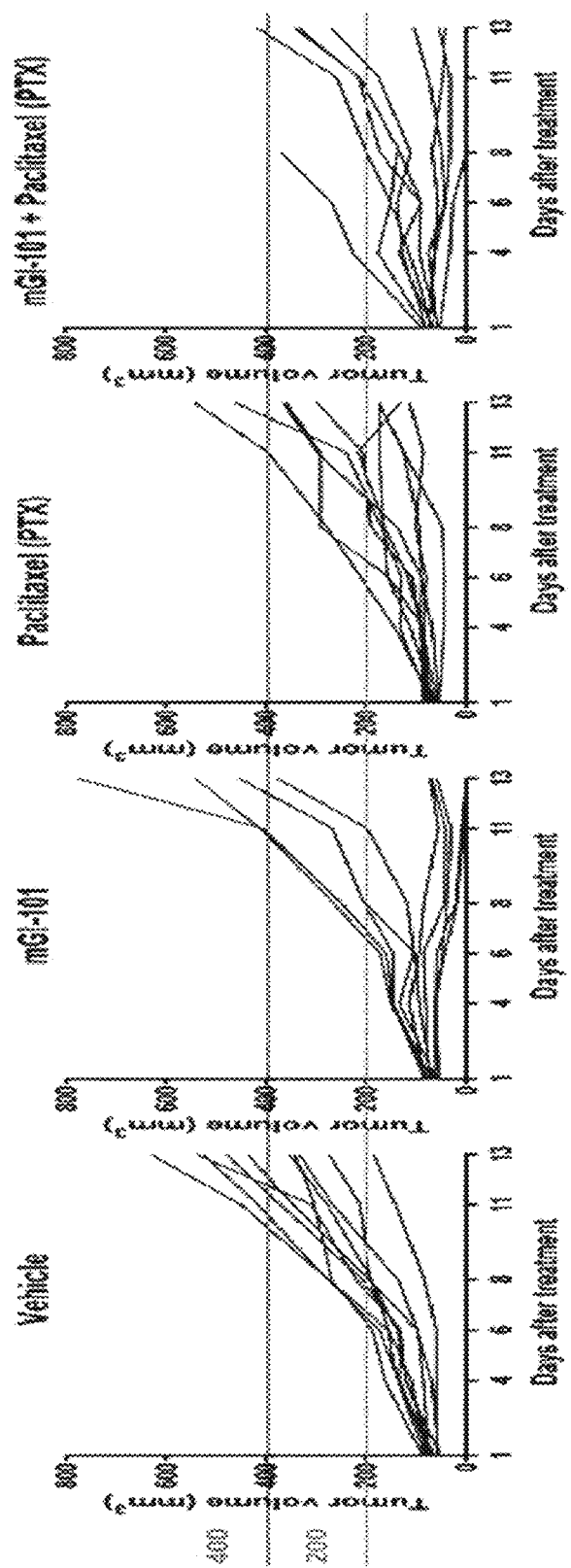
FIG. 109 illustrates the degree of tumor growth of individual experimental animals when mGI101 and Paclitaxel are administered in combination in mice transplanted with rodent-derived breast cancer cells (EMT6).

Individual tumor sizes for each test group are shown in FIG. 109. According to the results of individual tumor sizes, on day 13 after the start of administration of the test substance, the group having received mGI-101 alone exhibited complete remission in 2 mice, and the group having received a combination of mGI-101 and Paclitaxel exhibited complete remission in 1 mouse.

Figure 108:
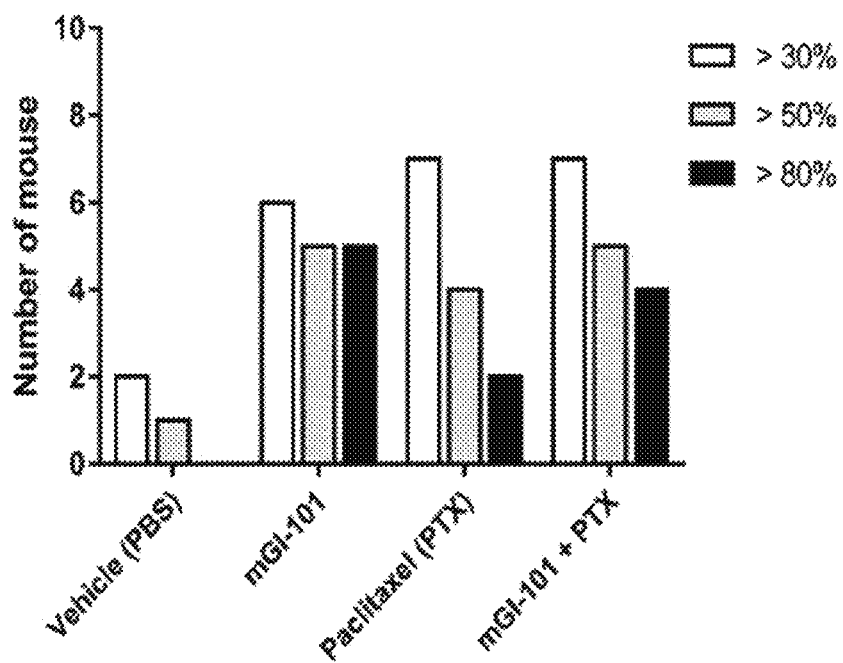
FIG. 108 illustrates a tumor growth inhibition rate when mGI101 and Paclitaxel are administered in combination in mice transplanted with rodent-derived breast cancer cells (EMT6).

FIG. 108 illustrates a tumor growth inhibition rate when mGI-101 and Paclitaxel are administered in combination in mice transplanted with EMT6. The vehicle control exhibited a tumor growth inhibition rate of 30% or more in 2 mice, 50% or more in 1 mouse, and 80% or more in no mouse. The group having received mGI-101 exhibited a tumor growth inhibition rate of 30% or more in 6 mice, 50% or more in 5 mice, and 80% or more in 5 mice. The group having received Paclitaxel exhibited a tumor growth inhibition rate of 30% or more in 7 mice, 50% or more in 4 mice, and 80% or more in 2 mice. The group having received a combination of mGI-101+Paclitaxel exhibited a tumor growth inhibition rate of 30% or more in 7 mice, 50% or more in 5 mice, and 80% or more in 4 mice.

XII. Identification of Anticancer Effect According to Administration of Combination: mGI-101+Anti-PD-1+Pemetrexed+Cisplatin (Chemotherapy, Maintaining Therapy)

Experimental Example 34. Identification of Anticancer Effect by Administration of Combination of mGI-101 and Anticancer Chemotherapeutic Agent and Anti-PD-1 Antibody in Mice Transplanted with Mouse-Derived Lung Cancer Cells This experiment was to evaluate the tumor growth inhibitory effect after intraperitoneal administration of mGI-101 as a test substance alone or in combination with an anticancer chemotherapeutic agent, Cisplastin (Selleck Chemicals, cat. no. S1166), Pemetrexed (Selleck Chemicals, cat. no. S1135), and an anti-PD-1 antibody (BioXcell, cat. no. BE0146) as a standard therapeutic agent in a tumor model allotransplanted with TC1 cells, lung cancer cell line, into C57BL/6 mice. Mouse-derived lung cancer cell line, TC1, was purchased from ATCC (USA) and used for the test.

TC1 cells were cultured in RPMI1640 medium (Gibco) containing 10% FBS (Gibco) and 1% antibiotic/antifungal agent (Gibco). The cultured cells were harvested using trypsin (Gibco), and then $1 \times 10^6$ of TC1 cells were subcutaneously injected into the right flank of C57BL/6 female mice (7-week-old) in order to establish an allotransplanted tumor model.

Figure 110:
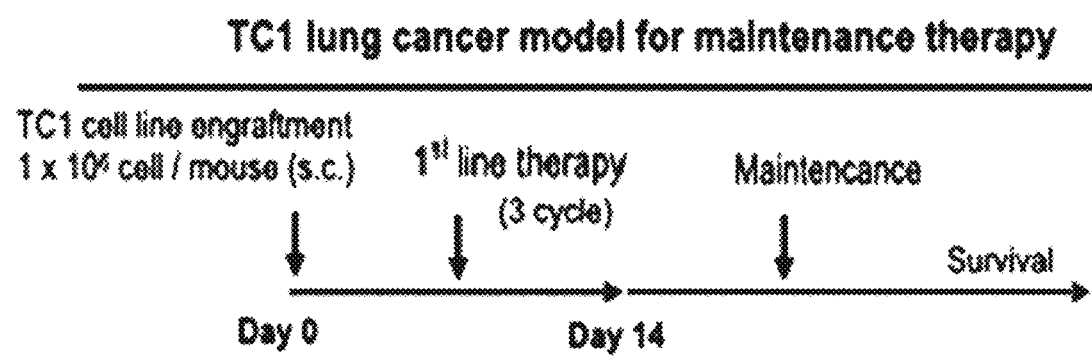
FIG. 110 is an experimental schedule for identifying an anticancer effect after mGI101, Cisplatin, Pemetrexed, and an anti-PD-1 antibody are administered in combination in mice transplanted with rodent-derived lung cancer cells (TC1). In addition, a schematic diagram of an experimental schedule for identifying an effect of maintenance therapy by mGI101 is also shown in the above figure.

The mice were randomly assigned based on tumor volume (~100 mm$^3$), each group including 13 to 19 mice. The tumor grafts were identified about day 2 after cell inoculation. The test groups were configured as shown in Table 25, and the test substances were administered according to the schedule shown in FIG. 110.

The test was divided into the 1$^{st}$ line treatment and the anticancer maintenance therapy. For the 1$^{st}$ line treatment, cisplatin (CDDP) at 5 mg/kg, pemetrexed at 100 mg/kg, and an anti-PD-1 antibody at 10 mg/kg were intraperitoneally administered twice a week, respectively, and in the case of the group having received a combination with mGI-101, it was intraperitoneally administered once a week, i.e., a total of 3 times, at 3 mg/kg.

In the anticancer maintenance therapy, mGI-101 was administered alone or mGI-101 was administered in combination with an anticancer chemotherapeutic agent and an anti-PD-1 antibody.

TABLE 25

| | Experimental group | Route of administration, dosing cycle | Dosage amount | Number of animals |
|---|---|---|---|---|
| G1 | mouse IgG4 | i.p. BIW | 3 mg/kg | 13 |
| G2 | 1) 1$^{st}$ line: Cisplatin + Pemetrexed + anti-PD-1 antibody  2) Maintenance therapy: Pemetrexed + anti-PD-1 antibody | mGI-101: i.p. QW Cisplatin: i.p. BIW Pemetrexed: i.p. BIW anti-PD-1 antibody: i.p. BI | mGI-101: 3 mg/kg Cisplatin: 5 mg/kg Pemetrexed: 100 mg/kg anti-PD-1 antibody: 10 mg/k | 19 |
| G3 | 1) 1$^{st}$ line: Cisplatin + Pemetrexed + anti-PD-1 antibody  2) Maintenance therapy: Pemetrexed + anti-PD-1 antibody + mGI-101 | | | 13 |
| G4 | 1) 1$^{st}$ line: Cisplatin + Pemetrexed + anti-PD-1 antibody 2) Maintenance therapy: mGI-101 | | | 13 |
| G5 | 1) 1$^{st}$ line: Cisplatin + Pemetrexed + anti-PD-1 antibody + mGI-101 2) Maintenance therapy: Pemetrexed + anti-PD-1 antibody + mGI-101 | | | 15 |

Clinical symptoms such as a disease and a behavioral change were observed once a day during the test period, and deceased animals were identified, and the mice were sacrificed when the tumor size reached a size of 4,000 mm$^3$. The size of the TC1 solid cancer was measured using a tumor 3D scanner (TM900, Peria, Belgium). For each experimental group, the average loss and percentage change of body weight and the average tumor growth inhibition were calculated. The anti-tumor efficacy was evaluated as compared with the mouse IgG4 control. All statistical calculations were performed using Prism 8.0 (Graph Pad Software Inc, USA). The comparison of tumor volume measurements was made through two-way analysis of variance followed by Bonferroni's multiple comparison test. A p value of less than 0.05 was considered significant.

Figure 111:
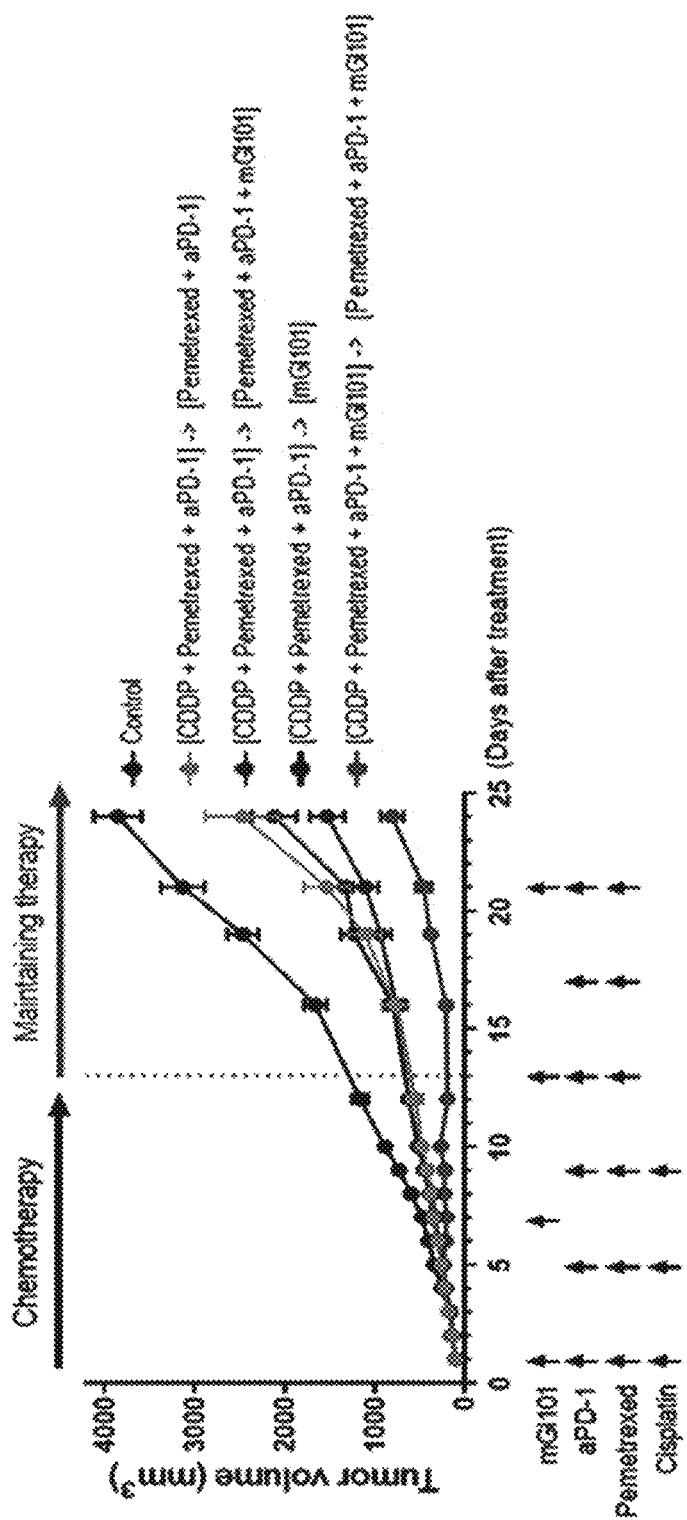
FIG. 111 illustrates a graph of tumor growth when mGI101, Cisplatin, Pemetrexed, and an anti-PD-1 antibody are administered in combination and maintenance therapy is performed in mice transplanted with rodent-derived lung cancer cells (TC1).
Figure 112:
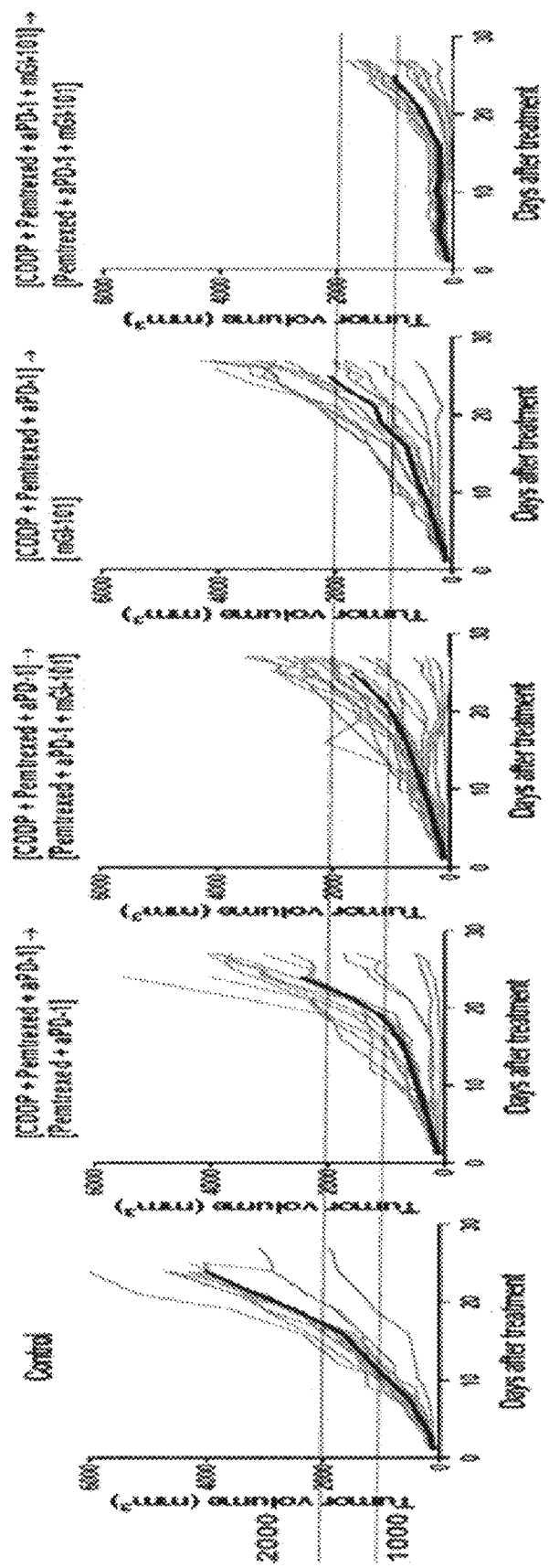
FIG. 112 illustrates the degree of tumor growth of individual experimental animals when mGI101, Cisplatin, Pemetrexed, and an anti-PD-1 antibody are administered in combination and maintenance therapy is performed in mice transplanted with rodent-derived lung cancer cells (TC1).
Figure 113:
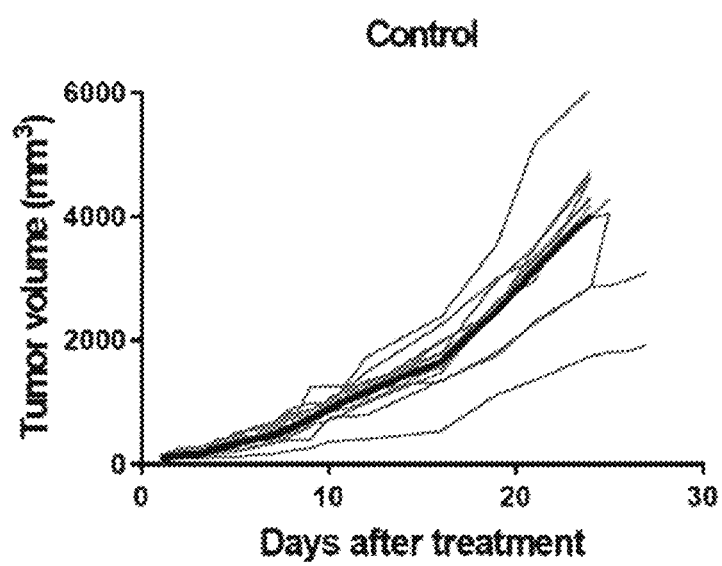
FIGS. 113 to 117 illustrate the degree of tumor growth of individual experimental animals for each experimental group when mGI101, Cisplatin, Pemetrexed, and an anti-PD-1 antibody are administered in combination and maintenance therapy is performed in mice transplanted with rodent-derived lung cancer cells (TC1).
Figure 114:
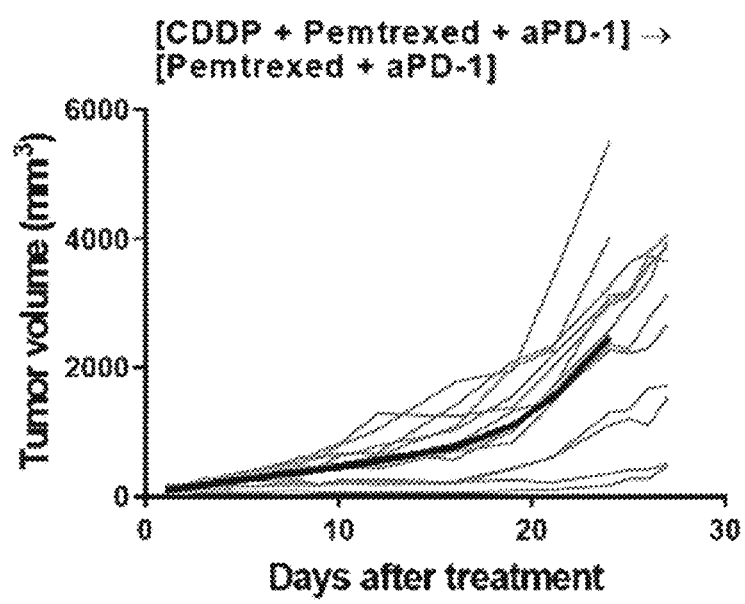
Figure 115:
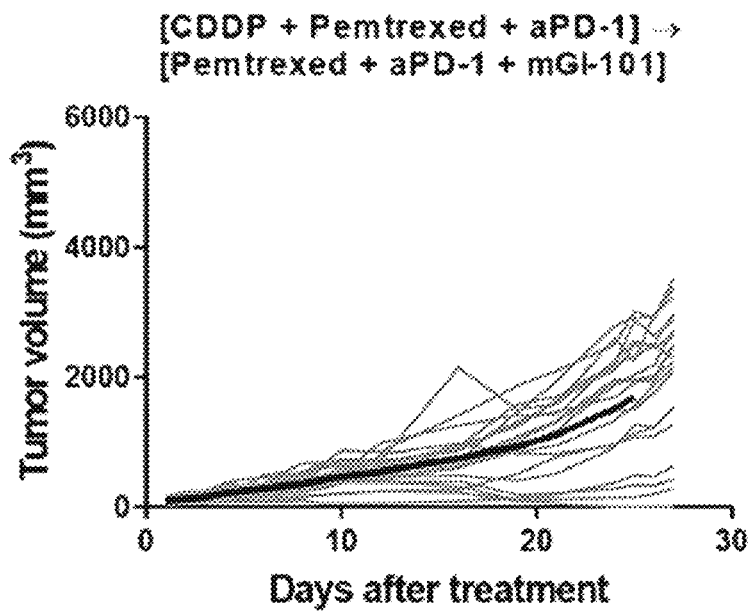
Figure 116:
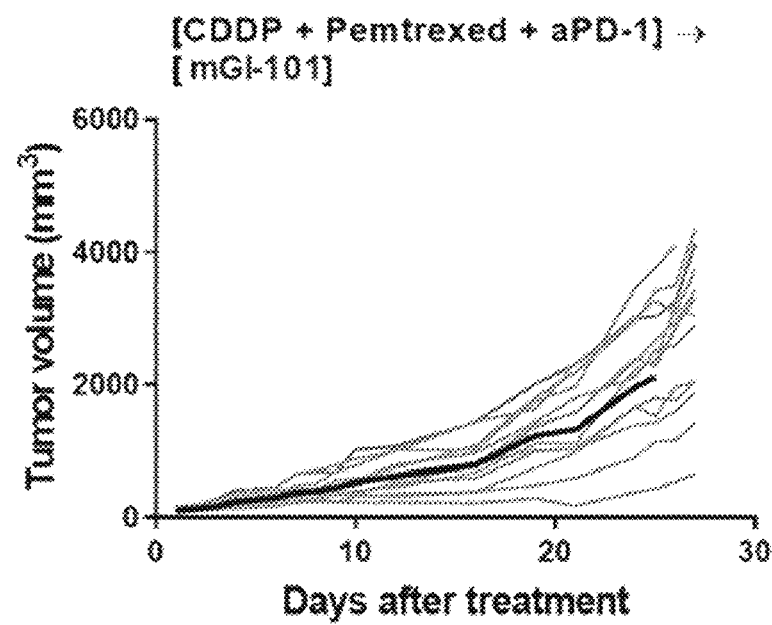
Figure 117:
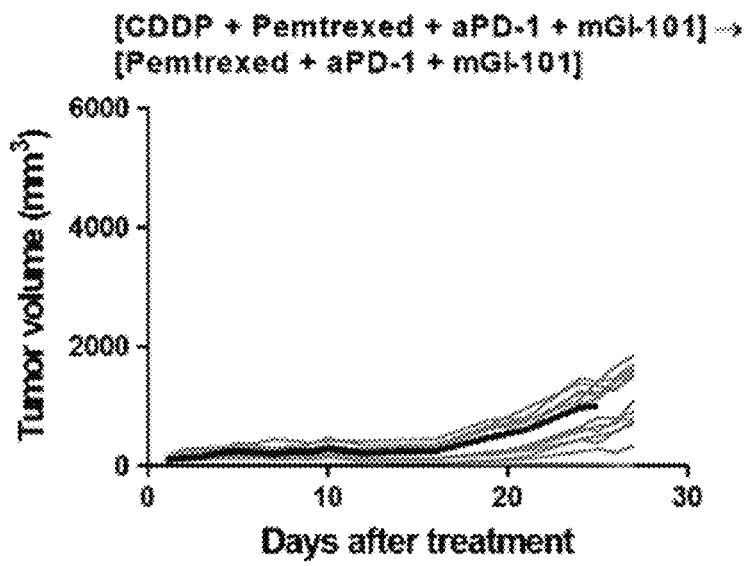

The results of administration of mGI-101 alone or in combination with an anticancer chemotherapeutic agent and an anti-PD-1 antibody against the TC1 tumor are shown in FIG. 111. The anticancer effect was observed in the group having received the drug as compared with the control, and the difference in tumor size was noticeable during the test period of 24 days. In the case of the 1$^{st}$ line treatment, the group having received mGI-101 in combination with an anticancer chemotherapeutic agent and an anti-PD-1 antibody exhibited a more excellent tumor growth inhibitory effect than that of the group having received only an anticancer chemotherapeutic agent and an anti-PD-1 antibody. In the case of the anticancer maintenance therapy, the group having received mGI-101 alone exhibited as much anticancer effect as the group having received an anticancer chemotherapeutic agent and an anti-PD-1 antibody, and the group having received mGI-101 in combination with an anticancer chemotherapeutic agent and an anti-PD-1 antibody exhibited a more excellent tumor growth inhibitory effect.

Individual tumor sizes for each test group are shown in FIGS. 112 to 117. According to the results of individual tumor sizes, in the 1$^{st}$ line treatment and the anticancer maintenance therapy, the group having received a combination with mGI-101 exhibited the most excellent tumor growth inhibitory effect.

Figure 118:
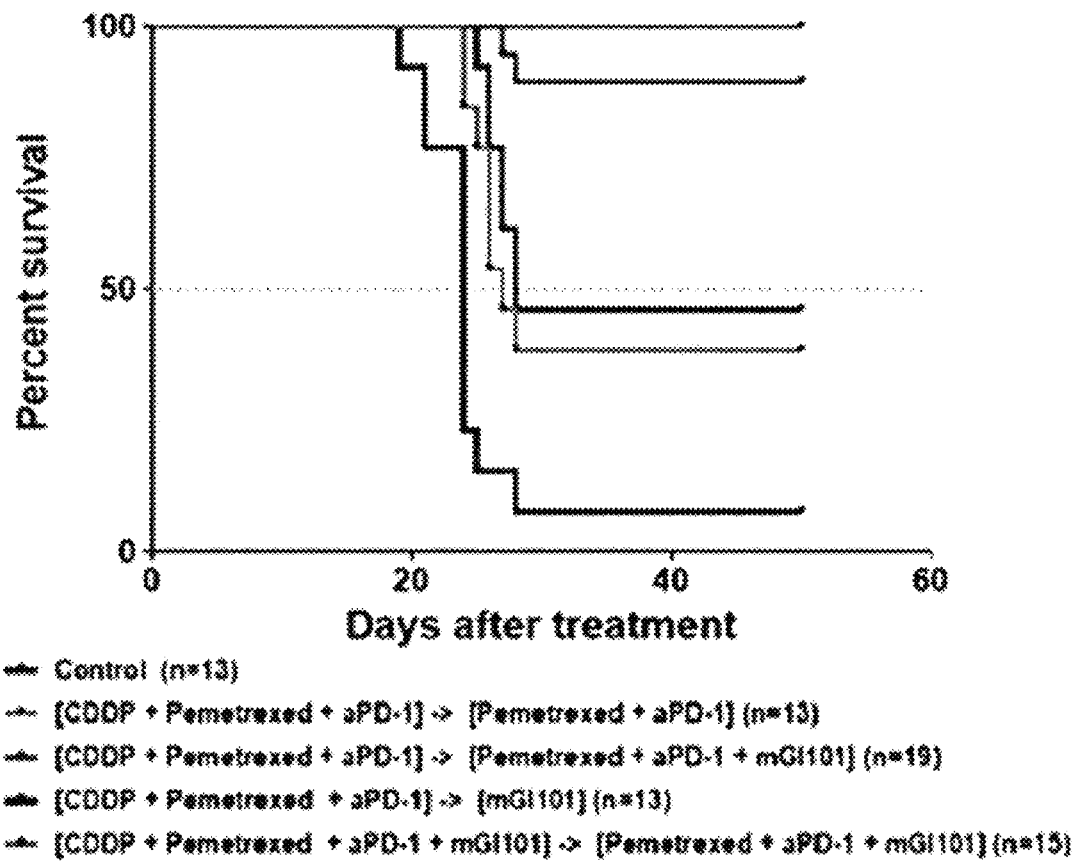
FIG. 118 illustrates a survival rate of mice after mGI101, Cisplatin, Pemetrexed, and an anti-PD-1 antibody are administered in combination and maintenance therapy is performed in mice transplanted with rodent-derived lung cancer cells (TC1).

FIG. 118 illustrates a result obtained by analyzing the survival rate of the mice according to the administration of a combination with mGI-101 during the 1$^{st}$ line treatment and the anticancer maintenance therapy in mice transplanted with TC1 cells. During the 1$^{st}$ line treatment and the anticancer maintenance therapy, a survival rate of 100% was identified in the group having received a combination with mGI-101. The average body weight of each test group is shown in Table 26.

TABLE 26

| | Treatment | | Body weight (g) on days | | | | | | | | | | | |
|---|---|---|---|---|---|---|---|---|---|---|---|---|---|---|
| | Treatment | | −2 | 1 | 3 | 5 | 7 | 10 | 12 | 13 | 15 | 20 | 23 | 26 |
| 1 | mouse IgG4 | Mean | 17.58 | 17.74 | 18.24 | 17.58 | 17.80 | 18.23 | 18.02 | 18.94 | 19.62 | 20.30 | 21.26 | 20.48 |
| 1 | mouse IgG4 | SEM | 1.00 | 1.07 | 0.95 | 1.14 | 1.08 | 1.09 | 1.01 | 1.08 | 1.32 | 1.35 | 1.61 | 1.71 |
| 2 | 1$^{st}$ line: Cisplatin + Pemetrexed + anti-PD-1 Maintenance: Pemetrexed + anti-PD-1 | Mean | 17.58 | 17.81 | 18.13 | 17.24 | 17.41 | 18.10 | 17.77 | 18.57 | 19.29 | 20.42 | 20.69 | 20.61 |
| 2 | 1$^{st}$ line: Cisplatin + Pemetrexed + anti-PD-1 Maintenance: Pemetrexed + anti-PD-1 | SEM | 0.82 | 0.77 | 0.98 | 0.94 | 1.15 | 1.56 | 1.47 | 1.56 | 1.71 | 1.91 | 2.01 | 1.61 |
| 3 | 1$^{st}$ line: Cisplatin + Pemetrexed + anti-PD-1 Maintenance: Pemetrexed + anti-PD-1 + mGI-101 | Mean | 17.42 | 17.73 | 18.06 | 17.42 | 17.78 | 18.54 | 18.11 | 19.01 | 19.23 | 19.72 | 20.28 | 20.18 |
| 3 | 1$^{st}$ line: Cisplatin + Pemetrexed + anti-PD-1 Maintenance: Pemetrexed + anti-PD-1 + mGI-101 | SEM | 1.25 | 1.08 | 1.39 | 1.66 | 1.70 | 1.57 | 1.42 | 1.70 | 1.44 | 1.88 | 1.88 | 1.90 |
| 4 | 1$^{st}$ line: Cisplatin + Pemetrexed + anti-PD-1 Maintenance: mGI-101 | Mean | 17.10 | 17.70 | 17.58 | 16.58 | 16.83 | 17.41 | 17.49 | 18.06 | 18.67 | 19.29 | 19.18 | 19.15 |
| 4 | 1$^{st}$ line: Cisplatin + Pemetrexed + anti-PD-1 Maintenance: mGI-101 | SEM | 1.05 | 1.04 | 1.04 | 1.18 | 1.19 | 1.02 | 1.02 | 1.22 | 1.39 | 1.23 | 1.63 | 1.59 |
| 5 | 1$^{st}$ line: Cisplatin + Pemetrexed + anti-PD-1 + mGI-101 Maintenance: Pemetrexed + anti-PD-1 + mGI-101 | Mean | 17.53 | 18.64 | 18.92 | 18.72 | 18.71 | 19.82 | 19.67 | 20.59 | 20.76 | 21.56 | 21.85 | 20.50 |
| 5 | 1$^{st}$ line: Cisplatin + Pemetrexed + anti-PD-1 + mGI-101 Maintenance: Pemetrexed + anti-PD-1 + mGI-101 | SEM | 0.99 | 0.85 | 1.01 | 0.96 | 0.89 | 1.18 | 1.15 | 0.94 | 1.34 | 1.67 | 1.69 | 0.71 |

XIII. Identification of Anticancer Effect According to Administration of Combination of Fusion Protein Dimer and Anti-HER Antibody

Experimental Example 35. Identification of Anticancer Effect by Administration of Combination of GI-101 and Trastuzumab This experiment was to evaluate the tumor growth inhibitory effect after administration of mGI-101 as a test substance alone or in combination with Herceptin (Trastuzumab) substance in a tumor model xenotransplanted with BT-474 cells (human breast cancer cells) into BALB/c nu/nu mice.

BT-474 cells were purchased from ATCC (USA) and cultured in RPMI1640 medium (Welgene) containing 10% FBS (Gibco) and 1% antibiotic/antifungal agent (Gibco). The cultured cells were harvested using trypsin (Gibco), and then a cell line was prepared by diluting in a medium to a concentration of $5.0 \times 10^6$ cells/0.05 mL.

In order to establish a xenotransplanted tumor model for BT-474 cells, it was subcutaneously injected into the left flank of BALB/c nu/nu female mice (7-week-old) by pulling the leather skin of the mice to make a space using a pellet transplant trochar (MP-182, Innovative Research of America, USA) so that it was located under the skin of the left flank. 7 days after the injection of the estrogen pellet, the prepared BT-474 cell suspension ($5 \times 10^6$ cells/0.05 mL) was dispensed, and 0.05 mL MATRIGEL™ matrix phenol red-free (356237, BD) was added, and the prepared solution was filled into a disposable syringe, and transplantation of the solution was performed by subcutaneous administration at 0.1 mL/head in the right dorsal region of the animals.

A certain period of time after cell inoculation of the tumor grafts of the mice, the tumor volume was measured for animals with no abnormalities in the health condition of the animals, and the subjects were selected so that the average of each group reached less than 60-120 mm³, and the selected animals were assigned as evenly as possible based on tumor volume and body weight, each group including 10 animals. As shown in Table 27, the test groups were configured and the test substances were administered.

TABLE 27

| Experimental group | | Route of administration | Dosing cycle | Dosage amount | Number of animals |
|---|---|---|---|---|---|
| G1 | Vehicle control (PBS) | i.v. | QW (once/week) | — mg/kg | 10 |
| G2 | mGI-101 | i.v. | QW (once/week) | 3 mg/kg | |
| G3 | Herceptin | i.p. | QW (once/week) | 1 mg/kg | 10 |
| G4 | mGI-101 + Herceptin | i.v. + i.p. | mGI-101: QW (once/week), Herceptin: QW (once/week) | 3 mg/kg + 1 mg/kg | 10 |

Clinical symptoms such as a disease and a behavioral change were observed once a day during the test period, and deceased animals were identified, and the mice were sacrificed when the tumor size reached a size of 4,000 mm³. The size of the solid cancer was measured twice a week during the observation period, and the major axis (maximum length, L) and minor axis (perpendicular width, W) of the tumor were measured using a caliper (Digital caliper, Mitutoyo, Japan), and the tumor volume (TV) and the tumor growth inhibition rate (TGI) were calculated by substituting them into the following equations.

$$TV \ (mm^3) = (W^2 \times L)/2 \quad \text{[Equation 1]}$$

$$\% \ TGI \ (\text{Tumor Growth Inhibition}) = (1-(Ti-T0)/(Vi-V0)) \times 100 \quad \text{[Equation 2]}$$

The tumor volume before administration of each subject was set as the value measured at the time of grouping.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 119:
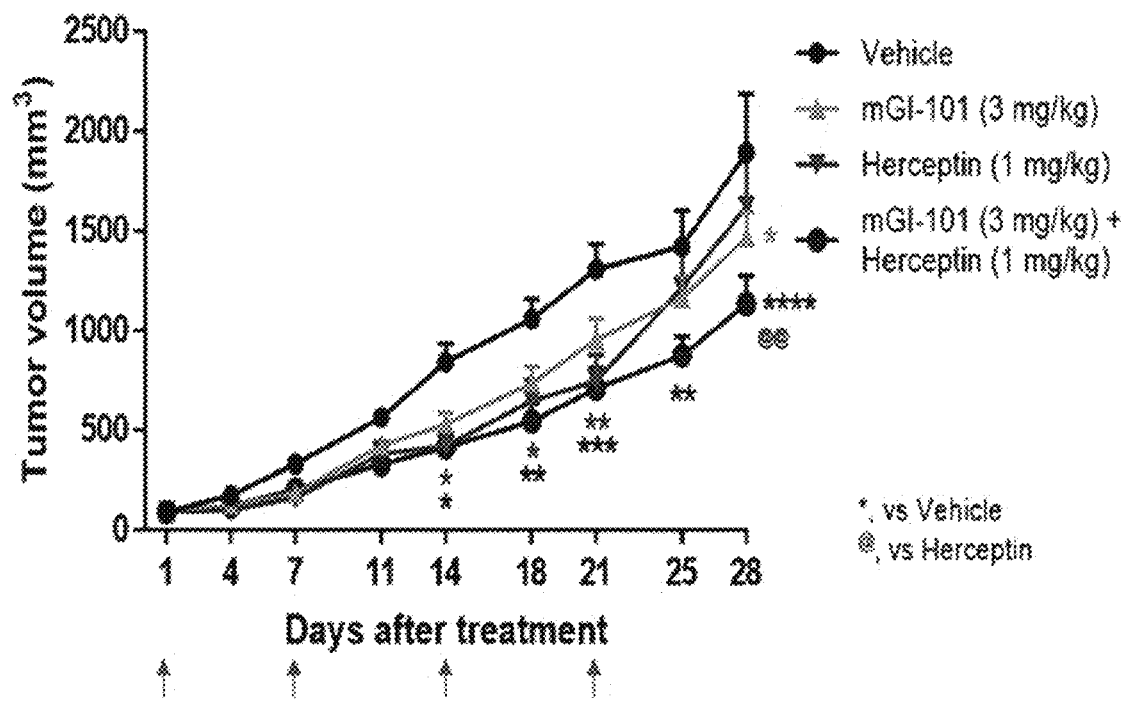
FIG. 119 illustrates a graph of tumor growth when GI101 and Trastuzumab are administered in combination in mice transplanted with human-derived breast cancer cells (BT-474).

The results of measuring the tumor size after administration of mGI-101 alone or in combination with Herceptin to mice transplanted with human-derived breast cancer cells are shown in FIG. 119. In the case of the group having received mGI-101 alone, a statistically significant reduction in tumor size was shown on day 28 after the start of administration of the test substance as compared with the vehicle control ($p<0.05$). In the case of the group having received Herceptin alone, a statistically significant reduction in tumor size was shown on day 14, day 18, and day 21 after the start of administration of the test substance as compared with the vehicle control (in the case of day 14 and day 18, $p<0.05$; in the case of day 21, $p<0.01$), but the tumor size tended to be increased rapidly on day 25 and day 28. In the case of the group having received a combination of mGI-101+Herceptin, a statistically significant reduction in tumor size was shown from day 14 to day 28 after the start of administration of the test substance as compared with the vehicle control, and a statistically significant reduction in tumor size was shown on day 28 after the start of administration of the test substance as compared with the group having received Herceptin alone ($p<0.01$).

Figure 121:
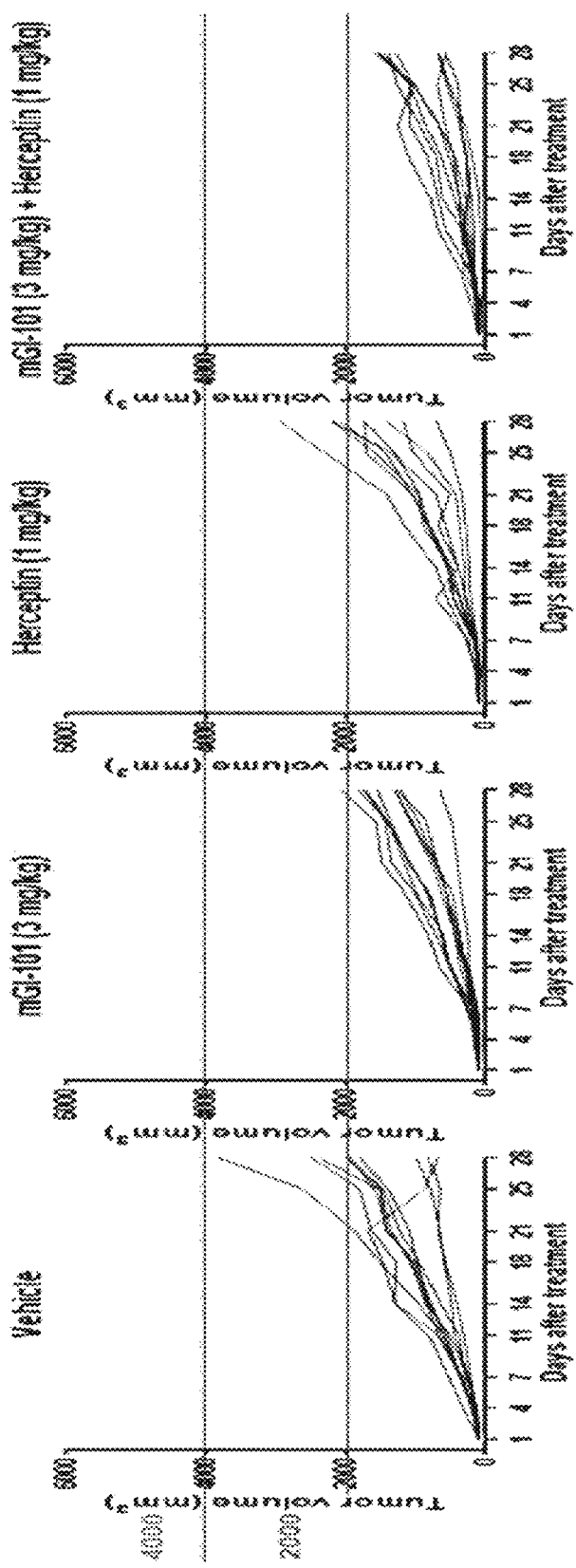
FIG. 121 illustrates the degree of tumor growth of individual experimental animals when GI101 and Trastuzumab are administered in combination in mice transplanted with human-derived breast cancer cells (BT-474).

Individual tumor sizes for each test group are shown in FIG. 121. According to the results of individual tumor sizes, the group having received the test substance exhibited a tumor growth inhibitory effect as compared with the vehicle control, and in particular, the group having received a combination of mGI-101+Herceptin exhibited an excellent tumor growth inhibitory effect as compared with the group having received mGI-101 alone.

Figure 120:
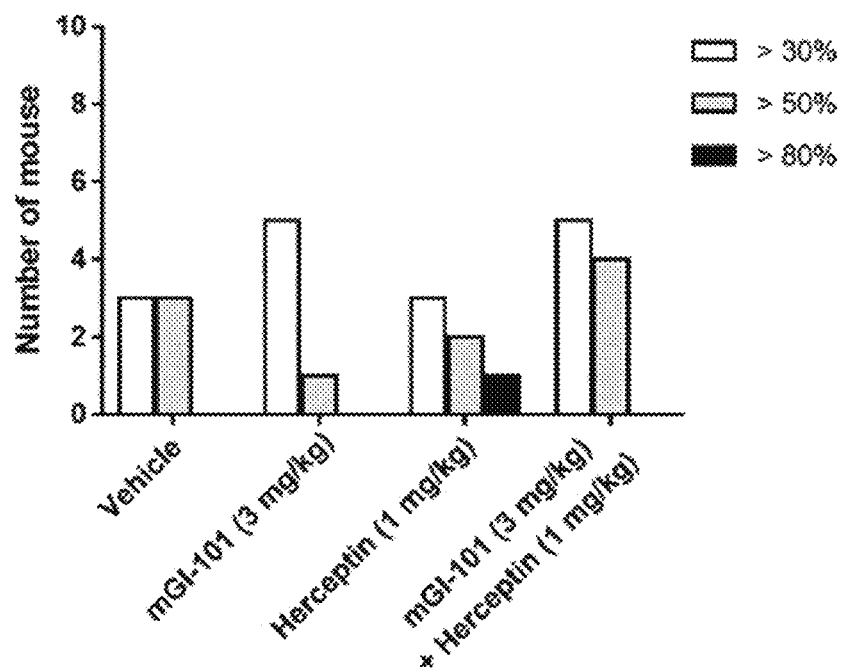
FIG. 120 illustrates a tumor growth inhibition rate when GI101 and Trastuzumab are administered in combination in mice transplanted with human-derived breast cancer cells (BT-474).

FIG. 120 illustrates a tumor growth inhibition rate when mGI-101 is administered alone or in combination with Herceptin in tumor mice xenotransplanted with BT-474 at the end of the test. The vehicle control exhibited a tumor growth inhibition rate of 30% or more in 3 mice, 50% or more in 3 mice, and 80% or more in no mouse. The group having received mGI-101 alone exhibited a tumor growth inhibition rate of 30% or more in 5 mice, 50% or more in 1 mouse, and 80% or more in no mouse. The group having received Herceptin alone exhibited a tumor growth inhibition rate of 30% or more in 3 mice, 50% or more in 2 mice, and 80% or more in 1 mouse. The group having received a combination of mGI-101+Herceptin exhibited a tumor growth inhibition rate of 30% or more in 5 mice, 50% or more in 4 mice, and 80% or more in no mouse.

Experimental Example 36. Identification of Anticancer Effect by Administration of Combination of GI-101 and Pertuzumab This experiment was to evaluate the effect of killing cancer cells by treating HCT116 cells (human colon cancer cells) with the test substance GI-101 alone or in combination with Pertuzumab substance in an in vitro environment.

HCT116 cells were purchased from the Korea cell line bank and cultured in McCoy's 5A medium (ATCC) containing 10% FBS (Gibco) and 1% antibiotic/antifungal agent (Gibco). For use in cancer cell killing test, the cells were harvested using trypsin (Gibco), and then suspended in McCoy's 5A medium, and then dead cells and debris were removed using Ficoll (GE Healthcare Life Sciences) solution. The cells suspended in McCoy's 5A medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was made into a suspension of $2\times10^5$ cells/mL with FBS-free RPMI1640 medium. The cancer cell suspension was stained at 37° C. for 1 hour using CELLTRACKER™ Deep Red Dye (Thermo) in order to track proliferation of cancer cells or inhibition of the proliferation. After staining, it was centrifuged at 1300 rpm for 5 minutes, and then it was washed with FBS-free RPMI1640 medium, and then suspended in RPMI1640 medium containing 5% human AB serum (Sigma) to a concentration of $2\times10^5$ cells/mL. The cancer cell suspension was added to each well of a 96-well microplate (Corning) by 50 μL ($1\times10^4$ cells), and then stabilized in an incubator (37° C., 5% $CO_2$) for 1 hour.

In order to identify the effect of killing cancer cells through antibody-dependent cellular cytotoxicity (ADCC) by the test substance, natural killer cells (NK cells) were isolated from human peripheral blood mononuclear cells (PBMCs) using a CD56+CD16+NK cell isolation kit (Miltenyi Biotec) and used. In isolated NK cells, dead cells and debris were removed using Ficoll (GE Healthcare Life Sciences) solution in the same manner as the cancer cell line. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was suspended in RPMI1640 medium containing 5% human AB serum (Sigma) to a concentration of $2\times10^5$ cells/mL. The PBMC suspension was dispensed 50 μl into each well of a 96-well microplate (Corning) in which cancer cell line has been dispensed, depending on the conditions.

In order to identify the effect of killing the cells, a CytoTox Green reagent (INCUCYTE™ CytoTox Green, Satorius) that binds to the DNA of cells to be killed was prepared in 1 μl per 1 mL of RPMI1640 medium containing 5% human AB serum (Sigma). The prepared medium was used for dilution of the test substance, and the effect of killing the cells could be quantitatively identified by staining the cells to be killed when the test substance was co-cultured with cancer cell lines and PBMCs.

Pertuzumab was diluted using RPMI1640 medium containing a CytoTox Green reagent, and then used in the experiment at a final concentration of 16.9 nM (50 μl) per well of a 96-well microplate.

GI-101 was diluted by ⅓ using RPMI1640 medium containing a CytoTox Green reagent, and then used in the experiment at final concentrations of 0.4 nM, 1.2 nM, 3.7 nM, 11.1 nM, 33.3 nM, and 100 nM by 50 μl per well of a 96-well microplate.

The prepared test substance was placed in each well of a 96-well microplate in which cancer cell lines and PBMCs were dispensed depending on the conditions, and cultured in an incubator (37° C., 5% $CO_2$) for 24 hours, and the proliferation or death of cancer cells was observed through the real-time cell imaging analysis equipment IncuCyte S3 (Satorious). The death of cancer cells was quantified by the integrated intensity of the cells stained in green with a CytoTox Green reagent.

Figure 122:
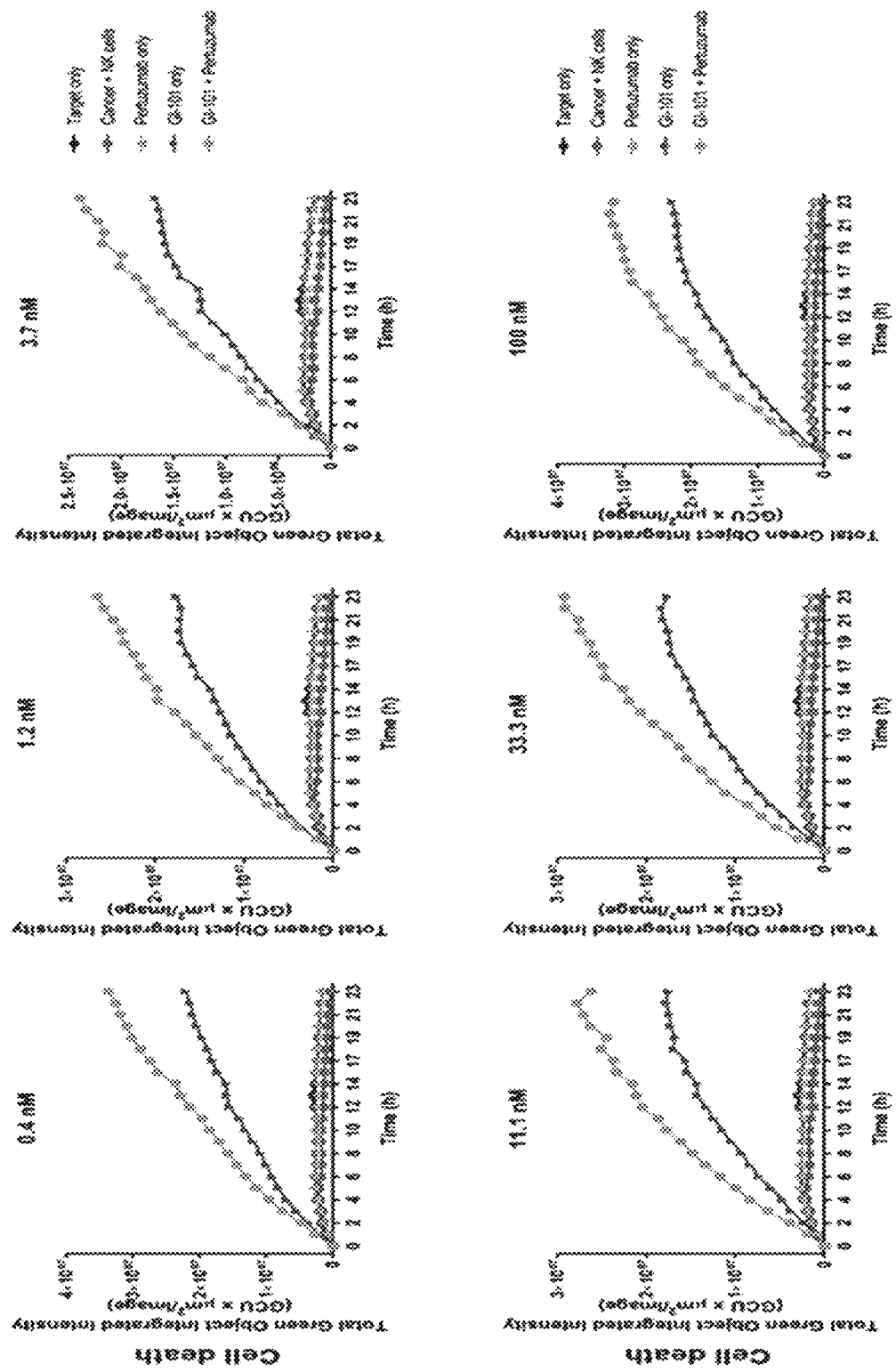
FIG. 122 illustrates the effect of killing cancer cell line depending on the concentrations of GI101 when GI101, Pertuzumab, a Her2 inhibitor, and a combination thereof are administered in human colorectal cancer cell line (HCT116).

FIG. 122 illustrates results obtained by measuring the degree of killing cancer cells after the HCT116 cells were treated with GI-101 at a concentration of 0.4 nM, 1.2 nM, 3.7 nM, 11.1 nM, 33.3 nM and 100 nM, respectively. In the case of co-culturing only cancer cells and NK cells and in the case of treatment of Pertuzumab alone, the effect of killing cancer cells was not shown as in the case of culturing only cancer cells. In the case of treatment with GI-101 alone and with a combination of GI-101+Pertuzumab, an excellent effect of killing cancer cells was shown, and in the case of treatment with a combination of GI-101+Pertuzumab, the most excellent effect of killing cancer cells was shown.

XIV. Identification of Anticancer Effect According to Administration of Combination of Fusion Protein Dimer and CDK4/6 Inhibitor Experimental Example 37. Identification of Anticancer Effect by Administration of Combination of GI-101 and Abemaciclib This experiment was to evaluate the tumor growth inhibitory effect after administration of mGI-101 as a test substance alone or in combination with Abemaciclib substance in a tumor model allotransplanted with 4T1 cells (mouse breast cancer cells) into BALB/c mice. 4T1 cells were purchased from ATCC (USA) and cultured in RPMI1640 medium (Gibco) containing 10% FBS (Gibco) and 1% antibiotic/antifungal agent (Gibco). The cultured cells were harvested using trypsin (Gibco) and then suspended in PBS. In order to establish an allotransplanted tumor model, $1\times10^5$ of 4T1 cells were subcutaneously injected into the back of BALB/c female mice (8-week-old). General symptoms were observed once a day during the engraftment and growth period after cell line transplantation.

A certain period of time after cell inoculation of the tumor grafts of the mice, the tumor volume was measured for animals with no abnormalities in the health condition of the animals, and the mice were randomly selected and assigned, each group including 11 mice. As shown in Table 28, the test groups were configured and the test substances were administered.

TABLE 28

| Experimental group | | Route of administration | Dosing cycle | Dosage amount | Number of animals |
|---|---|---|---|---|---|
| G1 | Vehicle control (PBS) | i.p. | QW (once/week) | — mg/kg | 11 |
| G2 | mGI-101 | i.p. | BIW (2 times/week) | 3 mg/kg | 11 |
| G3 | Abemaciclib | p.o. | 6 times/week | 50 mg/kg | 11 |
| G4 | mGI-101 + Abemaciclib | i.p. + p.o. | mGI-101: BIW (2 times/week), Abemaciclib: 6 times/week | 3 mg/kg + 50 mg/kg | 11 |

The death of the mouse, the type of general symptoms, the date of onset, and the severity of symptoms were observed once a day during the test period, and recorded for each subject. The size of the Renca solid cancer was measured twice a week during the observation period, and the major axis (maximum length, L) and minor axis (perpendicular width, W) of the tumor were measured using a vernier caliper, and the tumor volume (TV) and the tumor growth inhibition rate (TGI) were calculated by substituting them into the following equations.

$$TV\ (mm^3) = (W^2 \times L)/2 \quad \text{[Equation 1]}$$

$$\%\ TGI\ (Tumor\ Growth\ Inhibition) = (1-(Ti-T0)/(Vi-V0)) \times 100 \quad \text{[Equation 2]}$$

The tumor volume before administration of each subject was set as the value measured at the time of grouping, and the anti-tumor efficacy was evaluated as compared with the vehicle control.

All statistical calculations were performed using Prism 8.0 (Graph Pad Software Inc, USA). The comparison of tumor volume measurements was made through two-way analysis of variance followed by Tukey's multiple comparison test. A p value of less than 0.05 was considered significant.

Figure 123:
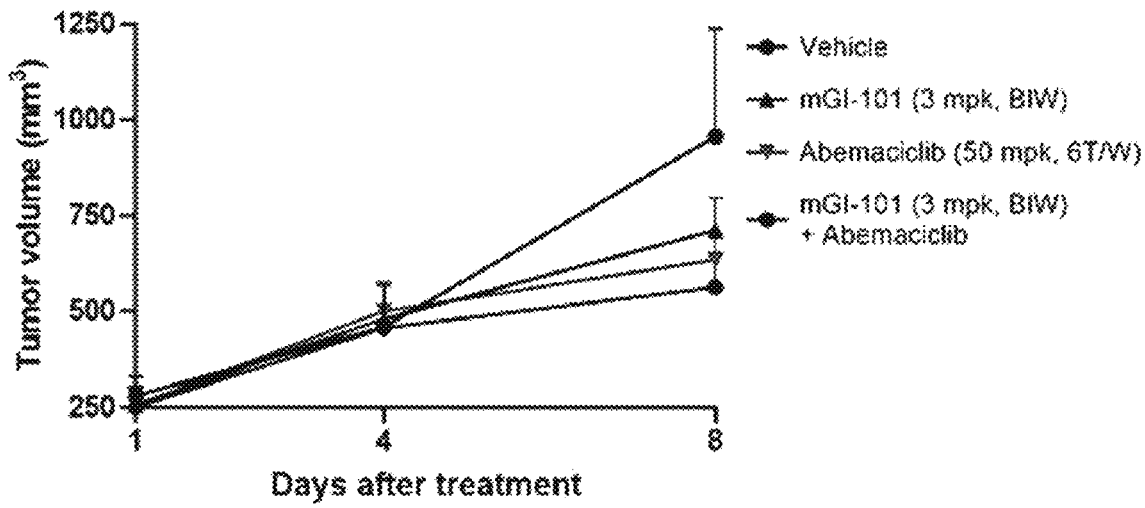
FIG. 123 illustrates a graph of tumor growth when mGI101 and Abemaciclib, a CDK4/6 inhibitor, are administered in combination in mice transplanted with rodent-derived breast cancer cells (4T1).

The results of measuring the tumor size after administration of mGI-101 alone or in combination with Abemaciclib substance in mice transplanted with mouse-derived breast cancer cells are shown in FIG. 123. In the case of the group having received a combination of mGI-101 (BIW)+Abemaciclib, the tumor growth inhibition tended to be highest.

Figure 125:
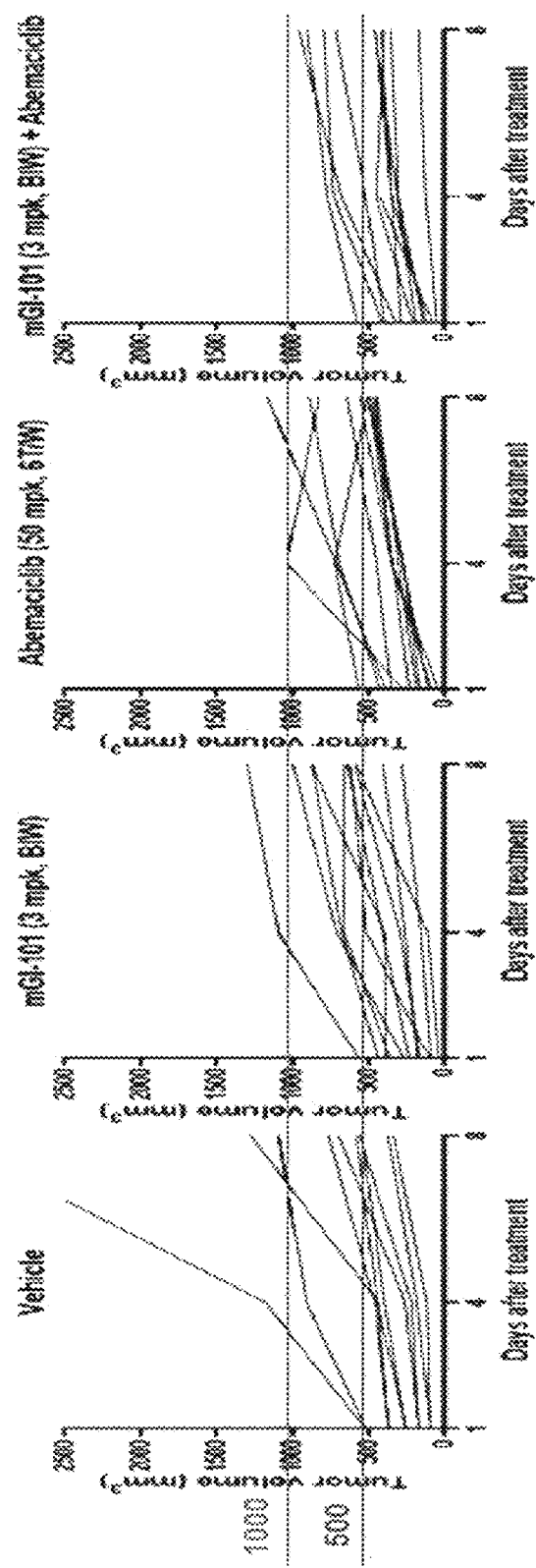
FIG. 125 illustrates the degree of tumor growth of individual experimental animals when mGI101 and Abemaciclib, a CDK4/6 inhibitor, are administered in combination in mice transplanted with rodent-derived breast cancer cells (4T1).

Individual tumor sizes for each test group are shown in FIG. 125. According to the results of individual tumor sizes, the group having received a combination of mGI-101 (BIW)+Abemaciclib exhibited the greatest tumor growth inhibitory effect.

Figure 124:
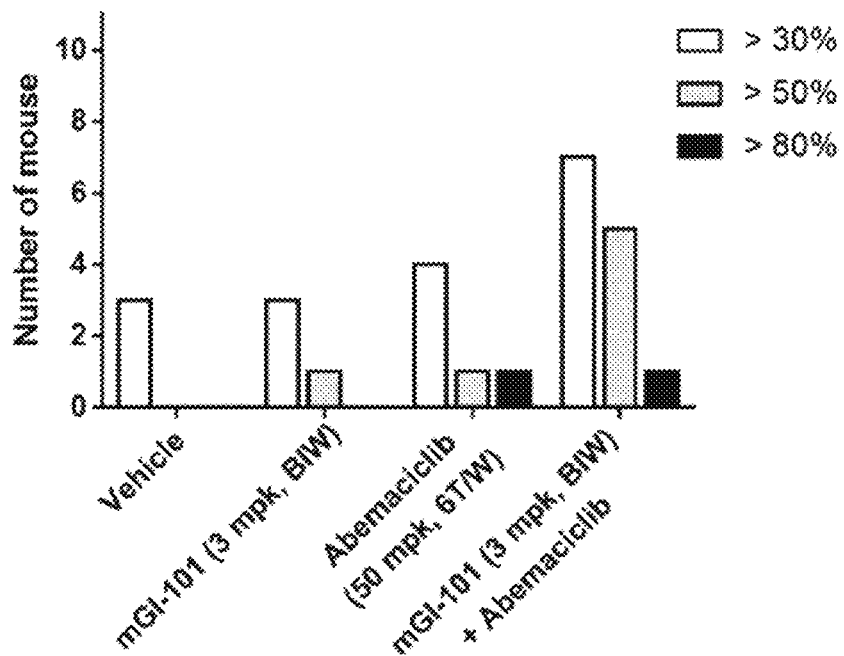
FIG. 124 illustrates a tumor growth inhibition rate when mGI101 and Abemaciclib, a CDK4/6 inhibitor, are administered in combination in mice transplanted with rodent-derived breast cancer cells (4T1).

FIG. 124 illustrates a tumor growth inhibition rate when mGI-101 and Abemaciclib are administered in combination in mice transplanted with 4T1. The vehicle control exhibited a tumor growth inhibition rate of 30% or more in 3 mice, and 50% or more and 80% or more in no mouse. The group having received mGI-101 (BIW) exhibited a tumor growth inhibition rate of 30% or more in 3 mice, 50% or more in 1 mouse, and 80% or more in no mouse. The group having received Abemaciclib exhibited a tumor growth inhibition rate of 30% or more in 4 mice, 50% or more in 1 mouse, and 80% or more in 1 mouse. The group having received a combination of mGI-101 (BIW)+Abemaciclib exhibited a tumor growth inhibition rate of 30% or more in 7 mice, 50% or more in 5 mice, and 80% or more in 1 mouse.

Experimental Example 38. Identification of Anticancer Effect by Administration of Combination of GI-101 and Ribociclib This experiment was to evaluate the effect of killing cancer cells by treating MDA-MB-231 cells (human breast cancer cells) with the test substance GI-101 alone or in combination with Ribociclib substance in an in vitro environment.

MDA-MB-231 cells were purchased from the Korea cell line bank and cultured in RPMI1640 medium (Gibco) containing 10% FBS (Gibco) and 1% antibiotic/antifungal agent (Gibco). For use in cancer cell killing test, the cells were harvested using trypsin (Gibco), and then suspended in RPMI1640 medium, and then dead cells and debris were removed using Ficoll (GE Healthcare Life Sciences) solution. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was made into a suspension of $2 \times 10^5$ cells/mL with FBS-free RPMI1640 medium. The cancer cell suspension was stained at 37° C. for 1 hour using CELLTRACKER™ Deep Red Dye (Thermo) in order to track proliferation of cancer cells or inhibition of the proliferation. After staining, it was centrifuged at 1300 rpm for 5 minutes, and then it was washed with FBS-free RPMI1640 medium, and then suspended in RPMI1640 medium containing 5% human AB serum (Sigma) to a concentration of $2 \times 10^5$ cells/mL. The cancer cell suspension was added to each well of a 96-well microplate (Corning) by 50 μl ($1 \times 10^4$ cells), and then stabilized in an incubator (37° C., 5% $CO_2$) for 1 hour.

Human peripheral blood mononuclear cells (PBMCs) were used in order to identify the effect of killing cancer cells by GI-101. The human PBMCs were purchased from Zen-Bio, and the PBMCs stored frozen were placed in a 37° C. water bath, and thawed as quickly as possible, and then transferred to RPMI1640 medium (Gibco) containing 10% FBS (Gibco) and 1% antibiotic/antifungal agent (Gibco), and centrifuged at 1300 rpm for 5 minutes. The separated cell layer was suspended in RPMI1640 medium, and then dead cells and debris were removed using Ficoll (GE Healthcare Life Sciences) solution in the same manner as the cancer cell line. The cells suspended in RPMI1640 medium were carefully layered on ficoll solution. The cell layer with a low specific gravity formed by centrifuging at room temperature at 350×g for 20 minutes was collected with a pipette, washed with PBS (Gibco), and then centrifuged at room temperature at 350×g for 5 minutes. The separated cell layer was suspended in RPMI1640 medium containing 5% human AB serum (Sigma) to a concentration of $5\times10^5$ cells/mL. The PBMC suspension was dispensed 50 µl into each well of a 96-well microplate (Corning) in which cancer cell line has been dispensed, depending on the conditions.

In order to identify the effect of killing the cells, a CytoTox Green reagent (INCUCYTE™ CytoTox Green, Satorius) that binds to the DNA of cells to be killed was prepared in 1 µl per 1 mL of RPMI1640 medium containing 5% human AB serum (Sigma). The prepared medium was used for dilution of the test substance, and the effect of killing the cells could be quantitatively identified by staining the cells to be killed when the test substance was co-cultured with cancer cell lines and PBMCs.

Ribociclib test substance was diluted using RPMI1640 medium containing a CytoTox Green reagent, and then used in the experiment at a final concentration of 913 nM (50 µl) per well of a 96-well microplate. GI-101 was diluted by ⅓ using RPMI1640 medium containing a CytoTox Green reagent, and then used in the experiment at a final concentration 100 nM by 50 µl per well of a 96-well microplate.

The prepared test substance was placed in each well of a 96-well microplate in which cancer cell lines and PBMCs were dispensed depending on the conditions, and cultured in an incubator (37° C., 5% $CO_2$) for 24 hours, and the proliferation or death of cancer cells was observed through the real-time cell imaging analysis equipment IncuCyte S3 (Satorious). The death of cancer cells was quantified by the integrated intensity of the cells stained in green with a CytoTox Green reagent.

Figure 126:
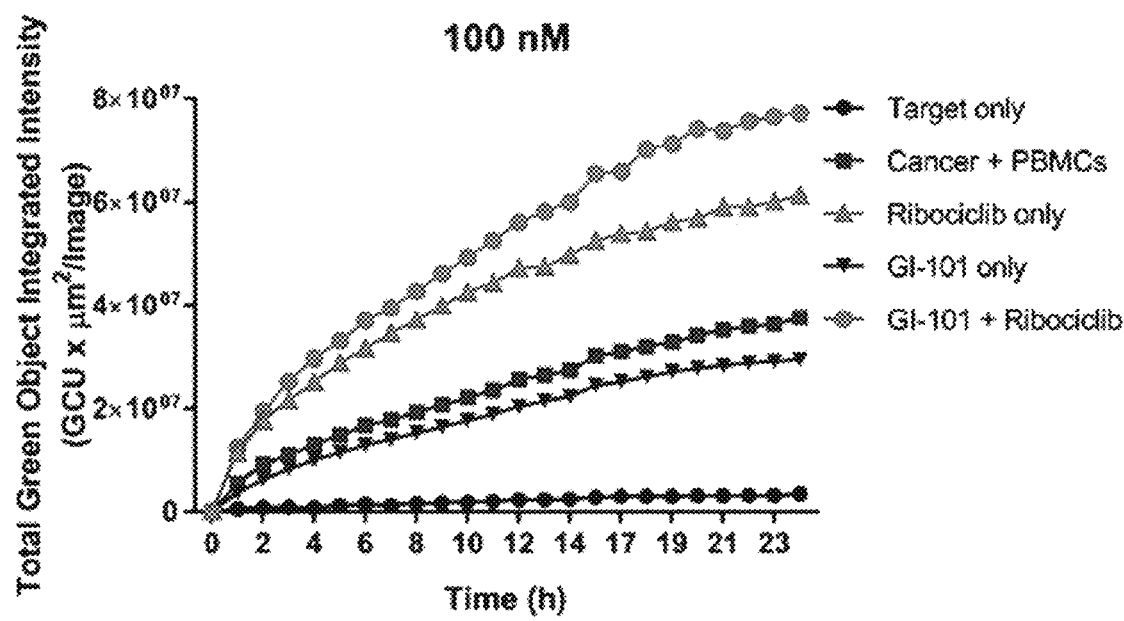
FIG. 126 illustrates the effect of killing cancer cell line when GI101, Ribociclib, a CDK4/6 inhibitor, and a combination thereof are administered in human-derived breast cancer cell line cells (MDA-MB-231).

FIG. 126 illustrates the effect of killing cancer cells in a condition of GI-101 at 100 nM. In the case of co-culturing only cancer cells and PBMCs, the effect of killing cancer cells was identified, and tended to be higher than that of treatment with GI-101 alone. In the case of treatment with Ribociclib alone and treatment with a combination of GI-101+Ribociclib, an excellent effect of killing cancer cells was shown as compared with the case of co-culturing only cancer cells and PBMCs, and in the case of treatment with a combination of GI-101+Ribociclib, the most excellent effect of killing cancer cells was shown.

XV. Identification of Anticancer Effect According to Administration of Combination of Fusion Protein Dimer and STING Agonist Experimental Example 39. Identification of Anticancer Effect by Administration of Combination of mGI-101 and DMXAA This experiment was to evaluate the anticancer efficacy according to administration of mGI-101 as a test substance alone or in combination with DMXAA substance, a STING agonist, in a tumor model allotransplanted with MC38 cells (mouse colon cancer cells) into C57BL/6 mice.

Figure 127:
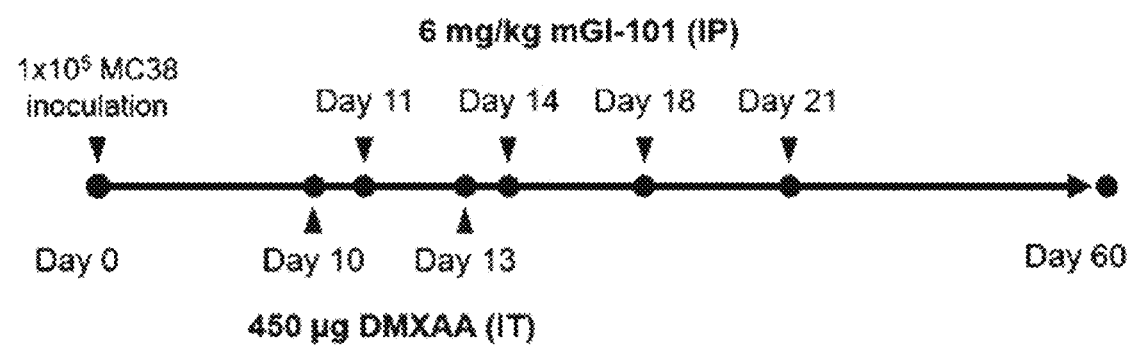
FIG. 127 illustrates a schematic diagram of an experimental schedule for the administration of mGI101 and DMXAA, a STING agonist, in combination in mice transplanted with rodent-derived colorectal cancer cells (MC38).

In order to establish an allotransplanted tumor model, $5\times10^5$ of MC38 cells were subcutaneously injected into C57BL/6 mice. The tumor grafts of the mice were identified to be a size of 100-200 mm³ about day 10 after cell inoculation, and the mice were assigned, each group including 5 mice. The test groups were configured as shown in Table 29, and the test substances were administered according to the schedule shown in FIG. 127.

TABLE 29

| Experimental group | Route of administration | Dosing cycle | Dosage amount | Number of animals |
|---|---|---|---|---|
| G1 Vehicle control (PBS) | | mGI-101: BIW (2 times/week), DMXAA: Day 10 and 13 | — mg/kg | 5 |
| G2 mGI-101 | i.p. | | 6 mg/kg | 5 |
| G3 DMXAA | I.T. | | 450 µg | 5 |
| G4 mGI-101 + DMXAA | i.p. + I.T. | | 6 mg/kg + 450 µg | 5 |

The size of the MC38 solid cancer was measured three times a week during the observation period, and the major axis (maximum length, L) and minor axis (perpendicular width, W) of the tumor were measured using a caliper, and the tumor volume (TV) was calculated by substituting them into the following equation, and once the tumor size was no less than 2 cm, the mice were sacrificed.

$$TV\ (mm^3) = (W^2 \times L)/2 \qquad [Equation\ 1]$$

Figure 128:
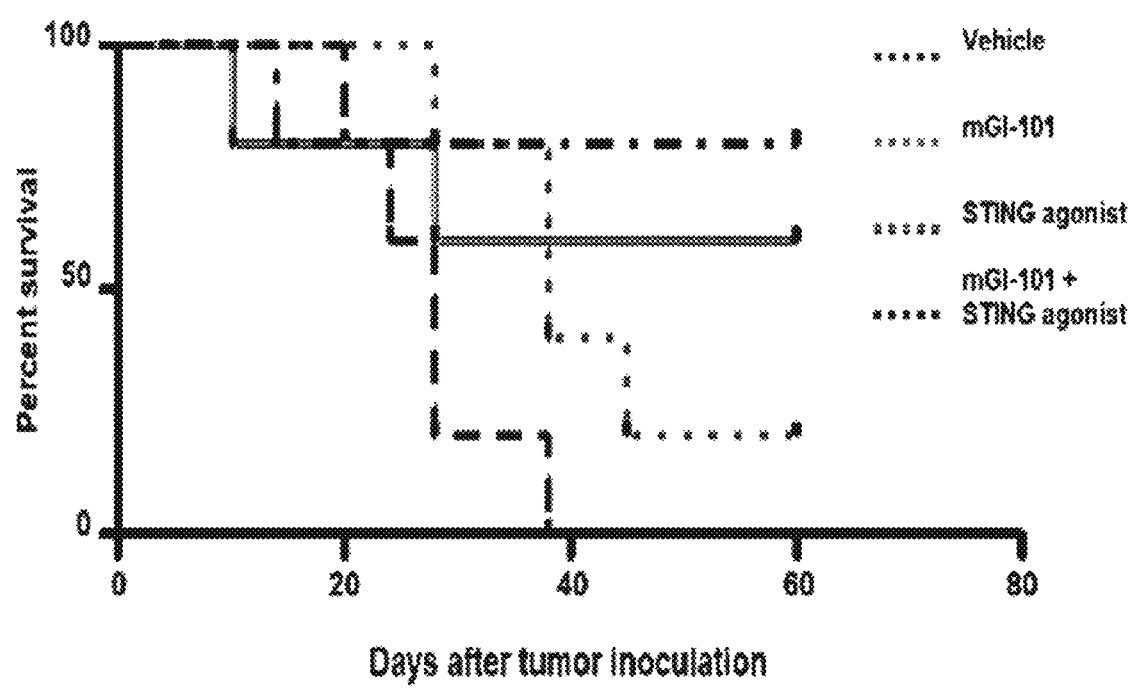
Figure 129:
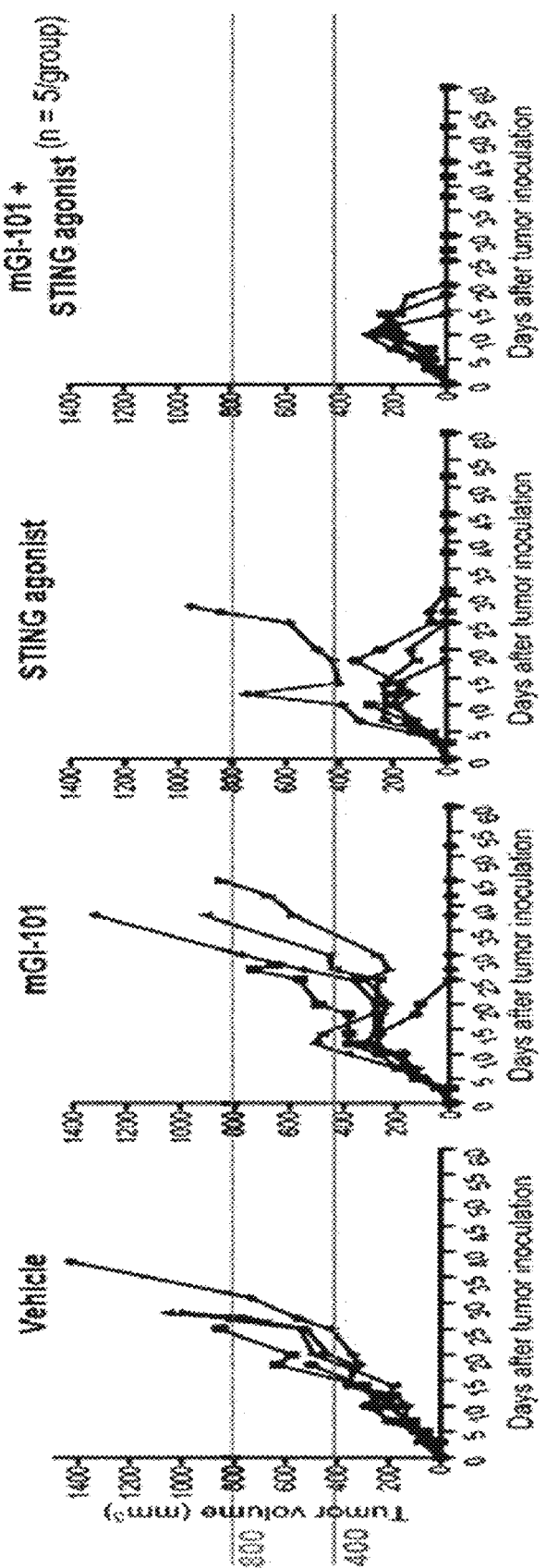
Figure 130:
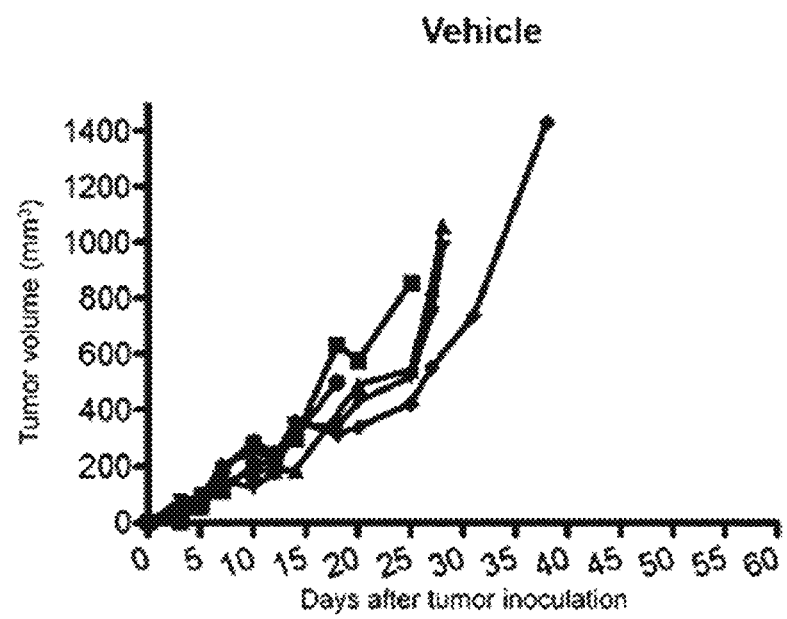
Figure 131:
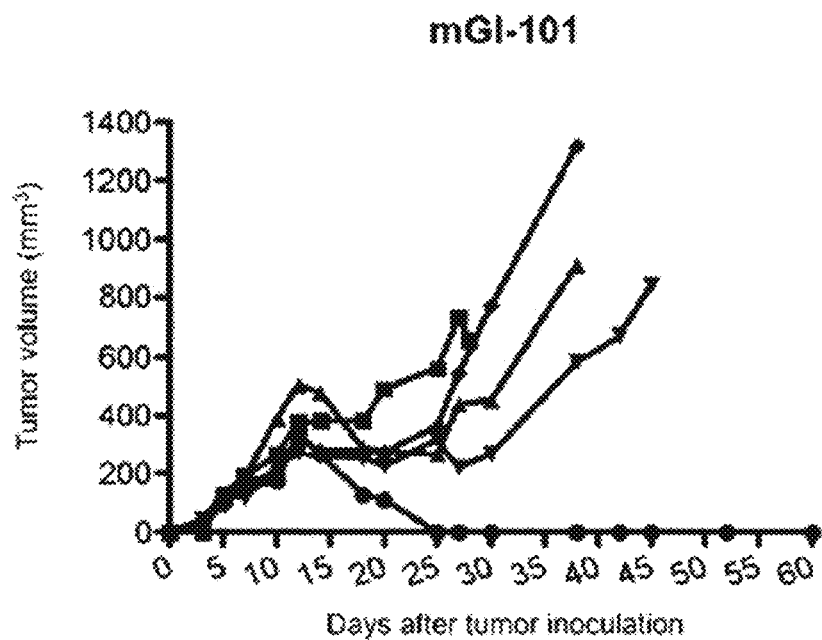
Figure 132:
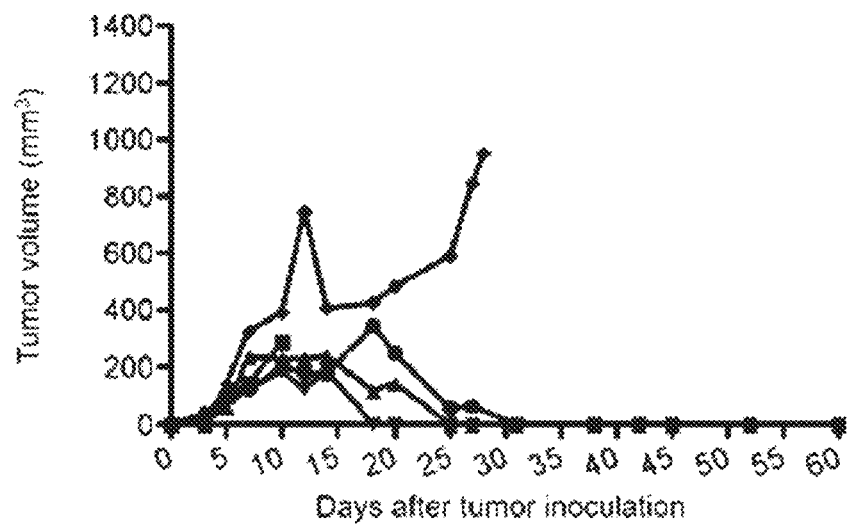
Figure 133:
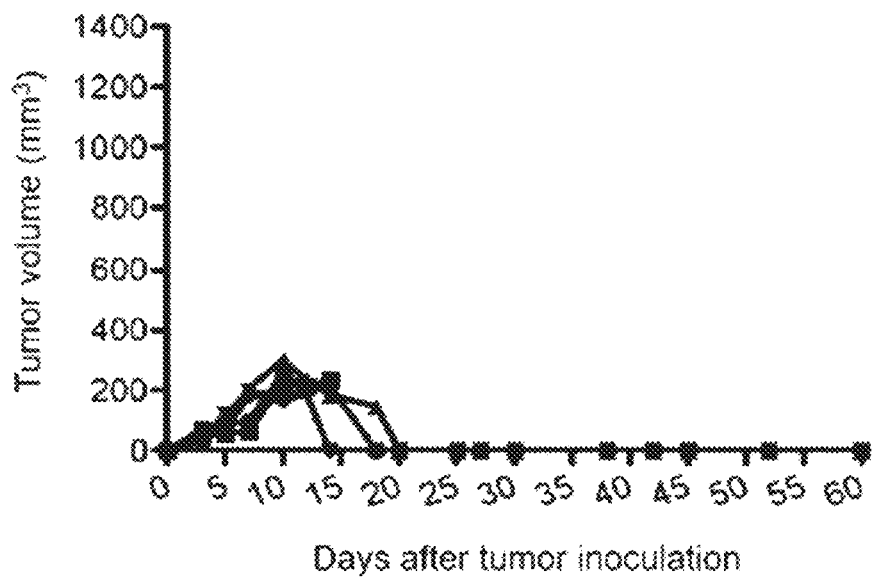

The survival rate upon administration of mGI-101 alone or in combination with DMXAA substance against the MC38 tumor is shown in FIG. 128. In the case of the vehicle control, all mice died before 40 days after tumor injection. In the case of the group having received mGI-101 alone, the survival rate on day 60 after tumor injection was 20%; and in the case of the group having received DMXAA, a STING agonist, alone, the survival rate on day 60 after tumor injection was 60%; and in the case of the group having received a combination of mGI-101+DMXAA, the survival rate on day 60 after tumor injection was 80%, indicating that the survival rate was higher than that of the other groups.

Individual tumor sizes for each test group are shown in FIGS. 129 to 133. The group having received a combination of mGI-101+DMXAA exhibited the greatest tumor growth inhibitory effect.

The invention claimed is:

1. A pharmaceutical composition comprising, as active ingredients, a fusion protein dimer comprising a CD80 fragment and an IL-2 variant; and an anticancer agent,
wherein the CD80 fragment is an extracellular domain of CD80 protein;
wherein the IL-2 variant comprises the amino acid sequence of SEQ ID NO: 10 with substitutions of R38A and F42A;
wherein the fusion protein has the following structural formula (I) or (II):

N'-X-[linker(1)]$_n$-Fc domain-[linker(2)]$_m$-Y-C'  (I)

N'-Y-[linker(1)]$_n$-Fc domain-[linker(2)]$_m$-X-C'  (II)

in the structural formulas (I) and (II),
N' is the N-terminus of the fusion protein,
C' is the C-terminus of the fusion protein,
X is the extracellular domain of CD80 protein,
Y is the IL-2 variant comprising the amino acid sequence of SEQ ID NO: 10 with substitutions of R38A and F42A,
the linkers (1) and (2) are peptide linkers, and
n and m are each independently 0 or 1,
and wherein the anticancer agent is selected form the group consisting of an anti-PD-1 (programmed cell death protein 1) antibody, an anti-PD-L1 (programmed cell death ligand 1) antibody, an anti-TIGIT (T cell immunoreceptor with Ig and ITIM domains) antibody, a VEGFR (vascular endothelial growth factor receptor) inhibitor, an EGFR (epidermal growth factor receptor) inhibitor, a PARP (poly (ADP-ribose) polymerase) inhibitor, a DNA methyltransferase inhibitor, a TGF-β (Transforming growth factor beta) receptor inhibitor, a CDK4/6 (cyclin-dependent kinase 4 and 6) inhibitor, a STING (stimulator of interferon genes) agonist, an alkylating agent, a microtubule inhibitor, an antimetabolite, a topoisomerase inhibitor, and combinations thereof.

2. The pharmaceutical composition of claim 1, wherein the VEGFR inhibitor is selected from the group consisting of Axitinib, Lenvatinib, Bevacizumab, Ramucirumab and Aflibercept.

3. The pharmaceutical composition of claim 1, wherein the EGFR inhibitor is selected from the group consisting of Cetuximab, Trastuzumab, Pertuzumab, Gefitinib, Elotinib and Panitumumab.

4. The pharmaceutical composition of claim 1, wherein the PARP inhibitor is selected from the group consisting of Olaparib, Talazoparib, Niraparib and Rucaparib.

5. The pharmaceutical composition of claim 1, wherein the DNA methyltransferase inhibitor is selected from the group consisting of Guadecitabine, Decitabine and Azacitidine.

6. The pharmaceutical composition of claim 1, wherein the TGF-β receptor inhibitor is selected from the group consisting of Galunisertib and Vactosertib.

7. The pharmaceutical composition of claim 1, wherein the CDK4/6 inhibitor is selected from the group consisting of Ribociclib, Abemaciclib and Palbociclib.

8. The pharmaceutical composition of claim 1, wherein the STING agonist is selected from the group consisting of DMXAA (5,6-dimethylxanthenone-4-acetic acid), a CDN (cyclic dinucleotide) and SB11285.

9. The pharmaceutical composition of claim 1, wherein the alkylating agent is selected from the group consisting of Cisplatin, Mechlorethamine, Cyclophosphamaide, Ifosfamide, Melphalan, Chlorambucil, Thiotepa, Altretamine, Procarbazine, Busulfan, Streptozocin, Carmustine, Iomustine, Dacabazine, Carboplatin and Oxaliplatin.

10. The pharmaceutical composition of claim 1, wherein the microtubule inhibitor is selected from the group consisting of Docetaxel, Velban, Oncovin and Navelbine.

11. The pharmaceutical composition of claim 1, wherein the antimetabolite is selected from the group consisting of Pemetrexed, Fluorouracil, Cytarabine, Fludarabine, Methotrexate, Mercaptopurine, Gemcitabine and Capecitabine.

* * * * *